(12) United States Patent
Blake et al.

(10) Patent No.: US 9,708,290 B2
(45) Date of Patent: Jul. 18, 2017

(54) SERINE/THREONINE KINASE INHIBITORS

(71) Applicants: ARRAY BIOPHARMA INC., Boulder, CO (US); GENENTECH, INC., South San Francisco, CA (US)

(72) Inventors: James F. Blake, Boulder, CO (US); Mark Joseph Chicarelli, Boulder, CO (US); Rustam Ferdinand Garrey, Boulder, CO (US); John Gaudino, Boulder, CO (US); Jonas Grina, Boulder, CO (US); David A. Moreno, Boulder, CO (US); Peter J. Mohr, Boulder, CO (US); Li Ren, Boulder, CO (US); Jacob Schwarz, South San Francisco, CA (US); Huifen Chen, South San Francisco, CA (US); Kirk Robarge, South San Francisco, CA (US); Aihe Zhou, South San Francisco, CA (US)

(73) Assignees: Array BioPharma Inc., Boulder, CO (US); Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/993,985

(22) Filed: Jan. 12, 2016

(65) Prior Publication Data
US 2016/0122316 A1 May 5, 2016

Related U.S. Application Data

(60) Continuation of application No. 14/181,418, filed on Feb. 14, 2014, now Pat. No. 9,259,470, which is a division of application No. 13/782,513, filed on Mar. 1, 2013, now Pat. No. 8,697,715.

(60) Provisional application No. 61/605,523, filed on Mar. 1, 2012.

(51) Int. Cl.
| | |
|---|---|
| *A61K 31/53* | (2006.01) |
| *C07D 401/04* | (2006.01) |
| *C07D 401/14* | (2006.01) |
| *C07D 405/14* | (2006.01) |
| *C07D 413/14* | (2006.01) |
| *C07D 409/14* | (2006.01) |
| *C07D 417/14* | (2006.01) |
| *C07D 471/04* | (2006.01) |
| *A61K 31/506* | (2006.01) |
| *A61K 45/06* | (2006.01) |
| *C07F 9/6558* | (2006.01) |
| *C07D 403/04* | (2006.01) |

(Continued)

(52) U.S. Cl.
CPC .......... *C07D 401/04* (2013.01); *A61K 31/506* (2013.01); *A61K 45/06* (2013.01); *C07D 401/14* (2013.01); *C07D 405/14* (2013.01); *C07D 409/14* (2013.01); *C07D 413/14* (2013.01); *C07D 417/14* (2013.01); *C07D 471/04* (2013.01); *C07F 9/65586* (2013.01); *A61K 31/444* (2013.01); *A61K 31/513* (2013.01); *A61K 31/53* (2013.01); *C07D 403/04* (2013.01)

(58) Field of Classification Search
CPC .. A61K 31/444; A61K 31/506; A61K 31/513; A61K 31/53; C07D 410/04; C07D 403/04
See application file for complete search history.

(56) References Cited

U.S. PATENT DOCUMENTS

| | | | | |
|---|---|---|---|---|
| 5,705,502 A | * | 1/1998 | Zimmermann | ...... C07D 401/04 514/252.02 |
| 8,697,715 B2 | * | 4/2014 | Blake | ................. C07F 9/65586 514/252.02 |
| 9,133,187 B2 | | 9/2015 | Blake et al. | |

(Continued)

FOREIGN PATENT DOCUMENTS

| | | |
|---|---|---|
| JP | 2005531501 A | 10/2005 |
| JP | 2015-179810 A | 10/2015 |

(Continued)

OTHER PUBLICATIONS

P. Stanetty et al., Journal of Organic Chemistry, 5215-5220 (2005).*

(Continued)

*Primary Examiner* — Alexander R Pagano
(74) *Attorney, Agent, or Firm* — Viksnins Harris & Padys PLLP

(57) ABSTRACT

Compounds of Formula I or a stereoisomer, tautomer, prodrug or pharmaceutically acceptable salt thereof are provided, which are useful for the treatment of hyperproliferative, pain and inflammatory diseases. Methods of using compounds of Formula I or a stereoisomer, tautomer, prodrug or pharmaceutically acceptable salt thereof, for in vitro, in situ, and in vivo diagnosis, prevention or treatment of such disorders in mammalian cells, or associated pathological conditions are disclosed.

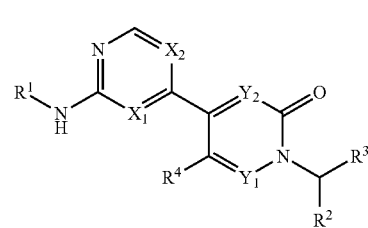

12 Claims, No Drawings

(51) Int. Cl.
    *A61K 31/513*    (2006.01)
    *A61K 31/444*    (2006.01)

(56) References Cited

U.S. PATENT DOCUMENTS

| | | | |
|---|---|---|---|
| 9,187,462 B2 | 11/2015 | Blake et al. | |
| 9,259,470 B2 * | 2/2016 | Blake | C07F 9/65586 |
| 9,388,171 B2 | 7/2016 | Blake et al. | |
| 2003/0171383 A1 | 9/2003 | Yasuda et al. | |
| 2009/0246198 A1 | 10/2009 | Dong et al. | |
| 2013/0252934 A1 | 9/2013 | Blake et al. | |
| 2013/0338140 A1 | 12/2013 | Blake et al. | |
| 2014/0066453 A1 | 3/2014 | Blake et al. | |
| 2015/0087664 A1 | 3/2015 | Blake et al. | |

FOREIGN PATENT DOCUMENTS

| | | |
|---|---|---|
| RU | 2288227 C2 | 11/2006 |
| RU | 2348627 C2 | 3/2009 |
| WO | 9509847 A1 | 4/1995 |
| WO | 9509851 A1 | 4/1995 |
| WO | 9824780 A2 | 6/1998 |
| WO | 0142241 A1 | 6/2001 |
| WO | 0162233 A2 | 8/2001 |
| WO | 0183448 A2 | 11/2001 |
| WO | 02087513 A2 | 11/2002 |
| WO | 03030909 A1 | 4/2003 |
| WO | 03057689 A1 | 7/2003 |
| WO | 03099808 A1 | 12/2003 |
| WO | 2004007468 A1 | 1/2004 |
| WO | 2005018557 A2 | 3/2005 |
| WO | 2005066139 A2 | 7/2005 |
| WO | 2005099711 A1 | 10/2005 |
| WO | 2005123680 A1 | 12/2005 |
| WO | 2006021458 A2 | 3/2006 |
| WO | 2006030032 A1 | 3/2006 |
| WO | 2006070208 A1 | 7/2006 |
| WO | 2006113704 A2 | 10/2006 |
| WO | 2007071348 A1 | 6/2007 |
| WO | 2007125405 A2 | 11/2007 |
| WO | 2007097937 A1 | 12/2007 |
| WO | 2008023239 A1 | 2/2008 |
| WO | 2008039882 A1 | 4/2008 |
| WO | 2008079933 A1 | 7/2008 |
| WO | 2008148889 A1 | 12/2008 |
| WO | 2009032861 A1 | 3/2009 |
| WO | 2009061761 A2 | 5/2009 |
| WO | 2009156484 A2 | 12/2009 |
| WO | 2009158571 A1 | 12/2009 |
| WO | 2010077275 A1 | 7/2010 |
| WO | 2011054837 A2 | 5/2011 |
| WO | 2012020786 A1 | 2/2012 |
| WO | 2012118850 A1 | 9/2012 |
| WO | 2013020062 A1 | 2/2013 |

OTHER PUBLICATIONS

P. Stanetty et al., 70 Journal of Organic Chemistry, 5215-5220 (2005).*
Aronov, et al., 50 Journal of Medical Chemistry, 1280-1287 (2007).
Ashton, et al., "Design and synthesis of novel amide AKT1 inhibitors with selectivity over CDK2", Bioorganic & Medical Chemistry Letters, vol. 21 (18), 5191-5196 (2011).
Bastian, "Genetic Progression", From Melanocytes to Melanoma the Progression to Malignancy 197, 201 (V.J. Hearing et al., eds., 2006).
Brinkmann, et al., "9 Nature reviews", Drug Discovery, 883-897 (2010).
Burkhard et al., "Development of Extracellular Signal-Regulated Kinase Inhibitors", Curr Top Med Chem 9(8), 678-689 (2009).
Cannistra, et al., "Ovarian Cancer, Fallopian Tube Carcinoma and Peritoneal Carcinoma", 2 Cancer Principles & Practice of Oncology 1568 (V.T. DeVita, Jr. et al. eds., 8th ed., 2008).
Carling, et al., "Thyroid Tumors", 2 Cancer Principles & Practice of Oncology 1503 (V.T. DeVita, Jr. et al. eds., 8th ed., 2008).
Collins, Current Signal Transduction Therapy, 1, 13-23, 13 (2006).
D'Ambrosio, et al., 273 Journal of Immunological Methods 3-13 (2003).
De Arruda, et al., Int. J. Radiation Oncology Biol. Phys., 64(2), 363-373 (2006).
Druker, et al., "Chronic Myelogenous Leukema", 2 Cancer Principles & Practice of Oncology 2121 (V. T. DeVita, Jr. et al., 7th ed., 2005).
Faderi, et al., "Myelodysplastic Syndromes", 2 Cancer Principles & Practice of Oncology 2133 (V.T. DeVita, Jr. et al. eds., 7th ed., 2005).
Friday, et al., 14 Clinical Cancer Research, 342-346, 344 (2008).
Hagan, et al., 11 Clinical Cancer Research, 7392-7397, 7393 (2005).
Hann, et al., Current Opinion in Cell Biology, 13, 778-784 (2001).
Judge, et al., 111 Pharmacology & Therapeutics, 224-259 (2006).
Kagaku-Dojin Publishing Co., Ltd, "Negishi Cross-Coupling", 1st edition, p. 310-311, 448-449 (Mar. 30, 2007). [English Translation.].
Keri, et al., "Rational Drug Design of Kinase Inhibitors for Signal Transduction Therapy", Protein Kinases as Drug Targets, 96 (B. Klebl et al., eds., 2011).
Kobel, et al., PLoS Medicine, 5(12) 1749-1760, 1749 (2008).
Koelink, et al., 133 Pharmacology & Therapeutics, 1-18 (2012).
Kohno, et al., "Pharmacological inhibitors of the ERK signaling pathway: application as anticancer drugs", Prog. Cell Cycle Res., vol. 5, 219-224 (2003).
Libutti, "Colon Cancer", 1 Cancer Principles & Practice of Oncology 1232, 1243(V.T. DeVita, Jr. et al. eds., 8th ed., 2008).
Ma, et al., "The ERK/MAPK pathway, as a target for the treatment of neuropathic pain", Expert Opin. Ther. Targets, 9(4), 699-713 (2005).
McCubrey, et al., 22 Leukemia, 708-722 (2008).
McIntyre, et al., "Pyridazine Based Inhibitors of p38 MAPK", Bioorganic & Medicinal Chemistry Letters. Pergamon, Elsevier Science, GB, vol. 12, 689-692, (2002).
Mizutani, et al., 580 FEBS Letters, 1417-1424 (2006).
Montagut, et al., 283 Cancer Letters 125-134 (2009).
O'Brien, et al., "Chronic Lymphoid Leukemias", 2 Cancer Principles & Practice of Oncology 2133 (V.T. DeVita, Jr. et al. eds., 7th ed., 2005).
Odunsi, et al., "Molecular Biology of Gynecological Cancers", 2 Cancer Principles & Practice of Oncology 1487, 1492 (V.T. DeVita, Jr. et al. eds., 8th ed., 2008).
Olive, et al., Clinical Cancer Reseach 12, 5277-5287 (2006).
Patent Cooperation Treaty, International Searching Authority, Search Report and Written Opinion for PCT/US2013/028622, 12 pages, Jun. 24, 2013.
Poupaert, "Drug Design: Basic Principles and Applications", 2 Encyclopedia of Pharmaceutical Technology 1362-1369, 1367 (James Swarbrick ed., 3rd ed., 2007).
Puszati, "Histopathologic and Molecular Markers of Prognosis and Response to Therapy", Breast Cancer 324, 326-328 (Kelly k. Hunt et al., ed., 2nd ed., 2008).
Raizer, Journal of Neuro-Oncology, 74(1), 77-86 (2005).
Ren, et al., "Discovery of Highly Potent, Selective and Efficacious Small Molecule Inhibitors of ERK/1/2", J. Med. Chem., Just accepted, 51 pages, published on Web Jan. 20, 2015.
Roberts, et al., 26 Oncogene, 3291-3310, 3305 (2007).
Rustgi, "Molecular Biology of the Esophagus and Stomach", 1 Cancer Principles & Practice of Oncology 989-993, 991(V.T. DeVita, Jr. et al. eds., 8th ed., 2008).
Scheinberg, et al., "Management of Acute Leukemias", 2 Cancer Principles & Practice of Oncology 2088, 2092 (V.T. DeVita, Jr. et al. eds., 7th ed., 2005).
Siefker-Radtke, "Uncommon Cancers of the Bladder", Textbook of Uncommon Cancer, 18-26 (D. Raghavan et al., eds., 3rd ed, 2006).
Sommer, et al., "Resolvins and inflammatory pain", F1000 Medicine Reports, 3, 19, 6 pages (2011).
Song, et al., "Cancer a Conceptual Framework", 1 Cancer Principles & Practice of Oncology 1, 5-6 (V. T. DeVita, Jr. et al. eds., 8th ed., 2008).

(56) References Cited

OTHER PUBLICATIONS

Stanetty, et al., "Novel and Efficient Access to Phenylaminopyrimidine Type Proten Kinase C Inhibitors Utilizing a Negishi Cross-Coupling Strategy", Journal of Organic Chemistry vol. 70, p. 5215-5220 (2005).
Steelman, et al., 22 Leukemia, 686-707 (2008).
Steelman, et al., 25 Leukemia, 1080-1094 (2011).
Sutherland, et al., 350 The New England Journal of Medicine, 2689-2697 (2004).
Testa, et al., "Prodrug Design", 5 Encyclopedia O Fpharmaceutical Technology, 3008-3014 (J. Swarbrick ed., 3rd ed., 2007).
Tiltman, Best Practice & Research Clinical Obstetrics & Gynaecology, 485-500, 19(4) (2005).
Traynor, et al., Drugs of Today, 40(8), 697-710, 698 (2004).
Tsai, et al., 105 PNAS 3041-3046, 3041 (2008).
Verhaak, et al., Cancer Cell, 17(1), 1-24 (2010).
Wong, et al., 4 Recent Patents on Anti-Cancer Drug Discovery, 28-35 (2009), Oct. 26, 2016.
Yap, et al., "Small Molecule Inhibitors of the ERK Signalling Pathway: Towards Novel Anti-cancer Therapeutics", ChemMedChem, 6(1), 38-48 (2011).
Zon, et al., Nature Reviews Drug Discovery 4, 35 (2005).

\* cited by examiner

SERINE/THREONINE KINASE INHIBITORS

RELATED APPLICATIONS

This application is a continuation of U.S. patent application Ser. No. 14/181,418 filed on Feb. 14, 2014, which is a divisional of U.S. patent application Ser. No. 13/782,513 filed on Mar. 1, 2013, and issued as U.S. Pat. No. 8,697,715 on Apr. 15, 2014, which claims priority to U.S. Provisional Application No. 61/605,523 filed on Mar. 1, 2012. The entire content of these applications is hereby incorporated herein by reference.

BACKGROUND OF THE INVENTION

Field of the Invention

The present invention relates to compounds that inhibit serine/threonine kinases and are useful for treating hyperproliferative and neoplastic diseases by inhibiting signal transduction pathways, which are commonly overactive or overexpressed in cancerous tissue. The present compounds are selective inhibitors of ERK (extracellular-signal regulated kinase). The present invention further relates to methods for treating cancer or hyperproliferative diseases with compounds of the present invention.

Description of the State of the Art

The processes involved in tumor growth, progression, and metastasis are mediated by signaling pathways that are activated in cancer cells. The ERK pathway plays a central role in regulating mammalian cell growth by relaying extracellular signals from ligand-bound cell surface receptor tyrosine kinase ("RTK's"), such as ErbB family, PDGF, FGF, and VEGF receptor tyrosine kinase. Activation of an RTK induces a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events, including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers, including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signaling pathway is an attractive pathway for anti-cancer therapies in a broad spectrum of human tumors (Kohno, M. and J. Pouyssegur. "Pharmacological inhibitors of the ERK signaling pathway: application as anticancer drugs." *Prog. Cell Cycle Res.* Vol. 5 (2003): pp. 219-224).

The ERK pathway has also been cited as a promising therapeutic target for the treatment of pain and inflammation (Ma, Weiya and Remi Quirion. "The ERK/MAPK pathway, as a target for the treatment of neuropathic pain." *Expert Opin. Ther. Targets.* 9(4) (2005): pp. 699-713; and Sommer, Claudia and Frank Birklein. "Resolvins and inflammatory pain." *F1000 Medicine Reports.* 3:19 (2011)).

Therefore, small-molecular inhibitors of ERK activity (i.e., ERK1 and/or ERK2 activity) would be useful for treating a broad spectrum of cancers, such as, for example, melanoma, pancreatic cancer, thyroid cancer, colorectal cancer, lung cancer, breast cancer, and ovarian cancer, as well as a treatment for pain and inflammation, such as arthritis, low back pain, inflammatory bowel disease, and rheumatism. Such a contribution is provided herein.

SUMMARY OF THE INVENTION

There is a continuing need for new and novel therapeutic agents that can be used for cancer and hyperproliferative conditions. The Raf/MEK/ERK pathway is an important signaling pathway, which is frequently overexpressed and/or overactive in many cancerous tissues. Design and development of new pharmaceutical compounds is essential.

More specifically, one aspect provides compounds of Formula I:

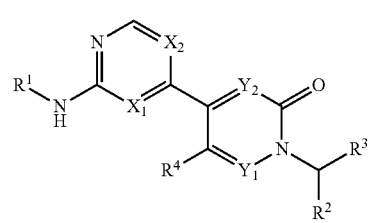

I or a stereoisomer, tautomer, prodrug or pharmaceutically acceptable salt thereof, wherein $X_1$, $X_2$, $Y_1$, $Y_2$, $R^1$, $R^2$, $R^3$ and $R^4$ are as defined herein.

Another aspect provides compounds of Formulas II, III, IV, V, VI, VII, VIII, IX and X, or a stereoisomer, tautomer or pharmaceutically acceptable salt thereof.

Another aspect provides a method for treating a hyperproliferative disorder by administering a therapeutically effective quantity of a compound according to Formula I, II, III, IV, V, VI, VII, VIII, IX or X, or a stereoisomer, tautomer or pharmaceutically acceptable salt thereof, to a patient in need thereof. The compound can be administered alone or co-administered with at least one other anti-hyperproliferative or chemotherapeutic compound.

Another aspect provides a method of inhibiting ERK protein kinase activity in a cell comprising treating the cell with a compound according to Formula I, II, III, IV, V, VI, VII, VIII, IX or X, or a stereoisomer, tautomer or pharmaceutically acceptable salt thereof, in an amount effective to attenuate or eliminate ERK kinase activity.

Another aspect provides methods of treating or preventing a disease or disorder modulated by ERK, comprising administering to a mammal in need of such treatment an effective amount of a compound of Formula I, II, III, IV, V, VI, VII, VIII, IX or X, or a stereoisomer, tautomer or pharmaceutically acceptable salt thereof. Examples of such diseases and disorders include, but are not limited to, hyperproliferative disorders, such as cancer.

Another aspect provides methods of treating or preventing cancer, comprising administering to a mammal in need of such treatment an effective amount of a compound of Formula I, II, III, IV, V, VI, VII, VIII, IX or X, or a stereoisomer, tautomer or pharmaceutically acceptable salt thereof, alone or in combination with one or more additional compounds having anti-cancer properties.

Another aspect provides a method of treating a hyperproliferative disease in a mammal comprising administering a therapeutically effective amount of a compound of Formula I, II, III, IV, V, VI, VII, VIII, IX or X, or a stereoisomer, tautomer or pharmaceutically acceptable salt thereof, to the mammal.

Another aspect provides the use of a compound of Formula I, II, III, IV, V, VI, VII, VIII, IX or X, or a stereoisomer, tautomer or pharmaceutically acceptable salt thereof, in the manufacture of a medicament for the treatment of a hyperproliferative disease.

Another aspect provides a compound of Formula I, II, III, IV, V, VI, VII, VIII, IX or X, or a stereoisomer, tautomer or pharmaceutically acceptable salt thereof, for use in the treatment of hyperproliferative diseases.

Another aspect provides a pharmaceutical composition comprising a compound of Formula I, II, III, IV, V, VI, VII, VIII, IX or X, or a stereoisomer, tautomer or pharmaceutically acceptable salt thereof, and a pharmaceutically acceptable carrier, diluent or excipient.

Another aspect provides intermediates for preparing compounds of Formula I, II, III, IV, V, VI, VII, VIII, IX or X. Certain compounds of the Formulas may be used as intermediates for other compounds of the Formulas.

Another aspect includes processes for preparing, methods of separation, and methods of purification of the compounds described herein.

DETAILED DESCRIPTION OF THE INVENTION

Reference will now be made in detail to certain embodiments, examples of which are illustrated in the accompanying structures and formulas. While enumerated embodiments will be described, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

DEFINITIONS

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein" refers to the broadest definition for each group as provided in the Detailed Description of the Invention or the broadest claim. In all other embodiments provided below, substituents that can be present in each embodiment, and which are not explicitly defined, retain the broadest definition provided in the Detailed Description of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components. Additionally, the words "include," "including," and "includes" when used in this specification and in the following claims are intended to specify the presence of stated features, integers, components, or steps, but they do not preclude the presence or addition of one or more other features, integers, components, steps, or groups thereof.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X_1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable that is inherently discrete, the variable can be equal to any integer value of the numerical range, including the end-points of the range. Similarly, for a variable that is inherently continuous, the variable can be equal to any real value of the numerical range, including the end-points of the range. As an example, a variable that is described as having values between 0 and 2, can be 0, 1 or 2 for variables that are inherently discrete, and can be 0.0, 0.1, 0.01, 0.001, or any other real value for variables that are inherently continuous.

Compounds of Formula I exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates; while in phenols, the enol form predominates. Common prototropic tautomers include keto/enol (—C(=O)—CH$_2$— ↔ —C(—OH)=CH—), amide/imidic acid (—C(=O)—NH— ↔ —

C(—OH)=N—) and amidine (—C(=NR)—NH— ↔ —C(—NHR)=N—) tautomers. The latter two are particularly common in heteroaryl and heterocyclic rings, and the present invention encompasses all tautomeric forms of the compounds.

It will be appreciated by the skilled artisan that some of the compounds of Formula I may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. The present invention includes all the individual stereoisomers (e.g., enantiomers), racemic mixtures or partially resolved mixtures of the compounds of Formula I and, where appropriate, the individual tautomeric forms thereof.

The compounds of Formula I may contain a basic center and suitable acid addition salts are formed from acids that form non-toxic salts. Examples of salts of inorganic acids include the hydrochloride, hydrobromide, hydroiodide, chloride, bromide, iodide, sulfate, bisulfate, nitrate, phosphate, and hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulfate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts, see Berge, Stephen M., et al. "Pharmaceutical salts." *J. Pharm. Sci*. Vol. 66, No. 1 (1977): 1-19, and Paulekuhn, G. Steffen, et al. "Trends in Active Pharmaceutical Ingredient Salt Selection based on Analysis of the Orange Book Database." *J. Med. Chem*. Vol. 50, No. 26 (2007): 6665-6672.

Technical and scientific terms used herein have the meaning commonly understood by one of skill in the art to which the present invention pertains, unless otherwise defined. Reference is made herein to various methodologies and materials known to those of skill in the art. A standard reference work setting forth the general principles of pharmacology include Hardman, Joel Griffith, et al. *Goodman & Gilman's The Pharmacological Basis of Therapeutics*. New York: McGraw-Hill Professional, 2001. The starting materials and reagents used in preparing these compounds generally are either available from commercial suppliers, such as Sigma-Aldrich (St. Louis, Mo.), or are prepared by methods known to those skilled in the art following procedures set forth in references. Materials, reagents and the like to which reference are made in the following description and examples are obtainable from commercial sources, unless otherwise noted. General synthetic procedures have been described in treatises, such as Louis F. Fieser and Mary Fieser, *Reagents for Organic Synthesis*. v. 1-23, New York: Wiley 1967-2006 ed. (also available via the Wiley InterScience® website); LaRock, Richard C., *Comprehensive Organic Transformations: A Guide to Functional Group Preparations*. New York: Wiley-VCH, 1999; B. Trost and I. Fleming, eds. *Comprehensive Organic Synthesis*. v. 1-9, Oxford: Pergamon 1991; A. R. Katritzky and C. W. Rees, eds. *Comprehensive Heterocyclic Chemistry*. Oxford: Pergamon 1984; A. R. Katritzky and C. W. Rees, eds. *Comprehensive Heterocyclic Chemistry II*. Oxford: Pergamon 1996; and Paquette, Leo A., ed. *Organic Reactions*. v. 1-40, New York: Wiley & Sons 1991; and will be familiar to those skilled in the art.

The term "alkyl" includes linear or branched-chain radicals of carbon atoms. Some alkyl moieties have been abbreviated, for example, methyl ("Me"), ethyl ("Et"), propyl ("Pr") and butyl ("Bu"), and further abbreviations are used to designate specific isomers of compounds, for example, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu") and the like. The abbreviations are sometimes used in conjunction with elemental abbreviations and chemical structures, for example, methanol ("MeOH") or ethanol ("EtOH"). In certain embodiments, alkyl is $C_{1-10}$ alkyl. In certain embodiments, alkyl is $C_{1-6}$ alkyl.

Additional abbreviations used throughout the application may include, for example, benzyl ("Bn"), phenyl ("Ph"), acetate ("Ac") and mesylate ("Ms").

The terms "alkenyl" and "alkynyl" also include linear or branched-chain radicals of carbon atoms.

The terms "heterocycle" and "heterocyclic" include four to seven membered saturated or partially unsaturated rings containing one, two or three heteroatoms selected from the group consisting of O, N, S, S(=O) and S(=O)$_2$. In certain instances, these terms may be specifically further limited, such as, "five to six membered heterocyclic" only including five and six membered rings.

The term "heteroaryl" includes five to six membered aromatic rings containing one, two, three or four heteroatoms selected from the group consisting of O, N and S. In certain instances, these terms may be specifically further limited, such as, five to six membered heteroaryl, wherein the heteroaryl contains one or two nitrogen heteroatoms. As well known to those skilled in the art, heteroaryl rings have less aromatic character than their all-carbon counter parts. Thus, for the purposes of the invention, a heteroaryl group need only have some degree of aromatic character.

A bond drawn into ring system (as opposed to connected at a distinct vertex) indicates that the bond may be attached to any of the suitable ring atoms.

The terms "treat" or "treatment" refer to therapeutic, prophylactic, palliative or preventative measures. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

The phrases "therapeutically effective amount" or "effective amount" mean an amount of a compound described herein that, when administered to a mammal in need of such treatment, sufficient to (i) treat or prevent the particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound that will correspond to such an amount will vary depending upon factors such as the particular compound, disease condition and its severity, the identity (e.g., weight) of the mammal in need of treatment, but can nevertheless be routinely determined by one skilled in the art.

The terms "cancer" and "cancerous" refer to or describe the physiological condition in mammals that is typically characterized by abnormal or unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, skin cancer, including melanoma, as well as head and neck cancer.

A "chemotherapeutic agent" is a chemical compound useful in the treatment of cancer. Examples of chemotherapeutic agents include erlotinib (TARCEVA®, Genentech/OSI Pharm.), bortezomib (VELCADE®, Millennium Pharm.), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors, such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens, such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Raf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

The phrase "pharmaceutically acceptable" indicates that the substance or composition is compatible chemically and/or toxicologically, with the other ingredients comprising a formulation, and/or the mammal being treated therewith.

The phrase "pharmaceutically acceptable salt," as used herein, refers to pharmaceutically acceptable organic or inorganic salts of a compound described herein.

The compounds described herein also include other salts of such compounds that are not necessarily pharmaceutically acceptable salts, and which may be useful as intermediates for preparing and/or purifying compounds described herein and/or for separating enantiomers of compounds described herein.

The term "mammal" means a warm-blooded animal that has or is at risk of developing a disease described herein and includes, but is not limited to, guinea pigs, dogs, cats, rats, mice, hamsters, and primates, including humans.

The term "prodrug" as used in this application refers to a precursor or derivative form of a compound of Formula I that is less active or inactive compared to the parent compound or drug and is capable of being metabolized in vivo into the more active parent form. See, e.g., Wilman, D E. "Prodrugs in Cancer Chemotherapy." *Biochem. Soc. Trans.* Vol. 14, No. 2 (1986): pp. 375-382; and Stella, Valentino J. and Kenneth J. Himmelstein. "Prodrugs: A Chemical Approach to Targeted Drug Delivery." In *Directed Drug Delivery*. Borchardt, Ronald T., Arnold J. Repta and Valentino J. Stella, eds. University of Michigan: Humana Press 1985, pp. 247-267. The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug.

ERK Inhibitors

Provided herein are compounds, and pharmaceutical formulations thereof, that are potentially useful in the treatment of diseases, conditions and/or disorders modulated by ERK.

One embodiment provides compounds of Formula I:

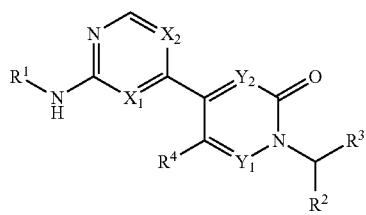

I or a stereoisomer, tautomer, prodrug or pharmaceutically acceptable salt thereof, wherein:

$X_1$ is selected from CH and N;
$X_2$ is selected from $CR^5$ and N;
$Y_1$ is selected from $CR^6$ and N;
$Y_2$ is selected from $CR^7$ and N;
$R^1$ is selected from (a) $C_1$-$C_6$ alkyl optionally substituted with one or more groups independently selected from halogen, $OR^a$, $NR^bR^c$, oxo, CN, $C_3$-$C_6$ cycloalkyl and a 3 to 7 membered heterocycle, (b) $C_3$-$C_7$ cycloalkyl optionally substituted with one or more groups independently selected from halogen, $OR^a$, CN and $C_1$-$C_3$ alkyl optionally substituted with one or more groups independently selected from halogen and $OR^d$, (c) phenyl optionally substituted with one or more groups independently selected from halogen, $OR^a$, CN, $C_3$-$C_6$ cycloalkyl and $C_1$-$C_3$ alkyl optionally substituted with one or more groups independently selected from halogen and $OR^d$, (d) a 3 to 7 membered saturated or partially unsaturated heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$, (e) a 5 to 6 membered heteroaryl optionally substituted with one or more groups independently selected from halogen, $OR^e$, oxide, CN, $C_3$-$C_6$ cycloalkyl and $C_1$-$C_3$ alkyl optionally substituted with one or more groups independently selected from halogen, oxo and $OR^d$, and (f) a 7 to 10 membered bicyclic heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$;

$R^2$ is selected from (a) hydrogen, (b) $C_1$-$C_6$ alkyl optionally substituted with one or more groups selected from $OR^f$, oxo, $NH_2$, $NH(C_1$-$C_3$ alkyl) and $N(C_1$-$C_3$ alkyl)$_2$, (c) $C_1$-$C_6$ alkenyl optionally substituted with one or more groups selected from $OR^f$, oxo, $NH_2$, $NH(C_1$-$C_3$ alkyl) and $N(C_1$-$C_3$ alkyl)$_2$, (d) $C_1$-$C_6$ alkynyl optionally substituted with one or more groups selected from $OR^f$, oxo, $NH_2$, $NH(C_1$-$C_3$ alkyl) and $N(C_1$-$C_3$ alkyl)$_2$, (e) $C_3$-$C_6$ cycloalkyl optionally substituted with one or more groups selected from $OR^f$ and $R^g$, (f) phenyl optionally substituted with one or more groups selected from $OR^f$ and $R^g$, (g) a 3 to 7 membered heterocycle optionally substituted with one or more groups selected from $OR^f$ and $R^g$, and (h) a 5 to 6 membered heteroaryl optionally substituted with one or more groups selected from $OR^f$ and $R^g$;

$R^3$ is selected from (a) $(CR^hR^i)_x$-phenyl, wherein the phenyl may be optionally substituted with one or more $R^j$ groups, (b) $(CR^hR^i)_x$-(5 to 6 membered heteroaryl), wherein the heteroaryl may be optionally substituted with one or more $R^j$ groups, (c) $(CR^hR^i)_x$-(9 to 10 membered bicyclic heterocycle), wherein the heterocycle may be optionally substituted with one or more $R^j$ groups, and (d) $(CR^hR^i)_x$-(9 to 10 membered bicyclic heteroaryl), wherein the heteroaryl may be optionally substituted with one or more $R^j$ groups;

each $R^4$, $R^5$, $R^6$ and $R^7$ is independently selected from hydrogen, halogen and $C_1$-$C_3$ alkyl;

each $R^a$, $R^b$, $R^c$, $R^d$ and $R^e$ are independently selected from hydrogen and $C_1$-$C_6$ alkyl;

$R^f$ is selected from hydrogen and $C_1$-$C_6$ alkyl optionally substituted with one or more groups selected from oxo, $NH_2$, $NH(C_1$-$C_3$ alkyl) and $N(C_1$-$C_3$ alkyl)$_2$;

each $R^g$ is $C_1$-$C_6$ alkyl;

$R^h$ and $R^i$ are independently selected from hydrogen, $OR^k$ and $C_1$-$C_6$ alkyl optionally substituted with $OR^m$;

each $R^j$ is independently selected from halogen, CN, cyclopropyl, $C_1$-$C_6$ alkyl optionally substituted with halogen, and $C_1$-$C_6$ alkoxy optionally substituted with halogen;

$R^k$ and $R^m$ are independently selected from hydrogen and $C_1$-$C_3$ alkyl; and x is 0 or 1.

In another embodiment, compounds of Formula I or a stereoisomer, tautomer or pharmaceutically acceptable salt thereof are provided.

In certain embodiments, $X_1$ is selected from CH and N; and $X_2$ is selected from $CR^5$ and N; wherein only one of $X_1$ and $X_2$ may be N.

In certain embodiments, $Y_1$ is selected from $CR^6$ and N; and $Y_2$ is selected from $CR^7$ and N; wherein only one of $Y_1$ and $Y_2$ may be N.

In certain embodiments, compounds of the invention have the stereochemical orientation represented by Formula II:

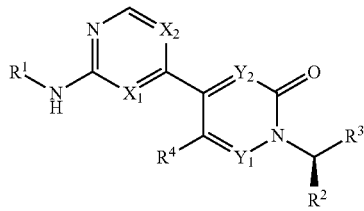

II or a stereoisomer, tautomer or pharmaceutically acceptable salt thereof, wherein $X_1$, $X_2$, $Y_1$ $Y_2$, $R^1$, $R^2$, $R^3$ and $R^4$ are as defined herein.

In certain embodiments, compounds of the invention have the stereochemical orientation represented by Formula III:

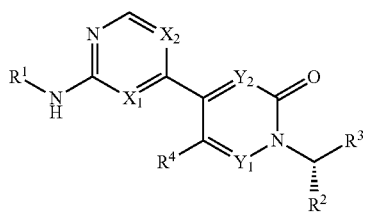

III or a stereoisomer, tautomer or pharmaceutically acceptable salt thereof, wherein $X_1$, $X_2$, $Y_1$ $Y_2$, $R^1$, $R^2$, $R^3$ and $R^4$ are as defined herein.

In certain embodiments, compounds of the invention have the stereochemical orientation represented by Formula IV:

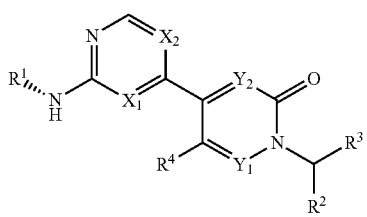

IV or a stereoisomer, tautomer or pharmaceutically acceptable salt thereof, wherein $X_1$, $X_2$, $Y_1$ $Y_2$, $R^1$, $R^2$, $R^3$ and $R^4$ are as defined herein.

In certain embodiments, compounds of the invention have the stereochemical orientation represented by Formula V:

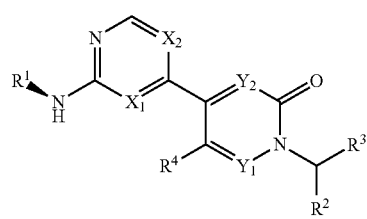

V or a stereoisomer, tautomer or pharmaceutically acceptable salt thereof, wherein $X_1$, $X_2$, $Y_1$ $Y_2$, $R^1$, $R^2$, $R^3$ and $R^4$ are as defined herein.

In certain embodiments, compounds of the invention have the Formula VI:

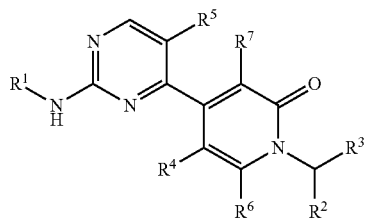

VI or a stereoisomer, tautomer or pharmaceutically acceptable salt thereof, wherein $R^1$, $R^2$, $R^3$, $R^4$, $R^5$, $R^6$ and $R^7$ are as defined herein.

In certain embodiments, compounds of the invention have the Formula VII:

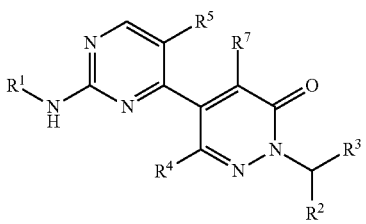

VII or a stereoisomer, tautomer or pharmaceutically acceptable salt thereof, wherein $R^1$, $R^2$, $R^3$, $R^4$, $R^5$ and $R^7$ are as defined herein.

In certain embodiments, compounds of the invention have the Formula VIII:

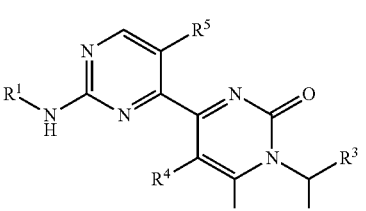

VIII or a stereoisomer, tautomer or pharmaceutically acceptable salt thereof, wherein $R^1$, $R^2$, $R^3$, $R^4$, $R^5$ and $R^6$ are as defined herein.

In certain embodiments, compounds of the invention have the Formula IX:

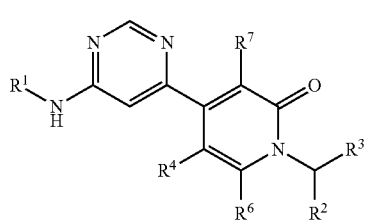

IX or a stereoisomer, tautomer or pharmaceutically acceptable salt thereof, wherein $R^1$, $R^2$, $R^3$, $R^4$, $R^6$ and $R^7$ are as defined herein.

In certain embodiments, compounds of the invention have the Formula X:

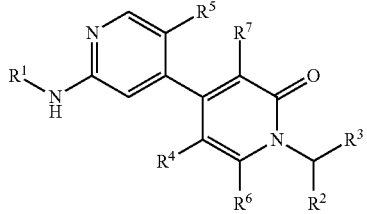

or a stereoisomer, tautomer or pharmaceutically acceptable salt thereof, wherein $R^1$, $R^2$, $R^3$, $R^4$, $R^5$, $R^6$ and $R^7$ are as defined herein.

In certain embodiments:

$X_1$ is selected from CH and N;
$X_2$ is selected from $CR^5$ and N;
$Y_1$ is selected from $CR^6$ and N;
$Y_2$ is selected from $CR^7$ and N;
$R^1$ is selected from (a) $C_1$-$C_6$ alkyl optionally substituted with one or more groups independently selected from halogen, $OR^a$, $NR^bR^c$, oxo, CN, $C_3$-$C_6$ cycloalkyl and a 3 to 7 membered heterocycle, (b) $C_3$-$C_7$ cycloalkyl optionally substituted with one or more groups independently selected from halogen, $OR^a$, CN and $C_1$-$C_3$ alkyl optionally substituted with one or more groups independently selected from halogen and $OR^d$, (c) phenyl optionally substituted with one or more groups independently selected from halogen, $OR^a$, CN, $C_3$-$C_6$ cycloalkyl and $C_1$-$C_3$ alkyl optionally substituted with one or more groups independently selected from halogen and $OR^d$, (d) a 3 to 7 membered saturated or partially unsaturated heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$, (e) a 5 to 6 membered heteroaryl optionally substituted with one or more groups independently selected from halogen, $OR^e$, oxide, CN, $C_3$-$C_6$ cycloalkyl and $C_1$-$C_3$ alkyl optionally substituted with one or more groups independently selected from halogen, oxo and $OR^d$, and (f) a 7 to 10 membered bicyclic heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$;
$R^2$ is selected from (a) hydrogen, (b) $C_1$-$C_6$ alkyl optionally substituted with one or more groups selected from $OR^f$, oxo, $NH_2$, $NH(C_1$-$C_3$ alkyl) and $N(C_1$-$C_3$ alkyl)$_2$, (c) $C_1$-$C_6$ alkenyl optionally substituted with one or more $OR^f$ groups, (d) $C_1$-$C_6$ alkynyl optionally substituted with one or more $OR^f$ groups, (e) $C_3$-$C_6$ cycloalkyl optionally substituted with one or more groups selected from $OR^f$ and $R^g$, (f) phenyl optionally substituted with one or more groups selected from $OR^f$ and $R^g$, (g) a 3 to 7 membered heterocycle optionally substituted with one or more groups selected from $OR^f$ and $R^g$, and (h) a 5 to 6 membered heteroaryl optionally substituted with one or more groups selected from $OR^f$ and $R^g$;
$R^3$ is selected from (a) $(CR^hR^i)_x$-phenyl, wherein the phenyl may be optionally substituted with one or more $R^j$ groups, (b) a 5 to 6 membered heteroaryl optionally substituted with one or more $R^j$ groups, (c) a 9 to 10 membered bicyclic heterocycle optionally substituted with one or more $R^j$ groups, and (d) a 9 to 10 membered bicyclic heteroaryl optionally substituted with one or more $R^j$ groups;
each $R^4$, $R^5$, $R^6$ and $R^7$ is independently selected from hydrogen, halogen and $C_1$-$C_3$ alkyl;
each $R^a$, $R^b$, $R^c$, $R^d$ and $R^e$ are independently selected from hydrogen and $C_1$-$C_6$ alkyl;
$R^f$ is selected from hydrogen and $C_1$-$C_6$ alkyl optionally substituted with one or more groups selected from oxo, $NH_2$, $NH(C_1$-$C_3$ alkyl) and $N(C_1$-$C_3$ alkyl)$_2$;
each $R^g$ is $C_1$-$C_6$ alkyl;
$R^h$ and $R^i$ are independently selected from hydrogen, $OR^k$ and $C_1$-$C_6$ alkyl optionally substituted with $OR^m$;
each $R^j$ is independently selected from halogen, CN, cyclopropyl, $C_1$-$C_6$ alkyl optionally substituted with halogen, and $C_1$-$C_6$ alkoxy optionally substituted with halogen;
$R^k$ and $R^m$ are independently selected from hydrogen and $C_1$-$C_3$ alkyl; and
x is 0 or 1.

In certain embodiments:

$X_1$ is selected from CH and N;
$X_2$ is selected from $CR^5$ and N;
$Y_1$ is selected from $CR^6$ and N;
$Y_2$ is selected from $CR^7$ and N;
$R^1$ is selected from (a) $C_1$-$C_6$ alkyl optionally substituted with one or more groups independently selected from halogen, $OR^a$, $NR^bR^c$, oxo, CN, $C_3$-$C_6$ cycloalkyl and a 3 to 7 membered heterocycle, (b) $C_3$-$C_7$ cycloalkyl optionally substituted with one or more groups independently selected from halogen, $OR^a$, CN and $C_1$-$C_3$ alkyl optionally substituted with one or more groups independently selected from halogen and $OR^d$, (c) phenyl optionally substituted with one or more groups independently selected from halogen, $OR^a$, CN, $C_3$-$C_6$ cycloalkyl and $C_1$-$C_3$ alkyl optionally substituted with one or more groups independently selected from halogen and $OR^d$, (d) a 3 to 7 membered saturated or partially unsaturated heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$, (e) a 5 to 6 membered heteroaryl optionally substituted with one or more groups independently selected from halogen, $OR^e$, oxide, CN, $C_3$-$C_6$ cycloalkyl and $C_1$-$C_3$ alkyl optionally substituted with one or more groups independently selected from halogen, oxo and $OR^d$, and (f) a 7 to 10 membered bicyclic heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$;
$R^2$ is selected from (a) hydrogen, (b) $C_1$-$C_6$ alkyl optionally substituted with one or more groups selected from $OR^f$ and oxo, (c) $C_1$-$C_6$ alkenyl optionally substituted with one or more $OR^f$ groups, (d) $C_1$-$C_6$ alkynyl optionally substituted with one or more $OR^f$ groups, (e) $C_3$-$C_6$ cycloalkyl optionally substituted with one or more groups selected from $OR^f$ and $R^g$, (f) phenyl optionally substituted with one or more groups selected from $OR^f$ and $R^g$, (g) a 3 to 7 membered heterocycle optionally substituted with one or more groups selected from $OR^f$ and $R^g$, and (h) a 5 to 6 membered heteroaryl optionally substituted with one or more groups selected from $OR^f$ and $R^g$;
$R^3$ is selected from (a) $(CR^hR^i)_x$-phenyl, wherein the phenyl may be optionally substituted with one or more $R^j$ groups, (b) a 5 to 6 membered heteroaryl optionally substituted with one or more $R^j$ groups, (c) a 9 to 10 membered heterocycle optionally substituted with one or more $R^j$ groups, and (d) a 9 to 10 membered heteroaryl optionally substituted with one or more $R^j$ groups;

each $R^4$, $R^5$, $R^6$ and $R^7$ is independently selected from hydrogen, halogen and $C_1$-$C_3$ alkyl;

each $R^a$, $R^b$, $R^c$, $R^d$, $R^e$ and $R^f$ are independently selected from hydrogen and $C_1$-$C_6$ alkyl;

each $R^g$ is $C_1$-$C_6$ alkyl;

$R^h$ and $R^i$ are independently selected from hydrogen, $OR^k$ and $C_1$-$C_6$ alkyl optionally substituted with $OR^m$;

each $R^j$ is independently selected from halogen, CN, cyclopropyl, $C_1$-$C_6$ alkyl optionally substituted with halogen, and $C_1$-$C_6$ alkoxy optionally substituted with halogen;

$R^k$ and $R^m$ are independently hydrogen or $C_1$-$C_3$ alkyl; and x is 0 or 1.

In certain embodiments, $R^1$ is selected from (a) $C_1$-$C_6$ alkyl optionally substituted with one or more groups independently selected from halogen, $OR^a$, $NR^bR^c$, oxo, CN, $C_3$-$C_6$ cycloalkyl and a 3 to 7 membered heterocycle, wherein the heterocycle contains one, two or three heteroatoms selected from the group consisting of O, N, S, S(=O) and S(=O)$_2$, (b) $C_3$-$C_7$ cycloalkyl optionally substituted with one or more groups independently selected from halogen, $OR^a$, CN and $C_1$-$C_3$ alkyl optionally substituted with one or more groups independently selected from halogen and $OR^d$, (c) phenyl optionally substituted with one or more groups independently selected from halogen, $OR^a$, CN, $C_3$-$C_6$ cycloalkyl and $C_1$-$C_3$ alkyl optionally substituted with one or more groups independently selected from halogen and $OR^d$, (d) a 3 to 7 membered saturated or partially unsaturated heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$, wherein the heterocycle contains one, two or three heteroatoms selected from the group consisting of O, N, S, S(=O) and S(=O)$_2$, (e) a 5 to 6 membered heteroaryl optionally substituted with one or more groups independently selected from halogen, $OR^e$, oxide, CN, $C_3$-$C_6$ cycloalkyl and $C_1$-$C_3$ alkyl optionally substituted with one or more groups independently selected from halogen, oxo and $OR^d$, wherein the heteroaryl contains one, two, three or four heteroatoms selected from the group consisting of O, N and S, and (f) a 7 to 10 membered bicyclic heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$, wherein the heterocycle contains one, two or three heteroatoms selected from the group consisting of O, N, S, S(=O) and S(=O)$_2$.

In certain embodiments, $R^1$ is selected from (a) $C_1$-$C_6$ alkyl optionally substituted with one to six groups independently selected from halogen, $OR^a$, $NR^bR^c$, $C_3$-$C_6$ cycloalkyl and a 3 to 7 membered heterocycle, wherein the heterocycle contains one, two or three heteroatoms selected from the group consisting of O, N, S, S(=O) and S(=O)$_2$, (b) $C_3$-$C_7$ cycloalkyl optionally substituted with one to four groups independently selected from halogen and $OR^a$, (c) phenyl optionally substituted with one to four groups independently selected from halogen and $C_1$-$C_3$ alkyl, (d) a 3 to 7 membered saturated or partially unsaturated heterocycle optionally substituted with one to four groups independently selected from halogen, oxo, $OR^a$ and $C_1$-$C_3$ alkyl optionally substituted with $OR^d$, wherein the heterocycle contains one, two or three heteroatoms selected from the group consisting of O, N, S, S(=O) and S(=O)$_2$, (e) a 5 to 6 membered heteroaryl optionally substituted with one to four groups independently selected from halogen, CN, $OR^e$, $C_3$-$C_6$ cycloalkyl, oxide and $C_1$-$C_3$ alkyl optionally substituted with one to three groups independently selected from hydroxyl, methoxy, oxo and halogen, wherein the heteroaryl contains one, two, three or four heteroatoms selected from the group consisting of O, N and S, and (f) a 7 to 10 membered bicyclic heterocycle optionally substituted with one or two groups selected from $C_1$-$C_3$ alkyl and oxo, wherein the heterocycle contains one, two or three heteroatoms selected from the group consisting of O, N, S, S(=O) and S(=O)$_2$.

In certain embodiments, each $R^a$ is independently selected from hydrogen and $C_1$-$C_6$ alkyl. In certain embodiments, each $R^a$ is independently selected from hydrogen and $C_1$-$C_3$ alkyl. In certain embodiments, each $R^a$ is independently selected from hydrogen and methyl.

In certain embodiments, each $R^b$ and $R^c$ are independently selected from hydrogen and $C_1$-$C_6$ alkyl. In certain embodiments, each $R^b$ and $R^c$ are independently selected from hydrogen and $C_1$-$C_3$ alkyl. In certain embodiments, each $R^b$ and $R^c$ are independently selected from hydrogen and methyl.

In certain embodiments, each $R^d$ is independently selected from hydrogen and $C_1$-$C_6$ alkyl. In certain embodiments, each $R^d$ is independently selected from hydrogen and $C_1$-$C_3$ alkyl. In certain embodiments, each $R^d$ is selected from hydrogen and methyl.

In certain embodiments, each $R^e$ is independently selected from hydrogen and $C_1$-$C_6$ alkyl. In certain embodiments, each $R^e$ is independently selected from hydrogen and $C_1$-$C_3$ alkyl. In certain embodiments, each $R^e$ is independently selected from methyl and ethyl.

In certain embodiments, $R^1$ is selected from 1-hydroxypropan-2-yl, isopropyl, 1-hydroxybutan-2-yl, 1-cyclopropylethyl, 1-hydroxy-3-methoxypropan-2-yl, 1,3-difluoropropan-2-yl, 1-cyclopropyl-2-hydroxyethyl, oxetan-3-ylmethyl, 4-methoxybutan-2-yl, 4,4,4-trifluoro-1-hydroxybutan-2-yl, 1-aminopropan-2-yl, 3-hydroxycyclopentyl, 3,3-difluorocyclobutyl, 3-hydroxycyclobutyl, 2-chloro-4-fluorophenyl, 4-fluoro-2-methylphenyl, tetrahydropyran-4-yl, 3-fluorotetrahydropyran-4-yl, tetrahydrodioxothiopyran-4-yl, 1,1-dioxotetrahydrothiophen-3-yl, oxetan-3-yl, tetrahydrofuran-3-yl, 2,2-dimethyltetrahydropyran-4-yl, 2-methyltetrahydropyran-4-yl, pyrrolidin-3-yl, azetidin-3-yl, piperdin-3-yl, 2-(hydroxymethyl)tetrahydropyran-4-yl, 6-oxo-1,6-dihydropyridin-3-yl, 1-methylpyrazol-4-yl, 2-methylpyrimidin-4-yl, 6-methylpyrimidin-4-yl, 6-methoxypyrimidin-4-yl, 2-methylpyridin-4-yl, 1,3-dimethylpyrazol-4-yl, 2-methoxypyridin-4-yl, 1-methylpyrazol-3-yl, 6-methoxypyridin-3-yl, 2-ethylpyrimidin-4-yl, 6-methylpyridin-2-yl, 2-cyclopropylpyrimidin-4-yl, 5-fluoro-6-methylpyridin-2-yl, 5-cyclopropyl-1-methylpyrazol-4-yl, 5-bromo-2-methylpyridin-4-yl, 1,5-dimethylpyrazol-4-yl, 1,3-dimethylpyrazol-5-yl, 4-(2-hydroxypropan-2-yl)pyridin-2-yl, 1-ethyl-3-methylpyrazol-4-yl, 5-ethoxy-2-methylpyridin-4-yl, 1-isopropylpyrazol-4-yl, 4-methylimidazol-5-yl, 1-methylimidazol-5-yl, 1-ethylpyrazol-4-yl, 2-(2-hydroxypropan-2-yl)pyridin-4-yl, 1-methyl-4-cyanopyrazol-5-yl, 3-methylpyridin-4-yl, 1-ethyl-3-methylpyrazol-5-yl, 1-methylpyrazol-5-yl, 1,4-dimethylpyrazol-5-yl, 1-ethylpyrazol-5-yl, 3-isopropyl-1-methylpyrazol-5-yl, 3-methylpyrazol-4-yl, 3-ethyl-1-methylpyrazol-4-yl, 1,3,5-trimethylpyrazol-4-yl, 3,5-dimethylpyrazol-4-yl, 2-cyclopropyl-5-methoxypyridin-4-yl, 5-ethyl-1-methylpyrazol-4-yl, 4-(2-methoxypyridine 1-oxide), 5-methoxy-2-methylpyridin-4- yl, 5-methyl-1,3,4-oxadizol-2-yl, 3-ethyl-1-methylpyrazol-5-yl, 1-(2-hydroxyethyl)-3-methylpyrazol-4-yl, 1-(2-hydroxyethyl)-5-methylpyrazol-4-yl, 1-methyl-3-(trifluoromethyl)pyrazol-4-yl, 1-methyl-3-(trifluoromethyl)pyrazol-5-yl, 1-methyl-1,2,3-triazol-5-yl, 2-methylpyridin-4-yl, 1-(2-hydroxyethyl)pyrazol-5-yl, methyl 4-picolinate, 4-picolinic acid, 1-cyclopropyl-5-methylpyrazol-4-yl, 1-cyclopropyl-3-methylpyrazol-4-yl, 2,3-dimethylpyridin-4-yl, 2,5-dimethylpyridin-4-yl, 1,3,4-oxadizol-2-yl, 3-methylpyridazin-4-yl, pyridazin-4-yl, tetrazol-5-yl, 1-methyltetrazol-5-yl, 2-methyl-2,4,5,6-tetrahydrocyclopentapyrazol-3-yl, 3-oxo-2-oxabicyclo[2.2.1]heptan-5-yl and 2-oxabicyclo[2.2.1]heptan-5-yl.

In certain embodiments, $R^1$ is selected from 1-hydroxypropan-2-yl, isopropyl, 1-hydroxybutan-2-yl, 1-cyclopropylethyl, 1-hydroxy-3-methoxypropan-2-yl, 1,3-difluoropropan-2-yl, 1-cyclopropyl-2-hydroxyethyl, oxetan-3-ylmethyl, 4-methoxybutan-2-yl, 4,4,4-trifluoro-1-hydroxybutan-2-yl, 1-aminopropan-2-yl, 3-hydroxycyclopentyl, 3,3-difluorocyclobutyl, 3-hydroxycyclobutyl, 2-chloro-4-fluorophenyl, 4-fluoro-2-methylphenyl, tetrahydropyran-4-yl, 3-fluorotetrahydropyran-4-yl, tetrahydrodioxothiopyran-4-yl, 1,1-dioxotetrahydrothiophen-3-yl, oxetan-3-yl, tetrahydrofuran-3-yl, 2,2-dimethyltetrahydropyran-4-yl, 2-methyltetrahydropyran-4-yl, pyrrolidin-3-yl, azetidin-3-yl, piperdin-3-yl, 2-(hydroxymethyl)tetrahydropyran-4-yl, 6-oxo-1,6-dihydropyridin-3-yl, 1-methylpyrazol-4-yl, 2-methylpyrimidin-4-yl, 6-methylpyrimidin-4-yl, 6-methoxypyrimidin-4-yl, 2-methylpyridin-4-yl, 1,3-dimethylpyrazol-4-yl, 2-methoxypyridin-4-yl, 1-methylpyrazol-3-yl, 6-methoxypyridin-3-yl, 2-ethylpyrimidin-4-yl, 6-methylpyridin-2-yl, 2-cyclopropylpyrimidin-4-yl, 5-fluoro-6-methylpyridin-2-yl, 5-cyclopropyl-1-methylpyrazol-4-yl, 5-bromo-2-methylpyridin-4-yl, 1,5-dimethylpyrazol-4-yl, 1,3-dimethylpyrazol-5-yl, 4-(2-hydroxypropan-2-yl)pyridin-2-yl, 1-ethyl-3-methylpyrazol-4-yl, 5-ethoxy-2-methylpyridin-4-yl, 1-isopropylpyrazol-4-yl, 4-methylimidazol-5-yl, 1-methylimidazol-5-yl, 1-ethylpyrazol-4-yl, 2-(2-hydroxypropan-2-yl)pyridin-4-yl, 1-methyl-4-cyanopyrazol-5-yl, 3-methylpyridin-4-yl, 1-ethyl-3-methylpyrazol-5-yl, 1-methylpyrazol-5-yl, 1,4-dimethylpyrazol-5-yl, 1-ethylpyrazol-5-yl, 3-isopropyl-1-methylpyrazol-5-yl, 3-methylpyrazol-4-yl, 3-ethyl-1-methylpyrazol-4-yl, 1,3,5-trimethylpyrazol-4-yl, 3,5-dimethylpyrazol-4-yl, 2-cyclopropyl-5-methoxypyridin-4-yl, 5-ethyl-1-methylpyrazol-4-yl, 4-(2-methoxypyridine 1-oxide), 5-methoxy-2-methylpyridin-4-yl, 5-methyl-1,3,4-oxadizol-2-yl, 3-ethyl-1-methylpyrazol-5-yl, 1-(2-hydroxyethyl)-3-methylpyrazol-4-yl, 1-(2-hydroxyethyl)-5-methylpyrazol-4-yl, 1-methyl-3-(trifluoromethyl)pyrazol-4-yl, 1-methyl-3-(trifluoromethyl)pyrazol-5-yl, 1-methyl-1,2,3-triazol-5-yl, 2-methylpyridin-4-yl, 1-(2-hydroxyethyl)pyrazol-5-yl, methyl 4-picolinate, 4-picolinic acid, 1-cyclopropyl-5-methylpyrazol-4-yl, 1-cyclopropyl-3-methylpyrazol-4-yl, 2,3-dimethylpyridin-4-yl, 2,5-dimethylpyridin-4-yl, 1,3,4-oxadizol-2-yl, 3-methylpyridazin-4-yl, pyridazin-4-yl, 2-methyl-2,4,5,6-tetrahydrocyclopentapyrazol-3-yl, 3-oxo-2-oxabicyclo[2.2.1]heptan-5-yl and 2-oxabicyclo[2.2.1]heptan-5-yl.

In certain embodiments, $R^1$ is selected from (a) $C_1$-$C_6$ alkyl optionally substituted with one or more groups independently selected from halogen, $OR^a$, $NR^bR^c$, oxo, CN, $C_3$-$C_6$ cycloalkyl and a 3 to 7 membered heterocycle, wherein the heterocycle contains one, two or three heteroatoms selected from the group consisting of O, N, S, S(=O) and S(=O)$_2$, (b) $C_3$-$C_7$ cycloalkyl optionally substituted with one or more groups independently selected from halogen, $OR^a$, CN and $C_1$-$C_3$ alkyl optionally substituted with one or more groups independently selected from halogen and $OR^d$, (c) phenyl optionally substituted with one or more groups independently selected from halogen, $OR^a$, CN, $C_3$-$C_6$ cycloalkyl and $C_1$-$C_3$ alkyl optionally substituted with one or more groups independently selected from halogen and $OR^d$, (d) a 3 to 7 membered saturated or partially unsaturated heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$, wherein the heterocycle contains one, two or three heteroatoms selected from the group consisting of O, N, S, S(=O) and S(=O)$_2$, (e) a 5 to 6 membered heteroaryl optionally substituted with one or more groups independently selected from halogen, $OR^e$, CN, $C_3$-$C_6$ cycloalkyl and $C_1$-$C_3$ alkyl optionally substituted with one or more groups independently selected from halogen, oxo and $OR^d$, wherein the heteroaryl contains one, two, three or four heteroatoms selected from the group consisting of O, N and S and (f) a 7 to 10 membered bicyclic heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$, wherein the heterocycle contains one, two or three heteroatoms selected from the group consisting of O, N, S, S(=O) and S(=O)$_2$.

In certain embodiments, $R^1$ is selected from (a) $C_1$-$C_6$ alkyl optionally substituted with one to six groups independently selected from halogen, $OR^a$, $NR^bR^c$, $C_3$-$C_6$ cycloalkyl and a 3 to 7 membered heterocycle, wherein the heterocycle contains one, two or three heteroatoms selected from the group consisting of O, N, S, S(=O) and S(=O)$_2$, (b) $C_3$-$C_7$ cycloalkyl optionally substituted with one to four groups independently selected from halogen and $OR^a$, (c) phenyl optionally substituted with one to four groups independently selected from halogen and $C_1$-$C_3$ alkyl, (d) a 3 to 7 membered saturated or partially unsaturated heterocycle optionally substituted with one to four groups independently selected from halogen, oxo, $OR^a$, and $C_1$-$C_3$ alkyl optionally substituted with $OR^d$, wherein the heterocycle contains one, two or three heteroatoms selected from the group consisting of O, N, S, S(=O) and S(=O)$_2$, (e) a 5 to 6 membered heteroaryl optionally substituted with one or to three groups independently selected from halogen, CN, $OR^e$, cyclopropyl, and $C_1$-$C_3$ alkyl optionally substituted with one to three groups independently selected from hydroxyl, methoxy, oxo and halogen, wherein the heteroaryl contains one, two, three or four heteroatoms selected from the group consisting of O, N and S, and (f) a 7 to 10 membered bicyclic heterocycle optionally substituted with one or two groups selected from $C_1$-$C_3$ alkyl and oxo.

In certain embodiments, $R^1$ is selected from 1-hydroxypropan-2-yl, isopropyl, 1-hydroxybutan-2-yl, 1-cyclopropylethyl, 1-hydroxy-3-methoxypropan-2-yl, 1,3-difluoropropan-2-yl, 1-cyclopropyl-2-hydroxyethyl, oxetan-3-ylmethyl, 4-methoxybutan-2-yl, 4,4,4-trifluoro-1-hydroxybutan-2-yl, 1-aminopropan-2-yl, 3-hydroxycyclopentyl, 3,3-difluorocyclobutyl, 3-hydroxycyclobutyl, 2-chloro-4-fluorophenyl, 4-fluoro-2-methylphenyl, tetrahydropyran-4-yl, 3-fluorotetrahydropyran-4-yl, tetrahydrodioxothiopyran-4-yl, 1,1-dioxotetrahydrothiophen-3-yl, oxetan-3-yl, tetrahydrofuran-3-yl, 2,2-dimethyltetrahydropyran-4-yl, 2-methyltetrahydropyran-4-yl, pyrrolidin-3-yl, azetidin-3-yl, piperdin-3-yl, 2-(hydroxymethyl)tetrahydropyran-4-yl, 6-oxo-1,6-dihydropyridin-3-yl, 1-methylpyrazol-4-yl, 2-methylpyrimidin-4-yl, 6-methylpyrimidin-4-yl, 6-methoxypyrimidin-4-yl, 2-methylpyridin-4-yl, 1,3-dimethylpyrazol-4-yl, 2-methoxypyridin-4-yl, 1-methylpyrazol-3-yl, 6-methoxypyridin-3-yl, 2-ethylpyrimidin-4-yl, 6-methylpyridin-2-yl, 2-cyclopropylpyrimidin-4-yl, 5-fluoro-6-methylpyridin-2-yl, 5-cyclopropyl-1-methylpyrazol-4-yl, 5-bromo-2-methylpyridin-4-yl, 1,5-dimethylpyrazol-4-yl, 1,3-dimethylpyrazol-5-yl, 4-(2-hydroxypropan-2-yl)pyridin-2-yl, 1-ethyl-3-methylpyrazol-4-yl, 5-ethoxy-2-methylpyridin-4-yl, 1-isopropylpyrazol-4-yl, 4-methylimidazol-5-yl, 1-methylimidazol-5-yl, 1-ethylpyrazol-4-yl, 2-(2-hydroxypropan-2-yl)pyridin-4-yl, 1-methyl-4-cyanopyrazol-5-yl, 3-methylpyridin-4-yl, 1-ethyl-3-methylpyrazol-5-yl, 1-methylpyrazol-5-yl, 1,4-dimethylpyrazol-5-yl, 1-ethylpyrazol-5-yl, 3-isopropyl-1-methylpyrazol-5-yl, 3-methylpyrazol-4-yl, 3-ethyl-1-methylpyrazol-4-yl, 1,3,5-trimethylpyrazol-4-yl, 3,5-dimethylpyrazol-4-yl, 2-cyclopropyl-5-methoxypyridin-4-yl, 5-ethyl-1-methylpyrazol-4-yl, 5-methoxy-2-methylpyridin-4-yl, 5-methyl-1,3,4-oxadizol-2-yl, 3-ethyl-1-methylpyrazol-5-yl, 1-(2-hydroxyethyl)-3-methylpyrazol-4-yl, 1-(2-hydroxyethyl)-5-methylpyrazol-4-yl, 1-methyl-3-(trifluoromethyl)pyrazol-4-yl, 1-methyl-3-(trifluoromethyl)pyrazol-5-yl and 1-methyl-1,2,3-triazol-5-yl, 2-methylpyridin-4-yl, 1-(2-hydroxyethyl)pyrazol-5-yl, methyl 4-picolinate, 4-picolinic acid, 1-cyclopropyl-5-methylpyrazol-4-yl, 1-cyclopropyl-3-methylpyrazol-4-yl, 2,3-dimethylpyridin-4-yl, 2,5-dimethylpyridin-4-yl, 1,3,4-oxadiazol-2-yl, 3-methylpyridazin-4-yl, pyridazin-4-yl, tetrazol-5-yl, 1-methyltetrazol-5-yl, 2-methyl-2,4,5,6-tetrahydrocyclopentapyrazol-3-yl, 3-oxo-2-oxabicyclo[2.2.1]heptan-5-yl and 2-oxabicyclo[2.2.1]heptan-5-yl.

In certain embodiments, $R^1$ is selected from 1-hydroxypropan-2-yl, isopropyl, 1-hydroxybutan-2-yl, 1-cyclopropylethyl, 1-hydroxy-3-methoxypropan-2-yl, 1,3-difluoropropan-2-yl, 1-cyclopropyl-2-hydroxyethyl, oxetan-3-ylmethyl, 4-methoxybutan-2-yl, 4,4,4-trifluoro-1-hydroxybutan-2-yl, 1-aminopropan-2-yl, 3-hydroxycyclopentyl, 3,3-difluorocyclobutyl, 3-hydroxycyclobutyl, 2-chloro-4-fluorophenyl, 4-fluoro-2-methylphenyl, tetrahydropyran-4-yl, 3-fluorotetrahydropyran-4-yl, tetrahydrodioxothiopyran-4-yl, 1,1-dioxotetrahydrothiophen-3-yl, oxetan-3-yl, tetrahydrofuran-3-yl, 2,2-dimethyltetrahydropyran-4-yl, 2-methyltetrahydropyran-4-yl, pyrrolidin-3-yl, azetidin-3-yl, piperdin-3-yl, 2-(hydroxymethyl)tetrahydropyran-4-yl, 6-oxo-1,6-dihydropyridin-3-yl, 1-methylpyrazol-4-yl, 2-methylpyrimidin-4-yl, 6-methylpyrimidin-4-yl, 6-methoxypyrimidin-4-yl, 2-methylpyridin-4-yl, 1,3-dimethylpyrazol-4-yl, 2-methoxypyridin-4-yl, 1-methylpyrazol-3-yl, 6-methoxypyridin-3-yl, 2-ethylpyrimidin-4-yl, 6-methylpyridin-2-yl, 2-cyclopropylpyrimidin-4-yl, 5-fluoro-6-methylpyridin-2-yl, 5-cyclopropyl-1-methylpyrazol-4-yl, 5-bromo-2-methylpyridin-4-yl, 1,5-dimethylpyrazol-4-yl, 1,3-dimethylpyrazol-5-yl, 4-(2-hydroxypropan-2-yl)pyridin-2-yl, 1-ethyl-3-methylpyrazol-4-yl, 5-ethoxy-2-methylpyridin-4-yl, 1-isopropylpyrazol-4-yl, 4-methylimidazol-5-yl, 1-methylimidazol-5-yl, 1-ethylpyrazol-4-yl, 2-(2-hydroxypropan-2-yl)pyridin-4-yl, 1-methyl-4-cyanopyrazol-5-yl, 3-methylpyridin-4-yl, 1-ethyl-3-methylpyrazol-5-yl, 1-methylpyrazol-5-yl, 1,4-dimethylpyrazol-5-yl, 1-ethylpyrazol-5-yl, 3-isopropyl-1-methylpyrazol-5-yl, 3-methylpyrazol-4-yl, 3-ethyl-1-methylpyrazol-4-yl, 1,3,5-trimethylpyrazol-4-yl, 3,5-dimethylpyrazol-4-yl, 2-cyclopropyl-5-methoxypyridin-4-yl, 5-ethyl-1-methylpyrazol-4-yl, 5-methoxy-2-methylpyridin-4-yl, 5-methyl-1,3,4-oxadizol-2-yl, 3-ethyl-1-methylpyrazol-5-yl, 1-(2-hydroxyethyl)-3-methylpyrazol-4-yl, 1-(2-hydroxyethyl)-5-methylpyrazol-4-yl, 1-methyl-3-(trifluoromethyl)pyrazol-4-yl, 1-methyl-3-(trifluoromethyl)pyrazol-5-yl and 1-methyl-1,2,3-triazol-5-yl, 2-methylpyridin-4-yl, 1-(2-hydroxyethyl)pyrazol-5-yl, methyl 4-picolinate, 4-picolinic acid, 1-cyclopropyl-5-methylpyrazol-4-yl, 1-cyclopropyl-3-methylpyrazol-4-yl, 2,3-dimethylpyridin-4-yl, 2,5-dimethylpyridin-4-yl, 1,3,4-oxadiazol-2-yl, 3-methylpyridazin-4-yl, pyridazin-4-yl, 2-methyl-2,4,5,6-tetrahydrocyclopentapyrazol-3-yl, 3-oxo-2-oxabicyclo[2.2.1]heptan-5-yl and 2-oxabicyclo[2.2.1]heptan-5-yl.

In certain embodiments, $R^1$ is selected from tetrahydropyran-4-yl, 3-fluorotetrahydropyran-4-yl, 2-(hydroxymethyl)tetrahydropyran-4-yl, 1,3-dimethylpyrazol-4-yl and 1-methylpyrazol-5-yl.

In certain embodiments, $R^1$ is $C_1$-$C_6$ alkyl optionally substituted with one to six groups independently selected from halogen, $OR^a$, $NR^bR^c$, $C_3$-$C_6$ cycloalkyl and a 3 to 7 membered heterocycle, wherein the heterocycle contains one, two or three heteroatoms selected from the group consisting of O, N, S, S(=O) and S(=O)$_2$. In certain embodiments, $R^1$ is $C_1$-$C_6$ alkyl optionally substituted with one to four groups independently selected from halogen, $OR^a$, $NR^bR^c$, $C_3$-$C_6$ cycloalkyl and a 3 to 7 membered heterocycle, wherein the heterocycle contains one O heteroatom. In certain embodiments, $R^1$ is $C_1$-$C_6$ alkyl optionally substituted with one to four groups independently selected from halogen, $OR^a$, $NR^bR^c$, cyclopropyl and oxetanyl. In certain embodiments, $R^1$ is selected from 1-hydroxypropan-2-yl, isopropyl, 1-hydroxybutan-2-yl, 1-cyclopropylethyl, 1-hydroxy-3-methoxypropan-2-yl, 1,3-difluoropropan-2-yl, 1-cyclopropyl-2-hydroxyethyl, oxetan-3-ylmethyl, 4-methoxybutan-2-yl, 4,4,4-trifluoro-1-hydroxybutan-2-yl and 1-aminopropan-2-yl.

In certain embodiments, $R^1$ is $C_3$-$C_7$ cycloalkyl optionally substituted with one or two groups independently selected from halogen, $C_1$-$C_3$ alkyl and $OR^a$. In certain embodiments, $R^1$ is $C_3$-$C_7$ cycloalkyl optionally substituted with one or two groups independently selected from halogen and $OR^a$. In certain embodiments, $R^1$ is selected from 3-hydroxycyclopentyl, 3,3-difluorocyclobutyl and 3-hydroxycyclobutyl.

In certain embodiments, $R^1$ is phenyl optionally substituted with one or two groups independently selected from halogen, $C_1$-$C_3$ alkyl and $OR^a$. In certain embodiments, $R^1$ is phenyl optionally substituted with one or two groups independently selected from halogen and $C_1$-$C_3$ alkyl. In certain embodiments, $R^1$ is selected from 2-chloro-4-fluorophenyl and 4-fluoro-2-methylphenyl.

In certain embodiments, $R^1$ is a 3 to 7 membered saturated or partially unsaturated heterocycle optionally substituted with one or two groups independently selected from halogen, oxo, $OR^a$, and $C_1$-$C_3$ alkyl optionally substituted with $OR^d$, wherein the heterocycle contains one, two or three heteroatoms selected from the group consisting of O, N, S, S(=O) and S(=O)$_2$. In certain embodiments, $R^1$ is a 3 to 7 membered saturated or partially unsaturated heterocycle optionally substituted with one or two groups independently selected from halogen, oxo and $C_1$-$C_3$ alkyl optionally substituted with $OR^d$, wherein the heterocycle contains one, two or three heteroatoms selected from the group consisting of O, N, S, S(=O) and S(=O)$_2$. In certain embodiments, $R^1$ is a 3 to 7 membered saturated or partially unsaturated heterocycle optionally substituted with one or two groups independently selected from halogen, oxo, $OR^a$, and $C_1$-$C_3$ alkyl optionally substituted with $OR^d$, wherein the heterocycle contains one heteroatom selected from the group consisting of O, N and S(=O)$_2$. In certain embodiments, R$^1$ is a 3 to 7 membered saturated or partially unsaturated heterocycle optionally substituted with one or two groups independently selected from halogen, oxo and C$_1$-C$_3$ alkyl optionally substituted with OR$^d$, wherein the heterocycle contains one heteroatom selected from the group consisting of O, N and S(=O)$_2$. In certain embodiments, R$^1$ is selected from tetrahydropyran-4-yl, 3-fluorotetrahydropyran-4-yl, tetrahydrodioxothiopyran-4-yl, 1,1-dioxotetrahydrothiophen-3-yl, oxetan-3-yl, tetrahydrofuran-3-yl, 2,2-dimethyltetrahydropyran-4-yl, 2-methyltetrahydropyran-4-yl, pyrrolidin-3-yl, azetidin-3-yl, piperdin-3-yl, 2-(hydroxymethyl) tetrahydropyran-4-yl and 6-oxo-1,6-dihydropyridin-3-yl.

In certain embodiments, R$^1$ is a 3 to 7 membered saturated heterocycle optionally substituted with one or two groups independently selected from halogen, oxo, OR$^a$, and C$_1$-C$_3$ alkyl optionally substituted with OR$^d$, wherein the heterocycle contains one, two or three heteroatoms selected from the group consisting of O, N, S, S(=O) and S(=O)$_2$. In certain embodiments, R$^1$ is a 3 to 7 membered saturated heterocycle optionally substituted with one or two groups independently selected from halogen and C$_1$-C$_3$ alkyl optionally substituted with OH, wherein the heterocycle contains one, two or three heteroatoms selected from the group consisting of O, N, S, S(=O) and S(=O)$_2$. In certain embodiments, R$^1$ is a 3 to 7 membered saturated heterocycle optionally substituted with one or two groups independently selected from halogen, oxo, OR$^a$, and C$_1$-C$_3$ alkyl optionally substituted with OR$^d$, wherein the heterocycle contains one heteroatom selected from the group consisting of O, N and S(=O)$_2$. In certain embodiments, R$^1$ is a 3 to 7 membered saturated heterocycle optionally substituted with one or two groups independently selected from halogen and C$_1$-C$_3$ alkyl optionally substituted with OH, wherein the heterocycle contains one heteroatom selected from the group consisting of O, N and S(=O)$_2$. In certain embodiments, R$^1$ is selected from tetrahydropyran-4-yl, 3-fluorotetrahydropyran-4-yl, tetrahydrodioxothiopyran-4-yl, 1,1-dioxotetrahydrothiophen-3-yl, oxetan-3-yl, tetrahydrofuran-3-yl, 2,2-dimethyltetrahydropyran-4-yl, 2-methyltetrahydropyran-4-yl, pyrrolidin-3-yl, azetidin-3-yl, piperdin-3-yl and 2-(hydroxymethyl)tetrahydropyran-4-yl.

In certain embodiments, R$^1$ is a 3 to 7 membered partially unsaturated heterocycle optionally substituted with one or two groups independently selected from halogen, oxo, OR$^a$, and C$_1$-C$_3$ alkyl optionally substituted with OR$^d$, wherein the heterocycle contains one, two or three heteroatoms selected from the group consisting of O, N, S, S(=O) and S(=O)$_2$. In certain embodiments, R$^1$ is a 3 to 7 membered partially unsaturated heterocycle optionally substituted with one oxo group, wherein the heterocycle contains one, two or three heteroatoms selected from the group consisting of O, N, S, S(=O) and S(=O)$_2$. In certain embodiments, R$^1$ is a 3 to 7 membered partially unsaturated heterocycle optionally substituted with one or two groups independently selected from halogen, oxo, OR$^a$, and C$_1$-C$_3$ alkyl optionally substituted with OR$^d$, wherein the heterocycle contains one N heteroatom. In certain embodiments, R$^1$ is a 3 to 7 membered partially unsaturated heterocycle optionally substituted with one oxo group, wherein the heterocycle contains one N heteroatom. In certain embodiments, R$^1$ is 6-oxo-1,6-dihydropyridin-3-yl.

In certain embodiments, R$^1$ is a 5 to 6 membered heteroaryl optionally substituted with one to three groups independently selected from halogen, CN, OR$^e$, cyclopropyl, oxide and C$_1$-C$_3$ alkyl optionally substituted with one to three groups independently selected from hydroxyl, methoxy, oxo and halogen, wherein the heteroaryl contains one, two, three or four heteroatoms selected from the group consisting of O, N and S. In certain embodiments, R$^1$ is a 5 to 6 membered heteroaryl optionally substituted with one to three groups independently selected from halogen, CN, OR$^e$, cyclopropyl, oxide and C$_1$-C$_3$ alkyl optionally substituted with one to three groups independently selected from hydroxyl, methoxy, oxo and halogen, wherein the heteroaryl contains one, two, three or four heteroatoms selected from the group consisting of O and N. In certain embodiments, R$^1$ is a 5 to 6 membered heteroaryl optionally substituted with one to three groups independently selected from halogen, CN, OR$^e$, cyclopropyl, oxide and C$_1$-C$_3$ alkyl optionally substituted with one to three groups independently selected from hydroxyl, methoxy, oxo and halogen, wherein the heteroaryl contains one, two or three heteroatoms selected from the group consisting of O and N. In certain embodiments, R$^1$ is a 5 to 6 membered heteroaryl optionally substituted with one to three groups independently selected from halogen, CN, OR$^e$, cyclopropyl and C$_1$-C$_3$ alkyl optionally substituted with one to three groups independently selected from hydroxyl, methoxy, oxo and halogen, wherein the heteroaryl contains one, two, three or four heteroatoms selected from the group consisting of O and N. In certain embodiments, R$^1$ is a 5 to 6 membered heteroaryl optionally substituted with one to three groups independently selected from halogen, CN, OR$^e$, cyclopropyl and C$_1$-C$_3$ alkyl optionally substituted with one to three groups independently selected from hydroxyl, methoxy, oxo and halogen, wherein the heteroaryl contains one, two or three heteroatoms selected from the group consisting of O and N. In certain embodiments, R$^1$ is a 5 to 6 membered heteroaryl optionally substituted with one or two groups independently selected from methyl, ethyl and CF$_3$, wherein the heteroaryl contains one or two N heteroatoms. In certain embodiments, R$^1$ is selected from 1-methylpyrazol-4-yl, 2-methylpyrimidin-4-yl, 6-methylpyrimidin-4-yl, 6-methoxypyrimidin-4-yl, 2-methylpyridin-4-yl, 1,3-dimethylpyrazol-4-yl, 2-methoxypyridin-4-yl, 1-methylpyrazol-3-yl, 6-methoxypyridin-3-yl, 2-ethylpyrimidin-4-yl, 6-methylpyridin-2-yl, 2-cyclopropylpyrimidin-4-yl, 5-fluoro-6-methylpyridin-2-yl, 5-cyclopropyl-1-methylpyrazol-4-yl, 5-bromo-2-methylpyridin-4-yl, 1,5-dimethylpyrazol-4-yl, 1,3-dimethylpyrazol-5-yl, 4-(2-hydroxypropan-2-yl)pyridin-2-yl, 1-ethyl-3-methylpyrazol-4-yl, 5-ethoxy-2-methylpyridin-4-yl, 1-isopropylpyrazol-4-yl, 4-methylimidazol-5-yl, 1-methylimidazol-5-yl, 1-ethylpyrazol-4-yl, 2-(2-hydroxypropan-2-yl)pyridin-4-yl, 1-methyl-4-cyanopyrazol-5-yl, 3-methylpyridin-4-yl, 1-ethyl-3-methylpyrazol-5-yl, 1-methylpyrazol-5-yl, 1,4-dimethylpyrazol-5-yl, 1-ethylpyrazol-5-yl, 3-isopropyl-1-methylpyrazol-5-yl, 3-methylpyrazol-4-yl, 3-ethyl-1-methylpyrazol-4-yl, 1,3,5-trimethylpyrazol-4-yl, 3,5-dimethylpyrazol-4-yl, 2-cyclopropyl-5-methoxypyridin-4-yl, 5-ethyl-1-methylpyrazol-4-yl, 4-(2-methoxypyridine 1-oxide), 5-methoxy-2-methylpyridin-4-yl, 5-methyl-1,3,4-oxadizol-2-yl, 3-ethyl-1-methylpyrazol-5-yl, 1-(2-hydroxyethyl)-3-methylpyrazol-4-yl, 1-(2-hydroxyethyl)-5-methylpyrazol-4-yl, 1-methyl-3-(trifluoromethyl)pyrazol-4-yl, 1-methyl-3-(trifluoromethyl)pyrazol-5-yl, 1-methyl-1,2,3-triazol-5-yl, 2-methylpyridin-4-yl, 1-(2-hydroxyethyl)pyrazol-5-yl, methyl 4-picolinate, 4-picolinic acid, 1-cyclopropyl-5-methylpyrazol-4-yl, 1-cyclopropyl-3-methylpyrazol-4-yl, 2,3-dimethylpyridin-4-yl, 2,5-dimethylpyridin-4-yl, 1,3,4-oxadizol-2-yl, 3-methylpyridazin-4-yl, pyridazin-4-yl, tetrazol-5-yl and 1-methyltetrazol-5-yl. In certain embodiments, R$^1$ is selected from 1-methylpyrazol-4-yl, 2-methylpyrimidin-4-yl, 6-methylpyrimidin-4-yl, 6-methoxypyrimidin-4-yl, 2-methylpyridin-4-yl, 1,3-dimethylpyrazol-4-yl, 2-methoxypyridin-4-yl, 1-methylpyrazol-3-yl, 6-methoxypyridin-3-yl, 2-ethylpyrimidin-4-yl, 6-methylpyridin-2-yl, 2-cyclopropylpyrimidin-4-yl, 5-fluoro-6-methylpyridin-2-yl, 5-cyclopropyl-1-methylpyrazol-4-yl, 5-bromo-2-methylpyridin-4-yl, 1,5-dimethylpyrazol-4-yl, 1,3-dimethylpyrazol-5-yl, 4-(2-hydroxypropan-2-yl)pyridin-2-yl, 1-ethyl-3-methylpyrazol-4-yl, 5-ethoxy-2-methylpyridin-4-yl, 1-isopropylpyrazol-4-yl, 4-methylimidazol-5-yl, 1-methylimidazol-5-yl, 1-ethylpyrazol-4-yl, 2-(2-hydroxypropan-2-yl)pyridin-4-yl, 1-methyl-4-cyanopyrazol-5-yl, 3-methylpyridin-4-yl, 1-ethyl-3-methylpyrazol-5-yl, 1-methylpyrazol-5-yl, 1,4-dimethylpyrazol-5-yl, 1-ethylpyrazol-5-yl, 3-isopropyl-1-methylpyrazol-5-yl, 3-methylpyrazol-4-yl, 3-ethyl-1-methylpyrazol-4-yl, 1,3,5-trimethylpyrazol-4-yl, 3,5-dimethylpyrazol-4-yl, 2-cyclopropyl-5-methoxypyridin-4-yl, 5-ethyl-1-methylpyrazol-4-yl, 5-methoxy-2-methylpyridin-4-yl, 5-methyl-1,3,4-oxadizol-2-yl, 3-ethyl-1-methylpyrazol-5-yl, 1-(2-hydroxyethyl)-3-methylpyrazol-4-yl, 1-(2-hydroxyethyl)-5-methylpyrazol-4-yl, 1-methyl-3-(trifluoromethyl)pyrazol-4-yl, 1-methyl-3-(trifluoromethyl)pyrazol-5-yl, 1-methyl-1,2,3-triazol-5-yl, 2-methylpyridin-4-yl, 1-(2-hydroxyethyl)pyrazol-5-yl, methyl 4-picolinate, 4-picolinic acid, 1-cyclopropyl-5-methylpyrazol-4-yl, 1-cyclopropyl-3-methylpyrazol-4-yl, 2,3-dimethylpyridin-4-yl, 2,5-dimethylpyridin-4-yl, 1,3,4-oxadizol-2-yl, 3-methylpyridazin-4-yl, pyridazin-4-yl, tetrazol-5-yl and 1-methyltetrazol-5-yl.

In certain embodiments, $R^1$ is selected from 1-methylpyrazol-4-yl, 2-methylpyrimidin-4-yl, 6-methylpyrimidin-4-yl, 6-methoxypyrimidin-4-yl, 2-methylpyridin-4-yl, 1,3-dimethylpyrazol-4-yl, 2-methoxypyridin-4-yl, 1-methylpyrazol-3-yl, 6-methoxypyridin-3-yl, 2-ethylpyrimidin-4-yl, 6-methylpyridin-2-yl, 2-cyclopropylpyrimidin-4-yl, 5-fluoro-6-methylpyridin-2-yl, 5-cyclopropyl-1-methylpyrazol-4-yl, 5-bromo-2-methylpyridin-4-yl, 1,5-dimethylpyrazol-4-yl, 1,3-dimethylpyrazol-5-yl, 4-(2-hydroxypropan-2-yl)pyridin-2-yl, 1-ethyl-3-methylpyrazol-4-yl, 5-ethoxy-2-methylpyridin-4-yl, 1-isopropylpyrazol-4-yl, 4-methylimidazol-5-yl, 1-methylimidazol-5-yl, 1-ethylpyrazol-4-yl, 2-(2-hydroxypropan-2-yl)pyridin-4-yl, 1-methyl-4-cyanopyrazol-5-yl, 3-methylpyridin-4-yl, 1-ethyl-3-methylpyrazol-5-yl, 1-methylpyrazol-5-yl, 1,4-dimethylpyrazol-5-yl, 1-ethylpyrazol-5-yl, 3-isopropyl-1-methylpyrazol-5-yl, 3-methylpyrazol-4-yl, 3-ethyl-1-methylpyrazol-4-yl, 1,3,5-trimethylpyrazol-4-yl, 3,5-dimethylpyrazol-4-yl, 2-cyclopropyl-5-methoxypyridin-4-yl, 5-ethyl-1-methylpyrazol-4-yl, 4-(2-methoxypyridine 1-oxide), 5-methoxy-2-methylpyridin-4-yl, 5-methyl-1,3,4-oxadizol-2-yl, 3-ethyl-1-methylpyrazol-5-yl, 1-(2-hydroxyethyl)-3-methylpyrazol-4-yl, 1-(2-hydroxyethyl)-5-methylpyrazol-4-yl, 1-methyl-3-(trifluoromethyl)pyrazol-4-yl, 1-methyl-3-(trifluoromethyl)pyrazol-5-yl, 1-methyl-1,2,3-triazol-5-yl, 2-methylpyridin-4-yl, 1-(2-hydroxyethyl)pyrazol-5-yl, methyl 4-picolinate, 4-picolinic acid, 1-cyclopropyl-5-methylpyrazol-4-yl, 1-cyclopropyl-3-methylpyrazol-4-yl, 2,3-dimethylpyridin-4-yl, 2,5-dimethylpyridin-4-yl, 1,3,4-oxadizol-2-yl, 3-methylpyridazin-4-yl and pyridazin-4-yl. In certain embodiments, $R^1$ is selected from 1-methylpyrazol-4-yl, 2-methylpyrimidin-4-yl, 6-methylpyrimidin-4-yl, 6-methoxypyrimidin-4-yl, 2-methylpyridin-4-yl, 1,3-dimethylpyrazol-4-yl, 2-methoxypyridin-4-yl, 1-methylpyrazol-3-yl, 6-methoxypyridin-3-yl, 2-ethylpyrimidin-4-yl, 6-methylpyridin-2-yl, 2-cyclopropylpyrimidin-4-yl, 5-fluoro-6-methylpyridin-2-yl, 5-cyclopropyl-1-methylpyrazol-4-yl, 5-bromo-2-methylpyridin-4-yl, 1,5-dimethylpyrazol-4-yl, 1,3-dimethylpyrazol-5-yl, 4-(2-hydroxypropan-2-yl)pyridin-2-yl, 1-ethyl-3-methylpyrazol-4-yl, 5-ethoxy-2-methylpyridin-4-yl, 1-isopropylpyrazol-4-yl, 4-methylimidazol-5-yl, 1-methylimidazol-5-yl, 1-ethylpyrazol-4-yl, 2-(2-hydroxypropan-2-yl)pyridin-4-yl, 1-methyl-4-cyanopyrazol-5-yl, 3-methylpyridin-4-yl, 1-ethyl-3-methylpyrazol-5-yl, 1-methylpyrazol-5-yl, 1,4-dimethylpyrazol-5-yl, 1-ethylpyrazol-5-yl, 3-isopropyl-1-methylpyrazol-5-yl, 3-methylpyrazol-4-yl, 3-ethyl-1-methylpyrazol-4-yl, 1,3,5-trimethylpyrazol-4-yl, 3,5-dimethylpyrazol-4-yl, 2-cyclopropyl-5-methoxypyridin-4-yl, 5-ethyl-1-methylpyrazol-4-yl, 5-methoxy-2-methylpyridin-4-yl, 5-methyl-1,3,4-oxadizol-2-yl, 3-ethyl-1-methylpyrazol-5-yl, 1-(2-hydroxyethyl)-3-methylpyrazol-4-yl, 1-(2-hydroxyethyl)-5-methylpyrazol-4-yl, 1-methyl-3-(trifluoromethyl)pyrazol-4-yl, 1-methyl-3-(trifluoromethyl)pyrazol-5-yl, 1-methyl-1,2,3-triazol-5-yl, 2-methylpyridin-4-yl, 1-(2-hydroxyethyl)pyrazol-5-yl, methyl 4-picolinate, 4-picolinic acid, 1-cyclopropyl-5-methylpyrazol-4-yl, 1-cyclopropyl-3-methylpyrazol-4-yl, 2,3-dimethylpyridin-4-yl, 2,5-dimethylpyridin-4-yl, 1,3,4-oxadizol-2-yl, 3-methylpyridazin-4-yl and pyridazin-4-yl.

In certain embodiments, $R^1$ is a 7 to 10 membered bicyclic heterocycle optionally substituted with one or two groups selected from $C_1$-$C_3$ alkyl and oxo, wherein the heterocycle contains one, two or three heteroatoms selected from the group consisting of O, N, S, S(=O) and S(=O)$_2$. In certain embodiments, $R^1$ is a 7 to 10 membered bicyclic heterocycle optionally substituted with one or two groups selected from $C_1$-$C_3$ alkyl and oxo, wherein the heterocycle contains one, two or three heteroatoms selected from O and N. In certain embodiments, $R^1$ is a 7 to 10 membered bicyclic heterocycle optionally substituted with one or two groups selected from $C_1$-$C_3$ alkyl and oxo, wherein the heterocycle contains one or two heteroatoms selected from O and N. In certain embodiments, $R^1$ is selected from 2-methyl-2,4,5,6-tetrahydrocyclopentapyrazol-3-yl, 3-oxo-2-oxabicyclo[2.2.1]heptan-5-yl and 2-oxabicyclo[2.2.1]heptan-5-yl.

In certain embodiments, $R^2$ is selected from (a) hydrogen, (b) $C_1$-$C_6$ alkyl optionally substituted with one or more groups selected from $OR^f$, oxo, $NH_2$, $NH(C_1$-$C_3$ alkyl) and $N(C_1$-$C_3$ alkyl)$_2$, (c) $C_1$-$C_6$ alkenyl optionally substituted with one or more groups selected from $OR^f$, oxo, $NH_2$, $NH(C_1$-$C_3$ alkyl) and $N(C_1$-$C_3$ alkyl)$_2$, (d) $C_1$-$C_6$ alkynyl optionally substituted with one or more groups selected from $OR^f$, oxo, $NH_2$, $NH(C_1$-$C_3$ alkyl) and $N(C_1$-$C_3$ alkyl)$_2$, (e) $C_3$-$C_6$ cycloalkyl optionally substituted with one or more groups selected from $OR^f$ and $R^g$, (f) phenyl optionally substituted with one or more groups selected from $OR^f$ and $R^g$, (g) a 3 to 7 membered heterocycle optionally substituted with one or more groups selected from $OR^f$ and $R^g$, wherein the heterocycle contains one, two or three heteroatoms selected from the group consisting of O, N, S, S(=O) and S(=O)$_2$, and (h) a 5 to 6 membered heteroaryl optionally substituted with one or more groups selected from $OR^f$ and $R^g$, wherein the heteroaryl contains one, two, three or four heteroatoms selected from the group consisting of O, N and S. In certain embodiments, $R^2$ is selected from (a) hydrogen, (b) $C_1$-$C_6$ alkyl optionally substituted with one or more groups selected from $OR^f$, oxo, $NH_2$, $NH(C_1$-$C_3$ alkyl) and $N(C_1$-$C_3$ alkyl)$_2$, (c) $C_1$-$C_6$ alkenyl optionally substituted with one or more $OR^f$ groups, (d) $C_1$-$C_6$ alkynyl optionally substituted with one or more $OR^f$ groups, (e) $C_3$-$C_6$ cycloalkyl optionally substituted with one or more groups selected from $OR^f$ and $R^g$, (f) phenyl optionally substituted with one or more groups selected from $OR^f$ and $R^g$, (g) a 3 to 7 membered heterocycle optionally substituted with one or more groups selected from $OR^f$ and $R^g$, wherein the heterocycle contains one, two or three heteroatoms selected from the group consisting of O, N, S, S(=O) and S(=O)$_2$, and (h) a 5 to 6 membered heteroaryl optionally substituted with one or more groups selected from $OR^f$ and $R^g$, wherein the heteroaryl contains one, two, three or four heteroatoms selected from the group consisting of O, N and S.

In certain embodiments, $R^2$ is selected from (a) hydrogen, (b) $C_1$-$C_6$ alkyl optionally substituted with one or more groups selected from $OR^f$ and oxo, (c) $C_1$-$C_6$ alkenyl optionally substituted with one or more $OR^f$ groups, (d) $C_1$-$C_6$ alkynyl optionally substituted with one or more $OR^f$ groups, (e) $C_3$-$C_6$ cycloalkyl optionally substituted with one or more groups selected from $OR^f$ and $R^g$, (f) phenyl optionally substituted with one or more groups selected from $OR^f$ and $R^g$, (g) a 3 to 7 membered heterocycle optionally substituted with one or more groups selected from $OR^f$ and $R^g$, wherein the heterocycle contains one, two or three heteroatoms selected from the group consisting of O, N, S, S(=O) and S(=O)$_2$, and (h) a 5 to 6 membered heteroaryl optionally substituted with one or more groups selected from $OR^f$ and $R^g$, wherein the heteroaryl contains one, two, three or four heteroatoms selected from the group consisting of O, N and S.

In certain embodiments, $R^2$ is selected from (a) hydrogen, (b) $C_1$-$C_6$ alkyl optionally substituted with one or more groups selected from $OR^f$, oxo, $NH_2$, $NH(C_1$-$C_3$ alkyl) and $N(C_1$-$C_3$ alkyl)$_2$, (c) $C_1$-$C_6$ alkenyl optionally substituted with one or more $OR^f$ groups, (f) phenyl optionally substituted with one or more groups selected from $OR^f$ and $R^g$, (g) a 3 to 7 membered heterocycle optionally substituted with one or more groups selected from $OR^f$ and $R^g$, wherein the heterocycle contains one, two or three heteroatoms selected from the group consisting of O, N, S, S(=O) and S(=O)$_2$, and (h) a 5 to 6 membered heteroaryl optionally substituted with one or more groups selected from $OR^f$ and $R^g$, wherein the heteroaryl contains one, two, three or four heteroatoms selected from the group consisting of O, N and S. In certain embodiments, $R^2$ is selected from (a) hydrogen, (b) $C_1$-$C_6$ alkyl optionally substituted with one or more groups selected from $OR^f$, oxo, and $NH_2$, (c) $C_1$-$C_6$ alkenyl optionally substituted with one or more $OR^f$ groups, (f) phenyl optionally substituted with one or more groups selected from $OR^f$ and $R^g$, (g) a 3 to 7 membered heterocycle optionally substituted with one or more groups selected from $OR^f$ and $R^g$, wherein the heterocycle contains one, two or three heteroatoms selected from the group consisting of O, N, S, S(=O) and S(=O)$_2$, and (h) a 5 to 6 membered heteroaryl optionally substituted with one or more groups selected from $OR^f$ and $R^g$, wherein the heteroaryl contains one, two, three or four heteroatoms selected from the group consisting of O, N and S.

In certain embodiments, $R^2$ is selected from (a) hydrogen, (b) $C_1$-$C_6$ alkyl optionally substituted with one or more groups selected from $OR^f$ and oxo, (c) $C_1$-$C_6$ alkenyl optionally substituted with one or more groups selected from $OR^f$, (f) phenyl optionally substituted with one or more groups selected from $OR^f$ and $R^g$, (g) a 3 to 7 membered heterocycle optionally substituted with one or more groups selected from $OR^f$ and $R^g$, wherein the heterocycle contains one, two or three heteroatoms selected from the group consisting of O, N, S, S(=O) and S(=O)$_2$, and (h) a 5 to 6 membered heteroaryl optionally substituted with one or more groups selected from $OR^f$ and $R^g$, wherein the heteroaryl contains one, two, three or four heteroatoms selected from the group consisting of O, N and S.

In certain embodiments, $R^f$ is selected from hydrogen and $C_1$-$C_6$ alkyl optionally substituted with one or more groups selected from oxo, $NH_2$, $NH(C_1$-$C_3$ alkyl) and $N(C_1$-$C_3$ alkyl)$_2$. In certain embodiments, $R^f$ is selected from hydrogen and $C_1$-$C_6$ alkyl optionally substituted with one or more groups selected from oxo and $NH_2$. In certain embodiments, $R^f$ is hydrogen, methyl, C(=O)C(CH$_3$)$_2$NH$_2$ or C(=O)CH$_3$.

In certain embodiments, $R^f$ is selected from hydrogen and $C_1$-$C_6$ alkyl. In certain embodiments, $R^f$ is hydrogen or methyl.

In certain embodiments, $R^g$ is methyl.

In certain embodiments, $R^2$ is selected from hydrogen, methyl, ethyl, CH$_2$OH, CH$_2$CH$_2$OH, CH$_2$CH(OH)CH$_3$, CH$_2$C(CH$_3$)$_2$OH, CH$_2$OCH$_3$, C(=O)OH, CH$_2$OC(=O)C(CH$_3$)$_2$NH$_2$, CH$_2$OC(=O)CH$_3$, CH$_2$NH$_2$, methylene, phenyl, pyrrolidin-2-yl, pyrrolidin-3-yl, oxazol-5-yl and 1-methyl-pyrazol-4-yl. In certain embodiments, $R^2$ is selected from methyl, ethyl, CH$_2$OH, CH$_2$CH$_2$OH, CH$_2$CH(OH)CH$_3$, CH$_2$C(CH$_3$)$_2$OH, CH$_2$OCH$_3$, CH$_2$OC(=O)C(CH$_3$)$_2$NH$_2$, CH$_2$OC(=O)CH$_3$, CH$_2$NH$_2$, pyrrolidin-2-yl, pyrrolidin-3-yl, oxazol-5-yl, and 1-methyl-pyrazol-4-yl. In certain embodiments, $R^2$ is selected from CH$_2$OH, CH$_2$CH$_2$OH, CH$_2$CH(OH)CH$_3$, CH$_2$C(CH$_3$)$_2$OH, CH$_2$OCH$_3$, CH$_2$OC(=O)C(CH$_3$)$_2$NH$_2$, CH$_2$OC(=O)CH$_3$, CH$_2$NH$_2$, pyrrolidin-2-yl, pyrrolidin-3-yl, oxazol-5-yl, and 1-methyl-pyrazol-4-yl. In certain embodiments, $R^2$ is selected from pyrrolidin-2-yl, pyrrolidin-3-yl, oxazol-5-yl and 1-methyl-pyrazol-4-yl. In certain embodiments, $R^2$ is selected from CH$_2$OH, CH$_2$CH$_2$OH, CH$_2$CH(OH)CH$_3$, CH$_2$C(CH$_3$)$_2$OH, CH$_2$OC(=O)C(CH$_3$)$_2$NH$_2$, CH$_2$OC(=O)CH$_3$, CH$_2$NH$_2$ and 1-methyl-pyrazol-4-yl.

In certain embodiments, $R^2$ is selected from hydrogen, methyl, ethyl, CH$_2$OH, CH$_2$CH$_2$OH, CH$_2$CH(OH)CH$_3$, CH$_2$C(CH$_3$)$_2$OH, CH$_2$OCH$_3$, C(=O)OH, methylene, phenyl, pyrrolidin-2-yl, pyrrolidin-3-yl, oxazol-5-yl and 1-methyl-pyrazol-4-yl. In certain embodiments, $R^2$ is selected from methyl, ethyl, CH$_2$OH, CH$_2$CH$_2$OH, CH$_2$CH(OH)CH$_3$, CH$_2$C(CH$_3$)$_2$OH, CH$_2$OCH$_3$, pyrrolidin-2-yl, pyrrolidin-3-yl, oxazol-5-yl, and 1-methyl-pyrazol-4-yl. In certain embodiments, $R^2$ is selected from CH$_2$OH, CH$_2$CH$_2$OH, CH$_2$CH(OH)CH$_3$, CH$_2$C(CH$_3$)$_2$OH, CH$_2$OCH$_3$, pyrrolidin-2-yl, pyrrolidin-3-yl, oxazol-5-yl, and 1-methyl-pyrazol-4-yl. In certain embodiments, $R^2$ is selected from pyrrolidin-2-yl, pyrrolidin-3-yl, oxazol-5-yl and 1-methyl-pyrazol-4-yl. In certain embodiments, $R^2$ is selected from CH$_2$OH, CH$_2$CH$_2$OH, CH$_2$CH(OH)CH$_3$, CH$_2$C(CH$_3$)$_2$OH and 1-methyl-pyrazol-4-yl.

In certain embodiments, $R^2$ is selected from (a) hydrogen, (b) $C_1$-$C_6$ alkyl optionally substituted with one or two groups selected from $OR^f$, oxo, and $NH_2$, (c) $C_1$-$C_6$ alkenyl, (f) phenyl, (g) a 3 to 7 membered heterocycle, wherein the heterocycle contains one, two or three heteroatoms selected from the group consisting of O, N, S, S(=O) and S(=O)$_2$, and (h) a 5 to 6 membered heteroaryl optionally substituted with one $R^g$ group, wherein the heteroaryl contains one, two, three or four heteroatoms selected from the group consisting of O, N and S.

In certain embodiments, $R^2$ is selected from (a) hydrogen, (b) $C_1$-$C_6$ alkyl optionally substituted with one or two groups selected from $OR^f$ and oxo, (c) $C_1$-$C_6$ alkenyl, (f) phenyl, (g) a 3 to 7 membered heterocycle, wherein the heterocycle contains one, two or three heteroatoms selected from the group consisting of O, N, S, S(=O) and S(=O)$_2$, and (h) a 5 to 6 membered heteroaryl optionally substituted with one $R^g$ group, wherein the heteroaryl contains one, two, three or four heteroatoms selected from the group consisting of O, N and S.

In certain embodiments, $R^2$ is selected from (b) $C_1$-$C_6$ alkyl optionally substituted with one or two groups selected from $OR^f$, oxo, and $NH_2$, (c) $C_1$-$C_6$ alkenyl, (f) phenyl, (g) a 3 to 7 membered heterocycle, wherein the heterocycle contains one, two or three heteroatoms selected from the group consisting of O, N, S, S(=O) and S(=O)$_2$, and (h) a 5 to 6 membered heteroaryl optionally substituted with one $R^g$ group, wherein the heteroaryl contains one, two, three or four heteroatoms selected from the group consisting of O, N and S. In certain embodiments, $R^2$ is selected from methyl, ethyl, $CH_2OH$, $CH_2CH_2OH$, $CH_2CH(OH)CH_3$, $CH_2C(CH_3)_2OH$, $CH_2OCH_3$, C(=O)OH, methylene, phenyl, pyrrolidin-2-yl, pyrrolidin-3-yl, oxazol-5-yl and 1-methyl-pyrazol-4-yl.

In certain embodiments, $R^2$ is selected from (b) $C_1$-$C_6$ alkyl optionally substituted with one or two groups selected from $OR^f$ and oxo, (c) $C_1$-$C_6$ alkenyl, (f) phenyl, (g) a 3 to 7 membered heterocycle, wherein the heterocycle contains one, two or three heteroatoms selected from the group consisting of O, N, S, S(=O) and S(=O)$_2$, and (h) a 5 to 6 membered heteroaryl optionally substituted with one $R^g$ group, wherein the heteroaryl contains one, two, three or four heteroatoms selected from the group consisting of O, N and S. In certain embodiments, $R^2$ is selected from methyl, ethyl, $CH_2OH$, $CH_2CH_2OH$, $CH_2CH(OH)CH_3$, $CH_2C(CH_3)_2OH$, $CH_2OCH_3$, C(=O)OH, $CH_2OC(=O)C(CH_3)_2NH_2$, $CH_2OC(=O)CH_3$, $CH_2NH_2$, methylene, phenyl, pyrrolidin-2-yl, pyrrolidin-3-yl, oxazol-5-yl and 1-methyl-pyrazol-4-yl.

In certain embodiments, $R^2$ is selected from (a) hydrogen, (b) $C_1$-$C_6$ alkyl optionally substituted with one or two groups selected from $OR^f$, oxo, and $NH_2$, (c) $C_1$-$C_6$ alkenyl, (f) phenyl, (g) a 3 to 7 membered heterocycle, wherein the heterocycle contains one N heteroatom, and (h) a 5 to 6 membered heteroaryl optionally substituted with one $R^g$ group, wherein the heteroaryl contains one or two heteroatoms selected from the group consisting of O and N.

In certain embodiments, $R^2$ is selected from (a) hydrogen, (b) $C_1$-$C_6$ alkyl optionally substituted with one or two groups selected from $OR^f$ and oxo, (c) $C_1$-$C_6$ alkenyl, (f) phenyl, (g) a 3 to 7 membered heterocycle, wherein the heterocycle contains one N heteroatom, and (h) a 5 to 6 membered heteroaryl optionally substituted with one $R^g$ group, wherein the heteroaryl contains one or two heteroatoms selected from the group consisting of O and N.

In certain embodiments, $R^2$ is selected from (b) $C_1$-$C_6$ alkyl optionally substituted with one or more groups selected from $OR^f$, oxo, $NH_2$, $NH(C_1$-$C_3$ alkyl) and $N(C_1$-$C_3$ alkyl)$_2$, (f) phenyl optionally substituted with one or more groups selected from $OR^f$ and $R^g$, (g) a 3 to 7 membered heterocycle optionally substituted with one or more groups selected from $OR^f$ and $R^g$, wherein the heterocycle contains one, two or three heteroatoms selected from the group consisting of O, N, S, S(=O) and S(=O)$_2$, and (h) a 5 to 6 membered heteroaryl optionally substituted with one or more groups selected from $OR^f$ and $R^g$, wherein the heteroaryl contains one, two, three or four heteroatoms selected from the group consisting of O, N and S. In certain embodiments, $R^2$ is selected from (b) $C_1$-$C_6$ alkyl optionally substituted with one or two groups selected from $OR^f$, oxo and $NH_2$, (f) phenyl, (g) a 3 to 7 membered heterocycle, wherein the heterocycle contains one N heteroatom, and a (h) 5 to 6 membered heteroaryl optionally substituted with one $R^g$ group, wherein the heteroaryl contains one or two heteroatoms selected from the group consisting of O and N. In certain embodiments, $R^2$ is selected from methyl, ethyl, $CH_2OH$, $CH_2CH_2OH$, $CH_2CH(OH)CH_3$, $CH_2C(CH_3)_2OH$, $CH_2OCH_3$, C(=O)OH, $CH_2OC(=O)C(CH_3)_2NH_2$, $CH_2OC(=O)CH_3$, $CH_2NH_2$, phenyl, pyrrolidin-2-yl, pyrrolidin-3-yl, oxazol-5-yl and 1-methyl-pyrazol-4-yl.

In certain embodiments, $R^2$ is selected from (b) $C_1$-$C_6$ alkyl optionally substituted with one or more groups selected from $OR^f$ and oxo, (f) phenyl optionally substituted with one or more groups selected from $OR^f$ and $R^g$, (g) a 3 to 7 membered heterocycle optionally substituted with one or more groups selected from $OR^f$ and $R^g$, wherein the heterocycle contains one, two or three heteroatoms selected from the group consisting of O, N, S, S(=O) and S(=O)$_2$, and (h) a 5 to 6 membered heteroaryl optionally substituted with one or more groups selected from $OR^f$ and $R^g$, wherein the heteroaryl contains one, two, three or four heteroatoms selected from the group consisting of O, N and S. In certain embodiments, $R^2$ is selected from (b) $C_1$-$C_6$ alkyl optionally substituted with one or two groups selected from $OR^f$ and oxo, (f) phenyl, (g) a 3 to 7 membered heterocycle, wherein the heterocycle contains one N heteroatom, and a (h) 5 to 6 membered heteroaryl optionally substituted with one $R^g$ group, wherein the heteroaryl contains one or two heteroatoms selected from the group consisting of O and N. In certain embodiments, $R^2$ is selected from methyl, ethyl, $CH_2OH$, $CH_2CH_2OH$, $CH_2CH(OH)CH_3$, $CH_2C(CH_3)_2OH$, $CH_2OCH_3$, C(=O)OH, phenyl, pyrrolidin-2-yl, pyrrolidin-3-yl, oxazol-5-yl and 1-methyl-pyrazol-4-yl.

In certain embodiments, $R^2$ is selected from (b) $C_1$-$C_6$ alkyl optionally substituted with one or more groups selected from $OR^f$ and oxo, (g) a 3 to 7 membered heterocycle optionally substituted with one or more groups selected from $OR^f$ and $R^g$, wherein the heterocycle contains one, two or three heteroatoms selected from the group consisting of O, N, S, S(=O) and S(=O)$_2$, and (h) a 5 to 6 membered heteroaryl optionally substituted with one or more groups selected from $OR^f$ and $R^g$, wherein the heteroaryl contains one, two, three or four heteroatoms selected from the group consisting of O, N and S. In certain embodiments, $R^2$ is selected from (b) $C_1$-$C_6$ alkyl optionally substituted with one or two groups selected from $OR^f$ and oxo, (g) a 3 to 7 membered heterocycle, wherein the heterocycle contains one N heteroatom, and a (h) 5 to 6 membered heteroaryl optionally substituted with one $R^g$ group, wherein the heteroaryl contains one or two heteroatoms selected from the group consisting of O and N. In certain embodiments, $R^2$ is selected from methyl, ethyl, $CH_2OH$, $CH_2CH_2OH$, $CH_2CH(OH)CH_3$, $CH_2C(CH_3)_2OH$, $CH_2OCH_3$, C(=O)OH, pyrrolidin-2-yl, pyrrolidin-3-yl, oxazol-5-yl and 1-methyl-pyrazol-4-yl.

In certain embodiments, $R^2$ is $C_1$-$C_6$ alkyl optionally substituted with one or two groups selected from $OR^f$, oxo, and $NH_2$. In certain embodiments, $R^2$ is selected from methyl, ethyl, $CH_2OH$, $CH_2CH_2OH$, $CH_2CH(OH)CH_3$, $CH_2C(CH_3)_2OH$, $CH_2OCH_3$, C(=O)OH, $CH_2OC(=O)C(CH_3)_2NH_2$, $CH_2OC(=O)CH_3$ and $CH_2NH_2$. In certain embodiments, $R^2$ is selected from $CH_2OH$, $CH_2CH_2OH$, $CH_2CH(OH)CH_3$, $CH_2C(CH_3)_2OH$, $CH_2OCH_3$, $CH_2OC(=O)C(CH_3)_2NH_2$, $CH_2OC(=O)CH_3$ and $CH_2NH_2$.

In certain embodiments, $R^2$ is $C_1$-$C_6$ alkyl optionally substituted with one or two groups selected from $OR^f$ and oxo. In certain embodiments, $R^2$ is selected from methyl, ethyl, $CH_2OH$, $CH_2CH_2OH$, $CH_2CH(OH)CH_3$, $CH_2C(CH_3)_2OH$, $CH_2OCH_3$ and C(=O)OH. In certain embodiments, $R^2$ is selected from $CH_2OH$, $CH_2CH_2OH$, $CH_2CH(OH)CH_3$, $CH_2C(CH_3)_2OH$ and $CH_2OCH_3$.

In certain embodiments, $R^2$ is $C_1$-$C_6$ alkenyl optionally substituted with one or more $OR^f$ groups. In certain embodiments, $R^2$ is $C_1$-$C_6$ alkenyl. In certain embodiments, $R^2$ is methylene.

In certain embodiments, $R^2$ is phenyl optionally substituted with one or more groups selected from $OR^f$ and $R^g$. In certain embodiments, $R^2$ is phenyl.

In certain embodiments, $R^2$ is a 5 to 6 membered heterocycle optionally substituted with one or two groups selected from $OR^f$ and $R^g$, wherein the heterocycle contains one, two or three heteroatoms selected from the group consisting of O, N, S, S(=O) and S(=O)$_2$. In certain embodiments, $R^2$ is a 5 to 6 membered heterocycle, wherein the heterocycle contains one or two heteroatoms selected from the group consisting of O, N, S, S(=O) and S(=O)$_2$. In certain embodiments, $R^2$ is a 5 to 6 membered heterocycle, wherein the heterocycle contains one or two heteroatoms selected from the group consisting of O, N and S. In certain embodiments, $R^2$ is a 5 to 6 membered heterocycle, wherein the heterocycle contains one N heteroatom. In certain embodiments, $R^2$ is selected from pyrrolidin-2-yl and pyrrolidin-3-yl.

In certain embodiments, $R^2$ is a 5 to 6 membered heteroaryl optionally substituted with one or two groups selected from $OR^f$ and $R^g$, wherein the heteroaryl contains one, two, three or four heteroatoms selected from the group consisting of O, N and S. In certain embodiments, $R^2$ is a 5 to 6 membered heteroaryl optionally substituted with one or two groups selected from $OR^f$ and $R^g$, wherein the heteroaryl contains one or two heteroatoms selected from the group consisting of O, N and S. In certain embodiments, $R^2$ is a 5 to 6 membered heteroaryl optionally substituted with one $R^g$ group, wherein the heteroaryl contains one or two heteroatoms selected from the group consisting of O, N and S. In certain embodiments, $R^2$ is a 5 to 6 membered heteroaryl optionally substituted with one $R^g$ group, wherein the heteroaryl contains one or two heteroatoms selected from the group consisting of O and N. In certain embodiments, $R^2$ is selected from oxazol-5-yl and 1-methyl-pyrazol-4-yl.

In certain embodiments, $R^3$ is selected from (a) $(CR^h R^i)_x$-phenyl, wherein the phenyl may be optionally substituted with one to three $R^j$ groups, (b) a 5 to 6 membered heteroaryl optionally substituted with one to three $R^j$ groups, (c) a 9 to 10 membered bicyclic heterocycle optionally substituted with one to three $R^j$ groups, and (d) a 9 to 10 membered bicyclic heteroaryl optionally substituted with one to three $R^j$ groups.

In certain embodiments, $R^3$ is selected from (a) $(CR^h R^i)_x$-phenyl, wherein the phenyl may be optionally substituted with one or two $R^j$ groups, (b) a 5 to 6 membered heteroaryl optionally substituted with one or two $R^j$ groups, (c) a 9 to 10 membered bicyclic heterocycle optionally substituted with one or two $R^j$ groups, and (d) a 9 to 10 membered bicyclic heteroaryl optionally substituted with one or two $R^j$ groups.

In certain embodiments, $R^3$ is selected from (a) $(CR^h R^i)_x$-phenyl, wherein the phenyl may be optionally substituted with one or two $R^j$ groups, (b) a 5 to 6 membered heteroaryl optionally substituted with one or two $R^j$ groups, wherein the heteroaryl contains one, two, three or four heteroatoms selected from O, N and S, (c) a 9 to 10 membered heterocycle optionally substituted with one or two $R^j$ groups, wherein the heterocycle contains one, two or three heteroatoms selected from the group consisting of O, N, S, S(=O) and S(=O)$_2$, and (d) a 9 to 10 membered heteroaryl optionally substituted with one or two $R^j$ groups, wherein the heteroaryl contains one, two, three or four heteroatoms selected from O, N and S.

In certain embodiments, each $R^j$ is independently selected from halogen, methyl, $CF_3$, $OCH_3$, $OCHF_2$, CN and cyclopropyl.

In certain embodiments, $R^3$ is selected from phenyl, 3-chlorophenyl, 3-fluorophenyl, 4-chlorophenyl, 3-(trifluoromethyl)phenyl, 3-methylphenyl, 3-cyanophenyl, 3-methoxyphenyl, 2-chlorophenyl, 4-(difluoromethoxy)phenyl, 4-methoxyphenyl, 3,4-dichlorophenyl, 2,3-difluorophenyl, 3,5-dichlorophenyl, 3,4-difluorophenyl, 3,5-difluorophenyl, 2,3-dichlorophenyl, 2,4-dichlorophenyl, 4-chloro-3-fluorophenyl, 3-chloro-4-fluorophenyl, 3-fluoro-4-methoxyphenyl, 3-chloro-2-fluorophenyl, 3-chloro-5-fluorophenyl, 4-chloro-2-fluorophenyl, 5-chloro-2-fluorophenyl, 3-fluoro-5-methoxyphenyl, 2-fluoro-3-methoxyphenyl, 2-fluoro-5-methoxyphenyl, 3-methoxy-4-cyanophenyl, 4-chloro-3-methoxyphenyl, 4-fluoro-3-methoxyphenyl, 5-chloropyridin-3-yl, 1,3-dimethylpyrazol-5-yl, indolin-6-yl, indol-2-yl, indol-3-yl, indol-4-yl, indol-5-yl, indol-6-yl, indol-7-yl, 3-chloroindol-6-yl, 5-chloroindol-2-yl, 3-methylindol-6-yl, 1-methylindol-6-yl, 5-fluoroindol-2-yl, 2-methylindol-6-yl, 7-fluoroindol-2-yl, 3-methylindol-2-yl, 3-chloroindol-2-yl, 2-methylindol-3-yl, 6-chloroindol-2-yl, 3-cyclopropylindol-6-yl, 6-fluoroindol-2-yl, 2,3-dimethylindol-6-yl, 4-fluoroindol-2-yl, 7-fluoroindol-6-yl, 4-fluoroindol-6-yl, 5-fluoroindol-6-yl, indazol-6-yl, benzothiazol-2-yl, benzoimidazol-2-yl, 1-methylbenzoimidazol-2-yl, benzoimidazol-6-yl, benzooxazol-2-yl, 5-chlorobenzooxazol-2-yl, 6-chlorobenzooxazol-2-yl, pyrrolo[2,3-c]pyridin-2-yl, (4-methoxyphenyl)methyl, (4-fluorophenyl)methyl, (3-chlorophenyl)methyl, (4-chlorophenyl)methyl, (4-methylphenyl)methyl, (3-methoxyphenyl)methyl, (4-(trifluoromethyl)phenyl)methyl, (3-methylphenyl)methyl, (3-(trifluoromethyl)phenyl)methyl, (4-(trifluoromethoxy)phenyl)methyl, (4-cyanophenyl)methyl, (3-fluorophenyl)methyl, (3-(trifluoromethoxy)phenyl)methyl, (3,4-dichlorophenyl)methyl, (4-chloro-3-fluorophenyl)methyl and 1-(4-chloro-3-fluorophenyl)-1,2-dihydroxyethyl.

In certain embodiments, $R^3$ is selected from phenyl, 3-chlorophenyl, 3-fluorophenyl, 4-chlorophenyl, 3-(trifluoromethyl)phenyl, 3-methylphenyl, 3-cyanophenyl, 3-methoxyphenyl, 2-chlorophenyl, 4-(difluoromethoxy)phenyl, 3,4-dichlorophenyl, 2,3-difluorophenyl, 3,5-dichlorophenyl, 3,4-difluorophenyl, 3,5-difluorophenyl, 2,3-dichlorophenyl, 2,4-dichlorophenyl, 4-chloro-3-fluorophenyl, 3-chloro-4-fluorophenyl, 3-fluoro-4-methoxyphenyl, 3-chloro-2-fluorophenyl, 3-chloro-5-fluorophenyl, 4-chloro-2-fluorophenyl, 5-chloro-2-fluorophenyl, 3-fluoro-5-methoxyphenyl, 2-fluoro-3-methoxyphenyl, 2-fluoro-5-methoxyphenyl, 3-methoxy-4-cyanophenyl, 4-chloro-3-methoxyphenyl, 5-chloropyridin-3-yl, 1,3-dimethylpyrazol-5-yl, indolin-6-yl, indol-2-yl, indol-3-yl, indol-4-yl, indol-5-yl, indol-6-yl, indol-7-yl, 3-chloroindol-6-yl, 5-chloroindol-2-yl, 3-methylindol-6-yl, 1-methylindol-6-yl, 5-fluoroindol-2-yl, 2-methylindol-6-yl, 7-fluoroindol-2-yl, 3-methylindol-2-yl, 3-chloroindol-2-yl, 2-methylindol-3-yl, 6-chloroindol-2-yl, 3-cyclopropylindol-6-yl, 6-fluoroindol-2-yl, 2,3-dimethylindol-6-yl, 4-fluoroindol-2-yl, 7-fluoroindol-6-yl, indazol-6-yl, benzothiazol-2-yl, benzoimidazol-2-yl, 1-methylbenzoimidazol-2-yl, benzoimidazol-6-yl, benzooxazol-2-yl, 5-chlorobenzooxazol-2-yl, 6-chlorobenzooxazol-2-yl, pyrrolo[2,3-c]pyridin-2-yl, (4-methoxyphenyl)methyl, (4-fluorophenyl)methyl, (3-chlorophenyl)methyl, (4-chlorophenyl)methyl, (4-methylphenyl)methyl, (3-methoxyphenyl)methyl, (4-(trifluoromethyl)phenyl)

methyl, (3-methylphenyl)methyl, (3-(trifluoromethyl)phenyl)methyl, (4-(trifluoromethoxy)phenyl)methyl, (4-cyanophenyl)methyl, (3-fluorophenyl)methyl, (3-(trifluoromethoxy)phenyl)methyl, (3,4-dichlorophenyl)methyl, (4-chloro-3-fluorophenyl)methyl and 1-(4-chloro-3-fluorophenyl)-1,2-dihydroxyethyl.

In certain embodiments, x is 0. In certain embodiments, $R^3$ is selected from phenyl, 3-chlorophenyl, 3-fluorophenyl, 4-chlorophenyl, 3-(trifluoromethyl)phenyl, 3-methylphenyl, 3-cyanophenyl, 3-methoxyphenyl, 2-chlorophenyl, 4-(difluoromethoxy)phenyl, 4-methoxyphenyl, 3,4-dichlorophenyl, 2,3-difluorophenyl, 3,5-dichlorophenyl, 3,4-difluorophenyl, 3,5-difluorophenyl, 2,3-dichlorophenyl, 2,4-dichlorophenyl, 4-chloro-3-fluorophenyl, 3-chloro-4-fluorophenyl, 3-fluoro-4-methoxyphenyl, 3-chloro-2-fluorophenyl, 3-chloro-5-fluorophenyl, 4-chloro-2-fluorophenyl, 5-chloro-2-fluorophenyl, 3-fluoro-5-methoxyphenyl, 2-fluoro-3-methoxyphenyl, 2-fluoro-5-methoxyphenyl, 3-methoxy-4-cyanophenyl, 4-chloro-3-methoxyphenyl, 4-fluoro-3-methoxyphenyl, 5-chloropyridin-3-yl, 1,3-dimethylpyrazol-5-yl, indolin-6-yl, indol-2-yl, indol-3-yl, indol-4-yl, indol-5-yl, indol-6-yl, indol-7-yl, 3-chloroindol-6-yl, 5-chloroindol-2-yl, 3-methylindol-6-yl, 1-methylindol-6-yl, 5-fluoroindol-2-yl, 2-methylindol-6-yl, 7-fluoroindol-2-yl, 3-methylindol-2-yl, 3-chloroindol-2-yl, 2-methylindol-3-yl, 6-chloroindol-2-yl, 3-cyclopropylindol-6-yl, 6-fluoroindol-2-yl, 2,3-dimethylindol-6-yl, 4-fluoroindol-2-yl, 7-fluoroindol-6-yl, 4-fluoroindol-6-yl, 5-fluoroindol-6-yl, indazol-6-yl, benzothiazol-2-yl, benzoimidazol-2-yl, 1-methylbenzoimidazol-2-yl, benzoimidazol-2-yl, benzooxazol-2-yl, 5-chlorobenzooxazol-2-yl, 6-chlorobenzooxazol-2-yl and pyrrolo[2,3-c]pyridin-2-yl.

In certain embodiments, x is 0. In certain embodiments, $R^3$ is selected from phenyl, 3-chlorophenyl, 3-fluorophenyl, 4-chlorophenyl, 3-(trifluoromethyl)phenyl, 3-methylphenyl, 3-cyanophenyl, 3-methoxyphenyl, 2-chlorophenyl, 4-(difluoromethoxy)phenyl, 3,4-dichlorophenyl, 2,3-difluorophenyl, 3,5-dichlorophenyl, 3,4-difluorophenyl, 3,5-difluorophenyl, 2,3-dichlorophenyl, 2,4-dichlorophenyl, 4-chloro-3-fluorophenyl, 3-chloro-4-fluorophenyl, 3-fluoro-4-methoxyphenyl, 3-chloro-2-fluorophenyl, 3-chloro-5-fluorophenyl, 4-chloro-2-fluorophenyl, 5-chloro-2-fluorophenyl, 3-fluoro-5-methoxyphenyl, 2-fluoro-3-methoxyphenyl, 2-fluoro-5-methoxyphenyl, 3-methoxy-4-cyanophenyl, 4-chloro-3-methoxyphenyl, 5-chloropyridin-3-yl, 1,3-dimethylpyrazol-5-yl, indolin-6-yl, indol-2-yl, indol-3-yl, indol-4-yl, indol-5-yl, indol-6-yl, indol-7-yl, 3-chloroindol-6-yl, 5-chloroindol-2-yl, 3-methylindol-6-yl, 1-methylindol-6-yl, 5-fluoroindol-2-yl, 2-methylindol-6-yl, 7-fluoroindol-2-yl, 3-methylindol-2-yl, 3-chloroindol-2-yl, 2-methylindol-3-yl, 6-chloroindol-2-yl, 3-cyclopropylindol-6-yl, 6-fluoroindol-2-yl, 2,3-dimethylindol-6-yl, 4-fluoroindol-2-yl, 7-fluoroindol-6-yl, indazol-6-yl, benzothiazol-2-yl, benzoimidazol-2-yl, 1-methylbenzoimidazol-2-yl, benzoimidazol-2-yl, benzooxazol-2-yl, 5-chlorobenzooxazol-2-yl, 6-chlorobenzooxazol-2-yl and pyrrolo[2,3-c]pyridin-2-yl.

In certain embodiments, x is 1. In certain embodiments, $R^h$ and $R^i$ are independently selected from hydrogen, OH and $CH_2OH$. In certain embodiments, $R^h$ is selected from hydrogen and OH, and $R^1$ is selected from hydrogen and $CH_2OH$. In certain embodiments, $R^h$ is OH and $R^i$ is $CH_2OH$, or $R^h$ and $R^i$ are hydrogen. In certain embodiments, $R^3$ is selected from (4-methoxyphenyl)methyl, (4-fluorophenyl)methyl, (3-chlorophenyl)methyl, (4-chlorophenyl)methyl, (4-methylphenyl)methyl, (3-methoxyphenyl)methyl, (4-(trifluoromethyl)phenyl)methyl, (3-methylphenyl)methyl, (3-(trifluoromethyl)phenyl)methyl, (4-(trifluoromethoxy)phenyl)methyl, (4-cyanophenyl)methyl, (3-fluorophenyl)methyl, (3-(trifluoromethoxy)phenyl)methyl, (3,4-dichlorophenyl)methyl, (4-chloro-3-fluorophenyl)methyl and 1-(4-chloro-3-fluorophenyl)-1,2-dihydroxyethyl.

In certain embodiments, $R^3$ is $(CR^hR^i)_x$-phenyl, wherein the phenyl may be optionally substituted with one to three $R^j$ groups. In certain embodiments, $R^3$ is $(CR^hR^i)_x$-phenyl, wherein the phenyl may be optionally substituted with one or two $R^j$ groups. In certain embodiments, x is 0. In certain embodiments, $R^3$ is phenyl optionally substituted with one to three $R^j$ groups. In certain embodiments, $R^3$ is phenyl optionally substituted with one or two $R^j$ groups. In certain embodiments, $R^3$ is selected from phenyl, 3-chlorophenyl, 3-fluorophenyl, 4-chlorophenyl, 3-(trifluoromethyl)phenyl, 3-methylphenyl, 3-cyanophenyl, 3-methoxyphenyl, 2-chlorophenyl, 4-(difluoromethoxy)phenyl, 4-methoxyphenyl, 3,4-dichlorophenyl, 2,3-difluorophenyl, 3,5-dichlorophenyl, 3,4-difluorophenyl, 3,5-difluorophenyl, 2,3-dichlorophenyl, 2,4-dichlorophenyl, 4-chloro-3-fluorophenyl, 3-chloro-4-fluorophenyl, 3-fluoro-4-methoxyphenyl, 3-chloro-2-fluorophenyl, 3-chloro-5-fluorophenyl, 4-chloro-2-fluorophenyl, 5-chloro-2-fluorophenyl, 3-fluoro-5-methoxyphenyl, 2-fluoro-3-methoxyphenyl, 2-fluoro-5-methoxyphenyl, 3-methoxy-4-cyanophenyl, 4-chloro-3-methoxyphenyl and 4-fluoro-3-methoxyphenyl. In certain embodiments, $R^3$ is selected from 3-chlorophenyl, 3-fluorophenyl, 4-chlorophenyl, 3-(trifluoromethyl)phenyl, 3,4-dichlorophenyl, 2,3-difluorophenyl, 3,4-difluorophenyl, 3,5-difluorophenyl, 4-chloro-3-fluorophenyl, 3-chloro-4-fluorophenyl, 3-chloro-2-fluorophenyl and 3-chloro-5-fluorophenyl. In certain embodiments, $R^3$ is selected from 3-chlorophenyl, 3-fluorophenyl, 4-chlorophenyl, 3,4-dichlorophenyl, 2,3-difluorophenyl, 3,4-difluorophenyl, 3,5-difluorophenyl, 4-chloro-3-fluorophenyl, 3-chloro-4-fluorophenyl, 3-chloro-2-fluorophenyl and 3-chloro-5-fluorophenyl.

In certain embodiments, $R^3$ is $(CR^hR^i)_x$-phenyl, wherein the phenyl may be optionally substituted with one to three $R^j$ groups. In certain embodiments, $R^3$ is $(CR^hR^i)_x$-phenyl, wherein the phenyl may be optionally substituted with one or two $R^j$ groups. In certain embodiments, x is 0. In certain embodiments, $R^3$ is phenyl optionally substituted with one to three $R^j$ groups. In certain embodiments, $R^3$ is phenyl optionally substituted with one or two $R^j$ groups. In certain embodiments, $R^3$ is selected from phenyl, 3-chlorophenyl, 3-fluorophenyl, 4-chlorophenyl, 3-(trifluoromethyl)phenyl, 3-methylphenyl, 3-cyanophenyl, 3-methoxyphenyl, 2-chlorophenyl, 4-(difluoromethoxy)phenyl, 3,4-dichlorophenyl, 2,3-difluorophenyl, 3,5-dichlorophenyl, 3,4-difluorophenyl, 3,5-difluorophenyl, 2,3-dichlorophenyl, 2,4-dichlorophenyl, 4-chloro-3-fluorophenyl, 3-chloro-4-fluorophenyl, 3-fluoro-4-methoxyphenyl, 3-chloro-2-fluorophenyl, 3-chloro-5-fluorophenyl, 4-chloro-2-fluorophenyl, 5-chloro-2-fluorophenyl, 3-fluoro-5-methoxyphenyl, 2-fluoro-3-methoxyphenyl, 2-fluoro-5-methoxyphenyl, 3-methoxy-4-cyanophenyl and 4-chloro-3-methoxyphenyl.

In certain embodiments, $R^3$ is $(CR^hR^i)_x$-phenyl, wherein the phenyl may be optionally substituted with one to three $R^j$ groups. In certain embodiments, $R^3$ is $(CR^hR^i)_x$-phenyl, wherein the phenyl may be optionally substituted with one or two $R^j$ groups. In certain embodiments, x is 1. In certain embodiments, $R^3$ is $(CR^hR^i)$-phenyl, wherein the phenyl may be optionally substituted with one to three $R^j$ groups. In certain embodiments, $R^3$ is $(CR^hR^i)$-phenyl, wherein the phenyl may be optionally substituted with one or two $R^j$ groups. In certain embodiments, $R^3$ is $(CH_2)$-phenyl, wherein the phenyl may be optionally substituted with one to three $R^j$ groups. In certain embodiments, $R^3$ is $(CH_2)$-phenyl, wherein the phenyl may be optionally substituted with one or two $R^j$ groups.

In certain embodiments, $R^3$ is a 5 to 6 membered heteroaryl optionally substituted with one to three $R^j$ groups, wherein the heteroaryl contains one, two, three or four heteroatoms selected from O, N and S. In certain embodiments, $R^3$ is a 5 to 6 membered heteroaryl optionally substituted with one or two $R^j$ groups, wherein the heteroaryl contains one, two, three or four heteroatoms selected from O, N and S. In certain embodiments, $R^3$ is a 5 to 6 membered heteroaryl optionally substituted with one or two $R^j$ groups, wherein the heteroaryl contains one or two N heteroatoms. In certain embodiments, $R^3$ is selected from 5-chloropyridin-3-yl and 1,3-dimethylpyrazol-5-yl.

In certain embodiments, $R^3$ is a 9 to 10 membered bicyclic heterocycle optionally substituted with one to four $R^j$ groups, wherein the heterocycle contains one, two or three heteroatoms selected from the group consisting of O, N, S, S(=O) and S(=O)$_2$. In certain embodiments, $R^3$ is a 9 to 10 membered bicyclic heterocycle optionally substituted with one or two $R^j$ groups, wherein the heterocycle contains one, two or three heteroatoms selected from the group consisting of O, N, S, S(=O) and S(=O)$_2$. In certain embodiments, $R^3$ is a 9 to 10 membered bicyclic heterocycle optionally substituted with one or two $R^j$ groups, wherein the heterocycle contains one N heteroatom. In certain embodiments, $R^3$ is a 9 to 10 membered bicyclic heterocycle, wherein the heterocycle contains one, two or three heteroatoms selected from the group consisting of O, N, S, S(=O) and S(=O)$_2$. In certain embodiments, $R^3$ is a 9 to 10 membered bicyclic heterocycle, wherein the heterocycle contains one N heteroatom. In certain embodiments, x is 0. In certain embodiments, $R^3$ is indolin-6-yl.

In certain embodiments, $R^3$ is a 9 to 10 membered bicyclic heteroaryl optionally substituted with one to four $R^j$ groups, wherein the heteroaryl contains one, two, three or four heteroatoms selected from O, N and S. In certain embodiments, $R^3$ is a 9 to 10 membered bicyclic heteroaryl optionally substituted with one or two $R^j$ groups, wherein the heteroaryl contains one, two, three or four heteroatoms selected from O, N and S. In certain embodiments, $R^3$ is a 9 to 10 membered bicyclic heteroaryl optionally substituted with one or two $R^j$ groups, wherein the heteroaryl contains one or two heteroatoms selected from O, N and S. In certain embodiments, x is 0. In certain embodiments, $R^3$ is selected from indol-2-yl, indol-3-yl, indol-4-yl, indol-5-yl, indol-6-yl, indol-7-yl, 3-chloroindol-6-yl, 5-chloroindol-2-yl, 3-methylindol-6-yl, 1-methylindol-6-yl, 5-fluoroindol-2-yl, 2-methylindol-6-yl, 7-fluoroindol-2-yl, 3-methylindol-2-yl, 3-chloroindol-2-yl, 2-methylindol-3-yl, 6-chloroindol-2-yl, 3-cyclopropylindol-6-yl, 6-fluoroindol-2-yl, 2,3-dimethylindol-6-yl, 4-fluoroindol-2-yl, 7-fluoroindol-6-yl, 4-fluoroindol-6-yl, 5-fluoroindol-6-yl, indazol-6-yl, benzothiazol-2-yl, benzoimidazol-2-yl, 1-methylbenzoimidazol-2-yl, benzoimidazol-2-yl, benzooxazol-2-yl, 5-chlorobenzooxazol-2-yl, 6-chlorobenzooxazol-2-yl and pyrrolo[2,3-c]pyridin-2-yl. In certain embodiments, $R^3$ is selected from indol-2-yl, indol-3-yl, indol-4-yl, indol-5-yl, indol-6-yl, indol-7-yl, 3-chloroindol-6-yl, 5-chloroindol-2-yl, 3-methylindol-6-yl, 1-methylindol-6-yl, 5-fluoroindol-2-yl, 2-methylindol-6-yl, 7-fluoroindol-2-yl, 3-methylindol-2-yl, 3-chloroindol-2-yl, 2-methylindol-3-yl, 6-chloroindol-2-yl, 3-cyclopropylindol-6-yl, 6-fluoroindol-2-yl, 2,3-dimethylindol-6-yl, 4-fluoroindol-2-yl, 7-fluoroindol-6-yl, 4-fluoroindol-6-yl and 5-fluoroindol-6-yl.

In certain embodiments, $R^3$ is a 9 to 10 membered bicyclic heteroaryl optionally substituted with one to four $R^j$ groups, wherein the heteroaryl contains one, two, three or four heteroatoms selected from O, N and S. In certain embodiments, $R^3$ is a 9 to 10 membered bicyclic heteroaryl optionally substituted with one or two $R^j$ groups, wherein the heteroaryl contains one, two, three or four heteroatoms selected from O, N and S. In certain embodiments, $R^3$ is a 9 to 10 membered bicyclic heteroaryl optionally substituted with one or two $R^j$ groups, wherein the heteroaryl contains one or two heteroatoms selected from O, N and S. In certain embodiments, x is 0. In certain embodiments, $R^3$ is selected from indol-2-yl, indol-3-yl, indol-4-yl, indol-5-yl, indol-6-yl, indol-7-yl, 3-chloroindol-6-yl, 5-chloroindol-2-yl, 3-methylindol-6-yl, 1-methylindol-6-yl, 5-fluoroindol-2-yl, 2-methylindol-6-yl, 7-fluoroindol-2-yl, 3-methylindol-2-yl, 3-chloroindol-2-yl, 2-methylindol-3-yl, 6-chloroindol-2-yl, 3-cyclopropylindol-6-yl, 6-fluoroindol-2-yl, 2,3-dimethylindol-6-yl, 4-fluoroindol-2-yl, 7-fluoroindol-6-yl, indazol-6-yl, benzothiazol-2-yl, benzoimidazol-2-yl, 1-methylbenzoimidazol-2-yl, benzoimidazol-2-yl, benzooxazol-2-yl, 5-chlorobenzooxazol-2-yl, 6-chlorobenzooxazol-2-yl and pyrrolo[2,3-c]pyridin-2-yl. In certain embodiments, $R^3$ is selected from indol-2-yl, indol-3-yl, indol-4-yl, indol-5-yl, indol-6-yl, indol-7-yl, 3-chloroindol-6-yl, 5-chloroindol-2-yl, 3-methylindol-6-yl, 1-methylindol-6-yl, 5-fluoroindol-2-yl, 2-methylindol-6-yl, 7-fluoroindol-2-yl, 3-methylindol-2-yl, 3-chloroindol-2-yl, 2-methylindol-3-yl, 6-chloroindol-2-yl, 3-cyclopropylindol-6-yl, 6-fluoroindol-2-yl, 2,3-dimethylindol-6-yl and 4-fluoroindol-2-yl.

In certain embodiments, $R^2$ is hydrogen and x is 1.

In certain embodiments, $R^2$ is hydrogen or $C_1$-$C_6$ alkyl optionally substituted with one or more groups selected from $OR^f$, oxo, $NH_2$, $NH(C_1$-$C_3$ alkyl) and $N(C_1$-$C_3$ alkyl)$_2$; x is 0; and $R^3$ is a 9 to 10 membered bicyclic heterocycle optionally substituted with one or more $R^j$ groups, or a 9 to 10 membered bicyclic heteroaryl optionally substituted with one or more $R^j$ groups. In certain embodiments, $R^2$ is hydrogen or $C_1$-$C_6$ alkyl optionally substituted with one or more groups selected from $OR^f$, oxo and $NH_2$; x is 0; and $R^3$ is a 9 to 10 membered bicyclic heterocycle optionally substituted with one or more $R^j$ groups, or a 9 to 10 membered bicyclic heteroaryl optionally substituted with one or more $R^j$ groups. In certain embodiments, $R^2$ is hydrogen or $C_1$-$C_6$ alkyl optionally substituted with one or more groups selected from $OR^f$ and oxo; x is 0; and $R^3$ is a 9 to 10 membered bicyclic heterocycle optionally substituted with one or more $R^j$ groups, or a 9 to 10 membered bicyclic heteroaryl optionally substituted with one or more $R^j$ groups. In certain embodiments, $R^2$ is hydrogen or $C_1$-$C_6$ alkyl; x is 0; and $R^3$ is a 9 to 10 membered bicyclic heterocycle optionally substituted with one or more $R^j$ groups, or a 9 to 10 membered bicyclic heteroaryl optionally substituted with one or more $R^j$ groups. In certain embodiments, $R^2$ is hydrogen or $C_1$-$C_6$ alkyl; x is 0; and $R^3$ is a 9 to 10 membered bicyclic heterocycle optionally substituted with one to four $R^j$ groups, or a 9 to 10 membered bicyclic heteroaryl optionally substituted with one to four $R^j$ groups. In certain embodiments, $R^2$ is hydrogen or methyl; x is 0; and $R^3$ is a 9 to 10 membered bicyclic heterocycle optionally substituted with one or more $R^j$ groups, or a 9 to 10 membered bicyclic heteroaryl optionally substituted with one or more $R^j$ groups. In certain embodiments, $R^2$ is hydrogen or methyl; x is 0; and $R^3$ is a 9 to 10 membered bicyclic heterocycle optionally substituted with one or two $R^j$ groups, or a 9 to 10 membered bicyclic heteroaryl optionally substituted with one or two $R^j$ groups.

In certain embodiments, $R^1$ is selected from (d) a 3 to 7 membered saturated or partially unsaturated heterocycle optionally substituted with one to four groups independently selected from halogen, oxo, $OR^a$ and $C_1$-$C_3$ alkyl optionally substituted with $OR^d$, wherein the heterocycle contains one, two or three heteroatoms selected from the group consisting of O, N, S, S(=O) and S(=O)$_2$, and (e) a 5 to 6 membered heteroaryl optionally substituted with one to four groups independently selected from halogen, CN, $OR^e$, $C_3$-$C_6$ cycloalkyl, oxide and $C_1$-$C_3$ alkyl optionally substituted with one to three groups independently selected from hydroxyl and halogen, wherein the heteroaryl contains one, two, three or four heteroatoms selected from the group consisting of O, N and S; $R^2$ is selected from (b) $C_1$-$C_6$ alkyl optionally substituted with one or more groups selected from $OR^f$, oxo, $NH_2$, $NH(C_1$-$C_3$ alkyl) and $N(C_1$-$C_3$ alkyl)$_2$, and (h) a 5 to 6 membered heteroaryl optionally substituted with one or more groups selected from $OR^f$ and $R^g$, wherein the heteroaryl contains one, two, three or four heteroatoms selected from the group consisting of O, N and S; and $R^3$ is phenyl optionally substituted with one or two $R^j$ groups.

In certain embodiments, $R^1$ is selected from (d) a 3 to 7 membered saturated or partially unsaturated heterocycle optionally substituted with one to four groups independently selected from halogen, oxo, $OR^a$ and $C_1$-$C_3$ alkyl optionally substituted with $OR^d$, wherein the heterocycle contains one, two or three heteroatoms selected from the group consisting of O, N, S, S(=O) and S(=O)$_2$, and (e) a 5 to 6 membered heteroaryl optionally substituted with one to four groups independently selected from halogen, CN, $OR^e$, $C_3$-$C_6$ cycloalkyl, oxide and $C_1$-$C_3$ alkyl optionally substituted with one to three groups independently selected from hydroxyl and halogen, wherein the heteroaryl contains one, two, three or four heteroatoms selected from the group consisting of O, N and S; $R^2$ is selected from (b) $C_1$-$C_6$ alkyl optionally substituted with one or more groups selected from $OR^f$, oxo and $NH_2$, and (h) a 5 to 6 membered heteroaryl optionally substituted with one or more groups selected from $OR^f$ and $R^g$, wherein the heteroaryl contains one, two, three or four heteroatoms selected from the group consisting of O, N and S; and $R^3$ is phenyl optionally substituted with one or two $R^j$ groups.

In certain embodiments, $R^1$ is selected from (d) a 3 to 7 membered saturated or partially unsaturated heterocycle optionally substituted with one to four groups independently selected from halogen, oxo, $OR^a$ and $C_1$-$C_3$ alkyl optionally substituted with $OR^d$, wherein the heterocycle contains one, two or three heteroatoms selected from the group consisting of O, N, S, S(=O) and S(=O)$_2$, and (e) a 5 to 6 membered heteroaryl optionally substituted with one to four groups independently selected from halogen, CN, $OR^e$, $C_3$-$C_6$ cycloalkyl, oxide and $C_1$-$C_3$ alkyl optionally substituted with one to three groups independently selected from hydroxyl and halogen, wherein the heteroaryl contains one, two, three or four heteroatoms selected from the group consisting of O, N and S; $R^2$ is selected from (b) $C_1$-$C_6$ alkyl optionally substituted with one or more groups selected from $OR^f$ and oxo, and (h) a 5 to 6 membered heteroaryl optionally substituted with one or more groups selected from $OR^f$ and $R^g$, wherein the heteroaryl contains one, two, three or four heteroatoms selected from the group consisting of O, N and S; and $R^3$ is phenyl optionally substituted with one or two $R^j$ groups.

In certain embodiments, $R^1$ is selected from (d) a 3 to 7 membered saturated heterocycle optionally substituted with one or two groups independently selected from halogen and $C_1$-$C_3$ alkyl optionally substituted with OH, wherein the heterocycle contains one heteroatom selected from the group consisting of O, N and S(=O)$_2$, and (e) a 5 to 6 membered heteroaryl optionally substituted with one to three groups independently selected from halogen, CN, $OR^e$, cyclopropyl and $C_1$-$C_3$ alkyl optionally substituted with one to three groups independently selected from hydroxyl and halogen, wherein the heteroaryl contains one, two or three heteroatoms selected from the group consisting of O and N; $R^2$ is selected from (b) $C_1$-$C_6$ alkyl optionally substituted with one or two groups selected from $OR^f$, oxo, $NH_2$, $NH(C_1$-$C_3$ alkyl) and $N(C_1$-$C_3$ alkyl)$_2$, and (h) a 5 to 6 membered heteroaryl optionally substituted with one $R^g$ group, wherein the heteroaryl contains one or two heteroatoms selected from the group consisting of O, N and S; and $R^3$ is phenyl optionally substituted with one or two $R^j$ groups.

In certain embodiments, $R^1$ is selected from (d) a 3 to 7 membered saturated heterocycle optionally substituted with one or two groups independently selected from halogen and $C_1$-$C_3$ alkyl optionally substituted with OH, wherein the heterocycle contains one heteroatom selected from the group consisting of O, N and S(=O)$_2$, and (e) a 5 to 6 membered heteroaryl optionally substituted with one to three groups independently selected from halogen, CN, $OR^e$, cyclopropyl and $C_1$-$C_3$ alkyl optionally substituted with one to three groups independently selected from hydroxyl and halogen, wherein the heteroaryl contains one, two or three heteroatoms selected from the group consisting of O and N; $R^2$ is selected from (b) $C_1$-$C_6$ alkyl optionally substituted with one or two groups selected from $OR^f$, oxo and $NH_2$, and (h) a 5 to 6 membered heteroaryl optionally substituted with one $R^g$ group, wherein the heteroaryl contains one or two heteroatoms selected from the group consisting of O, N and S; and $R^3$ is phenyl optionally substituted with one or two $R^j$ groups.

In certain embodiments, $R^1$ is selected from (d) a 3 to 7 membered saturated heterocycle optionally substituted with one or two groups independently selected from halogen and $C_1$-$C_3$ alkyl optionally substituted with OH, wherein the heterocycle contains one heteroatom selected from the group consisting of O, N and S(=O)$_2$, and (e) a 5 to 6 membered heteroaryl optionally substituted with one to three groups independently selected from halogen, CN, $OR^e$, cyclopropyl and $C_1$-$C_3$ alkyl optionally substituted with one to three groups independently selected from hydroxyl and halogen, wherein the heteroaryl contains one, two or three heteroatoms selected from the group consisting of O and N; $R^2$ is selected from (b) $C_1$-$C_6$ alkyl optionally substituted with one or two groups selected from $OR^f$ and oxo, and (h) a 5 to 6 membered heteroaryl optionally substituted with one $R^g$ group, wherein the heteroaryl contains one or two heteroatoms selected from the group consisting of O, N and S; and $R^3$ is phenyl optionally substituted with one or two $R^j$ groups.

In certain embodiments, $R^1$ is selected from tetrahydropyran-4-yl, 3-fluorotetrahydropyran-4-yl, 2-(hydroxymethyl)tetrahydropyran-4-yl, 1,3-dimethylpyrazol-4-yl and 1-methylpyrazol-5-yl; $R^2$ is selected from $CH_2OH$, $CH_2CH_2OH$ and 1-methyl-pyrazol-4-yl; and $R^3$ is selected from 3-chlorophenyl, 3-fluorophenyl, 4-chlorophenyl, 3-(trifluoromethyl)phenyl, 3,4-dichlorophenyl, 2,3-difluorophenyl, 3,4-difluorophenyl, 3,5-difluorophenyl, 4-chloro-3-fluorophenyl, 3-chloro-4-fluorophenyl, 3-chloro-2-fluorophenyl and 3-chloro-5-fluorophenyl.

In certain embodiments, $R^1$ is selected from (d) a 3 to 7 membered saturated or partially unsaturated heterocycle optionally substituted with one to four groups independently selected from halogen, oxo, $OR^a$ and $C_1$-$C_3$ alkyl optionally substituted with $OR^d$, wherein the heterocycle contains one, two or three heteroatoms selected from the group consisting of O, N, S, S(=O) and S(=O)$_2$, and (e) a 5 to 6 membered heteroaryl optionally substituted with one to four groups independently selected from halogen, CN, $OR^e$, $C_3$-$C_6$ cycloalkyl, oxide and $C_1$-$C_3$ alkyl optionally substituted with one to three groups independently selected from hydroxyl and halogen; $R^2$ is selected from (b) $C_1$-$C_6$ alkyl optionally substituted with one or more groups selected from $OR^f$, oxo, $NH_2$, $NH(C_1$-$C_3$ alkyl) and $N(C_1$-$C_3$ alkyl)$_2$, and (h) a 5 to 6 membered heteroaryl optionally substituted with one or more groups selected from $OR^f$ and $R^g$, wherein the heteroaryl contains one, two, three or four heteroatoms selected from the group consisting of O, N and S; and $R^3$ is a 9 to 10 membered bicyclic heteroaryl optionally substituted with one to four $R^j$ groups, wherein the heteroaryl contains one, two or three heteroatoms selected from the group consisting of O, N and S.

In certain embodiments, $R^1$ is selected from (d) a 3 to 7 membered saturated or partially unsaturated heterocycle optionally substituted with one to four groups independently selected from halogen, oxo, $OR^a$ and $C_1$-$C_3$ alkyl optionally substituted with $OR^d$, wherein the heterocycle contains one, two or three heteroatoms selected from the group consisting of O, N, S, S(=O) and S(=O)$_2$, and (e) a 5 to 6 membered heteroaryl optionally substituted with one to four groups independently selected from halogen, CN, $OR^e$, $C_3$-$C_6$ cycloalkyl, oxide and $C_1$-$C_3$ alkyl optionally substituted with one to three groups independently selected from hydroxyl and halogen; $R^2$ is selected from (b) $C_1$-$C_6$ alkyl optionally substituted with one or more groups selected from $OR^f$, oxo and $NH_2$, and (h) a 5 to 6 membered heteroaryl optionally substituted with one or more groups selected from $OR^f$ and $R^g$, wherein the heteroaryl contains one, two, three or four heteroatoms selected from the group consisting of O, N and S; and $R^3$ is a 9 to 10 membered bicyclic heteroaryl optionally substituted with one to four $R^j$ groups, wherein the heteroaryl contains one, two or three heteroatoms selected from the group consisting of O, N and S.

In certain embodiments, $R^1$ is selected from (d) a 3 to 7 membered saturated or partially unsaturated heterocycle optionally substituted with one to four groups independently selected from halogen, oxo, $OR^a$ and $C_1$-$C_3$ alkyl optionally substituted with $OR^d$, wherein the heterocycle contains one, two or three heteroatoms selected from the group consisting of O, N, S, S(=O) and S(=O)$_2$, and (e) a 5 to 6 membered heteroaryl optionally substituted with one to four groups independently selected from halogen, CN, $OR^e$, $C_3$-$C_6$ cycloalkyl, oxide and $C_1$-$C_3$ alkyl optionally substituted with one to three groups independently selected from hydroxyl and halogen; $R^2$ is selected from (b) $C_1$-$C_6$ alkyl optionally substituted with one or more groups selected from $OR^f$ and oxo, and (h) a 5 to 6 membered heteroaryl optionally substituted with one or more groups selected from $OR^f$ and $R^g$, wherein the heteroaryl contains one, two, three or four heteroatoms selected from the group consisting of O, N and S; and $R^3$ is a 9 to 10 membered bicyclic heteroaryl optionally substituted with one to four $R^j$ groups, wherein the heteroaryl contains one, two or three heteroatoms selected from the group consisting of O, N and S.

In certain embodiments, $R^1$ is selected from (d) a 3 to 7 membered saturated heterocycle optionally substituted with one or two groups independently selected from halogen and $C_1$-$C_3$ alkyl optionally substituted with OH, wherein the heterocycle contains one heteroatom selected from the group consisting of O, N and S(=O)$_2$, and (e) a 5 to 6 membered heteroaryl optionally substituted with one to three groups independently selected from halogen, CN, $OR^e$, cyclopropyl and $C_1$-$C_3$ alkyl optionally substituted with one to three groups independently selected from hydroxyl and halogen, wherein the heteroaryl contains one, two or three heteroatoms selected from the group consisting of O and N; $R^2$ is selected from (b) $C_1$-$C_6$ alkyl optionally substituted with one or two groups selected from $OR^f$, oxo, $NH_2$, $NH(C_1$-$C_3$ alkyl) and $N(C_1$-$C_3$ alkyl)$_2$, and (h) a 5 to 6 membered heteroaryl optionally substituted with one $R^g$ group, wherein the heteroaryl contains one or two heteroatoms selected from the group consisting of O, N and S; and $R^3$ is a 9 to 10 membered bicyclic heteroaryl optionally substituted with one or two $R^j$ groups, wherein the heteroaryl contains one N heteroatom.

In certain embodiments, $R^1$ is selected from (d) a 3 to 7 membered saturated heterocycle optionally substituted with one or two groups independently selected from halogen and $C_1$-$C_3$ alkyl optionally substituted with OH, wherein the heterocycle contains one heteroatom selected from the group consisting of O, N and S(=O)$_2$, and (e) a 5 to 6 membered heteroaryl optionally substituted with one to three groups independently selected from halogen, CN, $OR^e$, cyclopropyl and $C_1$-$C_3$ alkyl optionally substituted with one to three groups independently selected from hydroxyl and halogen, wherein the heteroaryl contains one, two or three heteroatoms selected from the group consisting of O and N; $R^2$ is selected from (b) $C_1$-$C_6$ alkyl optionally substituted with one or two groups selected from $OR^f$, oxo and $NH_2$, and (h) a 5 to 6 membered heteroaryl optionally substituted with one $R^g$ group, wherein the heteroaryl contains one or two heteroatoms selected from the group consisting of O, N and S; and $R^3$ is a 9 to 10 membered bicyclic heteroaryl optionally substituted with one or two $R^j$ groups, wherein the heteroaryl contains one N heteroatom.

In certain embodiments, $R^1$ is selected from (d) a 3 to 7 membered saturated heterocycle optionally substituted with one or two groups independently selected from halogen and $C_1$-$C_3$ alkyl optionally substituted with OH, wherein the heterocycle contains one heteroatom selected from the group consisting of O, N and S(=O)$_2$, and (e) a 5 to 6 membered heteroaryl optionally substituted with one to three groups independently selected from halogen, CN, $OR^e$, cyclopropyl and $C_1$-$C_3$ alkyl optionally substituted with one to three groups independently selected from hydroxyl and halogen, wherein the heteroaryl contains one, two or three heteroatoms selected from the group consisting of O and N; $R^2$ is selected from (b) $C_1$-$C_6$ alkyl optionally substituted with one or two groups selected from $OR^f$ and oxo, and (h) a 5 to 6 membered heteroaryl optionally substituted with one $R^g$ group, wherein the heteroaryl contains one or two heteroatoms selected from the group consisting of O, N and S; and $R^3$ is a 9 to 10 membered bicyclic heteroaryl optionally substituted with one or two $R^j$ groups, wherein the heteroaryl contains one N heteroatom.

In certain embodiments, $R^1$ is selected from tetrahydropyran-4-yl, 3-fluorotetrahydropyran-4-yl, 2-(hydroxymethyl)tetrahydropyran-4-yl, 1,3-dimethylpyrazol-4-yl and 1-methylpyrazol-5-yl; $R^2$ is selected from $CH_2OH$, $CH_2CH_2OH$ and 1-methyl-pyrazol-4-yl; and $R^3$ is selected from indol-2-yl, indol-3-yl, indol-4-yl, indol-5-yl, indol-6- yl, indol-7-yl, 3-chloroindol-6-yl, 5-chloroindol-2-yl, 3-methylindol-6-yl, 1-methylindol-6-yl, 5-fluoroindol-2-yl, 2-methylindol-6-yl, 7-fluoroindol-2-yl, 3-methylindol-2-yl, 3-chloroindol-2-yl, 2-methylindol-3-yl, 6-chloroindol-2-yl, 3-cyclopropylindol-6-yl, 6-fluoroindol-2-yl, 2,3-dimethylindol-6-yl and 4-fluoroindol-2-yl.

In certain embodiments, $R^4$ is selected from hydrogen, F and methyl. In certain embodiments, $R^4$ is selected from hydrogen and F. In certain embodiments, $R^4$ is selected from hydrogen and methyl. In certain embodiments, $R^4$ is selected from F and methyl. In certain embodiments, $R^4$ is hydrogen. In certain embodiments, $R^4$ is F. In certain embodiments, $R^4$ is methyl.

In certain embodiments, $R^5$ is selected from hydrogen, F, Cl and methyl. In certain embodiments, $R^5$ is selected from hydrogen, F and methyl. In certain embodiments, $R^5$ is selected from hydrogen and F. In certain embodiments, $R^5$ is selected from hydrogen and methyl. In certain embodiments, $R^5$ is hydrogen. In certain embodiments, $R^5$ is F. In certain embodiments, $R^5$ is Cl. In certain embodiments, $R^5$ is methyl.

In certain embodiments, $R^6$ is selected from hydrogen and $C_1$-$C_3$ alkyl. In certain embodiments, $R^6$ is selected from hydrogen and methyl. In certain embodiments, $R^6$ is hydrogen. In certain embodiments, $R^6$ is methyl.

In certain embodiments, $R^7$ is selected from hydrogen and halogen. In certain embodiments, $R^7$ is selected from hydrogen and F. In certain embodiments, $R^7$ is hydrogen. In certain embodiments, $R^7$ is F.

In certain embodiments:
$R^5$ is selected from hydrogen, halogen and $C_1$-$C_3$ alkyl; $R^6$ is hydrogen; and $R^7$ is hydrogen; or
$R^5$ is hydrogen; $R^6$ is selected from hydrogen and $C_1$-$C_3$ alkyl; and $R^7$ is hydrogen; or
$R^5$ is hydrogen; $R^6$ is hydrogen; and $R^7$ is selected from hydrogen and halogen.

In certain embodiments, a compound of Examples 1 to 323 is provided. In certain embodiments, a compound of Examples 1 to 310 is provided.

In certain embodiments, a compound of Examples 1 to 288 and 311 to 323 is provided. In certain embodiments, a compound of Examples 1 to 288 is provided.

In certain embodiments, a compound of Formula I, II, III, IV, V, VI, VII, VIII, IX or X is provided. In certain embodiments, a compound of Formula I, II, III, IV, V, VI, VII, VIII, IX, or X is provided, with the proviso that the compound is not Example 311 to 323.

It will be appreciated that certain compounds described herein may contain asymmetric or chiral centers, and therefore exist in different stereoisomeric forms. It is intended that all stereoisomeric forms of the compounds described herein, including but not limited to, diastereomers, enantiomers and atropisomers, as well as mixtures thereof such as racemic mixtures, form part of the present compounds.

In the structures shown herein, where the stereochemistry of any particular chiral atom is not specified, then all stereoisomers are contemplated and included as the compounds described herein. Where stereochemistry is specified by a solid wedge or dashed line representing a particular configuration, then that stereoisomer is so specified and defined.

It will also be appreciated that certain compounds of Formula I may be used as intermediates for further compounds of Formula I.

It will be further appreciated that the compounds described herein may exist in unsolvated, as well as solvated forms with pharmaceutically acceptable solvents, such as water, ethanol, and the like, and it is intended that the compounds embrace both solvated and unsolvated forms.

Prodrugs of compounds of Formula I are not as active as the compounds of Formula I in the assay as described in Example A (although some prodrugs may be converted in the assay to a more active form). However, the prodrugs are capable of being converted in vivo into more active metabolites, i.e., compounds of Formula I. Examples 290, 293, α and β are examples of prodrugs of Formula I. Prodrugs of compounds of Formula I include compounds having Formula XI:

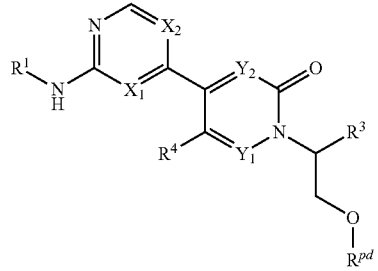

XI wherein $X_1$, $X_2$, $Y_1$, $Y_2$, $R^1$, $R^3$ and $R^4$ are as defined herein, and $R^{pd}$ is OP(=O)(OH)$_2$ or CH$_2$OP(=O)(OH)$_2$.

Synthesis of Compounds

Compounds described herein may be synthesized by synthetic routes that include processes analogous to those well-known in the chemical arts, particularly in light of the description contained herein. The starting materials are generally available from commercial sources such as Sigma-Aldrich (St. Louis, Mo.), Alfa Aesar (Ward Hill, Mass.), or TCI (Portland, Oreg.), or are readily prepared using methods well known to those skilled in the art (e.g., prepared by methods generally described in Louis F. Fieser and Mary Fieser, *Reagents for Organic Synthesis*. v. 1-23, New York: Wiley 1967-2006 ed. (also available via the Wiley InterScience® website), or *Beilsteins Handbuch der organischen Chemie*, 4, Aufl. ed. Springer-Verlag, Berlin, including supplements (also available via the Beilstein online database)).

For illustrative purposes, Schemes 1-10 show general methods for preparing the compounds described herein, as well as key intermediates. For a more detailed description of the individual reaction steps, see the Examples section below. Those skilled in the art will appreciate that other synthetic routes may be used to synthesize the compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1

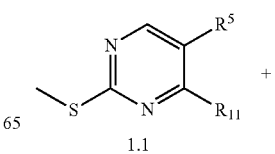

-continued

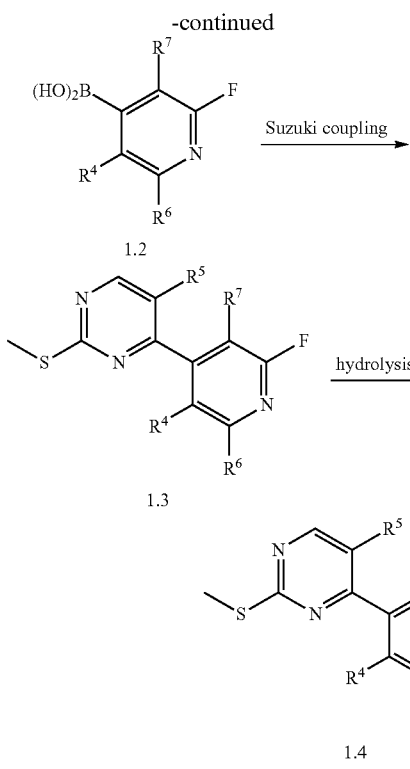

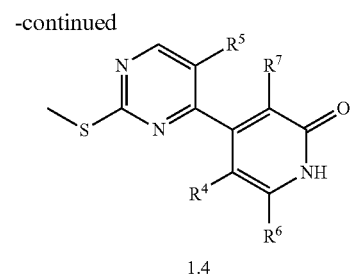

Scheme 2 shows an alternative scheme for preparing a compound 1.4, wherein $R^4$, $R^5$, $R^6$ and $R^7$ are as defined herein. A Stille coupling of stanane 2.1 with iodopyridine 2.2, in the presence of catalysts, such as $PdCl_2(PPh_3)_2$ and Cu(I)I, in a suitable solvent, such as N-methyl-2-pyrrolidone ("NMP"), may be used to obtain intermediate 1.3. Hydrolysis of compound 1.3 may be accomplished under acid conditions, such as aqueous HCl, to provide a pyridone 1.4.

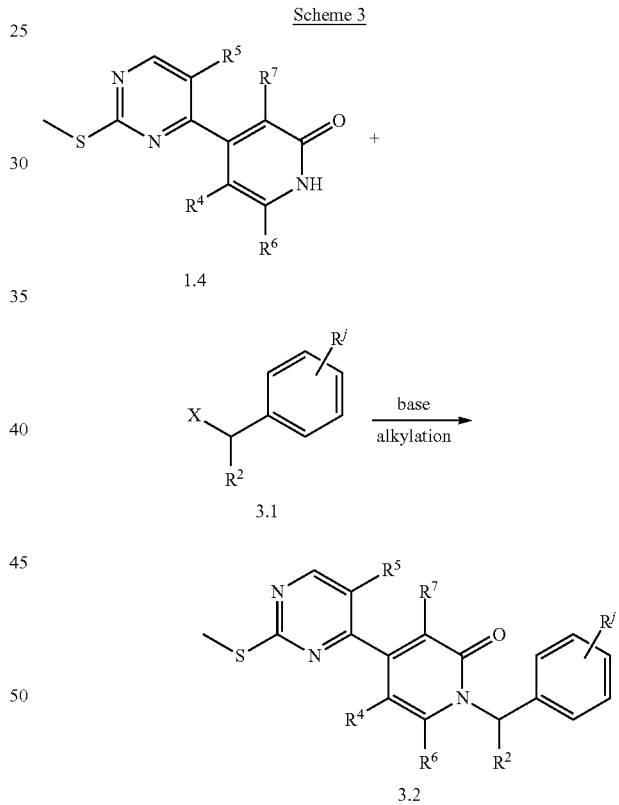

Scheme 1 shows a general scheme for the synthesis of compound 1.4, wherein $R^4$, $R^5$, $R^6$ and $R^7$ are as defined herein. A 4-halo pyrimidine 1.1, wherein $R^{11}$=Cl, Br or I, may be coupled to a 4-pyridine boronic acid 1.2 with a Pd catalyst, such as $PdCl_2(dppf)$, in the presence of a base, such as $Na_2CO_3$ to give intermediate 1.3. Hydrolysis of compound 1.3 may be accomplished under acid conditions, such as aqueous HCl, to provide a pyridone 1.4.

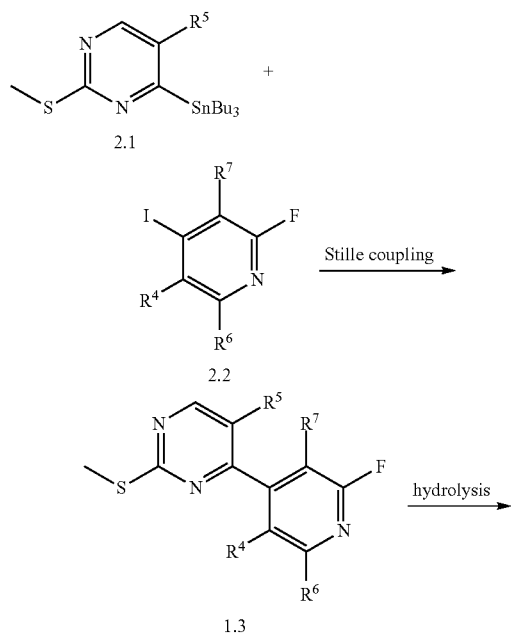

Scheme 3 shows a general scheme for preparing compound 3.2, wherein $R^2$, $R^4$, $R^5$, $R^6$, $R^7$ and $R^j$ are as defined herein. Pyridone 1.4 may be alkylated with a benzyl electrophile 3.1, wherein X is Cl, Br, I, mesylate ester ("OMs") or triflate ("OTf"), in the presence of a base, such as potassium bis(trimethylsilyl)amide ("KHMDS") or KOt-Bu with a suitable solvent, such as tetrahydrofuran ("THF"), 2-methyltetrahydrofuran or dioxane, with an optional catalyst, such as tetrabutylammonium iodide, to provide N-benzyl pyridone 3.2.

Scheme 4

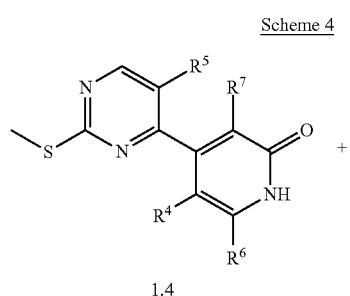

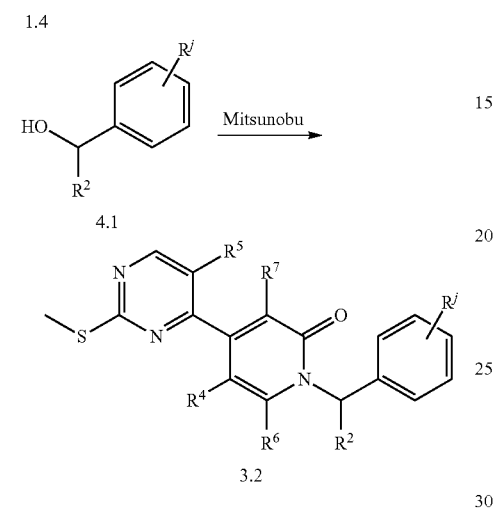

Scheme 4 shows an alternative scheme for preparing compound 3.2, wherein $R^2$, $R^4$, $R^5$, $R^6$, $R^7$ and $R^j$ are as defined herein. Benzyl alcohol 4.1 in a suitable solvent, such as THF, may be activated with diisopropyl azodicarboxylate ("DIAD") and triphenylphosphine ("PPh$_3$"). Subsequent treatment with pyridone 1.4 affords N-benzyl pyridone 3.2.

Scheme 5

Scheme 5 shows a general scheme for preparing compound 5.5, a subset of 3.1, wherein $R^j$ is as defined herein.

Treatment of aldehyde 5.1 with a Wittig reagent, such as methyltriphenylphosphonium bromide, and a base, such as NaH, in a suitable solvent, such as THF, yields alkene 5.2. Dihydroxylation of alkene 5.2 may be accomplished with Sharpless catalyst, AD-mix-β, to afford diol 5.3. The primary hydroxyl group may be selectively protected with tert-butyldimethylsilyl chloride ("TBSCl") to give alcohol 5.4, which may then be converted to the corresponding mesylate 5.5 with MsCl and a base, such as triethylamine.

Scheme 6

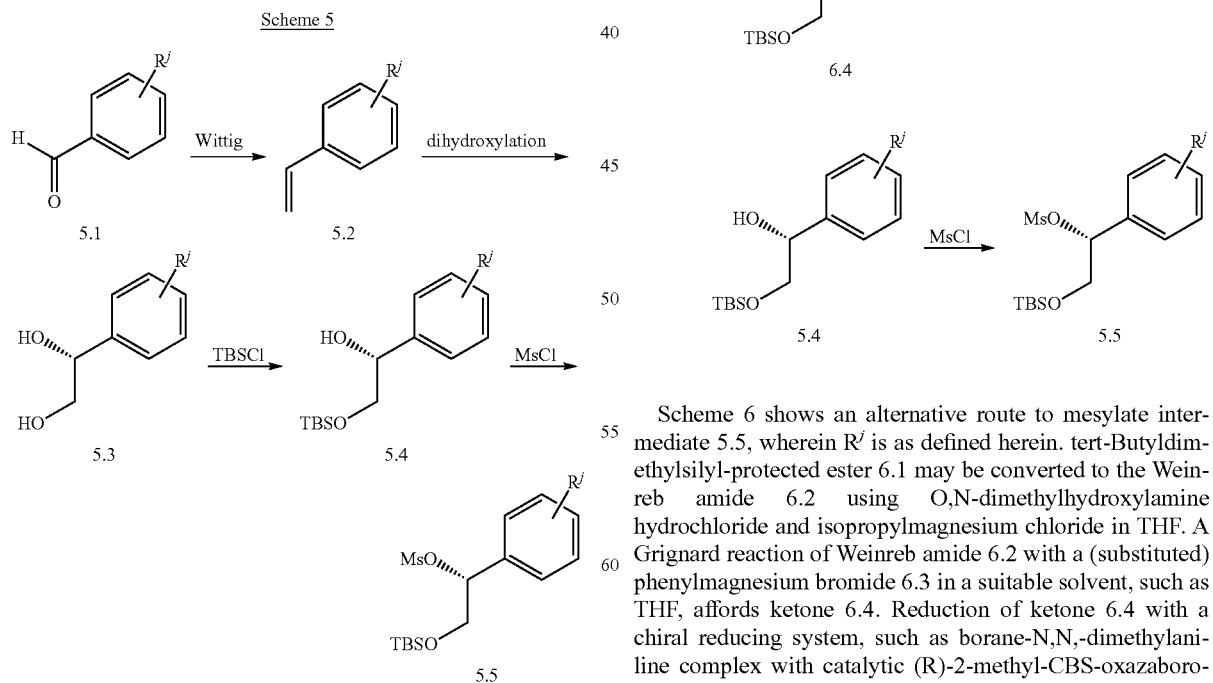

Scheme 6 shows an alternative route to mesylate intermediate 5.5, wherein $R^j$ is as defined herein. tert-Butyldimethylsilyl-protected ester 6.1 may be converted to the Weinreb amide 6.2 using O,N-dimethylhydroxylamine hydrochloride and isopropylmagnesium chloride in THF. A Grignard reaction of Weinreb amide 6.2 with a (substituted) phenylmagnesium bromide 6.3 in a suitable solvent, such as THF, affords ketone 6.4. Reduction of ketone 6.4 with a chiral reducing system, such as borane-N,N,-dimethylaniline complex with catalytic (R)-2-methyl-CBS-oxazaborolidine in a suitable solvent, such as methyl tert-butyl ether ("MTBE"), provides chiral alcohol 5.4. This may then be converted to the corresponding mesylate 5.5 as in Scheme 5.

Scheme 7

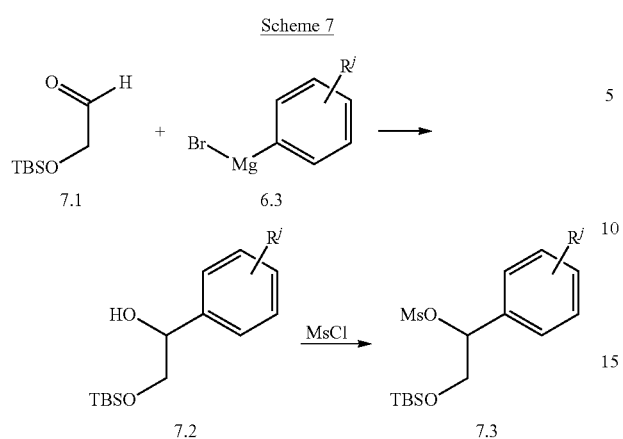

Scheme 7 shows a general scheme for preparing racemic mesylate intermediates 7.3, wherein $R^j$ is as defined herein. A Grignard reaction of 7.1 and 6.3 in a solvent, such as THF, affords alcohol 7.2, which may then be reacted with MsCl to provide 7.3, a racemic version of 5.5.

Scheme 8

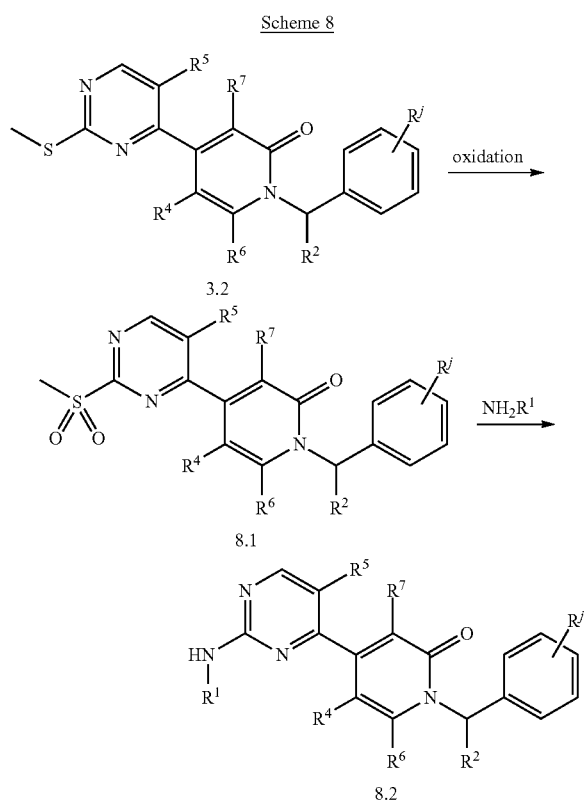

Scheme 8 shows a general scheme for preparing a compound 8.2, wherein $R^1$, $R^2$, $R^4$, $R^5$, $R^6$, $R^7$ and $R^j$ are as defined herein. Compound 3.2 may be oxidized to methyl sulfone intermediate 8.1 with an oxidant, such as meta-chloroperoxybenzoic acid ("mCPBA"), in a suitable solvent, such as dichloromethane ("DCM"). Subsequent displacement of the methyl sulfone moiety with amine $NH_2R^1$, in a suitable solvent, such as sec-BuOH, affords product 8.2.

Scheme 9

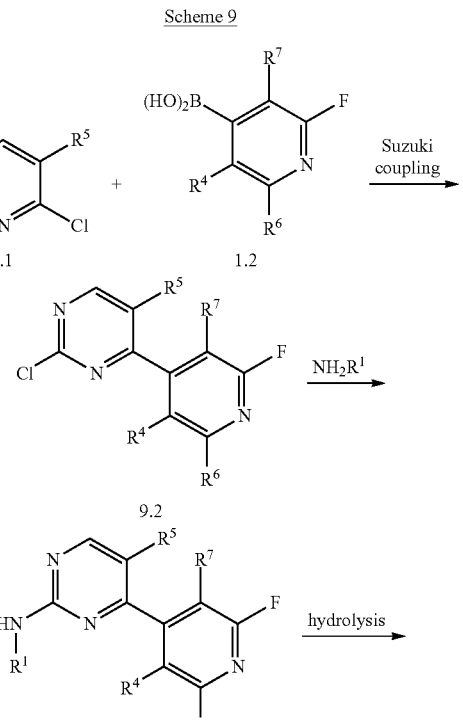

Scheme 9 shows a general method for preparing intermediate pyridone 9.4, wherein $R^1$, $R^4$, $R^5$, $R^6$ and $R^7$ are as defined herein. A 2,4-dichloropyrimidine 9.1 may be coupled to a 4-pyridine boronic acid 1.2 with a Pd catalyst, such as $PdCl_2(dppf)$, in the presence of a base, such as $Na_2CO_3$, to give intermediate 9.2. This intermediate may be reacted with an amine, $NH_2R^1$, in the presence of an optional base, such as Hunig's base, in a suitable solvent, N,N-dimethylacetamide or 2-butanol, either thermally or in a microwave to afford intermediate 9.3. Hydrolysis of 9.3 in either aqueous acid, such as 1M HCl, or base, such as 1M NaOH, yields intermediate pyridone 9.4.

Scheme 10

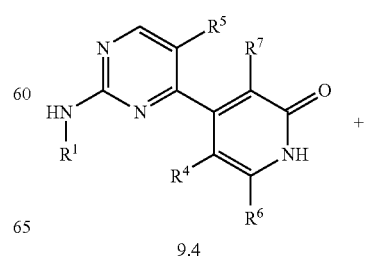

-continued

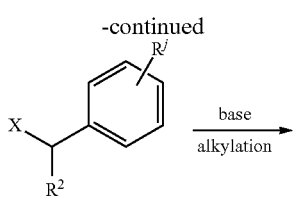

3.1

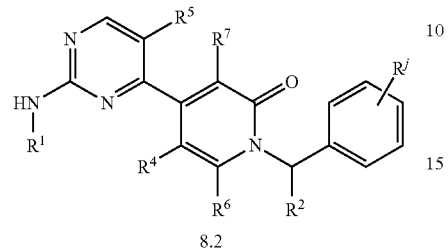

8.2

Scheme 10 shows an alternative method for preparing compound 8.2, wherein $R^1$, $R^2$, $R^4$, $R^5$, $R^6$, $R^7$ and $R^j$ are as defined herein. Pyridone 9.4 may be alkylated with benzyl electrophile 3.1, wherein X is Cl, Br, I, OMs or OTf, in the presence of a base, such as KHMDS or KOt-Bu with a suitable solvent, such as THF, 2-methyltetrahydrofuran or dioxane, with an optional catalyst, such as tetrabutylammonium iodide, to provide 8.2.

In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butyloxycarbonyl ("Boc"), benzyloxycarbonyl ("CBz") and 9-fluorenylmethyleneoxycarbonyl ("Fmoc"). The need for such protection is readily determined by one skilled in the art. For a general description of protecting groups and their use, see T. W. Greene, et al. *Greene's Protective Groups in Organic Synthesis*. New York: Wiley Interscience, 2006.

In certain embodiments, intermediate 1.4 is provided:

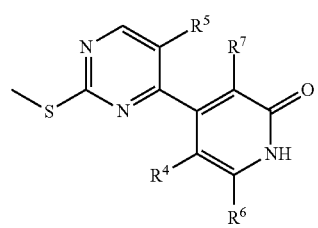

1.4 wherein $R^4$, $R^5$, $R^6$ and $R^7$ are as defined herein.

In certain embodiments, intermediate 3.2 is provided:

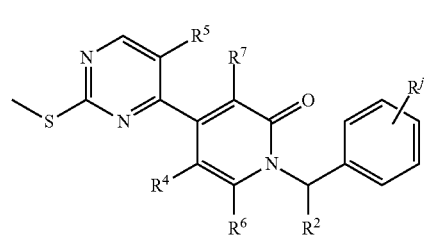

3.2 wherein $R^2$, $R^4$, $R^5$, $R^6$, $R^7$ and each $R^j$ are as defined herein. In certain embodiments, intermediate 3.2 is substituted with 0 to 3 $R^j$ groups. In certain embodiments, intermediate 3.2 is substituted with 1 or 2 $R^j$ groups.

In certain embodiments, intermediate 5.5 is provided:

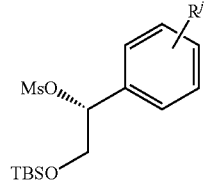

5.5 wherein each $R^j$ is as defined herein. In certain embodiments, intermediate 5.5 is substituted with 0 to 3 $R^j$ groups. In certain embodiments, intermediate 5.5 is substituted with 1 or 2 $R^j$ groups.

In certain embodiments, intermediate 7.3 is provided:

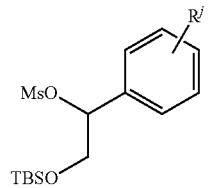

7.3 wherein each $R^j$ is as defined herein. In certain embodiments, intermediate 7.3 is substituted with 0 to 3 $R^j$ groups. In certain embodiments, intermediate 7.3 is substituted with 1 or 2 $R^j$ groups.

In certain embodiments, intermediate 8.1 is provided:

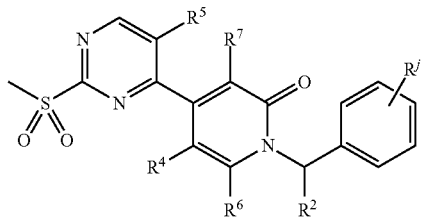

8.1 wherein $R^2$, $R^4$, $R^5$, $R^6$, $R^7$ and each $R^j$ are as defined herein. In certain embodiments, intermediate 8.1 is substituted with 0 to 3 $R^j$ groups. In certain embodiments, intermediate 8.1 is substituted with 1 or 2 $R^j$ groups.

In certain embodiments, intermediate 9.4 is provided:

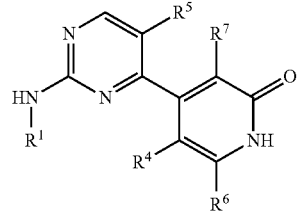

9.4 wherein $R^1$, $R^4$, $R^5$, $R^6$ and $R^7$ are as defined herein.

In certain embodiments, intermediate 10.1 is provided:

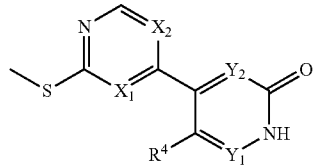

10.1 wherein $X^1$, $X^2$, $Y^1$, $Y^2$ and $R^4$ are as defined herein.

In certain embodiments, intermediate 10.2 is provided:

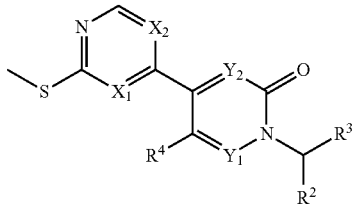

10.2 wherein $X^1$, $X^2$, $Y^1$, $Y^2$, $R^2$, $R^3$, and $R^4$ are as defined herein.

In certain embodiments, intermediate 10.3 is provided:

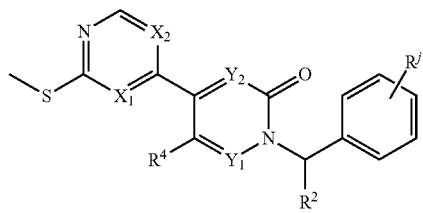

10.3 wherein $X^1$, $X^2$, $Y^1$, $Y^2$, $R^2$, $R^4$ and $R^j$ are as defined herein. In certain embodiments, intermediate 10.3 is substituted with 0 to 3 $R^j$ groups. In certain embodiments, intermediate 10.3 is substituted with 1 or 2 $R^j$ groups.

In certain embodiments, intermediate 10.4 is provided:

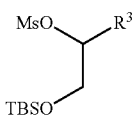

10.4 wherein $R^3$ is as defined herein.

In certain embodiments, intermediate 10.5 is provided:

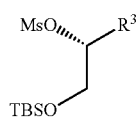

10.5 wherein $R^3$ is as defined herein.

In certain embodiments, intermediate 10.6 is provided:

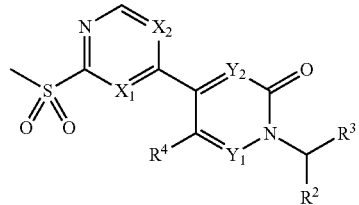

10.6 wherein $X_1$, $X_2$, $Y_1$, $Y_2$, $R^2$, $R^3$ and $R^4$ are as defined herein.

In certain embodiments, intermediate 10.7 is provided:

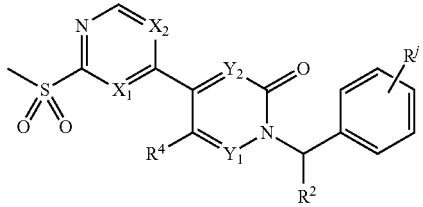

10.7 wherein $X_1$, $X_2$, $Y_1$, $Y_2$, $R^2$, $R^4$ and each $R^j$ are as defined herein. In certain embodiments, intermediate 10.7 is substituted with 0 to 3 $R^j$ groups. In certain embodiments, intermediate 10.7 is substituted with 1 or 2 $R^j$ groups.

In certain embodiments, intermediate 10.8 is provided:

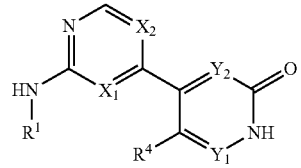

10.8 wherein $X_1$, $X_2$, $Y_1$, $Y_2$, $R^1$ and $R^4$ are as defined herein.

In certain embodiments, a process for preparing compounds of Formula 10.1 is provided, comprising:

(a) coupling a compound having the structure:

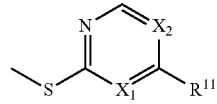

with a compound having the structure:

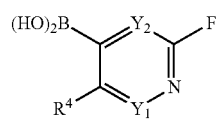

to prepare a compound having the structure:

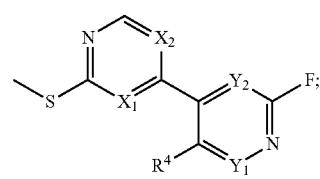

and (b) hydrolyzing the compound having the structure:

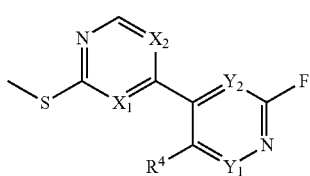

to prepare a compound of Formula 10.1:

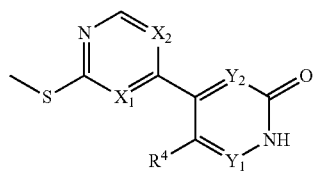

10.1 wherein $X_1$, $X_2$, $Y_1$, $Y_2$, $R^4$ and $R^{11}$ are as defined herein. In certain embodiments, the coupling in Step (a) is performed by a Suzuki reaction. In certain embodiments, the hydrolysis in Step (b) is performed under acidic conditions. In certain embodiments, the hydrolysis in Step (b) is performed by addition of aqueous HCl.

In certain embodiments, a process for preparing compounds of 1.4 is provided, comprising:

(a) coupling a compound of Formula 1.1:

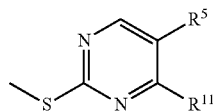

1.1 with a compound of Formula 1.2:

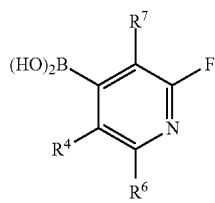

1.2 to prepare a compound of Formula 1.3:

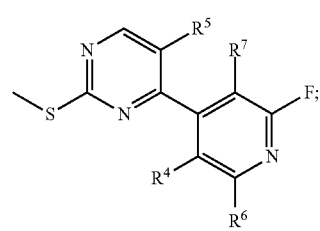

1.3 and (b) hydrolyzing the compound of Formula 1.3 to prepare a compound of Formula 1.4:

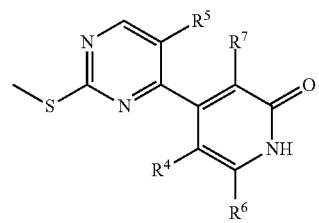

1.4 wherein $R^4$, $R^5$, $R^6$, $R^7$ and $R^{11}$ are as defined herein. In certain embodiments, the coupling in Step (a) is performed by a Suzuki reaction. In certain embodiments, the hydrolysis in Step (b) is performed under acidic conditions. In certain embodiments, the hydrolysis in Step (b) is performed by addition of aqueous HCl.

In certain embodiments, a process for preparing compounds of 10.2 is provided, comprising:

reacting a compound of Formula 10.1:

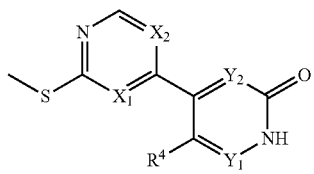

10.1 with a compound having the structure:

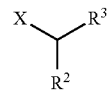

to prepare a compound of Formula 10.2:

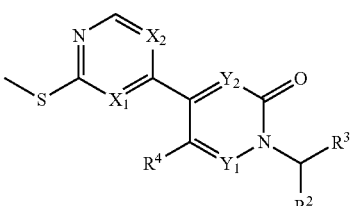

10.2 wherein $X_1$, $X_2$, $Y_1$, $Y_2$, $R^2$, $R^3$, $R^4$ and X are as defined herein. In certain embodiments, the reaction is an alkylation. In certain embodiments, the reaction takes place in the presence of a base. In certain embodiments, the base is KHMDS or KOt-Bu. In certain embodiments, the reaction takes place in a solvent. In certain embodiments, the solvent is THF, 2-methyltetrahydrofuran or dioxane. In certain embodiments, the reaction includes a catalyst. In certain embodiments, the catalyst is tetrabutylammonium iodide.

In certain embodiments, a process for preparing compounds of 10.3 is provided, comprising:

reacting a compound of Formula 10.1:

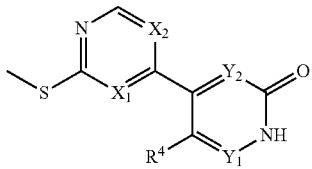
10.1 with a compound of Formula 3.1:

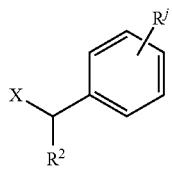
3.1 to prepare a compound of Formula 10.3:

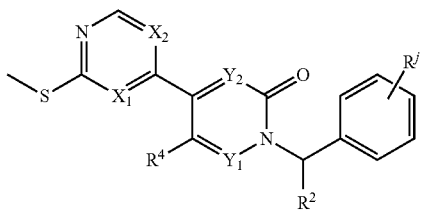
10.3 wherein $X_1$, $X_2$, $Y_1$, $Y_2$, $R^2$, $R^4$, $R^j$ and X are as defined herein. In certain embodiments, the reaction is an alkylation. In certain embodiments, the reaction takes place in the presence of a base. In certain embodiments, the base is KHMDS or KOt-Bu. In certain embodiments, the reaction takes place in a solvent. In certain embodiments, the solvent is THF, 2-methylthetrahydrofuran or dioxane. In certain embodiments, the reaction includes a catalyst. In certain embodiments, the catalyst is tetrabutylammonium iodide. In certain embodiments, intermediates 3.1 and 10.3 are substituted with 0 to 3 $R^j$ groups. In certain embodiments, intermediate 3.1 and 10.3 are substituted with 1 or 2 $R^j$ groups.

In certain embodiments, a process for preparing compounds of 3.2 is provided, comprising:
reacting a compound of Formula 1.4:

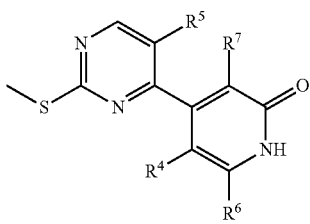
1.4 with a compound of Formula 3.1:

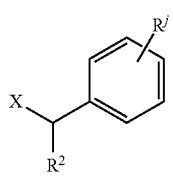
3.1 to prepare a compound of Formula 3.2:

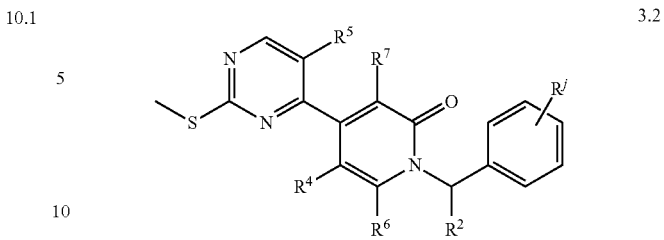
3.2 wherein $R^2$, $R^4$, $R^5$, $R^6$, $R^7$, $R^j$ and X are as defined herein. In certain embodiments, the reaction is an alkylation. In certain embodiments, the reaction takes place in the presence of a base. In certain embodiments, the base is KHMDS or KOt-Bu. In certain embodiments, the reaction takes place in a solvent. In certain embodiments, the solvent is THF, 2-methylthetrahydrofuran or dioxane. In certain embodiments, the reaction includes a catalyst. In certain embodiments, the catalyst is tetrabutylammonium iodide. In certain embodiments, intermediates 3.1 and 10.3 are substituted with 0 to 3 $R^j$ groups. In certain embodiments, intermediate 3.1 and 10.3 are substituted with 1 or 2 $R^j$ groups.

In certain embodiments, a process for preparing compounds of 10.2 is provided, comprising:
reacting a compound of Formula 10.1:

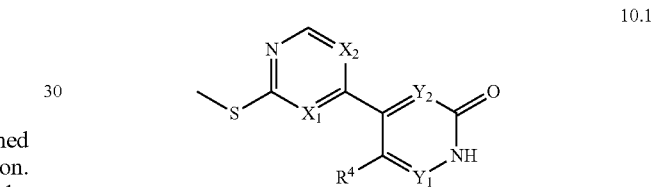
10.1 with a compound having the structure:

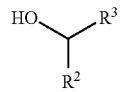

to prepare a compound of Formula 10.2:

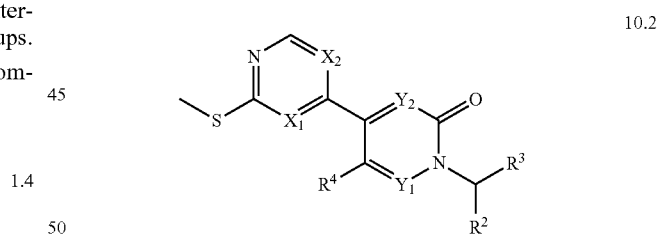
10.2 wherein $X_1$, $X_2$, $Y_1$, $Y_2$, $R^2$, $R^3$ and $R^4$ are as defined herein. In certain embodiments, the reaction is a Mitsunobu reaction. In certain embodiments, the reaction includes DIAD and $PPh_3$. In certain embodiments, the reaction is in a solvent. In certain embodiments, the solvent is THF.

In certain embodiments, a process for preparing compounds of 10.3 is provided, comprising:
reacting a compound of Formula 10.1:

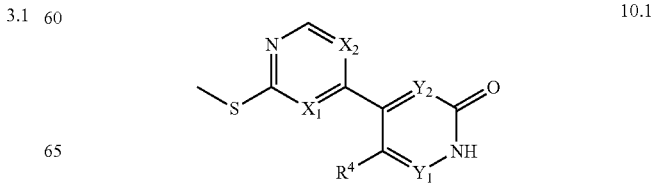
10.1 with a compound of Formula 4.1:

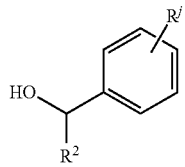

to prepare a compound of Formula 10.3:

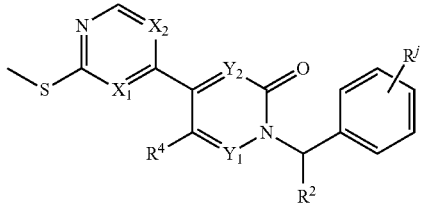

wherein $X_1$, $X_2$, $Y_1$, $Y_2$, $R^2$, $R^4$ and $R^j$ are as defined herein. In certain embodiments, the reaction is a Mitsunobu reaction. In certain embodiments, the reaction includes DIAD and $PPh_3$. In certain embodiments, the reaction is in a solvent. In certain embodiments, the solvent is THF. In certain embodiments, intermediates 4.1 and 10.3 are substituted with 0 to 3 $R^j$ groups. In certain embodiments, intermediate 4.1 and 10.3 are substituted with 1 or 2 $R^j$ groups.

In certain embodiments, a process for preparing compounds of 3.2 is provided, comprising:
reacting a compound of Formula 1.4:

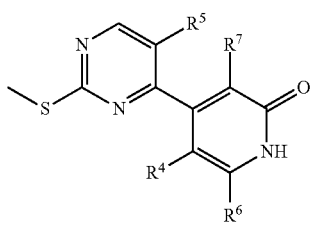

with a compound of Formula 4.1:

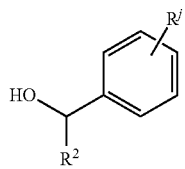

to prepare a compound of Formula 3.2:

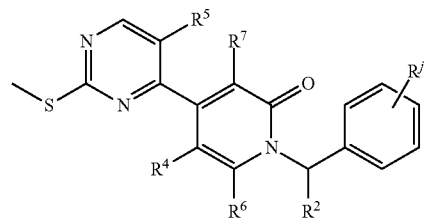

wherein $R^2$, $R^4$, $R^5$, $R^6$, $R^7$ and $R^j$ are as defined herein. In certain embodiments, the reaction is a Mitsunobu reaction. In certain embodiments, the reaction includes DIAD and $PPh_3$. In certain embodiments, the reaction is in a solvent. In certain embodiments, the solvent is THF. In certain embodiments, intermediates 4.1 and 3.2 are substituted with 0 to 3 $R^j$ groups. In certain embodiments, intermediate 4.1 and 3.2 are substituted with 1 or 2 $R^j$ groups.

In certain embodiments, a process for preparing compounds of Formula 10.6 is provided, comprising:
oxidizing a compound of Formula 10.2:

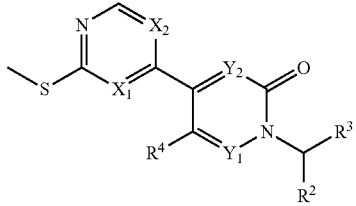

to prepare a compound of Formula 10.6:

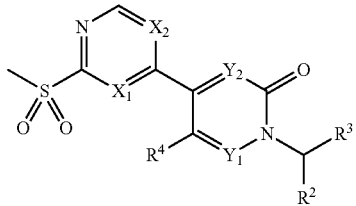

wherein $X_1$, $X_2$, $Y_1$, $Y_2$, $R^2$, $R^3$ and $R^4$ are as defined herein. In certain embodiments, the oxidation is with mCPBA. In certain embodiments, the oxidation is in a solvent. In certain embodiments, the solvent is DCM.

In certain embodiments, a process for preparing compounds of Formula 10.7 is provided, comprising:
oxidizing a compound of Formula 10.3:

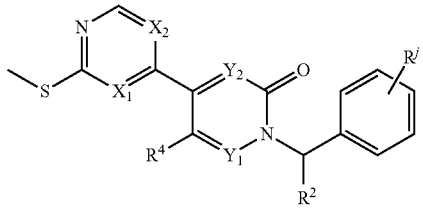

to prepare a compound of Formula 10.7:

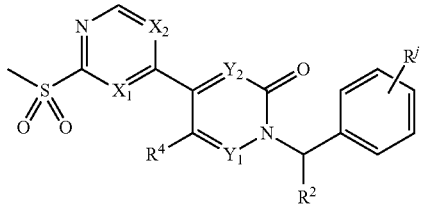

wherein $X_1$, $X_2$, $Y_1$, $Y_2$, $R^2$, $R^4$ and $R^j$ are as defined herein. In certain embodiments, the oxidation is with mCPBA. In certain embodiments, the oxidation is in a solvent. In certain embodiments, the solvent is DCM. In certain embodiments, intermediates 10.3 and 10.7 are substituted with 0 to 3 $R^j$ groups. In certain embodiments, intermediate 10.3 and 10.7 are substituted with 1 or 2 $R^j$ groups.

In certain embodiments, a process for preparing compounds of Formula 8.1 is provided, comprising:

oxidizing a compound of Formula 3.2:

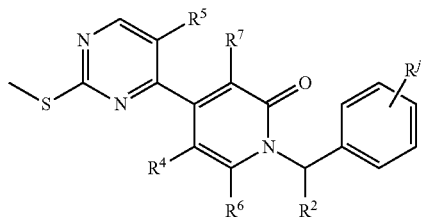

3.2 to prepare a compound of Formula 8.1:

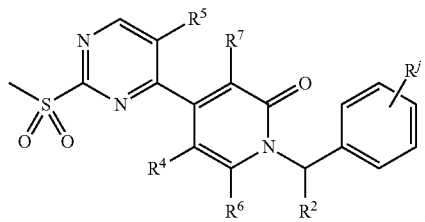

8.1 wherein $R^2$, $R^4$, $R^5$, $R^6$, $R^7$ and $R^j$ are as defined herein. In certain embodiments, the oxidation is with mCPBA. In certain embodiments, the oxidation is in a solvent. In certain embodiments, the solvent is DCM. In certain embodiments, intermediates 3.2 and 8.1 are substituted with 0 to 3 $R^j$ groups. In certain embodiments, intermediate 3.2 and 8.1 are substituted with 1 or 2 $R^j$ groups.

In certain embodiments, a process for preparing compounds of Formula 10.8 is provided, comprising:

(a) coupling a compound having the structure:

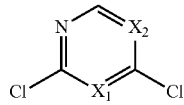

with a compound having the structure:

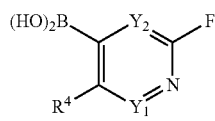

to prepare a compound having the structure:

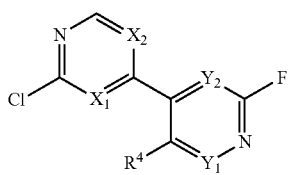

(b) reacting the compound having the structure:

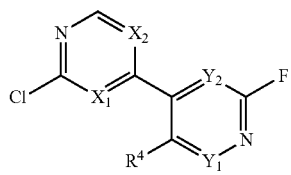

with $NH_2R^1$ to prepare a compound having the structure:

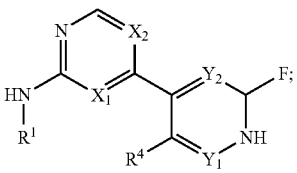

and (c) hydrolyzing the compound having the structure:

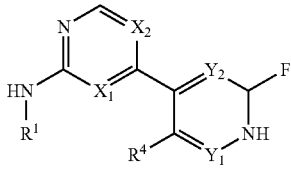

to prepare a compound of Formula 10.8:

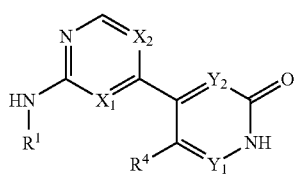

10.8 wherein $X_1$, $X_2$, $Y_1$, $Y_2$, $R^1$ and $R^4$ are as defined herein. In certain embodiments, the coupling in Step (a) is a Suzuki coupling. In certain embodiments, the coupling in Step (a) includes a Pd catalyst. In certain embodiments, the Pd catalyst in Step (a) is $PdCl_2(dppf)$. In certain embodiments, the coupling in Step (a) is done in the presence of a base. In certain embodiments, the base in Step (a) is $Na_2CO_3$. In certain embodiments, the reaction in Step (b) is done in the presence of a base. In certain embodiments, the base in Step (b) is Hunig's base. In certain embodiments, the reaction in Step (b) is done in a solvent. In certain embodiments, the solvent in Step (b) is N,N-dimethylacetamide or 2-butanol. In certain embodiments, the reaction in Step (b) is done with heat. In certain embodiments, the hydrolysis in Step (c) is done with an aqueous acid. In certain embodiments, the acid in Step (c) is HCl. In certain embodiments, the hydrolysis in Step (c) is done with a base. In certain embodiments, the base in Step (c) is NaOH.

In certain embodiments, a process for preparing compounds of Formula 9.4 is provided, comprising:
(a) coupling a compound of Formula 9.1:

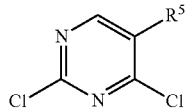

9.1 with a compound of Formula 1.2:

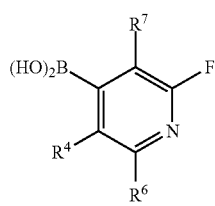

9.1 to prepare a compound of Formula 9.2:

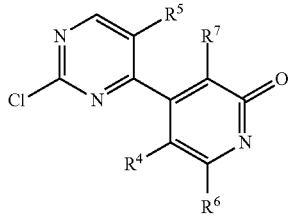

9.2

(b) reacting the compound of Formula 9.2 with NH$_2$R$^1$ to prepare a compound of Formula 9.3:

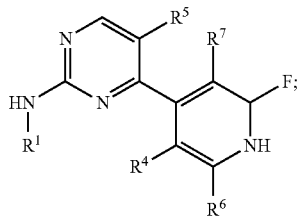

9.3 and
(c) hydrolyzing the compound of Formula 9.3 to prepare a compound of Formula 9.4:

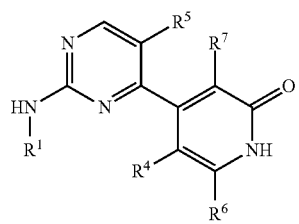

9.4 wherein R$^1$, R$^4$, R$^5$, R$^6$ and R$^7$ are as defined herein. In certain embodiments, the coupling in Step (a) is a Suzuki coupling. In certain embodiments, the coupling in Step (a) includes a Pd catalyst. In certain embodiments, the Pd catalyst in Step (a) is PdCl$_2$(dppf). In certain embodiments, the coupling in Step (a) is done in the presence of a base. In certain embodiments, the base in Step (a) is Na$_2$CO$_3$. In certain embodiments, the reaction in Step (b) is done in the presence of a base. In certain embodiments, the base in Step (b) is Hunig's base. In certain embodiments, the reaction in Step (b) is done in a solvent. In certain embodiments, the solvent in Step (b) is N,N-dimethylacetamide or 2-butanol. In certain embodiments, the reaction in Step (b) is done with heat. In certain embodiments, the hydrolysis in Step (c) is done with an aqueous acid. In certain embodiments, the acid in Step (c) is HCl. In certain embodiments, the hydrolysis in Step (c) is done with a base. In certain embodiments, the base in Step (c) is NaOH.

In certain embodiments, a process for preparing a compound of Formula I is provided, comprising:
reacting a compound of Formula 10.6:

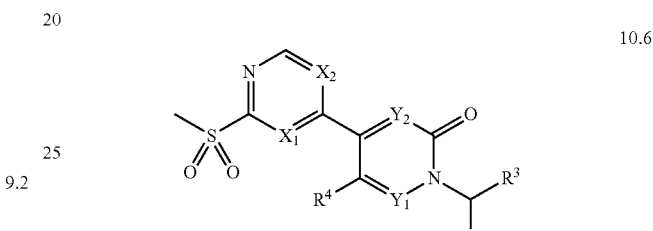

10.6 with NH$_2$R$^1$ to prepare a compound of Formula I:

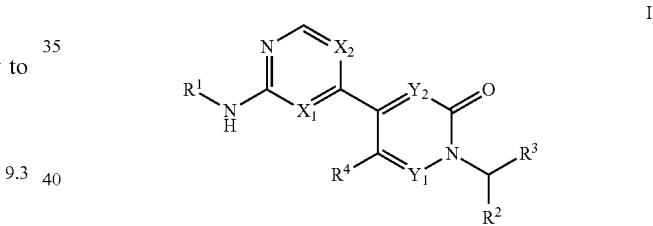

I wherein X$_1$, X$_2$, Y$_1$, Y$_2$, R$^1$, R$^2$, R$^3$ and R$^4$ are as defined herein. In certain embodiments, the reaction is performed in a solvent. In certain embodiments, the solvent is sec-BuOH.

In certain embodiments, a process for preparing compounds of Formula I is provided, comprising:
reacting a compound of Formula 10.8:

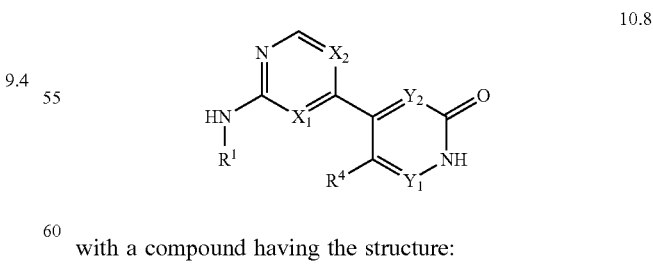

10.8 with a compound having the structure:

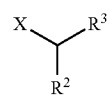

to prepare a compound of Formula I:

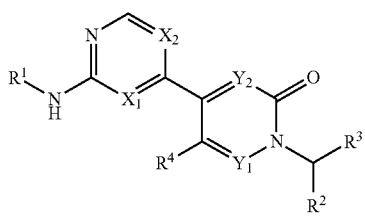

wherein $X_1$, $X_2$, $Y_1$, $Y_2$, $R^1$, $R^2$, $R^3$, $R^4$ and X are as defined herein. In certain embodiments, the reaction is performed in the presence of a base. In certain embodiments, the base is KHMDS or KOt-Bu. In certain embodiments, the reaction is performed in a solvent. In certain embodiments, the solvent is THF, 2-methyltetrahydrofuran or dioxane. In certain embodiments, the reaction is performed with a catalyst. In certain embodiments, the catalyst is tetrabutylammonium iodide.

Methods of Separation

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. *Stereochemistry of Organic Compounds*. New York: John Wiley & Sons, Inc., 1994; Lochmuller, C. H., et al. "Chromatographic resolution of enantiomers: Selective review." *J. Chromatogr*. Vol. 113, No. 3 (1975): pp. 283-302). Racemic mixtures of chiral compounds described herein may be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., ed. *Drug Stereochemistry: Analytical Methods and Pharmacology*. New York: Marcel Dekker, Inc., 1993.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid, can result in formation of the diastereomeric salts.

Alternatively, by method (2), the substrate to be resolved is reacted with one enantiomer of a chiral compound to form a diastereomeric pair (Eliel, E. and Wilen, S. *Stereochemistry of Organic Compounds*. New York: John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III, Peyton. "Resolution of (±)-5-Bromonornicotine. Synthesis of (R)- and (S)-Nornicotine of High Enantiomeric Purity." *J. Org. Chem*. Vol. 47, No. 21 (1982): pp. 4165-4167), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111).

By method (3), a racemic mixture of two enantiomers can be separated by chromatography using a chiral stationary phase (Lough, W. J., ed. *Chiral Liquid Chromatography*. New York: Chapman and Hall, 1989; Okamoto, Yoshio, et al. "Optical resolution of dihydropyridine enantiomers by high-performance liquid chromatography using phenylcarbamates of polysaccharides as a chiral stationary phase." *J. of Chromatogr*. Vol. 513 (1990): pp. 375-378). Enriched or purified enantiomers can be distinguished by methods used to distinguish other chiral molecules with asymmetric carbon atoms, such as optical rotation and circular dichroism.

Biological Evaluation

Determination of the activity of ERK activity of a compound of Formula I is possible by a number of direct and indirect detection methods. Certain exemplary compounds described herein were assayed for their ERK inhibition assay (Biological Example 1). The range of ERK binding activities was less than 1 nM (nanomolar) to about 10 μM (micromolar). A cell-based function assay (Biological Example 2) was used to determine the effect of ERK inhibitors on down-stream signaling by assaying phosphorylation of P90RSK.

Administration and Pharmaceutical Formulations

The compounds described herein may be administered by any convenient route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal.

The compounds may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents. If parenteral administration is desired, the compositions will be sterile and in a solution or suspension form suitable for injection or infusion.

A typical formulation is prepared by mixing a compound described herein and a carrier, diluent or excipient. Suitable carriers, diluents and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound described herein or pharmaceutical composition thereof) or aid in the manufacturing of the pharmaceutical product (i.e., medicament).

One embodiment includes a pharmaceutical composition comprising a compound of Formula I, II, III, IV, V, VI, VII, VIII, IX or X, or a stereoisomer, tautomer or pharmaceutically acceptable salt thereof. A further embodiment provides a pharmaceutical composition comprising a compound of Formula I, II, III, IV, V, VI, VII, VIII, IX or X, or a stereoisomer, tautomer or pharmaceutically acceptable salt thereof, together with a pharmaceutically acceptable carrier, diluent or excipient.

Methods of Treatment with Compounds of the Invention

Also provided are methods of treating or preventing a disease or condition by administering one or more compounds described herein, or a stereoisomer, tautomer or pharmaceutically acceptable salt thereof. In one embodiment, a method of treating a hyperproliferative disease in a mammal comprising administering a therapeutically effective amount of the compound of Formula I, II, III, IV, V, VI, VII, VIII, IX or X, or a stereoisomer, tautomer or pharmaceutically acceptable salt thereof, to the mammal is provided.

Another embodiment provides a method of treating or preventing cancer in a mammal in need of such treatment, wherein the method comprises administering to said mammal a therapeutically effective amount of a compound of Formula I, II, III, IV, V, VI, VII, VIII, IX or X, or a stereoisomer, tautomer or pharmaceutically acceptable salt thereof.

Another embodiment provides a method of treating or preventing pain in a mammal in need of such treatment, wherein the method comprises administering to said mammal a therapeutically effective amount of a compound of Formula I, II, III, IV, V, VI, VII, VIII, IX or X, or a stereoisomer, tautomer or pharmaceutically acceptable salt thereof.

Another embodiment provides a method of treating or preventing an inflammatory disorder in a mammal in need of such treatment, wherein the method comprises administering to said mammal a therapeutically effective amount of a compound of Formula I, II, III, IV, V, VI, VII, VIII, IX or X, or a stereoisomer, tautomer or pharmaceutically acceptable salt thereof.

Another embodiment provides a method of inhibiting ERK protein kinase activity in a cell comprising treating the cell with a compound according to Formula I, II, III, IV, V, VI, VII, VIII, IX or X, or a stereoisomer, tautomer or pharmaceutically acceptable salt thereof.

Another embodiment provides a method of inhibiting ERK protein kinase activity in a cell comprising treating the cell with a compound according to Formula I, II, III, IV, V, VI, VII, VIII, IX or X, or a stereoisomer, tautomer or pharmaceutically acceptable salt thereof, in an amount effective to attenuate or eliminate ERK kinase activity.

Another embodiment provides a method of inhibiting ERK protein kinase activity in a patient in need thereof comprising the step of administering to said patient a compound according to Formula I, II, III, IV, V, VI, VII, VIII, IX or X, or a stereoisomer, tautomer or pharmaceutically acceptable salt thereof.

Another embodiment provides a method of treating or ameliorating the severity of a hyperproliferative disorder in a patient in need thereof comprising administering to said patient a compound according to Formula I, II, III, IV, V, VI, VII, VIII, IX or X, or a stereoisomer, tautomer or pharmaceutically acceptable salt thereof.

Another embodiment provides a method of treating or ameliorating the severity of a hyperproliferative disorder in a patient in need thereof comprising co-administering to said patient a compound according to Formula I, II, III, IV, V, VI, VII, VIII, IX or X, or a stereoisomer, tautomer or pharmaceutically acceptable salt thereof, with at least one other chemotherapeutic agent used to treat or ameliorate the hyperproliferative disorder.

Another embodiment provides a method of treating or ameliorating the severity of pain in a patient in need thereof comprising administering to said patient a compound according to Formula I, II, III, IV, V, VI, VII, VIII, IX or X, or a stereoisomer, tautomer or pharmaceutically acceptable salt thereof.

Another embodiment provides a method of treating or ameliorating the severity of an inflammatory disorder in a patient in need thereof comprising administering to said patient a compound according to Formula I, II, III, IV, V, VI, VII, VIII, IX or X, or a stereoisomer, tautomer or pharmaceutically acceptable salt thereof.

In another embodiment, a method of treating or preventing a disease or disorder modulated by ERK, comprising administering to a mammal in need of such treatment an effective amount of a compound of Formula I, II, III, IV, V, VI, VII, VIII, IX or X, or a stereoisomer, tautomer or pharmaceutically acceptable salt thereof. Examples of such diseases and disorders include, but are not limited to, hyperproliferative diseases, such as cancer, and pain or inflammatory diseases.

Another embodiment provides the use of a compound of Formula I, II, III, IV, V, VI, VII, VIII, IX or X, or a stereoisomer, tautomer or pharmaceutically acceptable salt thereof, in the manufacture of a medicament for the treatment of a hyperproliferative disease. Another embodiment provides the use of a compound of Formula I, II, III, IV, V, VI, VII, VIII, IX or X, or a stereoisomer, tautomer or pharmaceutically acceptable salt thereof, in the manufacture of a medicament for the treatment of cancer.

Another embodiment provides the use of a compound of Formula I, II, III, IV, V, VI, VII, VIII, IX or X, or a stereoisomer, tautomer or pharmaceutically acceptable salt thereof, in the manufacture of a medicament for the treatment of pain.

Another embodiment provides the use of a compound of Formula I, II, III, IV, V, VI, VII, VIII, IX or X, or a stereoisomer, tautomer or pharmaceutically acceptable salt thereof, in the manufacture of a medicament for the treatment of an inflammatory disease.

Another embodiment provides the use of a compound of Formula I, II, III, IV, V, VI, VII, VIII, IX or X, or a stereoisomer, tautomer or pharmaceutically acceptable salt thereof, for use in the treatment of hyperproliferative diseases. Another embodiment provides the use of a compound of Formula I, II, III, IV, V, VI, VII, VIII, IX or X, or a stereoisomer, tautomer or pharmaceutically acceptable salt thereof, for use in the treatment of cancer.

Another embodiment provides the use of a compound of Formula I, II, III, IV, V, VI, VII, VIII, IX or X, or a stereoisomer, tautomer or pharmaceutically acceptable salt thereof, for use in the treatment of pain.

Another embodiment provides the use of a compound of Formula I, II, III, IV, V, VI, VII, VIII, IX or X, or a stereoisomer, tautomer or pharmaceutically acceptable salt thereof, for use in the treatment of inflammatory diseases.

In certain embodiments, the hyperproliferative disease is cancer. In certain embodiments, the cancer may be selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, NSCLC, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia. In certain embodiments, the cancer disorder is melanoma. In certain embodiments, the cancer is pancreatic cancer. In certain embodiments, the cancer is thyroid cancer. In certain embodiments, the cancer is colorectal cancer. In certain embodiments, the cancer is lung cancer. In certain embodiments, the cancer is breast cancer. In certain embodiments, the cancer is ovarian cancer. In certain embodiments, the cancer is acute myelogenous leukemia. In certain embodiments, the cancer is chronic myelomonocytic leukemia. In certain embodiments, the cancer is chronic myelogenous leukemia. In certain embodiments, the cancer is multiple myeloma. In certain embodiments, the cancer is myeloid leukemia.

In certain embodiments, the inflammatory disorder may be selected from arthritis, low back pain, inflammatory bowel disease, and rheumatism.

Combination Therapy

The compounds described herein and stereoisomers, tautomers and pharmaceutically acceptable salts thereof may be employed alone or in combination with other therapeutic agents for treatment. The compounds described herein may be used in combination with one or more additional drugs, for example an anti-hyperproliferative (or anti-cancer) agent that works through action on a different target protein. The second compound of the pharmaceutical combination formulation or dosing regimen preferably has complementary activities to the compound described herein, such that they do not adversely affect each other. Such molecules are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

EXAMPLES

For illustrative purposes, the following Examples are included. However, it is to be understood that these Examples do not limit the invention and are only meant to suggest a method of practicing the invention. Persons skilled in the art will recognize that the chemical reactions described may be readily adapted to prepare a number of other compounds described herein, and alternative methods for preparing the compounds are deemed to be within the scope of this invention. For example, the synthesis of non-exemplified compounds may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds described herein.

In the Examples described below, unless otherwise indicated all temperatures are set forth in degrees Celsius. Reagents were purchased from commercial suppliers such as Sigma-Aldrich, Alfa Aesar, or TCI, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters) (unless otherwise stated). $^1$H NMR spectra were recorded on a Varian instrument operating at 400 MHz. $^1$H-NMR spectra were obtained as $CDCl_3$, $CD_3OD$, $D_2O$, $(CD_3)_2SO$, $(CD_3)_2CO$, $C_6D_6$, $CD_3CN$ solutions (reported in ppm), using tetramethylsilane (0.00 ppm) or residual solvent ($CDCl_3$: 7.26 ppm; $CD_3OD$: 3.31 ppm; $D_2O$: 4.79 ppm; $(CD_3)_2SO$: 2.50 ppm; $(CD_3)_2CO$: 2.05 ppm; $C_6D_6$: 7.16 ppm; $CD_3CN$: 1.94 ppm) as the reference standard. When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

Biological Example 1

ERK-2 Enzymatic Assay

Compounds were tested in an enzymatic assay using human ERK-2 (Mitogen Activated Kinase 1), recombinantly expressed as an n-terminal 6-His fusion protein in *E. coli* and corresponding to aa 8-360. The substrate used was the fluorescent Omnia peptide S/T17 (Invitrogen of Carlsbad, Calif.; Cat. KNZ1171C). Test compounds were diluted in dimethylsulfoxide ("DMSO") in 3-fold serial dilutions at 100× final concentrations. In addition to compound, the assay contained 50 mM HEPES [pH 7.3], 10 mM $MgCl_2$, 1 mM DTT, 0.005% Triton-X100, 5 nM ERK-2 enzyme, 6.25 µM S/T17 peptide substrate and 25 µM ATP (corresponding to the observed $K_m$) for a total reaction volume of 25 µL. The assay was run at ambient temperature in a white 384-well polypropylene plate (Nunc, Inc of Naperville, Ill.; Cat. 267462) collecting data every 50 seconds for approximately 30 minutes on an Envision plate reader (PerkinElmer, Inc. of Waltham, Mass.); Excitation 340 nm/Emission 495 nm. The data collected from each well was fit to a straight line and the resulting rates were used to calculate percent of control. Percent of control was plotted against compound concentration and $IC_{50}$ values were determined using a four-parameter fit. Table 1 contains representative data for Examples disclosed herein. The reported $IC_{50}$ in Table 1 may be from a single assay or the mean of multiple assays. Examples 1-310 were tested in the above assay and were found to have an $IC_{50}$ of less than 1 µM.

Biological Example 2

Cellular P90RSK(Ser380) Phosphorylation Assay

Inhibition of PMA-stimulated P90RSK(Ser380) phosphorylation was determined by the following in vitro cellular mechanistic assay, which comprises incubating cells with a compound for 1.5 hours and quantifying fluorescent pP90RSK(Ser380) signal on fixed cells and normalizing to GAPDH signal.

HepG2 cells were obtained from ATCC and grown in DMEM supplemented with 10% fetal bovine serum. Cells were plated in 96-well plates at 35,000 cells/well and allowed to attach overnight at 37° C./5% $CO_2$. Diluted compounds were then added at a final concentration of 0.5% DMSO. After 1.5 hours compound incubation, cells were stimulated with the addition of phorbol 12-myristate 13-acetate ("PMA") at a final concentration of 100 ng/mL; the PMA stimulation was a 30-minute incubation at 37° C./5% $CO_2$. After the 30-minute PMA stimulation, cells were washed with phosphate buffered saline ("PBS") and fixed in 3.7% formaldehyde in PBS at room temperature for 15-20 minutes. This was followed by another wash in PBS and then permeabilization in 100% MeOH at room temperature for 10-15 minutes. Following the permeabilization incubation, cells were washed in PBS/0.05% Tween-20, followed by a block in Odyssey blocking buffer (LI-COR Biosciences) for at least 1 hour. Antibodies to phosphorylated P90RSK(Ser380) (Cell Signaling #9335, rabbit monoclonal) and GAPDH (Fitzgerald 10R-G109a, mouse monoclonal) were added to the cells and incubated overnight at 4° C. pP90RSK(Ser380) antibody was used at a 1:250 dilution; GAPDH was used at a 1:10,000 dilution. After washing with PBS/0.05% Tween-20, the cells were incubated with fluorescently-labeled secondary antibodies (Anti-rabbit-Alexa Flour680, Invitrogen Cat#A21109; Anti-mouse-IRDye800CW, Rockland Inc. Cat#610-131-121) for 1 hour. Both secondary antibodies were used at a 1:1000 dilution. Cells were then washed and analyzed for fluorescence at both wavelengths using the Odyssey Infrared Imaging System (LI-COR Biosciences). Phosphorylated P90RSK (Ser380) signal was normalized to GAPDH signal. Table 1 contains representative data for Examples disclosed herein. The reported $IC_{50}$ in Table 1 may be from a single assay or the mean of multiple assays.

Table 1 contains Examples tested in the above assays:

TABLE 1

| Example # | Biological Example 1 $IC_{50}$ (nM) | Biological Example 2 $IC_{50}$ (nM) |
| --- | --- | --- |
| Example 1 | 3.9 | 31.9 |
| Example 2 | 3.2 | 59.1 |

TABLE 1-continued

| Example # | Biological Example 1 $IC_{50}$ (nM) | Biological Example 2 $IC_{50}$ (nM) |
| --- | --- | --- |
| Example 3 | 4.0 | 40.3 |
| Example 4 | 3.8 | 8.5 |
| Example 11 | 13.6 | 295.8 |
| Example 12 | 51.8 | 931.7 |
| Example 14 | 15.6 | 842.5 |
| Example 20 | 145.6 | >5000 |
| Example 21 | 3.0 | 118.5 |
| Example 39 | 3.3 | 15.5 |
| Example 42 | 6.3 | 74.0 |
| Example 50 | 11.5 | 292.4 |
| Example 57 | 35.7 | 1774.6 |
| Example 58 | 13.9 | 708.2 |
| Example 60 | 53.0 | 1614.5 |
| Example 65 | 6.3 | 67.5 |
| Example 68 | 3.3 | 185.1 |
| Example 87 | 3.0 | 152.6 |
| Example 102 | 39.5 | >5000 |
| Example 103 | 10.4 | 511.0 |
| Example 109 | 15.9 | 572.0 |
| Example 120 | 3.8 | 86.6 |
| Example 134 | 5.5 | 543.5 |
| Example 139 | 13.7 | 371.8 |
| Example 157 | 8.7 | 46.3 |
| Example 166 | 2.9 | 12.9 |
| Example 167 | 3.1 | 100.1 |
| Example 172 | 2.9 | 12.9 |
| Example 173 | 5.7 | 110.2 |
| Example 185 | 3.9 | 19.6 |
| Example 209 | 0.8 | 6.7 |
| Example 250 | 1.6 | 15.2 |
| Example 266 | 2.4 | 8.6 |
| Example 270 | 2.2 | 22 |
| Example 289 | 8.5 | 20.4 |
| Example 290 | 15.8 | 26.5 |
| Example 291 | 12.1 | 55.9 |
| Example 293 | 9.8 | 16.8 |
| Example 295 | 14.5 | 203.5 |
| Example 305 | 4 | 53 |
| Example α | 249.1 | 954.7 |
| Example β | 2.6 | 99.6 |

Intermediate Example A

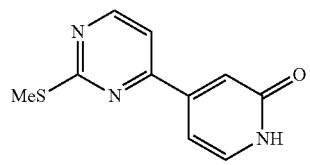

4-(2-(methylthio)pyrimidin-4-yl)pyridin-2(1H)-one

Step A: A suspension of 4-bromo-2-(methylthio)pyrimidine (7.00 g, 34.1 mmol), 2-fluoropyridin-4-ylboronic acid (5.05 g, 35.8 mmol), $Na_2CO_3$ (10.9 g, 102 mmol) and Pd(dppf)$Cl_2 \cdot CH_2Cl_2$ (1.40 g, 1.71 mmol) in dioxane/$H_2O$ (100 mL; 1:1) was heated to 85° C. under an Ar balloon for 2 hours. The reaction mixture was cooled to room temperature and concentrated. The residue was diluted with ethyl acetate (200 mL) and water (100 mL). The layers were separated, and the aqueous layer was extracted with ethyl acetate (1×). The organics were dried, filtered and concentrated. The crude product was purified via column chromatography, eluting with hexanes/ethyl acetate (3:1) to give 4-(2-fluoropyridin-4-yl)-2-(methylthio)pyrimidine (6.83 g, 90%) as a solid. ¹H NMR (400 MHz, (CD₃)₂SO) δ 8.85 (d, J=5.2 Hz, 1H), 8.46 (d, J=5.2 Hz, 1H), 8.11 (m, 1H), 7.96 (d, J=5.2 Hz, 1H), 7.92 (s, 1H), 2.62 (s, 3H); m/z (APCI-pos) M+1=222.1.

Step B: A suspension of 4-(2-fluoropyridin-4-yl)-2-(methylthio)pyrimidine (6.83 g, 30.9 mmol) in 2N HCl (100 mL) was heated to reflux for 2 hours. The reaction mixture was cooled to room temperature and placed in an ice bath. The pH was adjusted to about 7 with 2N NaOH (about 100 mL). The resulting solids were collected by filtration, washed with water and dried to give 4-(2-(methylthio)pyrimidin-4-yl)pyridin-2(1H)-one (5.07 g) as a solid. This material was placed in the thimble of a Soxhlet apparatus and was attached to a 1 L flask charged with ethyl acetate (500 mL). The material was continuously extracted for 3 days. The resulting white precipitate from the ethyl acetate layer was collected by filtration (3.3 grams, 49% yield). ¹H NMR (400 MHz, (CD₃)₂SO) δ 11.85 (br, s, 1H), 8.75 (d, J=5.0 Hz, 1H), 7.79 (d, J=5.0 Hz, 1H), 7.54 (d, J=7.0 Hz, 1H), 7.13 (s, 1H), 6.86 (d, J=7.0 Hz, 1H), 2.58 (s, 3H); m/z (APCI-pos) M+1=220.0.

Intermediate Example B

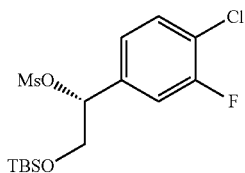

(R)-2-(tert-butyldimethylsilyloxy)-1-(4-chloro-3-fluorophenyl)ethyl methanesulfonate Step A: Sodium hydride (8.549 g, 213.7 mmol, 60% suspension in mineral oil) was added portionwise to a cold (0° C.) solution of 4-chloro-3-fluorobenzaldehyde (26.07 g, 164.4 mmol) and methyltriphenylphosphonium bromide (70.48 g, 197.3 mmol) in THF (400 mL). The reaction mixture was allowed to warm up to room temperature overnight. The solids were removed by filtration, and the filter cake was washed with ether. The filtrate was concentrated (water bath about 20° C.), and the residue was suspended in hexanes and stirred for 30 minutes. The solids (mostly PPh₃O) were removed by filtration, and the filter cake was washed with hexanes. The filtrate was concentrated, and the crude product was purified by column chromatography, eluting with hexanes/ethyl acetate (25:1) to give 1-chloro-2-fluoro-4-vinylbenzene (12.1 g, 47%) as an oil. ¹H NMR (400 MHz, CDCl₃) δ 7.33 (m, 1H), 7.18 (m, 1H), 7.10 (m, 1H), 6.63 (m, 1H), 5.74 (d, J=17.4 Hz, 1H), 5.32 (d, J=10.8 Hz, 1H).

Step B: 1-Chloro-2-fluoro-4-vinylbenzene (12.1 g, 77.3 mmol) was added to a cold (0° C.) solution of AD-mix-β (108 g, 139 mmol) in t-BuOH/H₂O (600 mL; 1:1), and the mixture was allowed to warm up to room temperature overnight. The next day, the reaction was placed in an ice bath and quenched with solid Na₂SO₃ (114 g). The mixture was stirred for 1 hour and then extracted with ethyl acetate (3×500 mL). The combined organics were dried, filtered and concentrated to give (R)-1-(4-chloro-3-fluorophenyl)ethane-1,2-diol as an oil. The crude product was used in Step C without purification.

Step C: Imidazole (13.1 g, 193 mmol) was added to a cold (0° C.) solution of (R)-1-(4-chloro-3-fluorophenyl)ethane-1,2-diol (14.7 g, 77.1 mmol) in DCM (100 mL), followed by TBSCl (12.8 g, 84.8 mmol). The reaction mixture was stirred at 0° C. for 1 hour and then quenched with water (50 mL). The layers were separated, and the organics were dried, filtered and concentrated. The crude product was purified via column chromatography, eluting with hexanes/ethyl acetate (100:1) to give (R)-2-(tert-butyldimethylsilyloxy)-1-(4-chloro-3-fluorophenyl)ethanol (11.0 g, 47% over two steps). ¹H NMR (400 MHz, CDCl₃) δ 7.36 (m, 1H), 7.20 (m, 1H), 7.08 (m, 1H), 4.71 (m, 1H), 3.75 (m, 1H), 3.49 (m, 1H), 2.96 (d, J=2.6 Hz, 1H), 0.90 (s, 9H), 0.07 (s, 3H), 0.06 (s, 3H).

Step D: Triethylamine (2.09 mL, 15.0 mmol) was added to a cold (0° C.) solution of (R)-2-(tert-butyldimethylsilyloxy)-1-(4-chloro-3-fluorophenyl)ethanol (3.05 g, 10.0 mmol) in DCM (100 mL), followed by methanesulfonyl chloride (0.929 mL, 12.0 mmol). The reaction mixture was stirred at 0° C. for 30 minutes and then quenched with water (50 mL). The layers were separated, and the organic layer was washed with saturated NaHCO₃, dried, filtered and concentrated to give the crude product. The crude product was purified via column chromatography, eluting with hexanes/ethyl acetate (25:1) to give (R)-2-(tert-butyldimethylsilyloxy)-1-(4-chloro-3-fluorophenyl)ethyl methanesulfonate (3.80 g, 99%) as an oil. ¹H NMR (400 MHz, CDCl₃) δ 7.42 (m, 1H), 7.20 (m, 1H), 7.12 (m, 1H), 5.50 (m, 1H), 3.91 (m, 1H), 3.80 (m, 1H), 2.98 (s, 3H), 0.88 (s, 9H), 0.05 (s, 3H), 0.04 (s, 3H).

Intermediate Example C

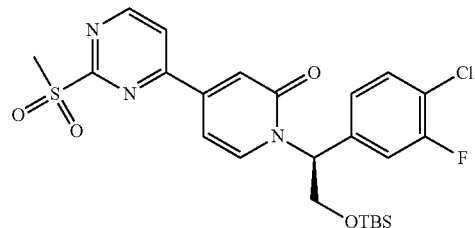 [SMILES: CC(C)(C)[Si](C)(C)OC[C@H](c1ccc(Cl)c(F)c1)n1ccc(-c2ccnc(S(C)(=O)=O)n2)cc1=O]

(S)-1-(2-(tert-butyldimethylsilyloxy)-1-(4-chloro-3-fluorophenyl)ethyl)-4-(2-(methylsulfonyl)pyrimidin-4-yl)pyridin-2(1H)-one Step A: 1.0M KHMDS (5.09 mL, 5.09 mmol) as a solution in THF was added to a cold (0° C.) suspension of 4-(2-(methylthio)pyrimidin-4-yl)pyridin-2(1H)-one (0.93 g, 4.24 mmol) in THF (20 mL). The reaction mixture was stirred at 0° C. for 10 minutes before (R)-2-(tert-butyldimethylsilyloxy)-1-(4-chloro-3-fluorophenyl)ethyl methanesulfonate (2.44 g, 6.36 mmol) was added as a solution in THF (5 mL). The reaction was heated to reflux for 30 hours and then cooled to room temperature and concentrated. The residue was taken up in ethyl acetate (200 mL) and washed with water. The organics were dried, filtered and concentrated. The crude product was purified via column chromatography, eluting with hexanes/ethyl acetate (4:1) to give (S)-1-(2-(tert-butyldimethylsilyloxy)-1-(4-chloro-3-fluorophenyl)ethyl)-4-(2-(methylthio)pyrimidin-4-yl)pyridin-2 (1H)-one (1.35 g, 63%) as a solid. ¹H NMR (400 MHz, CDCl₃) δ 8.66 (d, J=5.0 Hz, 1H), 7.43 (m, 2H), 7.34 (d, J=5.0 Hz, 1H), 7.32-7.28 (m, 2H), 7.16 (m, 1H), 6.85 (m, 1H), 6.24 (m, 1H), 4.35 (m, 1H), 4.23 (m, 1H), 2.65 (s, 3H), 0.88 (s, 9H), 0.03 (s, 3H), −0.03 (s, 3H); m/z (APCI-pos) M+1=506.1, 508.1.

Step B: mCPBA (7.1 g, 29 mmol) was added to a cold (0° C.) solution of (S)-1-(2-(tert-butyldimethylsilyloxy)-1-(4-chloro-3-fluorophenyl)ethyl)-4-(2-(methylthio)pyrimidin-4-yl)pyridin-2(1H)-one (5.8 g, 11 mmol) in DCM (100 mL), and the mixture was stirred for 2 hours. The reaction mixture was washed with saturated $Na_2S_2O_3$ (1×), $NaHCO_3$ (1×), dried, filtered, and evaporated. The crude product was purified via column chromatography, eluting with hexanes/ethyl acetate (1:1) to give (S)-1-(2-(tert-butyldimethylsilyloxy)-1-(4-chloro-3-fluorophenyl)ethyl)-4-(2-(methylsulfonyl)pyrimidin-4-yl)pyridin-2(1H)-one (5.5 g, 89%) as a solid. $^1H$ NMR (400 MHz, $CDCl_3$) δ 9.06 (d, J=5.2 Hz, 1H), 7.91 (d, J=5.4 Hz, 1H), 7.55 (d, J=7.4 Hz, 1H), 7.43 (m, 1H), 7.32 (d, J=2.4 Hz, 1H), 7.27 (m, 1H), 7.15 (m, 1H), 6.93 (m, 1H), 6.22 (m, 1H), 4.35 (m, 1H), 4.24 (m, 1H), 3.45 (s, 3H), 0.88 (s, 9H), 0.03 (s, 3H), −0.03 (s, 3H); m/z (APCI-pos) M+1=538.1, 540.0.

Intermediate Example D

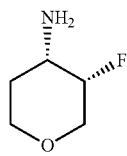

(3S,4S)-3-fluorotetrahydro-2H-pyran-4-amine

Step A: 1-Chloromethyl-4-fluoro-1,4-diazoniabicyclo[2.2.2]octane bis-tetrafluoroborate (147 g, 414 mmol; Selectfluor®) was placed in acetonitrile/water (800 mL; 1:1) in a 3 L round bottom flask and cooled to 0° C. A well stirred acetonitrile ("ACN") (120 mL) solution of 4-methoxy-3,6-dihydro-2H-pyran (45.0 g, 394 mmol) was then added dropwise. The reaction was stirred for 30 minutes under the ice bath, and then the bath was removed. The reaction was stirred for an additional 1 hour. Solid NaCl (200 g) was then added to the reaction, along with DCM (300 mL). A saturated $Na_2CO_3$ solution was then added slowly until the pH was 10. The reaction was then poured into a 4 L separation funnel and extracted into DCM (3×). The aqueous layer was then placed in a continuous liquid-liquid extractor with DCM and heated to 58° C. for 18 hours. The combined organics were then dried ($MgSO_4$), filtered and concentrated at 20° C. on the rotovap to give the crude product. Purification by column chromatography (500:3-500:5 DCM:MeOH) gave the product 3-fluorodihydro-2H-pyran-4(3H)-one (30 g, 64.4% yield).

Step B: 3-Fluorodihydro-2H-pyran-4(3H)-one (30 g, 254 mmol) was placed in 1,2-dichloroethane ("DCE") (800 mL) and cooled to 0° C. Phenylmethanamine (29.8 mL, 267 mmol) was added, and the mixture was stirred for 10 minutes. The addition of $NaBH(OAc)_3$ (75.4 g, 356 mmol) followed, and dropwise addition of acetic acid (14.5 mL, 254 mmol; d 1.049) was then added. The reaction was stirred for 2 hours, then poured into 1M NaOH and extracted with DCM. The combined organic fractions were dried ($MgSO_4$), filtered, and concentrated to give the crude product, which was purified by reverse phase column chromatography (0-40% ACN in water to give the racemic cis product (3S,4S)- and (3R,4R)—N-benzyl-3-fluorotetrahydro-2H-pyran-4-amine (39 g, 73.4% yield).

Step C: The enantiomers were separated by chromatography on a Chiralpak IC, 5×25 cm column eluting with 10% IPA (0.1% $NH_4OH$)/90% $CO_2$ at a flow rate of 300 mL/min and a temperature of 40° C. The back pressure was 100 Bar.

Step D: (3S,4S)—N-Benzyl-3-fluorotetrahydro-2H-pyran-4-amine (3.7 g, 18 mmol) was placed in MeOH (40 mL) at room temperature. Pd/C (3.8 g, 1.8 mmol) was added, stirred under $H_2$ for 18 hours, filtered, washed with MeOH, and concentrated to give the product (3S,4S)-3-fluorotetrahydro-2H-pyran-4-amine (2.1 g, 100% yield). $^1H$ NMR (400 MHz, $CDCl_3$) δ 4.58-4.44 (m, 1H), 4.19-4.09 (m, 1H), 4.05-3.95 (m, 1H), 3.56-3.38 (m, 2H), 2.96-2.84 (m, 1H), 1.88-1.77 (m, 1H), 1.72-1.65 (m, 1H).

Intermediate Example E

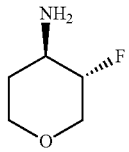

(3S,4R)-3-fluorotetrahydro-2H-pyran-4-amine

Step A: 3-Fluorodihydro-2H-pyran-4(3H)-one (34.58 g, 292.8 mmol) was placed in THF (350 mL) and cooled to −78° C. L-Selectride® (307.4 mL, 307.4 mmol) was then added dropwise, and the reaction was stirred for 30 minutes. MeOH (35.58 mL, 878.4 mmol) and 1N NaOH (878.4 mL, 878.4 mmol) were then added, and the reaction was allowed to warm to 0° C. $H_2O_2$ (99.59 mL, 1464 mmol) was then carefully added dropwise, and the reaction was stirred for an additional 30 minutes. A saturated brine (50 mL) solution was then added, and the reaction was concentrated to remove THF and then diluted with DCM (500 mL). The reaction was then transferred to a liquid-liquid continuous extractor, which was heated at 58° C. for 24 hours. The organic fraction was then separated, dried ($MgSO_4$), and concentrated to give the crude product, which was purified by column chromatography (5:1-3:1 DCM/ethyl acetate) to give the racemic cis product (3R,4S)- and (3S,4R)-3-fluorotetrahydro-2H-pyran-4-ol (21 g, 60.2% yield).

Step B: Racemic (3R,4S)- and (3S,4R)-3-fluorotetrahydro-2H-pyran-4-ol (15.0 g, 125 mmol), isoindoline-1,3-dione (20.2 g, 137 mmol) and 2-(diphenylphosphino)pyridine (42.7 g, 162 mmol) were placed in THF (550 mL) at 0° C. (E)-Di-tert-butyl diazene-1,2-dicarboxylate (37.4 g, 162 mmol) was added, and the reaction was then warmed to room temperature for 24 hours. HCl (156 mL, 624 mmol; 4M in dioxane) was added, and the reaction was stirred for 2 hours and then concentrated to dryness. The resulting residue was dissolved in ether and washed with 4M HCl (6×). Solids that did not dissolve in ether were set aside for later purification (batch 1). The organics were then dried ($MgSO_4$), filtered and concentrated. The crude material was suspended in THF and filtered, giving solid product (batch 2). The filtrate was next concentrated, then suspended in DCM and filtered. The solid was discarded. The filtrate was combined with the first two batches of solids (batches 1 and 2), concentrated and purified by chromatography 500:2-500:5 DCM/MeOH to give the racemic product 2-((3S,4R)-

3-fluorotetrahydro-2H-pyran-4-yl)isoindoline-1,3-dione and 2-((3R,4S)-3-fluorotetrahydro-2H-pyran-4-yl)isoindoline-1,3-dione (14 g, 45.0% yield).

Step C: The enantiomers were separated by chromatography on a Chiralpak IA, 5×25 cm column eluting with 10% MeOH/DCM (1:1)/90% CO₂ at a flow rate of 300 mL/min and a temperature of 40° C. The back pressure was 100 Bar.

Step D: 2-((3S,4R)-3-Fluorotetrahydro-2H-pyran-4-yl)isoindoline-1,3-dione (8.4 g, 34 mmol) was placed in THF/MeOH (160 mL; 1:1). Hydrazine monohydrate (17 g, 337 mmol) was then added. The reaction was stirred at 50° C. for 6 hours, cooled to room temperature for 24 hours, filtered, washed with THF and concentrated to give the crude product, which was purified by column chromatography (500: 20-500:25 DCM/MeOH) to give the product (3S,4R)-3-fluorotetrahydro-2H-pyran-4-amine (4.0 g, 100% yield). ¹H NMR (400 MHz, CDCl₃) δ 4.28-4.04 (m, 2H), 3.94-3.85 (m, 1H), 3.45-3.35 (m, 1H), 3.30-3.20 (m, 1H), 3.05-2.92 (m, 1H), 1.97-1.88 (m, 1H), 1.58-1.48 (m, 1H).

Intermediate Example F

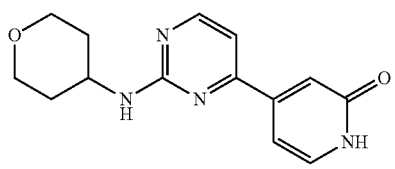 [SMILES: O=c1cc(-c2ccnc(NC3CCOCC3)n2)cc[nH]1]

4-(2-((tetrahydro-2H-pyran-4-yl)amino)pyrimidin-4-yl)pyridin-2(1H)-one

Step A: Sodium carbonate (4.91 g, 46.3 mmol) was added to 2-fluoropyridin-4-ylboronic acid (2.61 g, 18.5 mmol) and 2,4-dichloropyrimidine (77.2 mL, 15.4 mmol) in dioxane/water (77 mL, 4:1), and the suspension was purged with argon. PdCl₂(dppf)*DCM (0.630 g, 0.772 mmol) was added to the mixture, and the mixture was heated at 80° C. under argon. After 3 hours, the reaction mixture was diluted with water, and the resulting solid was collected by vacuum filtration to yield 2-chloro-4-(2-fluoropyridin-4-yl)pyrimidine (3.12 g, 14.9 mmol, 96.4% yield) with minor impurities.

Step B: N-Ethyl-N-isopropylpropan-2-amine (0.496 mL, 2.86 mmol) was added to tetrahydro-2H-pyran-4-amine (0.265 g, 2.62 mmol) and 2-chloro-4-(2-fluoropyridin-4-yl)pyrimidine (0.50 g, 2.39 mmol) in 2-butanol (2 mL) in a sealed tube (microwave vial). The vial was sealed and heated at 100° C. in an oil bath overnight. The reaction mixture was evaporated, and the dark residue was treated with ethyl acetate ("EtOAc") and water, filtered through Celite®, and the layers were separated. The EtOAc was washed with brine, dried over MgSO₄, filtered and evaporated to yield a glass (0.56 g). This was chromatographed on a 50 g Biotage SNAP column with 2:1 EtOAc/hexane. Fractions 28-82 contained 4-(2-fluoropyridin-4-yl)-N-(tetrahydro-2H-pyran-4-yl)pyrimidin-2-amine (0.32 g, 1.17 mmol, 48.9% yield).

Step C: 1M HCl (35 mL) was added to 4-(2-fluoropyridin-4-yl)-N-(tetrahydro-2H-pyran-4-yl)pyrimidin-2-amine (0.32 g, 1.2 mmol). The mixture was heated at reflux overnight. The cooled reaction mixture was neutralized with solid NaHCO₃. The resulting solid was collected by vacuum filtration, washed into a flask with EtOAc/MeOH, evaporated and dried to afford 4-(2-((tetrahydro-2H-pyran-4-yl)amino)pyrimidin-4-yl)pyridin-2(1H)-one (0.30 g, 1.1 mmol, 94% yield). ¹H NMR (400 MHz, (CD₃)₂SO) δ 11.74 (br s, 1H), 8.40 (d, 1H), 7.48 (d, 1H), 7.33 (d, 1H), 7.11 (d, 1H), 6.99 (br s, 1H), 6.85-6.76 (m, 1H), 4.04-3.92 (m, 1H), 3.92-3.85 (m, 2H), 3.45-3.36 (m, 2H), 1.90-1.81 (m, 2H), 1.59-1.48 (m, 2H); m/z (APCI-pos) M+1=273.1.

Intermediate Example G

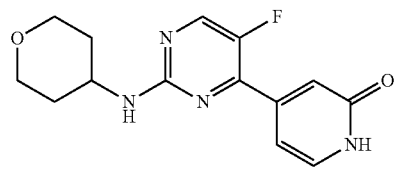 [SMILES: O=c1cc(-c2nc(NC3CCOCC3)ncc2F)cc[nH]1]

4-(5-fluoro-2-((tetrahydro-2H-pyran-4-yl)amino)pyrimidin-4-yl)pyridin-2(1H)-one

Step A: Sodium carbonate (1.3 g, 13 mmol) to 2-fluoropyridin-4-ylboronic acid (0.71 g, 5.0 mmol) and 2,4-dichloro-5-fluoropyrimidine (0.70 g, 4.2 mmol) in dioxane/water (17 mL, 4:1), and the mixture was purged with nitrogen. PdCl₂(dppf)*DCM (0.17 g, 0.21 mmol) was added to the mixture, and the sealed vial was heated at 80° C. After 1.5 hours, the cooled reaction mixture was partitioned between water and EtOAc. The EtOAc was washed with brine, dried over MgSO₄, filtered, and evaporated to yield a crude product (1.7 g) as an oil. The crude product was absorbed on silica gel and chromatographed on a 50 g Biotage SNAP column with 2:1 hexane/EtOAc. Fractions 14-17 contained 2-chloro-5-fluoro-4-(2-fluoropyridin-4-yl)pyrimidine (0.82 g, 3.6 mmol, 86% yield).

Step B: N-Ethyl-N-isopropylpropan-2-amine (0.459 mL, 2.64 mmol) and tetrahydro-2H-pyran-4-amine (0.196 g, 1.93 mmol) were added to 2-chloro-5-fluoro-4-(2-fluoropyridin-4-yl)pyrimidine (0.40 g, 1.76 mmol) in dimethylacetamide ("DMA") (2 mL) in a microwave vial. The mixture was heated at 120° C. for 30 minutes in a microwave. The reaction mixture was partitioned between EtOAc and water. The EtOAc was washed with water, brine, dried over MgSO₄, filtered, and evaporated to yield a crude product (0.52 g) as an oil. The crude product was chromatographed on a 50 g Biotage SNAP column with 2:1 EtOAc/hexane. Fractions 14-26 contained 5-fluoro-4-(2-fluoropyridin-4-yl)-N-(tetrahydro-2H-pyran-4-yl)pyrimidin-2-amine (0.26 g, 0.890 mmol, 50.6% yield).

Step C: 1M HCl (15 mL) was added to 5-fluoro-4-(2-fluoropyridin-4-yl)-N-(tetrahydro-2H-pyran-4-yl)pyrimidin-2-amine (0.26 g, 0.89 mmol). The suspension was heated at reflux. After 2.5 hours, the suspension was neutralized with NaHCO₃, and the solid was collected by vacuum filtration. This was suspended in MeOH and evaporated to yield 4-(5-fluoro-2-((tetrahydro-2H-pyran-4-yl)amino)pyrimidin-4-yl)pyridin-2(1H)-one (0.25 g, 0.86 mmol, 97% yield). ¹H NMR (400 MHz, (CD₃)₂SO) δ 11.80 (br s, 1H), 8.48 (d, 1H), 7.52 (d, 1H), 7.40 (d, 1H), 6.83 (br s, 1H), 6.65-6.61 (m, 1H), 3.90-3.84 (m, 3H), 3.43-3.36 (m, 2H), 1.88-1.81 (m, 2H), 1.57-1.46 (m, 2H); m/z (APCI-pos) M+1=291.1.

Intermediate Example H

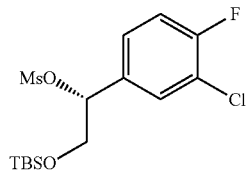 [SMILES: CC(C)(C)[Si](C)(C)OC[C@H](OS(C)(=O)=O)c1ccc(F)c(Cl)c1]

(R)-2-((tert-butyldimethylsilyl)oxy)-1-(3-chloro-4-fluorophenyl)ethyl methanesulfonate Step A: 2M Isopropylmagnesium chloride in THF (91.6 mL, 183 mmol) was added dropwise to ethyl 2-(tert-butyldimethylsilyloxy)acetate (10.0 g, 45.8 mmol) and N,O-dimethylhydroxylamine hydrochloride (9.38 g, 96.2 mmol) in THF (500 mL) cooled in ice. The mixture was stirred for 4.5 hours allowing to slowly warm to ambient temperature. The reaction mixture was quenched with aqueous NH$_4$Cl and concentrated to ⅓ volume. The residue was diluted with water and extracted with EtOAc. The EtOAc was washed with brine, dried over MgSO$_4$, filtered, and evaporated to yield 2-(tert-butyldimethylsilyloxy)-N-methoxy-N-methylacetamide (8.51 g, 36.5 mmol, 79.6% yield) as an oil.

Step B: 0.5M (3-Chloro-4-fluorophenyl)magnesium bromide in THF (27.4 mL, 13.7 mmol) was added dropwise to 2-(tert-butyldimethylsilyloxy)-N-methoxy-N-methylacetamide (2.00 g, 8.57 mmol) in THF (20 mL) cooled in ice. The mixture became turbid after about half of the Grignard reagent was added. This was stirred in an ice bath for 2 hours, quenched with saturated aqueous NH$_4$Cl, and concentrated to remove the THF. The aqueous residue was extracted with 2 portions DCM. The combined DCM layers were dried over MgSO$_4$, filtered, and evaporated to yield a crude product (3.62 g) as an oil. This was taken up in hexane and purified on a silica gel plug with hexane until product started eluting, then 15:1 hexane/EtOAc. Product-containing fractions yielded 2-(tert-butyldimethylsilyloxy)-1-(3-chloro-4-fluorophenyl)ethanone (2.28 g, 7.53 mmol, 87.9% yield) as an oil.

Step C: Diethylaniline-borane complex (1.34 mL, 7.53 mmol) was added to 1.0M (R)-1-methyl-3,3-diphenylhexahydropyrrolo[1,2-c][1,3,2]oxazaborole in toluene (0.753 mL, 0.753 mmol) in MTBE (45 mL). The mixture was heated at 40° C. for 15 minutes (the solution became cloudy), then a solution of 2-(tert-butyldimethylsilyloxy)-1-(3-chloro-4-fluorophenyl)ethanone (2.28 g, 7.53 mmol) in MTBE (25 mL) was added dropwise to the mixture at 40° C. The resulting mixture was heated at 40° C. for 30 minutes, cooled, and was treated with MeOH (3 mL) added dropwise. The resulting solution was treated with 1M HCl (10 mL), diluted with water, and extracted with 2 portions DCM. The DCM was dried over MgSO$_4$, filtered, and evaporated to yield a crude product as an oil. The crude product was chromatographed on a 50 g Biotage SNAP column with 50:1 hexane/EtOAc for 48 fractions, then 15:1 hexane/EtOAc for 36 fractions. Fractions 40-68 contained (R)-2-(tert-butyldimethylsilyloxy)-1-(3-chloro-4-fluorophenyl)ethanol (2.60 g, 8.53 mmol, 113% yield) as an oil with minor impurities.

Step D: Triethylamine (0.480 mL, 3.44 mmol) was added to (R)-2-(tert-butyldimethylsilyloxy)-1-(3-chloro-4-fluorophenyl)ethanol (0.70 g, 2.30 mmol) in DCM (10 mL) cooled in ice, and then methanesulfonyl chloride (0.213 mL, 2.76 mmol) was added. After 1 hour, the reaction mixture was diluted with DCM, washed with aqueous NaHCO$_3$, dried over MgSO$_4$, filtered, and evaporated to yield (R)-2-(tert-butyldimethylsilyloxy)-1-(3-chloro-4-fluorophenyl)ethyl methanesulfonate (0.87 g, 2.27 mmol, 98.9% yield) as an oil. $^1$H NMR (400 MHz, CDCl$_3$) δ 7.47-7.44 (m, 1H), 7.29-7.24 (m, 1H), 7.16 (t, 1H), 5.51-5.47 (m, 1H), 3.94-3.89 (m, 1H), 3.81-3.76 (m, 1H), 2.97 (s, 3H), 0.88 (s, 9H), 0.04 (d, 6H).

Intermediate Example I

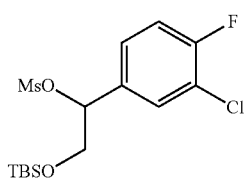 [SMILES: CC(C)(C)[Si](C)(C)OCC(OS(C)(=O)=O)c1ccc(F)c(Cl)c1]

2-((tert-butyldimethylsilyl)oxy)-1-(3-chloro-4-fluorophenyl)ethyl methanesulfonate Step A: A solution of 2-(tert-butyldimethylsilyloxy)acetaldehyde (2.00 g, 10.3 mmol) in dry THF (40 mL) was placed in an ice bath, and (4-chloro-3-fluorophenyl)magnesium bromide (24.8 mL, 12.4 mmol) was added dropwise via a syringe. The reaction mixture was stirred at 0° C. for 1 hour and then carefully quenched by dropwise addition of water. The reaction mixture was concentrated, and the residue was partitioned between EtOAc and saturated aqueous NH$_4$Cl. The organics were dried, filtered and concentrated. The crude product was purified by column chromatography, eluting with hexanes/EtOAc (20:1) to give 2-(tert-butyldimethylsilyloxy)-1-(4-chloro-3-fluorophenyl)ethanol (2.92 g, 9.58 mmol, 92.8% yield) as an oil.

Step B: Triethylamine ("TEA") (0.741 mL, 5.31 mmol; d. 0.726) was added to a cold (0° C.) solution of 2-(tert-butyldimethylsilyloxy)-1-(4-chloro-3-fluorophenyl)ethanol (1.08 g, 3.54 mmol) in DCM (10 mL), followed by addition of methanesulfonyl chloride (0.329 mL, 4.25 mmol). After 1 hour, the reaction mixture was diluted with DCM, and the organic layer was washed with saturated aqueous NaHCO$_3$, dried, filtered and concentrated to afford 2-(tert-butyldimethylsilyloxy)-1-(4-chloro-3-fluorophenyl)ethyl methanesulfonate (1.30 g, 3.39 mmol, 95.8% yield). $^1$H NMR (400 MHz, CDCl$_3$) δ 7.33 (m, 1H), 7.18 (m, 1H), 7.10 (m, 1H), 6.63 (m, 1H), 5.74 (d, 1H), 5.32 (d, 1H).

Intermediate Example J

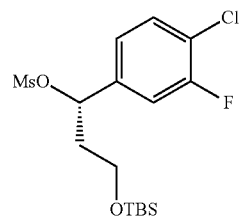 [SMILES: CC(C)(C)[Si](C)(C)OCC[C@H](OS(C)(=O)=O)c1ccc(Cl)c(F)c1]

(S)-3-(tert-butyldimethylsilyloxy)-1-(4-chloro-3-fluorophenyl)propyl methanesulfonate Step A: 4-Chloro-3-fluorobenzaldehyde (15.0 g, 94.6 mmol) was combined with malonic acid (10.8 g, 104 mmol)

and pyridine (11.5 mL, 142 mmol). The mixture was heated to 50° C. and agitated 1 hour. Then it was heated to 100° C. and agitated 16 hours. Ice (100 g) and 6M HCl (25 mL) were added, and the mixture was agitated one hour. Precipitation was filtered, washed with water and dried in vacuo to give (E)-3-(4-chloro-3-fluorophenyl)acrylic acid (17.6 g, 87.7 mmol, 92.7% yield) as a solid.

Step B: (E)-3-(4-Chloro-3-fluorophenyl)acrylic acid (17.3 g, 86.24 mmol) was suspended in ethanol (200 mL), and chlorotrimethylsilane (24.00 mL, 189.7 mmol) was added. The mixture was then agitated for 20 hours and evaporated, to give (E)-ethyl 3-(4-chloro-3-fluorophenyl)acrylate (19.65 g, 85.94 mmol, 99.65% yield) as an oil, which solidified later.

Step C: (E)-Ethyl 3-(4-chloro-3-fluorophenyl)acrylate (18.3 g, 80.0 mmol) was combined with toluene (200 mL) and cooled to −78° C. Diisobutylaluminium hydride ("DIBAL-H") (100 g, 176 mmol) (25% in toluene) was then added over one hour. The reaction was then allowed to agitate and warm up to ambient temperature over 2 hours. After agitating for an additional hour, the reaction was quenched with ice (200 g), and 6M HCl (100 mL) was added slowly. The aqueous layer was separated and extracted once with ethyl acetate. The combined organics were washed with brine, dried and evaporated to give a waxy solid, which was triturated with hexanes to give (E)-3-(4-chloro-3-fluorophenyl)prop-2-en-1-ol (14.0 g, 75.0 mmol, 93.7% yield) as a solid.

Step D: Diisopropyl D-tartrate (1.690 mL, 8.038 mmol) was dissolved in dichloromethane (500 mL) and cooled to −20° C. Activated powdered 4 Å molecular sieves (3 g), titanium(IV) isopropoxide (1.570 mL, 5.359 mmol) and tert-butyl hydroperoxide (19.49 mL, 107.2 mmol; in decane) were added sequentially, and the mixture was agitated for 1 hour at −20° C. (E)-3-(4-Chloro-3-fluorophenyl)prop-2-en-1-ol (10.0 g, 53.59 mmol) was dissolved in dichloromethane (25 mL) and treated with 4 Å molecular sieves (1.0 g) for 1 hour. This mixture was added to the initial mixture over 20 minutes and agitation was continued for another 3 hours at −20° C. The reaction was then quenched by addition of a mixture of a saturated NaCl solution (3 mL) and 50% w/v NaOH (3 mL). Ether was added (100 mL), and the mixture was allowed to warm up to 10° C. After agitating for 10 minutes at this temperature, MsSO₄ (5 g) and Celite® (2 g) were added, and the mixture was agitated for an additional 15 minutes. The mixture was then allowed to settle and filtered through a pad of Celite®, washing with ether. Solvents were then evaporated, and resulting solid was triturated with hexane to give ((2R,3R)-3-(4-chloro-3-fluorophenyl)oxiran-2-yl)methanol (10.55 g, 52.07 mmol, 97.17% yield) as a solid.

Step E: ((2R,3R)-3-(4-Chloro-3-fluorophenyl)oxiran-2-yl)methanol (10.55 g, 52.07 mmol) was dissolved in 1,2-dimethoxyethane (150 mL) and cooled to 0° C. Sodium bis(2-methoxyethoxy)aluminum hydride ("Red-Al") (17.46 mL, 57.28 mmol) was added dropwise. The mixture was agitated for 3 hours at room temperature, diluted with ether (250 mL) and quenched with HCl solution (20 mL, 6M HCl+60 mL water). After agitating for 30 minutes, the aqueous phase was separated and extracted twice with ethyl acetate. The combined organics were washed with brine, dried with MgSO₄, and evaporated to give (S)-1-(4-chloro-3-fluorophenyl)propane-1,3-diol (10.5 g, 51.31 mmol, 98.55% yield) as thick oil.

Step F: (S)-1-(4-Chloro-3-fluorophenyl)propane-1,3-diol (10.5 g, 51.3 mmol) was dissolved in dichloromethane (200 mL), and imidazole (8.73 g, 128 mmol) was added. The mixture was then cooled to 0° C., and tert-butyldimethylsilyl chloride (9.67 g, 64.1 mmol) was added. The mixture was agitated for 1 hour, diluted with dichloromethane to 250 mL and washed with water, sodium bicarbonate solution, dried and evaporated. Purified by chromatography on silica gel, eluted with 5-10% ethyl acetate/hexanes to give (S)-3-(tert-butyldimethylsilyloxy)-1-(4-chloro-3-fluorophenyl)propan-1-ol (8.40 g, 26.3 mmol, 51.3% yield) as an oil.

Step G: (S)-3-(tert-Butyldimethylsilyloxy)-1-(4-chloro-3-fluorophenyl)propan-1-ol (0.600 g, 1.88 mmol) was dissolved in dichloromethane (10 mL) and cooled to 0° C. TEA (0.393 mL, 2.82 mmol; d. 0.726) was added, followed by methanesulfonic acid chloroanhydride (0.175 mL, 2.26 mmol), and the mixture was agitated for 2 hours. The mixture was diluted with dichloromethane to 100 mL, washed with water, sodium bicarbonate solution, dried and evaporated to give (S)-3-(tert-butyldimethylsilyloxy)-1-(4-chloro-3-fluorophenyl)propyl methanesulfonate (0.74 g, 1.86 mmol, 99.1% yield) as an oil.

Intermediate Example K

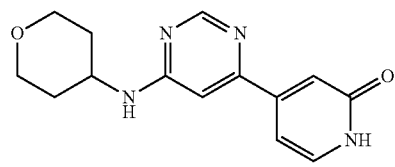 [SMILES: O=c1cc(-c2cc(NC3CCOCC3)ncn2)cc[nH]1]

4-(6-((tetrahydro-2H-pyran-4-yl)amino)pyrimidin-4-yl)pyridin-2(1H)-one

Step A: 4,6-Dichloropyrimidine (3.06 g, 20.5 mmol) was dissolved in dimethylformamide ("DMF") (20 mL) and Cs₂CO₃ (10.0 g, 30.8 mmol) was added. Tetrahydro-2H-pyran-4-amine (1.87 g, 18.5 mmol) combined with DMF (5 mL) was added dropwise. A slight exotherm was observed. After agitating at ambient temperature for 2 hours, product peak was seen in LC/MS. Agitation continued overnight. The mixture was then diluted with ethyl acetate (250 mL) and washed 4 times with water, brine, dried and evaporated to give 6-chloro-N-(tetrahydro-2H-pyran-4-yl)pyrimidin-4-amine (2.86 g, 13.4 mmol, 65.2% yield) as a solid.

Step B: Sodium carbonate (4.24 g, 40.0 mmol) was added to 2-fluoropyridin-4-ylboronic acid (2.26 g, 16.0 mmol) and 6-chloro-N-(tetrahydro-2H-pyran-4-yl)pyrimidin-4-amine (2.85 g, 13.3 mmol) in 4:1 dioxane/water (100 mL), and the suspension was purged with argon. PdCl₂(dppf)*DCM (0.545 g, 0.667 mmol) was added, and the mixture was heated at 80° C. under nitrogen. After agitating for 6 hours, the reaction mixture was cooled, diluted with water and extracted with ethyl acetate two times. The extract was washed with water, brine, dried and evaporated. Purified by chromatography on silica gel, eluted with 50-70% ethyl acetate/hexane to give 6-(2-fluoropyridin-4-yl)-N-(tetrahydro-2H-pyran-4-yl)pyrimidin-4-amine (2.50 g, 9.11 mmol, 68.3% yield) as a solid.

Step C: 6-(2-Fluoropyridin-4-yl)-N-(tetrahydro-2H-pyran-4-yl)pyrimidin-4-amine (2.50 g, 9.11 mmol) was dissolved in 1M HCl (50 mL) and heated to 90° C. The mixture was agitated overnight, cooled and neutralized with 1M NaOH (50 mL). The resulting slurry was cooled to 5° C., and the solids were filtered off, washed with ice cold water and Intermediate Example L

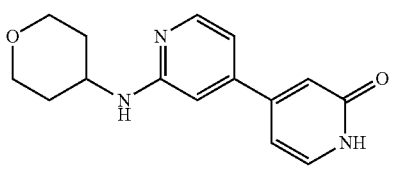 [SMILES: O=c1cc(-c2ccnc(NC3CCOCC3)c2)cc[nH]1]

4-(2-((tetrahydro-2H-pyran-4-yl)amino)pyridin-4-yl)pyridin-2(1H)-one

Step A: 4-Bromo-2-fluoropyridine (1.38 g, 7.84 mmol) was dissolved in DMSO (20 mL), and (tetrahydro-pyran-4-yl)amine (0.912 g, 9.02 mmol) was added, followed by cesium carbonate (5.11 g, 15.7 mmol). The mixture was heated to 90° C. and agitated 3 hours. After cooling, the mixture was diluted with ethyl acetate (200 mL) and washed with water (5×), brine, dried and evaporated to give 4-bromo-N-(tetrahydro-2H-pyran-4-yl)pyridin-2-amine (1.12 g, 4.36 mmol, 55.5% yield) as an oil.

Step B: Sodium carbonate (0.989 g, 9.33 mmol) was added to 2-fluoropyridin-4-ylboronic acid (0.570 g, 4.04 mmol) and 4-bromo-N-(tetrahydro-2H-pyran-4-yl)pyridin-2-amine (0.80 g, 3.11 mmol) in 4:1 dioxane/water (25 mL), and the suspension was purged with nitrogen. PdCl$_2$(dppf)*DCM (0.127 g, 0.156 mmol) was added, and the mixture was heated at 80° C. under nitrogen. After agitating for 6 hours, the reaction mixture was cooled, diluted with water and extracted with ethyl acetate (2×). The extract was washed with water, brine, dried and evaporated. Purified by chromatography on silica gel, eluted with 50-70% ethyl acetate/hexane to give 2'-fluoro-N-(tetrahydro-2H-pyran-4-yl)-4,4'-bipyridin-2-amine (0.64 g, 2.34 mmol, 75.3% yield) as a solid.

Step C: 2'-Fluoro-N-(tetrahydro-2H-pyran-4-yl)-4,4'-bipyridin-2-amine (0.64 g, 2.3 mmol) was combined with 1M HCl (25 mL, 25 mmol) and heated to 95° C. for 3 hours. Upon cooling, the mixture was neutralized (pH 7-8) with of 1M NaOH (25 mL). The resulting slurry was cooled to 0° C. and filtered. The solids were washed with water and dried to give 4-(2-(tetrahydro-2H-pyran-4-ylamino)pyridin-4-yl)pyridin-2(1H)-one (0.62 g, 2.3 mmol, 98% yield) as a solid.

Intermediate Example M

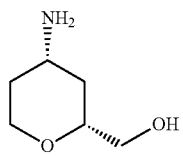

cis-(4-aminotetrahydro-2H-pyran-2-yl)methanol

Step A: A solution of ZnCl (0.63 g, 4.6 mmol) in anhydrous THF (15 mL) was added to a solution of 1-methoxy-3-(trimethylsilyloxy)-1,3-butadiene (7.94 g, 46.0 mmol) and ethyl glyoxalate (7.05 g, 69.0 mmol) in toluene (30 mL) at room temperature. After stirring for 30 minutes, water (30 mL) and TFA (2 mL) were added, and the mixture was stirred vigorously for 20 minutes. After concentration, the residue was partitioned between EtOAc (200 mL) and water (100 mL). The separated organic layer was washed with brine, dried over sodium sulfate, and concentrated to give 4-oxo-3,4-dihydro-2H-pyran-2-carboxylic acid ethyl ester (8.0 g, 100% yield) as an oil, which was carried to the next step without further purification. $^1$H NMR (500 MHz, CDCl$_3$) δ 7.40 (d, J=1.0 Hz, 1H), 5.48 (d, J=6.5 Hz, 1H), 5.02 (t, J=8.0 Hz, 1H), 4.26 (q, J=7.0 Hz, 2H), 2.85 (d, J=8.0 Hz, 2H), 1.32 (t, J=7.5 Hz 3H); LCMS (ESI) m/z: 171 [M+H]$^+$.

Step B: A mixture of 4-oxo-3,4-dihydro-2H-pyran-2-carboxylic acid ethyl ester (8.0 g, 46 mmol) and Pd/C (10%, 0.20 g) in ethyl acetate (70 mL) was stirred under hydrogen (1 atm) for 4 hours. The mixture was filtered through a pad of Celite®. The filtrate was concentrated, and the residue was purified by silica gel column using 30% EtOAc in petroleum ether to give 4-oxo-tetrahydro-pyran-2-carboxylic acid ethyl ester (2.62 g, 33% yield) as an oil. $^1$H NMR (500 MHz, CDCl$_3$) δ 4.40 (m, 1H), 4.23-4.31 (m, 3H), 3.79 (m, 1H), 2.61-2.74 (m, 3H), 2.40 (d, J=15.0 Hz, 1H), 1.31 (t, J=7.5 Hz, 3H).

Step C: Ti(Oi-Pr)$_4$ (4.26 g, 15.0 mol) was added to a stirred solution of ethyl 4-oxo-tetrahydro-2H-pyran-2-carboxylate (1.8 g, 10 mol) in THF and CH$_3$OH (v/v=3:1, 100 mL). After stirring at room temperature for 1 hour, NaBH(CH$_3$COO)$_3$ (4.22 g, 20.0 mol) was added at −20° C. The reaction mixture was then kept in a refrigerator at −20° C. overnight. Ethyl acetate (100 mL) was added to the reaction mixture, followed by adding brine (2 mL) slowly. After being stirred for 30 minutes, the solid was filtered off, and the filtrate was concentrated to afford the crude product, which was purified by silica gel column using 1% methanol in ethyl acetate to give cis-ethyl 4-(benzylamino)-tetrahydro-2H-pyran-2-carboxylate (1.4 g, 51% yield) as a solid. $^1$H NMR (500 MHz, CDCl$_3$) δ 7.34-7.28 (m, 5H), 4.23 (q, J=7.0 Hz, 2H), 4.17 (m, 1H), 3.94 (d, J=11.5 Hz, 2H), 3.84 (m, 1H), 3.46 (m, 1H), 2.81 (m, 1H), 2.29 (d, J=10.0 Hz, 2H), 1.86 (d, J=14.5 Hz, 2H), 1.37 (m, 1H), 1.29 (t, J=7.0 Hz, 3H); LCMS (ESI) m/z: 264.2 [M+H]$^+$.

Step D: LiAlH$_4$ (1.0 g, 26 mol) was added at 0° C. to a stirred solution of cis-ethyl 4-(benzylamino)-tetrahydro-2H-pyran-2-carboxylate (1.3 g, 5.0 mol) in anhydrous THF (50 mL). After stirring for 1 hour, the reaction was quenched by slow, sequential addition of water (1 mL), 15% NaOH (1 mL), and water (3 mL). The inorganic salt was filtered off, and the filtrated was diluted with EtOAc (50 mL), dried and concentrated to give cis-4-(benzylamino)-(tetrahydro-2H-pyran-2-yl)methanol (1.1 g, 100% yield). LCMS (ESI) m/z: 222.3 [M+H]$^+$.

Step E: A mixture of cis-4-(benzylamino)-(tetrahydro-2H-pyran-2-yl)methanol (1.1 g, 5.0 mol) and Pd/C (10%, 0.10 g) in methanol (20 mL) was stirred under hydrogen (1 atm) for 2 hours. The resulting mixture was filtered through a pad of Celite®. The filtrate was concentrated to give cis-(4-aminotetrahydro-2H-pyran-2-yl)methanol (500 mg, 77% yield). LCMS (ESI) m/z: 132.2 [M+H]$^+$.

Example 1

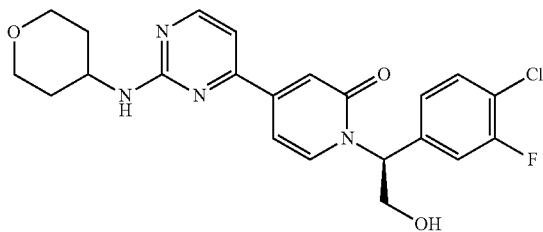 [SMILES: O=c1cc(-c2ccnc(NC3CCOCC3)n2)ccn1[C@H](CO)c1ccc(Cl)c(F)c1]

(S)-1-(1-(4-chloro-3-fluorophenyl)-2-hydroxyethyl)-
4-(2-((tetrahydro-2H-pyran-4-yl)amino)pyrimidin-4-
yl)pyridin-2(1H)-one Step A: A suspension of (S)-1-(2-(tert-butyldimethylsilyloxy)-1-(4-chloro-3-fluorophenyl)ethyl)-4-(2-(methylsulfonyl)pyrimidin-4-yl)pyridin-2(1H)-one (5.77 g, 10.7 mmol) and tetrahydro-2H-pyran-4-amine (2.17 g, 21.4 mmol) in sec-BuOH (30 mL) was heated to 120° C. for 4 hours in a sealed tube. The reaction mixture was cooled to room temperature and concentrated. The crude (S)-1-(2-(tert-butyldimethylsilyloxy)-1-(4-chloro-3-fluorophenyl)ethyl)-4-(2-(tetrahydro-2H-pyran-4-ylamino)pyrimidin-4-yl)pyridin-2(1H)-one was used without purification in Step B. m/z (APCI-pos) M+1=559.2, 560.2.

Step B: A solution of (S)-1-(2-(tert-butyldimethylsilyloxy)-1-(4-chloro-3-fluorophenyl)ethyl)-4-(2-(tetrahydro-2H-pyran-4-ylamino)pyrimidin-4-yl)pyridin-2(1H)-one (6.00 g, 10.7 mmol) in THF (20 mL) was treated with tetrabutyl ammonium fluoride (12.9 mL, 12.9 mmol) at room temperature for 30 minutes. The reaction mixture was concentrated, and the residue was taken up with ethyl acetate and water. The organic layer was washed with water (1×). The combined organics were dried, filtered and concentrated. The crude product was purified via column chromatography, eluting with ethyl acetate to give (S)-1-(1-(4-chloro-3-fluorophenyl)-2-hydroxyethyl)-4-(2-((tetrahydro-2H-pyran-4-ylamino))pyrimidin-4-yl)pyridin-2(1H)-one as a solid (4.14 g, 87%; 96% enantiomeric excess ("e.e.") by chiral HPLC (Chiral Tech, column OJ-H, 4.6 mm×250 mm, 5 u, 30% ethanol/70% hexanes, 1 mL/minute)). $^1$H NMR (400 MHz, CDCl$_3$) δ 8.38 (d, J=5.0 Hz, 1H), 7.40 (m, 2H), 7.20 (m, 2H), 7.10 (d, J=8.2 Hz, 1H), 6.88 (d, J=5.0 Hz, 1H), 6.78 (m, 1H), 6.20 (m, 1H), 5.16 (d, J=8.0 Hz, 1H), 4.31 (m, 2H), 4.10 (m, 1H), 4.00 (m, 2H), 3.55 (m, 2H), 2.74 (br, s, 1H), 2.06 (m, 2H), 1.58 (m, 2H); m/z (APCI-pos) M+1=445.1, 447.0.

Example 2

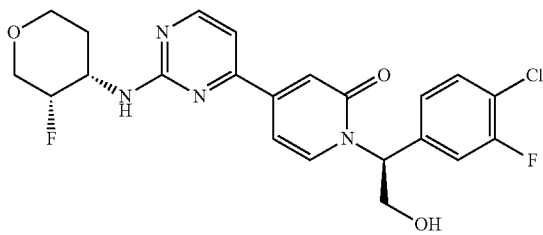 [SMILES: O=c1cc(-c2ccnc(N[C@H]3CCOC[C@H]3F)n2)ccn1[C@H](CO)c1ccc(Cl)c(F)c1]

1-((S)-1-(4-chloro-3-fluorophenyl)-2-hydroxyethyl-
4-(2-(((3S,4S)-3-fluorotetrahydro-2H-pyran-4-yl)
amino)pyrimidin-4-yl)pyridin-2(1H)-one Step A: A mixture of (3S,4S)-3-fluorotetrahydro-2H-pyran-4-amine (2.8 g, 24 mmol), N-ethyl-N-isopropylpropan-2-amine (2.9 g, 22 mmol) and (S)-1-(2-(tert-butyldimethylsilyloxy)-1-(4-chloro-3-fluorophenyl)ethyl)-4-(2-(methylsulfonyl)pyrimidin-4-yl)pyridin-2(1H)-one (8.0 g, 15 mmol) in sec-BuOH (25 mL) was placed in a sealed tube and heated to 120° C. for 68 hours. The reaction mixture was cooled to room temperature and concentrated. The crude 1-((S)-2-(tert-butyldimethylsilyloxy)-1-(4-chloro-3-fluorophenyl)ethyl)-4-(2-((3S,4S)-3-fluorotetrahydro-2H-pyran-4-ylamino)pyrimidin-4-yl)pyridin-2(1H)-one was used in Step B without purification. m/z (APCI-pos) M+1=577.2, 579.2.

Step B: A 4.0M solution of hydrogen chloride (18.6 mL, 74.5 mmol) in dioxane was slowly added to a cold (0° C.) solution of 1-((S)-2-(tert-butyldimethylsilyloxy)-1-(4-chloro-3-fluorophenyl)ethyl)-4-(2-((3S,4S)-3-fluorotetrahydro-2H-pyran-4-ylamino)pyrimidin-4-yl)pyridin-2(1H)-one (8.6 g, 14.9 mmol) in MeOH (40 mL), and the mixture was stirred for 1 hour. The reaction mixture was concentrated, and the residue was taken up in saturated NaHCO$_3$ and extracted with ethyl acetate (2×). The organic layer was dried, filtered and concentrated. The crude product was purified by column chromatography, eluting with hexanes/ethyl acetate (1:4) to give 1-((S)-1-(4-chloro-3-fluorophenyl)-2-hydroxyethyl)-4-(2-(((3S,4S)-3-fluorotetrahydro-2H-pyran-4-yl)amino)pyrimidin-4-yl)pyridin-2(1H)-one as a solid (4.58 g, 66%; 97% e.e. by chiral HPLC (Chiral Tech, column OD-H, 4.6 mm×250 mm, 5 u, 30% ethanol/70% hexanes, 1 mL/minute)). $^1$H NMR (400 MHz, CDCl$_3$) δ 8.38 (d, J=5.0 Hz, 1H), 7.41 (m, 2H), 7.21-7.09 (m, 3H), 6.89 (d, J=5.0 Hz, 1H), 6.76 (d, J=7.0 Hz, 1H), 6.20 (m, 1H), 5.55 (d, J=8.2 Hz, 1H), 4.75 (d, J=50 Hz, 1H), 4.38-4.18 (m, 4H), 4.05 (m, 1H), 3.69-3.53 (m, 2H), 3.12 (br, s, 1H), 2.08-1.84 (m, 2H); m/z (APCI-pos) M+1=463.1, 465.0.

Example 3

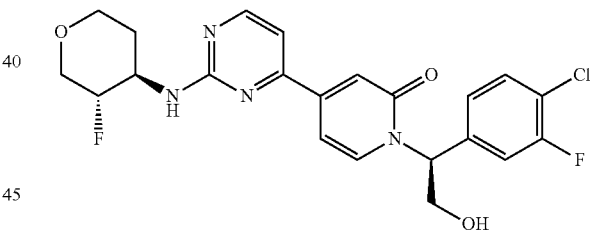

1-((S)-1-(4-chloro-3-fluorophenyl)-2-hydroxyethyl)-
4-(2-(((3S,4R)-3-fluorotetrahydro-2H-pyran-4-yl)
amino)pyrimidin-4-yl)pyridin-2(1H)-one Step A: 1-((S)-2-(tert-Butyldimethylsilyloxy)-1-(4-chloro-3-fluorophenyl)ethyl)-4-(2-((3S,4R)-3-fluorotetrahydro-2H-pyran-4-ylamino)pyrimidin-4-yl)pyridin-2(1H)-one was prepared according to the general procedure of Example 2, Step A, substituting (3S,4R)-3-fluorotetrahydro-2H-pyran-4-amine for (3S,4S)-3-fluorotetrahydro-2H-pyran-4-amine. m/z (APCI-pos) M+1=577.2, 579.2.

Step B: 1-((S)-1-(4-Chloro-3-fluorophenyl)-2-hydroxyethyl)-4-(2-((3S,4R)-3-fluorotetrahydro-2H-pyran-4-ylamino)pyrimidin-4-yl)pyridin-2(1H)-one (56%, 2 steps; 96% e.e. by chiral HPLC (Chiral Tech, column OJ-H, 4.6 mm×250 mm, 5 u, 20% ethanol/80% hexanes, 1 mL/minute)) was prepared according to the general procedure of Example 2, Step B, substituting 1-((S)-2-(tert-butyldimethylsilyloxy)-1-(4-chloro-3-fluorophenyl)ethyl)-4-(2-(((3S,4R)-3-fluorotetrahydro-2H-pyran-4-yl)amino)pyrimidin-4-yl)pyridin-2(1H)-one for 1-((S)-2-(tert-butyldimethylsilyloxy)-1-(4-chloro-3-fluorophenyl)ethyl)-4-(2-((3S,4S)-3-fluorotetrahydro-2H-pyran-4-ylamino)pyrimidin-4-yl)pyridin-2(1H)-one. ¹H NMR (400 MHz, CDCl₃) δ 8.39 (d, J=5.0 Hz, 1H), 7.40 (m, 2H), 7.21-7.09 (m, 3H), 6.91 (d, J=5.2 Hz, 1H), 6.79 (m, 1H), 6.19 (m, 1H), 5.34 (d, J=7.8 Hz, 1H), 4.61-4.42 (m, 1H), 4.38-4.26 (m, 3H), 4.10 (m, 1H), 3.90 (m, 1H), 3.61-3.51 (m, 2H), 3.05 (br, s, 1H), 2.33 (m, 1H), 1.63 (m, 1H); m/z (APCI-pos) M+1=463.1, 465.1.

Example 4

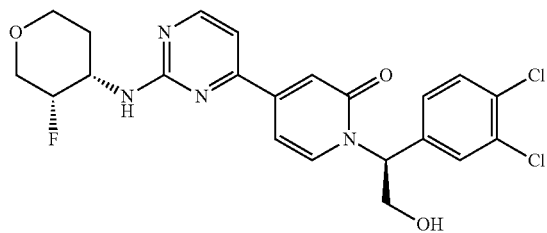 [SMILES: O=c1cc(-c2ccnc(N[C@H]3CCOC[C@H]3F)n2)ccn1[C@H](CO)c1ccc(Cl)c(Cl)c1]

1-((S)-1-(3,4-dichlorophenyl)-2-hydroxyethyl)-4-(2-(((3S,4S)-3-fluorotetrahydro-2H-pyran-4-yl)amino)pyrimidin-4-yl)pyridin-2(1H)-one Step A: 1-((S)-2-(tert-Butyldimethylsilyloxy)-1-(3,4-dichlorophenyl)ethyl)-4-(2-((3S,4S)-3-fluorotetrahydro-2H-pyran-4-ylamino)pyrimidin-4-yl)pyridin-2(1H)-one was prepared according to the general procedure of Example 2, Step A, substituting (S)-1-(2-(tert-butyldimethylsilyloxy)-1-(3,4-dichlorophenyl)ethyl)-4-(2-(methylsulfonyl)pyrimidin-4-yl)pyridin-2(1H)-one for (S)-1-(2-(tert-butyldimethylsilyloxy)-1-(4-chloro-3-fluorophenyl)ethyl)-4-(2-(methylsulfonyl)pyrimidin-4-yl)pyridin-2(1H)-one. m/z (APCI-pos) M+1=593.1, 595.2.

Step B: 1-((S)-1-(3,4-Dichlorophenyl)-2-hydroxyethyl)-4-(2-(((3S,4S)-3-fluorotetrahydro-2H-pyran-4-yl)amino)pyrimidin-4-yl)pyridin-2(1H)-one (74%, 2 steps; 98% e.e. by chiral HPLC (Chiral Tech, column OD-H, 4.6 mm×250 mm, 5 u, 30% ethanol/70% hexanes, 1 mL/minute)) was prepared according to the general procedure of Example 2, Step B, substituting 1-((S)-2-(tert-butyldimethylsilyloxy)-1-(3,4-dichlorophenyl)ethyl)-4-(2-((3S,4S)-3-fluorotetrahydro-2H-pyran-4-ylamino)pyrimidin-4-yl)pyridin-2(1H)-one for 1-((S)-2-(tert-butyldimethylsilyloxy)-1-(4-chloro-3-fluorophenyl)ethyl)-4-(2-(((3S,4S)-3-fluorotetrahydro-2H-pyran-4-yl)amino)pyrimidin-4-yl)pyridin-2(1H)-one. ¹H NMR (400 MHz, CDCl₃) δ 8.39 (d, J=5.4 Hz, 1H), 7.50-7.38 (m, 3H), 7.24-7.15 (m, 2H), 6.91 (d, J=5.2 Hz, 1H), 6.77 (m, 1H), 6.19 (m, 1H), 5.53 (d, J=8.6 Hz, 1H), 4.75 (d, J=49 Hz, 1H), 4.40-4.18 (m, 4H), 4.10 (m, 1H), 3.70-3.54 (m, 2H), 2.65 (br, s, 1H), 2.08-01.88 (m, 2H); m/z (APCI-pos) M+1=479.0, 481.0.

Example 5

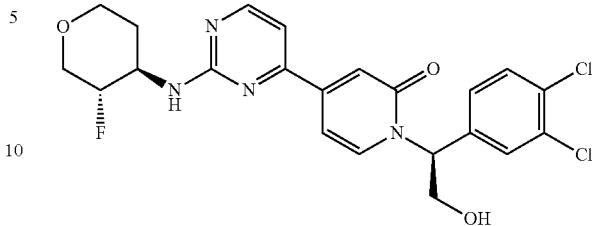

1-((S)-1-(3,4-dichlorophenyl)-2-hydroxyethyl)-4-(2-(((3S,4R)-3-fluorotetrahydro-2H-pyran-4-yl)amino)pyrimidin-4-yl)pyridin-2(1H)-one Step A: 1-((S)-2-(tert-Butyldimethylsilyloxy)-1-(3,4-dichlorophenyl)ethyl)-4-(2-((3S,4R)-3-fluorotetrahydro-2H-pyran-4-ylamino)pyrimidin-4-yl)pyridin-2(1H)-one was prepared according to the general procedure of Example 2, Step A, substituting (3S,4R)-3-fluorotetrahydro-2H-pyran-4-amine for tetrahydro-2H-pyran-4-amine and (S)-1-(2-(tert-butyldimethylsilyloxy)-1-(3,4-dichlorophenyl)ethyl)-4-(2-(methylsulfonyl)pyrimidin-4-yl)pyridin-2(1H)-one for (S)-1-(2-(tert-butyldimethylsilyloxy)-1-(4-chloro-3-fluorophenyl)ethyl)-4-(2-(methylsulfonyl)pyrimidin-4-yl)pyridin-2(1H)-one. m/z (APCI-pos) M+1=593.1, 595.2.

Step B: 1-((S)-1-(3,4-Dichlorophenyl)-2-hydroxyethyl)-4-(2-(((3S,4R)-3-fluorotetrahydro-2H-pyran-4-yl)amino)pyrimidin-4-yl)pyridin-2(1H)-one (54%, 2 steps; 98% e.e. by chiral HPLC (Chiral Tech, column OD-H, 4.6 mm×250 mm, 5 u, 30% ethanol/70% hexanes, 1 mL/minute)) was prepared according to the general procedure of Example 2, Step B, substituting 1-((S)-2-(tert-butyldimethylsilyloxy)-1-(3,4-dichlorophenyl)ethyl)-4-(2-((3S,4R)-3-fluorotetrahydro-2H-pyran-4-ylamino)pyrimidin-4-yl)pyridin-2(1H)-one for 1-((S)-2-(tert-butyldimethylsilyloxy)-1-(4-chloro-3-fluorophenyl)ethyl)-4-(2-((3S,4S)-3-fluorotetrahydro-2H-pyran-4-ylamino)pyrimidin-4-yl)pyridin-2(1H)-one. ¹H NMR (400 MHz, CDCl₃) δ 8.39 (d, J=5.0 Hz, 1H), 7.49-7.45 (m, 2H), 7.39 (d, J=7.4 Hz, 1H), 7.23-7.17 (m, 2H), 6.93 (d, J=5.2 Hz, 1H), 6.79 (m, 1H), 6.19 (m, 1H), 5.31 (d, J=7.5 Hz, 1H), 4.61-4.42 (m, 1H), 4.38-4.26 (m, 3H), 4.10 (m, 1H), 3.90 (m, 1H), 3.65-3.51 (m, 2H), 2.68 r, s, 1H), 2.33 (m, 1H), 1.66 (m, 1H); m/z (APCI-pos) M+1=479.0, 481.0.

Example 6

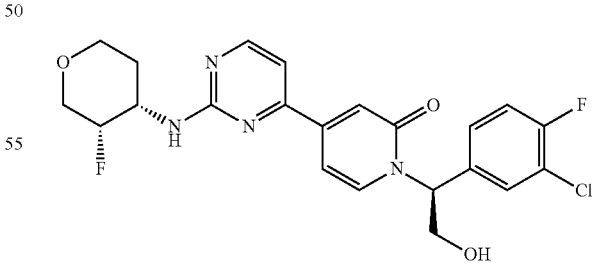

1-((S)-1-(3-chloro-4-fluorophenyl)-2-hydroxyethyl)-4-(2-(((3S,4S)-3-fluorotetrahydro-2H-pyran-4-yl)amino)pyrimidin-4-yl)pyridin-2(1H)-one Step A: 1-((S)-2-(tert-Butyldimethylsilyloxy)-1-(3-chloro-4-fluorophenyl)ethyl)-4-(2-((3S,4S)-3-fluorotetrahydro-2H-pyran-4-ylamino)pyrimidin-4-yl)pyridin-2(1H)-one was prepared according to the general procedure of Example 2, Step A, substituting (S)-1-(2-(tert-butyldimethylsilyloxy)-1-(3-chloro-4-fluorophenyl)ethyl)-4-(2-(methylsulfonyl)pyrimidin-4-yl)pyridin-2(1H)-one for (S)-1-(2-(tert-butyldimethylsilyloxy)-1-(4-chloro-3-fluorophenyl)ethyl)-4-(2-(methylsulfonyl)pyrimidin-4-yl)pyridin-2(1H)-one. m/z (APCI-pos) M+1=577.2, 579.2.

Step B: 1-((S)-1-(3-Chloro-4-fluorophenyl)-2-hydroxyethyl)-4-(2-(((3S,4S)-3-fluorotetrahydro-2H-pyran-4-yl)amino)pyrimidin-4-yl)pyridin-2(1H)-one (66%, 2 steps; 99% e.e. by chiral HPLC (Chiral Tech, column OD-H, 4.6 mm×250 mm, 5 u, 20% ethanol/80% hexanes, 1 mL/minute)) was prepared according to the general procedure of Example 2, Step B, substituting 1-((S)-2-(tert-butyldimethylsilyloxy)-1-(3-chloro-4-fluorophenyl)ethyl)-4-(2-((3S,4S)-3-fluorotetrahydro-2H-pyran-4-ylamino)pyrimidin-4-yl)pyridin-2(1H)-one for 1-((S)-2-(tert-butyldimethylsilyloxy)-1-(4-chloro-3-fluorophenyl)ethyl)-4-(2-(((3S,4S)-3-fluorotetrahydro-2H-pyran-4-yl)amino)pyrimidin-4-yl)pyridin-2(1H)-one. $^1$H NMR (400 MHz, CDCl$_3$) δ 8.38 (d, J=5.0 Hz, 1H), 7.46 (d, J=7.0 Hz, 1H), 7.38 (d, J=7.8 Hz, 1H), 7.25 (m, 1H), 7.19-7.14 (m, 2H), 6.92 (d, J=5.0 Hz, 1H), 6.76 (d, J=6.6 Hz, 1H), 6.20 (m, 1H), 5.55 (d, J=9.4 Hz, 1H), 4.75 (d, J=50 Hz, 1H), 4.38-4.18 (m, 4H), 4.08 (m, 1H), 3.69-3.53 (m, 2H), 2.68 (br, s, 1H), 2.08-1.87 (m, 2H); m/z (APCI-pos) M+1=463.1, 465.1.

Example 7

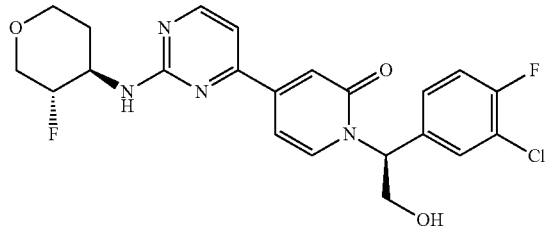 [SMILES: O=c1cc(-c2ccnc(N[C@@H]3CCOC[C@H]3F)n2)ccn1[C@H](CO)c1ccc(F)c(Cl)c1]

1-((S)-1-(3-chloro-4-fluorophenyl)-2-hydroxyethyl)-4-(2-(((3S,4R)-3-fluorotetrahydro-2H-pyran-4-yl)amino)pyrimidin-4-yl)pyridin-2(1H)-one Step A: 1-((S)-2-(tert-Butyldimethylsilyloxy)-1-(3-chloro-4-fluorophenyl)ethyl)-4-(2-((3S,4R)-3-fluorotetrahydro-2H-pyran-4-ylamino)pyrimidin-4-yl)pyridin-2(1H)-one was prepared according to the general procedure of Example 2, Step A, substituting (3S,4R)-3-fluorotetrahydro-2H-pyran-4-amine for tetrahydro-2H-pyran-4-amine and (S)-1-(2-(tert-butyldimethylsilyloxy)-1-(3-chloro-4-fluorophenyl)ethyl)-4-(2-(methylsulfonyl)pyrimidin-4-yl)pyridin-2(1H)-one for (S)-1-(2-(tert-butyldimethylsilyloxy)-1-(4-chloro-3-fluorophenyl)ethyl)-4-(2-(methylsulfonyl)pyrimidin-4-yl)pyridin-2(1H)-one. m/z (APCI-pos) M+1=577.2, 579.2.

Step B: 1-((S)-1-(3-Chloro-4-fluorophenyl)-2-hydroxyethyl)-4-(2-(((3S,4R)-3-fluorotetrahydro-2H-pyran-4-yl)amino)pyrimidin-4-yl)pyridin-2(1H)-one (59%, 2 steps; 99% e.e. by chiral HPLC (Chiral Tech, column OJ-H, 4.6 mm×250 mm, 5 u, 20% ethanol/80% hexanes, 1 mL/minute)) was prepared according to the general procedure of Example 2, Step B, substituting 1-((S)-2-(tert-butyldimethylsilyloxy)-1-(3-chloro-4-fluorophenyl)ethyl)-4-(2-((3S,4R)-3-fluorotetrahydro-2H-pyran-4-ylamino)pyrimidin-4-yl)pyridin-2(1H)-one for 1-((S)-2-(tert-butyldimethylsilyloxy)-1-(4-chloro-3-fluorophenyl)ethyl)-4-(2-(((3S,4S)-3-fluorotetrahydro-2H-pyran-4-yl)amino)pyrimidin-4-yl)pyridin-2(1H)-one. $^1$H NMR (400 MHz, CDCl$_3$) δ 8.38 (d, J=5.0 Hz, 1H), 7.46 (d, J=7.0 Hz, 1H), 7.38 (d, J=7.8 Hz, 1H), 7.25 (m, 1H), 7.19-7.14 (m, 2H), 6.92 (d, J=5.0 Hz, 1H), 6.76 (d, J=6.6 Hz, 1H), 6.20 (m, 1H), 5.34 (d, J=7.8 Hz, 1H), 4.61-4.42 (m, 1H), 4.38-4.26 (m, 3H), 4.10 (m, 1H), 3.90 (m, 1H), 3.61-3.51 (m, 2H), 3.05 (br, s, 1H), 2.33 (m, 1H), 1.63 (m, 1H); m/z (APCI-pos) M+1=463.1, 465.1.

Example 8

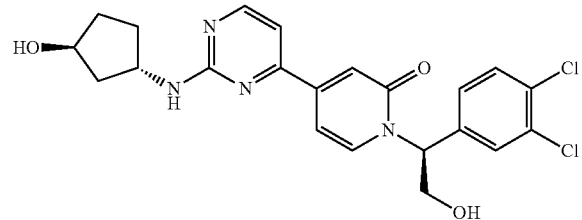 [SMILES: O=c1cc(-c2ccnc(N[C@H]3CC[C@H](O)C3)n2)ccn1[C@H](CO)c1ccc(Cl)c(Cl)c1]

1-((S)-1-(3,4-dichlorophenyl)-2-hydroxyethyl)-4-(2-(((1S,3S)-3-hydroxycyclopentyl)amino)pyrimidin-4-yl)pyridin-2(1H)-one Step A: 1-((S)-2-(tert-Butyldimethylsilyloxy)-1-(3,4-dichlorophenyl)ethyl)-4-(2-((1S,3S)-3-hydroxycyclopentylamino)pyrimidin-4-yl)pyridin-2(1H)-one was prepared according to the general procedure of Example 2, Step A, substituting (1S,3S)-3-aminocyclopentanol for tetrahydro-2H-pyran-4-amine and (S)-1-(2-(tert-butyldimethylsilyloxy)-1-(3,4-dichlorophenyl)ethyl)-4-(2-(methylsulfonyl)pyrimidin-4-yl)pyridin-2(1H)-one for (S)-1-(2-(tert-butyldimethylsilyloxy)-1-(4-chloro-3-fluorophenyl)ethyl)-4-(2-(methylsulfonyl)pyrimidin-4-yl)pyridin-2(1H)-one. m/z (APCI-pos) M+1=575.2, 577.1.

Step B: 1-((S)-1-(3,4-Dichlorophenyl)-2-hydroxyethyl)-4-(2-(((1S,3S)-3-hydroxycyclopentyl)amino)pyrimidin-4-yl)pyridin-2(1H)-one (78%, 2 steps; 97% e.e. by chiral HPLC (Chiral Tech, column OD-H, 4.6 mm×250 mm, 5 u, 30% ethanol/70% hexanes, 1 mL/minute)) was prepared according to the general procedure of Example 1, Step B, substituting 1-((S)-2-(tert-butyldimethylsilyloxy)-1-(3,4-dichlorophenyl)ethyl)-4-(2-((1S,3S)-3-hydroxycyclopentylamino)pyrimidin-4-yl)pyridin-2(1H)-one for (S)-1-(2-(tert-butyldimethylsilyloxy)-1-(4-chloro-3-fluorophenyl)ethyl)-4-(2-(tetrahydro-2H-pyran-4-ylamino)pyrimidin-4-yl)pyridin-2(1H)-one. $^1$H NMR (400 MHz, CDCl$_3$) δ 8.31 (d, J=4.2 Hz, 1H), 7.48 (s, 1H), 7.44 (d, J=8.0 Hz, 1H), 7.39 (d, J=7.2 Hz, 1H), 7.21 (m, 1H), 7.13 (s, 1H), 6.80 (m, 2H), 6.17 (m, 1H), 5.22 (d, J=7.2 Hz, 1H), 4.60-4.43 (m, 2H), 4.30 (m, 2H), 3.50 (br, s, 2H), 2.36 (m, 1H), 2.22 (m, 1H), 2.11 (m, 1H), 1.77-1.64 (m, 2H), 1.52 (m, 1H); m/z (APCI-pos) M+1=461.0, 463.1.

Example 9

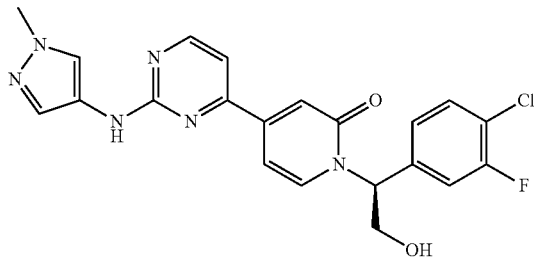 [SMILES: Cn1cc(Nc2nccc(-c3ccn([C@H](CO)c4ccc(Cl)c(F)c4)c(=O)c3)n2)cn1]

(S)-1-(1-(4-chloro-3-fluorophenyl)-2-hydroxyethyl)-
4-(2-((1-methyl-1H-pyrazol-4-yl)amino)pyrimidin-
4-yl)pyridin-2(1H)-one A solution of 1-methyl-1H-pyrazol-4-amine (0.054 g, 0.56 mmol) and (S)-1-(2-(tert-butyldimethylsilyloxy)-1-(4-chloro-3-fluorophenyl)ethyl)-4-(2-(methylsulfonyl)pyrimidin-4-yl)pyridin-2(1H)-one (0.060 g, 0.11 mmol) in sec-BuOH (1 mL) was heated to 120° C. in a microwave reactor for 2 hours. The reaction mixture was cooled to room temperature and concentrated. The residue was diluted with ethyl acetate and washed with $H_2O$ (2×). The organic layer was dried, filtered and concentrated. The crude product was purified by column chromatography, eluting with DCM/MeOH (25:1) to give (S)-1-(1-(4-chloro-3-fluorophenyl)-2-hydroxyethyl)-4-(2-((1-methyl-1H-pyrazol-4-yl)amino)pyrimidin-4-yl)pyridin-2(1H)-one (0.013 g, 26%). $^1$H NMR (400 MHz, CD$_3$OD) δ 8.50 (d, J=5.0 Hz, 1H), 7.96 (s, 1H), 7.85 (d, J=7.0 Hz, 1H), 7.58 (s, 1H), 7.48 (m, 1H), 7.34-7.28 (m, 2H), 7.20-7.17 (m, 2H), 7.06 (m, 1H), 6.12 (m, 1H), 4.28 (m, 1H), 4.19 (m, 1H), 3.88 (s, 3H); m/z (APCI-pos) M+1=441.1, 443.1.

Example 10

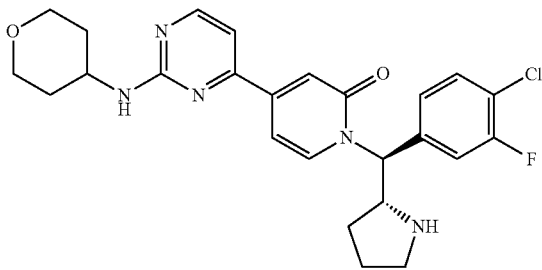 [SMILES: O=c1cc(-c2ccnc(NC3CCOCC3)n2)ccn1[C@@H](c1ccc(Cl)c(F)c1)[C@H]1CCCN1]

1-((S)-(4-chloro-3-fluorophenyl)((R)-pyrrolidin-2-
yl)methyl)-4-(2-((tetrahydro-2H-pyran-4-yl)amino)
pyrimidin-4-yl)pyridin-2(1H)-one Step A: (R)-1-(tert-Butoxycarbonyl)pyrrolidine-2-carboxylic acid (5.00 g, 23.2 mmol), O,N-dimethylhydroxylamine hydrochloride (2.49 g, 25.6 mmol), diisopropyl ethyl amine (8.09 mL, 46.5 mmol) and 2-(1H-7-azabenzotriazol-1-yl)-1,1,3,3-tetramethyl uronium hexafluorophosphate methanaminium ("HATU") (9.72 g, 25.6 mmol) in DCM (50 mL) were stirred at room temperature for 2 hours. The reaction mixture was quenched with water, and the layers were separated. The aqueous layer was extracted with DCM (1×), and the combined organics were dried, filtered and concentrated. The crude product was purified via column chromatography, eluting with hexanes/ethyl acetate (1:1) to give (R)-tert-butyl 2-(methoxy(methyl)carbamoyl)pyrrolidine-1-carboxylate as an oil (5.5 g, 92%). m/z (APCI-pos) (M+1)-Boc=159.0.

Step B: 0.5M (4-Chloro-3-fluorophenyl)magnesium bromide (22.5 mL, 11.2 mmol) as a solution in THF was added dropwise to a cold (0° C.) solution of (R)-tert-butyl 2-(methoxy(methyl)carbamoyl)pyrrolidine-1-carboxylate (1.45 g, 5.61 mmol) in THF (25 mL) under $N_2$, and the reaction was allowed to warm up to room temperature overnight. The next morning, the mixture was placed in an ice bath and carefully quenched with ice. The reaction mixture was concentrated. The residue was treated for 1 hour with a solution of 30% sodium potassium and then extracted with ethyl acetate (2×). The organic layer was dried, filtered and concentrated. The crude product was purified via column chromatography, eluting with hexanes/ethyl acetate (5:1) to give (R)-tert-butyl 2-(4-chloro-3-fluorobenzoyl)pyrrolidine-1-carboxylate (1.12 g, 61%). m/z (APCI-pos) (M+1)-Boc=228.1, 230.1.

Step C: (R)-tert-Butyl 2-(4-chloro-3-fluorobenzoyl)pyrrolidine-1-carboxylate (1.12 g, 3.42 mmol) was placed in THF (50 mL) at −78° C., and 1.0M L-Selectride® (5.13 mL, 5.13 mmol) as a solution in THF was added. The reaction was stirred at −78° C. for 1 hour and then 0° C. for 2 hours. The reaction was quenched with 1N HCl, and the pH was adjusted to about 7 with saturated NaHCO$_3$. The mixture was concentrated to remove most of the THF, and the residue was extracted with ethyl acetate (2×). The combined organics were dried, filtered and concentrated. The crude product was purified via column chromatography, eluting with hexanes/ethyl acetate (12:1) to give (R)-tert-butyl 2-((R)-(4-chloro-3-fluorophenyl)(hydroxy)methyl)pyrrolidine-1-carboxylate (0.67 g, 60%). m/z (APCI-pos) (M+1)-Boc=230.1, 232.1.

Step D: A solution of (R)-tert-butyl 2-((R)-(4-chloro-3-fluorophenyl)(hydroxy)methyl)pyrrolidine-1-carboxylate (0.662 g, 2.01 mmol) and triphenylphosphine (0.658 g, 2.51 mmol) in THF (40 mL) was placed in an ice bath, and diisopropyl azodicarboxylate (0.518 mL, 2.51 mmol) was added. The cold bath was removed after 10 minutes, and the reaction mixture was stirred at room temperature for 10 minutes. 4-(2-(Methylthio)pyrimidin-4-yl)pyridin-2(1H)-one (0.22 g, 1.00 mmol) was added, and the reaction was left at room temperature for 1 hour. The reaction mixture was concentrated, and the crude product was purified via column chromatography, eluting with hexanes/ethyl acetate (1:1) to give (R)-tert-butyl 2-((S)-(4-chloro-3-fluorophenyl)(4-(2-(methylthio)pyrimidin-4-yl)-2-oxopyridin-1(2H)-yl)methyl)pyrrolidine-1-carboxylate (contaminated with large amounts of PPh$_3$O). m/z (APCI-pos) (M+1)-Boc=431.2, 433.2.

Step E: (R)-tert-Butyl 2-((S)-(4-chloro-3-fluorophenyl)(4-(2-(methylsulfonyl)pyrimidin-4-yl)-2-oxopyridin-1(2H)-yl)methyl)pyrrolidine-1-carboxylate (33%, 2 steps) was prepared according to the general procedure of Intermediate Example C, Step B, substituting (R)-tert-butyl 2-((S)-(4-chloro-3-fluorophenyl)(4-(2-(methylthio)pyrimidin-4-yl)-2-oxopyridin-1(2H)-yl)methyl)pyrrolidine-1-carboxylate for (S)-1-(2-(tert-butyldimethylsilyloxy)-1-(4-chloro-3-fluorophenyl)ethyl)-4-(2-(methylthio)pyrimidin-4-yl)pyridin-2(1H)-one. m/z (APCI-pos) (M+1)-Boc=463.0, 465.0.

Step F: (R)-tert-Butyl 2-((S)-(4-chloro-3-fluorophenyl)(2-oxo-4-(2-(tetrahydro-2H-pyran-4-ylamino)pyrimidin-4-yl)pyridin-1(2H)-yl)methyl)pyrrolidine-1-carboxylate was prepared according to the general procedure of Example 1, Step A, substituting (R)-tert-butyl 2-((S)-(4-chloro-3-fluorophenyl)(4-(2-(methylsulfonyl)pyrimidin-4-yl)-2-oxopyridin-1(2H)-yl)methyl)pyrrolidine-1-carboxylate for (S)-1-(2-(tert-butyldimethylsilyloxy)-1-(4-chloro-3-fluorophenyl)ethyl)-4-(2-(methylsulfonyl)pyrimidin-4-yl)pyridin-2(1H)-one. m/z (APCI-pos) (M+1)-Boc=484.1, 486.1.

Step G: 1-((S)-(4-Chloro-3-fluorophenyl)((R)-pyrrolidin-2-yl)methyl)-4-(2-((tetrahydro-2H-pyran-4-yl)amino)pyrimidin-4-yl)pyridin-2(1H)-one (74%, 2 steps) was prepared according to the general procedure of Example 2, Step B, substituting (R)-tert-butyl 2-((S)-(4-chloro-3-fluorophenyl)(2-oxo-4-(2-((tetrahydro-2H-pyran-4-yl)amino)pyrimidin-4-yl)pyridin-1(2H)-yl)methyl)pyrrolidine-1-carboxylate for 1-((S)-2-(tert-butyldimethylsilyloxy)-1-(4-chloro-3-fluorophenyl)ethyl)-4-(2-(((3S,4S)-3-fluorotetrahydro-2H-pyran-4-yl)amino)pyrimidin-4-yl)pyridin-2(1H)-one. $^1$H NMR (400 MHz, CDCl$_3$) δ 8.37 (d, J=5.0 Hz, 1H), 7.52 (d, J=7.0 Hz, 1H), 7.41-7.36 (m, 2H), 7.30 (m, 1H), 7.15 (s, 1H), 6.87 (d, J=5.2 Hz, 1H), 6.75 (m, 1H), 6.03 (d, J=9.0 Hz, 1H), 5.13 (d, J=7.6 Hz, 1H), 4.10 (m, 1H), 4.01 (m, 2H), 3.92 (m, 1H), 3.55 (m, 2H), 3.00 (m, 2H), 2.07 (m, 2H), 1.87 (m, 2H), 1.73 (m, 1H), 1.60 (m, 4H); m/z (APCI-pos) M+1=484.1, 486.1.

Example 11

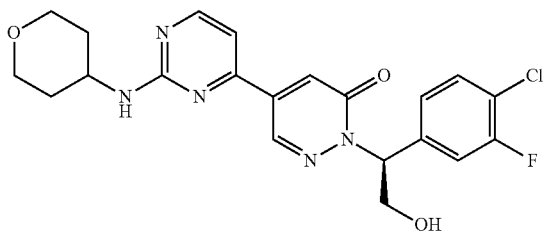 [SMILES: O=c1cc(-c2ccnc(NC3CCOCC3)n2)cnn1[C@H](CO)c1ccc(Cl)c(F)c1]

(S)-2-(1-(4-chloro-3-fluorophenyl)-2-hydroxyethyl)-5-(2-((tetrahydro-2H-pyran-4-yl)amino)pyrimidin-4-yl)pyridazin-3(2H)-one Step A: 1.0M KOt-Bu (2.64 mL, 2.64 mmol) in THF and tetrabutylammonium iodide (0.0749 g, 0.203 mmol) were added to a solution of 5-iodopyridazin-3(2H)-one (0.45 g, 2.03 mmol) in THF (10 mL). The mixture was stirred at room temperature for 10 minutes before (R)-2-(tert-butyldimethylsilyloxy)-1-(4-chloro-3-fluorophenyl)ethyl methanesulfonate (1.16 g, 3.04 mmol) was added as a solution in THF (10 mL). The reaction was heated to reflux for 90 hours, then cooled to room temperature and concentrated. The residue was taken up in ethyl acetate and washed with water (2×). The organics were dried, filtered and concentrated. The crude product was purified via column chromatography, eluting with hexanes/ethyl acetate (25:1) to give (S)-2-(2-(tert-butyldimethylsilyloxy)-1-(4-chloro-3-fluorophenyl)ethyl)-5-iodopyridazin-3(2H)-one (0.65 g, 63%). $^1$H NMR (400 MHz, CDCl$_3$) δ 7.98 (d, J=2.0 Hz, 1H), 7.45 (d, J=2.2 Hz, 1H), 7.35 (m, 1H), 7.23 (m, 1H), 7.16 (m, 1H), 6.09 (m, 1H), 4.34 (m, 1H), 4.01 (m, 1H), 0.81 (s, 9H), 0.01 (s, 3H), −0.01 (s, 3H).

Step B: A solution of (S)-2-(2-(tert-butyldimethylsilyloxy)-1-(4-chloro-3-fluorophenyl)ethyl)-5-iodopyridazin-3(2H)-one (0.402 g, 0.790 mmol), 2-(methylthio)-4-(tributylstannyl)pyrimidine (0.361 g, 0.869 mmol), copper(I) iodide (0.0150 g, 0.0790 mmol) and PdCl$_2$(PPh$_3$)$_2$ (0.0555 g, 0.0790 mmol) in NMP (4 mL) was heated to 120° C. under Ar for 16 hours. The reaction mixture was cooled to room temperature and diluted with ethyl acetate (200 mL). The organics were washed with brine (3×50 mL), dried, filtered and concentrated. The crude product was purified via column chromatography, eluting with hexanes/ethyl acetate (1:1) to give (S)-2-(1-(4-chloro-3-fluorophenyl)-2-hydroxyethyl)-5-(2-(methylthio)pyrimidin-4-yl)pyridazin-3(2H)-one (0.25 g, 79%). m/z (APCI-pos) M+1=393.0, 395.0.

Step C: (S)-2-(1-(4-Chloro-3-fluorophenyl)-2-hydroxyethyl)-5-(2-(methylsulfonyl)pyrimidin-4-yl)pyridazin-3(2H)-one (58%) was prepared according to the general procedure of Intermediate Example C, Step B, substituting (S)-2-(1-(4-chloro-3-fluorophenyl)-2-hydroxyethyl)-5-(2-(methylthio)pyrimidin-4-yl)pyridazin-3(2H)-one for (S)-1-(2-(tert-butyldimethylsilyloxy)-1-(4-chloro-3-fluorophenyl)ethyl)-4-(2-(methylthio)pyrimidin-4-yl)pyridin-2(1H)-one. m/z (APCI-pos) M+1=425.0, 427.0.

Step D: (S)-2-(1-(4-Chloro-3-fluorophenyl)-2-hydroxyethyl)-5-(2-((tetrahydro-2H-pyran-4-yl)amino)pyrimidin-4-yl)pyridazin-3(2H)-one (78%) was prepared according to the general procedure of Example 1, Step A, substituting (S)-2-(1-(4-chloro-3-fluorophenyl)-2-hydroxyethyl)-5-(2-(methylsulfonyl)pyrimidin-4-yl)pyridazin-3(2H)-one for (S)-1-(2-(tert-butyldimethylsilyloxy)-1-(4-chloro-3-fluorophenyl)ethyl)-4-(2-(methylsulfonyl)pyrimidin-4-yl)pyridin-2(1H)-one. $^1$H NMR (400 MHz, CD$_3$OD) δ 8.68 (d, J=2.2 Hz, 1H), 8.41 (d, J=5.2 Hz, 1H), 7.56 (d, J=2.2 Hz, 1H), 7.45 (m, 1H), 7.34 (m, 1H), 7.24 (m, 1H), 7.15 (d, J=5.4 Hz, 1H), 6.18 (m, 1H), 4.42 (m, 1H), 4.06-3.97 (m, 4H), 3.56 (m, 2H), 2.00 (m, 2H), 1.62 (m, 2H); m/z (APCI-pos) M+1=446.1, 448.1.

Example 12

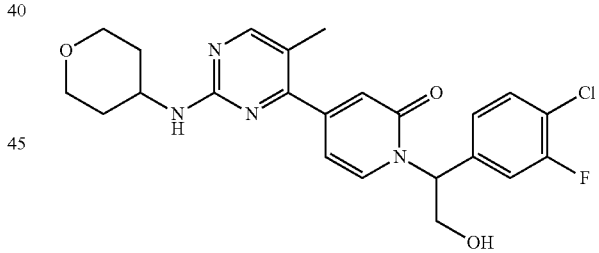

1-(1-(4-chloro-3-fluorophenyl)-2-hydroxyethyl)-4-(5-methyl-2-((tetrahydro-2H-pyran-4-yl)amino)pyrimidin-4-yl)pyridin-2(1H)-one Step A: Sodium carbonate (0.575 g, 5.43 mmol) was added to 2-fluoropyridin-4-ylboronic acid (0.306 g, 2.17 mmol) and 2,4-dichloro-5-methylpyrimidine (0.212 mL, 1.81 mmol) in dioxane/water (10 mL; 4:1), and the suspension was purged with nitrogen. PdCl$_2$(dppf)*DCM (0.0739 g, 0.0905 mmol) was added, and the vial was sealed and heated at 80° C. After 3 hours, the cooled reaction mixture was partitioned between water and EtOAc. The EtOAc was washed with brine, dried over MgSO$_4$, filtered, and evaporated to yield a crude product (0.50 g) as a solid. The crude product was absorbed on silica gel and chromatographed on a 50 g Biotage SNAP column with 1:1 hexane/EtOAc.

Fractions 16-34 contained 2-chloro-4-(2-fluoropyridin-4-yl)-5-methylpyrimidine (0.22 g, 0.984 mmol, 54.4% yield) with minor impurities.

Step B: Tetrahydro-2H-pyran-4-amine (0.109 g, 1.08 mmol) and N-ethyl-N-isopropylpropan-2-amine (0.258 mL, 1.48 mmol) were added to 2-chloro-4-(2-fluoropyridin-4-yl)-5-methylpyrimidine (0.22 g, 0.984 mmol) in DMA (2 mL). The mixture was heated in a microwave at 180° C. for 30 minutes. The reaction mixture was partitioned between water and EtOAc. The EtOAc was washed with water, brine, dried over MgSO₄, filtered, and evaporated to yield a crude product (0.28 g) as a film. The crude product was chromatographed on a 50 g Biotage SNAP column with EtOAc. Fractions 17-32 contained 4-(2-fluoropyridin-4-yl)-5-methyl-N-(tetrahydro-2H-pyran-4-yl)pyrimidin-2-amine (0.158 g, 0.548 mmol, 55.7% yield) as a solid.

Step C: 1M HCl (10 mL) was added to 4-(2-fluoropyridin-4-yl)-5-methyl-N-(tetrahydro-2H-pyran-4-yl)pyrimidin-2-amine (0.158 g, 0.548 mmol). The mixture was heated at reflux. After 2 hours, the cooled reaction mixture was neutralized with solid NaHCO₃. The resulting solid was collected by vacuum filtration and dried to afford 4-(5-methyl-2-(tetrahydro-2H-pyran-4-ylamino)pyrimidin-4-yl)pyridin-2(1H)-one (0.126 g, 0.440 mmol, 80.3% yield) as a solid.

Step D: 0.55 g PS-triphenylphosphine 1.99 mmol/g (0.289 g, 1.10 mmol) was added to 2-(tert-butyldimethylsilyloxy)-1-(4-chloro-3-fluorophenyl)ethanol (0.268 g, 0.880 mmol) in DCM (15 mL) cooled in ice. (E)-Diisopropyl diazene-1,2-dicarboxylate (0.216 mL, 1.10 mmol) was added dropwise to the mixture. After 10 minutes allowing the reaction mixture to warm to ambient temperature, a suspension of 4-(5-methyl-2-(tetrahydro-2H-pyran-4-ylamino)pyrimidin-4-yl)pyridin-2(1H)-one (0.126 g, 0.440 mmol) in DCM (5 mL) was added. The mixture was stirred at ambient temperature. After 4 hours, an additional 1 equivalent DIAD was added, and the mixture stirred overnight. The reaction mixture was filtered and evaporated. The residue was partitioned between water and EtOAc. The EtOAc was washed with brine, dried over MgSO₄, filtered, and evaporated to yield a crude product (0.64 g) as an oil. The crude product was chromatographed on a 50 g Biotage SNAP column with 2:1 EtOAc/hexane. Fractions 60-84 contained 1-(2-(tert-butyldimethylsilyloxy)-1-(4-chloro-3-fluorophenyl)ethyl)-4-(5-methyl-2-((tetrahydro-2H-pyran-4-yl)amino)pyrimidin-4-yl)pyridin-2(1H)-one (0.033 g, 0.0576 mmol, 13.1% yield) as a glass.

Step E: 1M Tetrabutylammonium fluoride in THF (0.173 mL, 0.173 mmol) was added to 1-(2-(tert-butyldimethylsilyloxy)-1-(4-chloro-3-fluorophenyl)ethyl)-4-(5-methyl-2-((tetrahydro-2H-pyran-4-yl)amino)pyrimidin-4-yl)pyridin-2(1H)-one (0.033 g, 0.0576 mmol) in THF (3 mL). The mixture was stirred at ambient temperature. After 1 hour, the reaction mixture was evaporated, and the residue was partitioned between water and EtOAc. The EtOAc was washed with brine, dried over MgSO₄, filtered, and evaporated to yield a crude product (0.0394 g) as a solid. The crude product was purified by chromatography on a 10 g Biotage SNAP column with 10:1 EtOAc/MeOH. Fractions 7-12 contained 1-(1-(4-chloro-3-fluorophenyl)-2-hydroxyethyl)-4-(5-methyl-2-((tetrahydro-2H-pyran-4-yl)amino)pyrimidin-4-yl)pyridin-2(1H)-one (0.0206 g, 0.0449 mmol, 78.0% yield) as a glass. ¹H NMR (400 MHz, CD₃OD) δ 8.21 (s, 1H), 7.82 (d, 1H), 7.50-7.46 (m, 1H), 7.35-7.31 (m, 1H), 7.21-7.18 (m, 1H), 6.72 (d, 1H), 6.59 (dd, 1H), 4.32-4.26 (m, 1H), 4.22-4.17 (m, 1H), 4.12-4.07 (m, 1H), 4.00-3.92 (m, 2H), 3.54-3.47 (m, 2H), 2.17 (s, 3H), 1.99-1.93 (m, 2H), 1.62-1.52 (m, 2H); m/z (APCI-pos) M+1=459.1.

Example 13

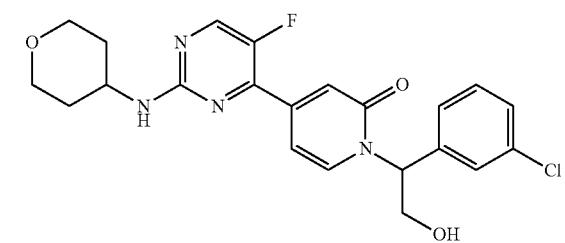 [SMILES: O=c1cc(-c2nc(NC3CCOCC3)ncc2F)ccn1C(CO)c1cccc(Cl)c1]

1-(1-(3-chlorophenyl)-2-hydroxyethyl)-4-(5-fluoro-2-((tetrahydro-2H-pyran-4-yl)amino)pyrimidin-4-yl)pyridin-2(1H)-one Step A: Triphenylphosphine (0.565 g, 2.15 mmol) was added to 2-(tert-butyldimethylsilyloxy)-1-(3-chlorophenyl)ethanol (0.494 g, 1.72 mmol; prepared as Intermediate Example I, Steps A and B, substituting (3-chlorophenyl)magnesium bromide for (4-chloro-3-fluorophenyl)magnesium bromide in Step A) in DCM (20 mL) cooled in ice. (E)-Diisopropyl diazene-1,2-dicarboxylate (0.423 mL, 2.15 mmol) was added dropwise to the mixture. After 10 minutes allowing the reaction mixture to warm to room temperature, the solution was added to 4-(5-fluoro-2-(tetrahydro-2H-pyran-4-ylamino)pyrimidin-4-yl)pyridin-2(1H)-one (0.25 g, 0.861 mmol), washing in with DCM (10 mL). The suspension was stirred at ambient temperature overnight. The reaction mixture was filtered, and the filtrate was evaporated to provide a crude product. The crude product was chromatographed on a 50 g Biotage SNAP column with 2:1 EtOAc/hexane. Fractions 20-36 contained 1-(2-(tert-butyldimethylsilyloxy)-1-(3-chlorophenyl)ethyl)-4-(5-fluoro-2-(tetrahydro-2H-pyran-4-ylamino)pyrimidin-4-yl)pyridin-2(1H)-one (0.0307 g, 0.0549 mmol, 6.38% yield) as a film.

Step B: 1M Tetrabutylammonium fluoride in THF (0.165 mL, 0.165 mmol) was added to 1-(2-(tert-butyldimethylsilyloxy)-1-(3-chlorophenyl)ethyl)-4-(5-fluoro-2-(tetrahydro-2H-pyran-4-ylamino)pyrimidin-4-yl)pyridin-2(1H)-one (0.0307 g, 0.0549 mmol) in THF (3 mL). The mixture was stirred at room temperature for 30 minutes. The reaction mixture was evaporated, and the residue was partitioned between water and EtOAc. The EtOAc was washed with brine, dried over MgSO₄, filtered, and evaporated to yield a crude product as a film. The crude product was purified by chromatography on a 10 g Biotage SNAP column with EtOAc. Fractions 17-32 contained a glass (16.2 mg). The glass was triturated with water and dried to afford 1-(1-(3-chlorophenyl)-2-hydroxyethyl)-4-(5-fluoro-2-((tetrahydro-2H-pyran-4-yl)amino)pyrimidin-4-yl)pyridin-2(1H)-one (0.0129 g, 0.0290 mmol, 52.8% yield) as a film. ¹H NMR (400 MHz, CD₃OD) δ 8.33 (d, 1H), 7.84 (d, 1H), 7.43-7.24 (m, 5H), 7.03-6.99 (m, 1H), 6.16-6.12 (m, 1H), 4.32-4.27 (m, 1H), 4.22-4.17 (m, 1H), 4.02-3.94 (m, 3H), 3.57-3.49 (m, 2H), 2.02-1.96 (m, 2H), 1.64-1.54 (m, 2H); m/z (APCI-pos) M+1=445.1.

Example 14

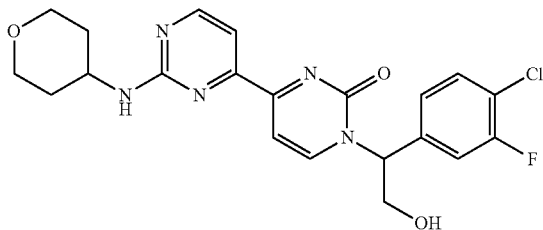 [SMILES: O=c1nc(-c2ccnc(NC3CCOCC3)n2)ccn1C(CO)c1ccc(Cl)c(F)c1]

1-(1-(4-chloro-3-fluorophenyl)-2-hydroxyethyl)-4-(2-((tetrahydro-2H-pyran-4-yl)amino)pyrimidin-4-yl)pyrimidin-2(1H)-one Step A: 1,1-Dimethoxy-N,N-dimethylmethanamine (9.87 mL, 74.3 mmol) was added to 1-(2-(methylthio)pyrimidin-4-yl)ethanone (0.50 g, 2.97 mmol). The mixture was heated at reflux overnight. The reaction mixture was concentrated to half volume and treated with $Et_2O$. The resulting solid was collected by vacuum filtration to yield the desired (E)-3-(dimethylamino)-1-(2-(methylthio)pyrimidin-4-yl)prop-2-en-1-one (0.46 g, 2.06 mmol, 69.3% yield).

Step B: A well-stirred solid mixture of (E)-3-(dimethylamino)-1-(2-(methylthio)pyrimidin-4-yl)prop-2-en-1-one (0.206 g, 0.923 mmol), urea (1.11 g, 18.5 mmol), and 60% sodium hydride (0.0922 g, 2.31 mmol) was heated in a sand bath preheated to 140° C. for 3 minutes until complete melting and then 2 additional minutes as a melt. The cooled reaction mixture was treated with water. The solution was acidified to pH 3 with 1M HCl, and the resulting solid was collected by vacuum filtration to yield a crude product (0.082 g). The crude was chromatographed on a 50 g Biotage SNAP column with 10:1 DCM/MeOH. Fractions 16-48 contained the desired 4-(2-(methylthio)pyrimidin-4-yl)pyrimidin-2(1H)-one (0.04 g, 0.182 mmol, 19.7% yield) as a solid.

Step C: Potassium 2-methylpropan-2-olate (0.026 g, 0.24 mmol) and tetrabutylammonium iodide (0.0067 g, 0.018 mmol) were added to 4-(2-(methylthio)pyrimidin-4-yl)pyrimidin-2(1H)-one (0.040 g, 0.18 mmol) suspended in THF (4 mL) cooled in ice. After 10 minutes, a solution of 2-(tert-butyldimethylsilyloxy)-1-(4-chloro-3-fluorophenyl)ethyl methanesulfonate (0.10 g, 0.27 mmol) in THF (1 mL) was added. The mixture was stirred at room temperature overnight and then heated at 90° C. for 3 days. Due to incomplete reaction, the material was transferred to a microwave vial and heated in a microwave at 130° C. for 1 hour. The reaction mixture was evaporated, and the residue was chromatographed on a 10 g Biotage SNAP column with 1:1 hexane/EtOAc. Fractions 8-13 contained the desired 1-(2-(tert-butyldimethylsilyloxy)-1-(4-chloro-3-fluorophenyl)ethyl)-4-(2-(methylthio)pyrimidin-4-yl)pyrimidin-2(1H)-one (0.030 g, 0.059 mmol, 33% yield) as a film.

Step D: 3-Chlorobenzoperoxoic acid (0.0306 g, 0.177 mmol) was added to 1-(2-(tert-butyldimethylsilyloxy)-1-(4-chloro-3-fluorophenyl)ethyl)-4-(2-(methylthio)pyrimidin-4-yl)pyrimidin-2(1H)-one (0.030 g, 0.0592 mmol) in DCM (5 mL). The mixture was stirred at room temperature. After 2 hours, the reaction mixture was evaporated. The residue was taken up in EtOAc, washed twice with a mixture of saturated aqueous $Na_2S_2O_3$ and saturated aqueous $NaHCO_3$, brine, dried over $MgSO_4$, filtered, and evaporated to yield 1-(2-(tert-butyldimethylsilyloxy)-1-(4-chloro-3-fluorophenyl)ethyl)-4-(2-(methylsulfonyl)pyrimidin-4-yl)pyrimidin-2(1H)-one (0.0349 g, 0.0647 mmol, 109% yield).

Step E: Tetrahydro-2H-pyran-4-amine (0.0327 g, 0.324 mmol) was added to 1-(2-(tert-butyldimethylsilyloxy)-1-(4-chloro-3-fluorophenyl)ethyl)-4-(2-(methylsulfonyl)pyrimidin-4-yl)pyrimidin-2(1H)-one (0.0349 g, 0.0647 mmol) in THF (5 mL). The mixture was heated in a microwave at 120° C. for 1 hour and then at 130° C. for 1.5 hours. The reaction mixture was evaporated, and the residue partitioned between EtOAc and water. The EtOAc was washed with brine, dried over $MgSO_4$, filtered, and evaporated to yield a crude product (30.2 mg) as a film. The crude product was chromatographed on a 10 g Biotage SNAP column with 2:1 EtOAc/hexane. Fractions 23-34 contained the desired 1-(2-(tert-butyldimethylsilyloxy)-1-(4-chloro-3-fluorophenyl)ethyl)-4-(2-((tetrahydro-2H-pyran-4-yl)amino)pyrimidin-4-yl)pyrimidin-2(1H)-one (0.0048 g, 0.00857 mmol, 13.2% yield) as a film.

Step F: 1M Tetrabutylammonium fluoride in THF (0.026 mL, 0.026 mmol) was added to 1-(2-(tert-butyldimethylsilyloxy)-1-(4-chloro-3-fluorophenyl)ethyl)-4-(2-((tetrahydro-2H-pyran-4-yl)amino)pyrimidin-4-yl)pyrimidin-2(1H)-one (0.0048 g, 0.0086 mmol) in THF (2 mL). The mixture was stirred at room temperature for 1 hour. The reaction mixture was evaporated, and the residue was partitioned between water and EtOAc. The EtOAc was washed with brine, dried over $MgSO_4$, filtered, and evaporated to yield a crude product (2.8 mg) as a film. The crude product was purified by chromatography on a preparative thin layer chromatography ("TLC") plate, eluting with 10:1 DCM/MeOH. The major band contained the desired 1-(1-(4-chloro-3-fluorophenyl)-2-hydroxyethyl)-4-(2-(tetrahydro-2H-pyran-4-ylamino)pyrimidin-4-yl)pyrimidin-2(1H)-one (0.0006 g, 0.0013 mmol, 16% yield). m/z (APCI-pos) M+1=446.1.

Example 15

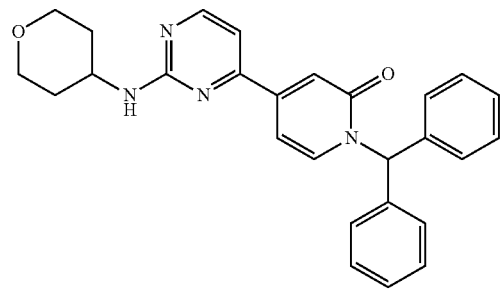 [SMILES: O=c1cc(-c2ccnc(NC3CCOCC3)n2)ccn1C(c1ccccc1)c1ccccc1]

1-benzhydryl-4-(2-((tetrahydro-2H-pyran-4-ylamino)pyrimidin-4-yl)pyridin-2(1H)-one Step A: 60% Sodium hydride (0.036 g, 0.89 mmol) was added to a suspension of (bromomethylene)dibenzene (0.19 g, 0.75 mmol) and 4-(2-(methylthio)pyrimidin-4-yl)pyridin-2(1H)-one (0.15 g, 0.68 mmol) in DMF (3 mL). The mixture was stirred at ambient temperature overnight. The mixture was then heated at 50° C. overnight. The reaction mixture was diluted with dilute aqueous NaCl and extracted with EtOAc. The EtOAc was washed with brine, dried over $MgSO_4$, filtered, and evaporated to yield a crude product (0.28 g) as a film. This was chromatographed on a 10 g Biotage SNAP column with 1:1 EtOAc/hexane. Fractions 13-22 contained the desired 1-benzhydryl-4-(2-(methylthio)pyrimidin-4-yl)pyridin-2(1H)-one (0.11 g, 0.29 mmol, 42% yield) as a solid foam.

Step B: 3-Chlorobenzoperoxoic acid (0.15 g, 0.86 mmol) was added to 1-benzhydryl-4-(2-(methylthio)pyrimidin-4-yl)pyridin-2(1H)-one (0.11 g, 0.29 mmol) in DCM (10 mL). The mixture was stirred at ambient temperature. After 5 hours, the reaction mixture was evaporated. The residue was taken up in EtOAc, washed twice with a mixture of saturated aqueous $Na_2S_2O_3$ and saturated aqueous $NaHCO_3$, brine, dried over $MgSO_4$, filtered, and evaporated to yield the desired 1-benzhydryl-4-(2-(methylsulfonyl)pyrimidin-4-yl)pyridin-2(1H)-one (0.12 g, 0.29 mmol, 101% yield) as a film.

Step C: Tetrahydro-2H-pyran-4-amine (0.20 g, 2.0 mmol) was added to 1-benzhydryl-4-(2-(methylsulfonyl)pyrimidin-4-yl)pyridin-2(1H)-one (0.12 g, 0.29 mmol) in DMA (3 mL) in a microwave vial. The mixture was heated at 120° C. for 1 hour in a microwave. The reaction mixture was diluted with water and extracted with EtOAc. The EtOAc was washed with water, twice with brine, dried over $MgSO_4$, filtered, and evaporated to yield a crude product (0.09 g) as a film. This was chromatographed on a 10 g Biotage SNAP column with EtOAc. Fractions 9-20 contained a film (0.0764 g). This was triturated with water, dried, then triturated with hexane and dried to afford the desired 1-benzhydryl-4-(2-((tetrahydro-2H-pyran-4-yl)amino)pyrimidin-4-yl)pyridin-2(1H)-one (0.072 g, 0.16 mmol, 57% yield) as a film. $^1$H NMR (400 MHz, $CDCl_3$) δ 8.38 (d, 1H), 7.52 (s, 1H), 7.40-7.15 (m, 9H), 6.91 (d, 1H), 6.76-6.72 (m, 1H), 5.25-5.21 (m, 1H), 4.15-4.06 (m, 1H), 4.02-3.96 (m, 2H), 3.59-3.51 (m, 2H), 2.09-2.03 (m, 2H), 1.62-1.52 (m, 2H); m/z (APCI-pos) M+1=439.2.

Example 16

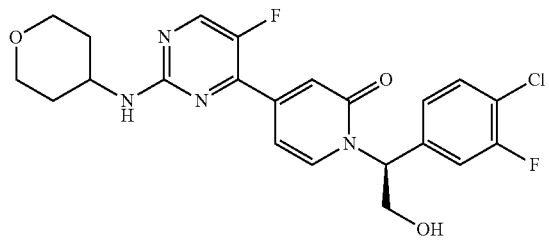 [SMILES: O=c1cc(-c2nc(NC3CCOCC3)ncc2F)ccn1[C@H](CO)c1ccc(Cl)c(F)c1]

(S)-1-(1-(4-chloro-3-fluorophenyl)-2-hydroxyethyl)-4-(5-fluoro-2-((tetrahydro-2H-pyran-4-yl)amino)pyrimidin-4-yl)pyridin-2(1H)-one Step A: 1.0M Potassium 2-methylpropan-2-olate in THF (0.49 mL, 0.49 mmol) and tetrabutylammonium iodide (0.017 g, 0.045 mmol) were added to 4-(5-fluoro-2-(tetrahydro-2H-pyran-4-ylamino)pyrimidin-4-yl)pyridin-2(1H)-one (0.13 g, 0.45 mmol) in THF (8 mL) cooled in ice. The mixture was stirred 10 minutes. A solution of (R)-2-(tert-butyldimethylsilyloxy)-1-(4-chloro-3-fluorophenyl)ethyl methanesulfonate (0.31 g, 0.81 mmol) in THF (2 mL) was added, and the mixture was heated at 60° C. in a sealed vial overnight. The reaction mixture was evaporated, and the residue was partitioned between water and EtOAc. The EtOAc was washed with brine, dried over $MgSO_4$, filtered, and evaporated to yield a crude product (0.31 g) as an oil. This was chromatographed on a 50 g Biotage SNAP column with 4:1 DCM/EtOAc, then 1:1 DCM/EtOAc. Fractions 76-96 contained the desired (S)-1-(2-(tert-butyldimethylsilyloxy)-1-(4-chloro-3-fluorophenyl)ethyl)-4-(5-fluoro-2-((tetrahydro-2H-pyran-4-yl)amino)pyrimidin-4-yl)pyridin-2(1H)-one (0.08 g, 0.14 mmol, 31% yield) as a film.

Step B: 1M Tetrabutylammonium fluoride in THF (0.42 mL, 0.42 mmol) was added to (S)-1-(2-(tert-butyldimethylsilyloxy)-1-(4-chloro-3-fluorophenyl)ethyl)-4-(5-fluoro-2-((tetrahydro-2H-pyran-4-yl)amino)pyrimidin-4-yl)pyridin-2(1H)-one (0.08 g, 0.14 mmol) in THF (10 mL). The mixture was stirred at room temperature. After 1 hour, the reaction mixture was evaporated, and the residue was partitioned between dilute aqueous NaCl and EtOAc. The EtOAc was washed with water, brine, dried over $MgSO_4$, filtered, and evaporated to yield a crude product (0.10 g) as a film. The crude product was purified by chromatography on a 10 g Biotage SNAP column with EtOAc. Fractions 13-23 contained the desired (S)-1-(1-(4-chloro-3-fluorophenyl)-2-hydroxyethyl)-4-(5-fluoro-2-((tetrahydro-2H-pyran-4-yl)amino)pyrimidin-4-yl)pyridin-2(1H)-one (0.050 g, 0.11 mmol, 78% yield) as a glass. $^1$H NMR (400 MHz, $CDCl_3$) δ 8.24 (d, 1H), 7.42-7.37 (m, 2H), 7.25-7.19 (m, 2H), 7.12-7.08 (m, 1H), 6.83-6.80 (m, 1H), 6.23-6.19 (m, 1H), 5.27-5.24 (m, 1H), 4.30-4.25 (m, 1H), 4.15-4.09 (m, 1H), 4.03-3.95 (m, 3H), 3.57-3.50 (m, 2H), 2.05-2.00 (m, 2H), 1.61-1.50 (m, 2H).

Example 17

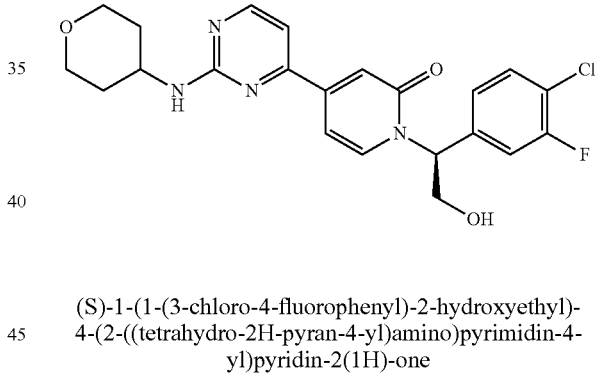

(S)-1-(1-(3-chloro-4-fluorophenyl)-2-hydroxyethyl)-4-(2-((tetrahydro-2H-pyran-4-yl)amino)pyrimidin-4-yl)pyridin-2(1H)-one Step A: 1.0M Potassium 2-methylpropan-2-olate in THF (2.02 mL, 2.02 mmol) and tetrabutylammonium iodide (0.0573 g, 0.155 mmol) were added to a suspension of 4-(2-(methylthio)pyrimidin-4-yl)pyridin-2(1H)-one (0.340 g, 1.55 mmol) in THF (20 mL) cooled in ice. After 10 minutes stirring in ice, a solution of (R)-2-(tert-butyldimethylsilyloxy)-1-(3-chloro-4-fluorophenyl)ethyl methanesulfonate (1.07 g, 2.79 mmol) in THF (5 mL) was added. The mixture was heated at 60° C. overnight. The reaction mixture was evaporated, and the residue partitioned between water and EtOAc. The EtOAc was washed with brine, dried over $MgSO_4$, filtered, and evaporated to yield a crude product (1.14 g) as an oil. This was chromatographed on a 50 g Biotage SNAP column with 4:1 DCM/EtOAc. Fractions 19-46 contained the desired (S)-1-(2-(tert-butyldimethylsilyloxy)-1-(3-chloro-4-fluorophenyl)ethyl)-4-(2-(methylthio)pyrimidin-4-yl)pyridin-2(1H)-one (0.45 g, 0.889 mmol, 57.3% yield) as a film.

Step B: 3-Chlorobenzoperoxoic acid (0.46 g, 2.7 mmol) was added to (S)-1-(2-(tert-butyldimethylsilyloxy)-1-(3- chloro-4-fluorophenyl)ethyl)-4-(2-(methylthio)pyrimidin-4-yl)pyridin-2(1H)-one (0.45 g, 0.89 mmol) in DCM (20 mL). The mixture was stirred at room temperature for 3 hours. The reaction mixture was evaporated, and the residue taken up in EtOAc, washed twice with a mixture of saturated aqueous Na$_2$S$_2$O$_3$ and saturated aqueous NaHCO$_3$, brine, dried over MgSO$_4$, filtered, and evaporated to yield the desired (S)-1-(2-(tert-butyldimethylsilyloxy)-1-(3-chloro-4-fluorophenyl)ethyl)-4-(2-(methylsulfonyl)pyrimidin-4-yl)pyridin-2(1H)-one (0.48 g, 0.89 mmol, 100% yield) as a film.

Step C: Tetrahydro-2H-pyran-4-amine (0.45 g, 4.5 mmol) was added to (S)-1-(2-(tert-butyldimethylsilyloxy)-1-(3-chloro-4-fluorophenyl)ethyl)-4-(2-(methylsulfonyl)pyrimidin-4-yl)pyridin-2(1H)-one (0.48 g, 0.89 mmol) in DMA (4 mL) in a microwave vial. The mixture was heated at 120° C. for 1 hour in a microwave. The reaction mixture was diluted with water and extracted with EtOAc. The EtOAc was washed three times with dilute aqueous NaCl, water, twice with brine, dried over MgSO$_4$, filtered, and evaporated to yield the desired (S)-1-(2-(tert-butyldimethylsilyloxy)-1-(3-chloro-4-fluorophenyl)ethyl)-4-(2-((tetrahydro-2H-pyran-4-yl)amino)pyrimidin-4-yl)pyridin-2(1H)-one (0.46 g, 0.82 mmol, 92% yield) as a film.

Step D: 1M Tetrabutylammonium fluoride in THF (2.5 mL, 2.5 mmol) was added to (S)-1-(2-(tert-butyldimethylsilyloxy)-1-(3-chloro-4-fluorophenyl)ethyl)-4-(2-((tetrahydro-2H-pyran-4-yl)amino)pyrimidin-4-yl)pyridin-2(1H)-one (0.46 g, 0.82 mmol) in THF (40 mL). The mixture was stirred at room temperature. After 45 minutes, the reaction mixture was evaporated, and the residue was partitioned between dilute aqueous NaCl and EtOAc. The EtOAc was washed with water, brine, dried over MgSO$_4$, filtered, and evaporated to yield a crude product (0.43 g) as a film. The crude product was purified by chromatography on a 50 g Biotage SNAP column with 10:1 EtOAc/MeOH. Fractions 19-29 contained the desired (S)-1-(1-(3-chloro-4-fluorophenyl)-2-hydroxyethyl)-4-(2-((tetrahydro-2H-pyran-4-yl)amino)pyrimidin-4-yl)pyridin-2(1H)-one (0.25 g, 0.56 mmol, 68% yield) as a solid foam. $^1$H NMR (400 MHz, CDCl$_3$) δ 8.38 (d, 1H), 7.47-7.44 (m, 1H), 7.38 (d, 1H), 7.29-7.24 (m, 1H), 7.18-7.14 (m, 1H), 6.88 (d, 1H), 6.80-6.77 (m, 1H), 6.21-6.17 (m, 1H), 5.17-5.14 (m, 1H), 4.32-4.29 (m, 2H), 4.15-4.08 (m, 2H), 4.03-3.98 (m, 2H), 3.60-3.52 (m, 2H), 2.70-2.66 (m, 1H), 2.09-2.03 (m, 2H), 1.63-1.53 (m, 2H); m/z (APCI-pos) M+1=445.1; 81.6% e.e. by chiral HPLC (Chiral Tech, column OD-H, 4.6 mm×250 mm, 5 u, 15% ethanol/85% hexanes, 1 mL/minute).

Example 18

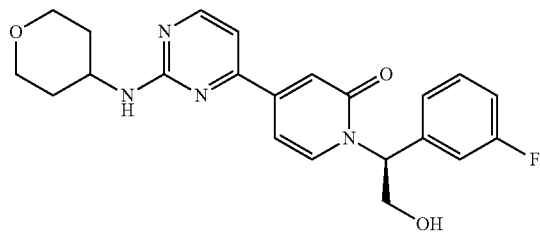 [SMILES: O=c1cc(-c2ccnc(NC3CCOCC3)n2)ccn1[C@H](CO)c1cccc(F)c1]

(S)-1-(1-(3-fluorophenyl)-2-hydroxyethyl)-4-(2-((tetrahydro-2H-pyran-4-yl)amino)pyrimidin-4-yl)pyridin-2(1H)-one Step A: 1M Potassium 2-methylpropan-2-olate in THF (0.815 mL, 0.815 mmol; solution) and tetrabutylammonium iodide (0.0251 g, 0.0679 mmol) were added to 4-(2-((tetrahydro-2H-pyran-4-yl)amino)pyrimidin-4-yl)pyridin-2(1H)-one (0.185 g, 0.679 mmol) suspended in dioxane (10 mL) in a sealed vial. After 10 minutes stirring, a solution of (R)-2-(tert-butyldimethylsilyloxy)-1-(3-fluorophenyl)ethyl methanesulfonate (0.355 g, 1.02 mmol; prepared as described in Intermediate Example B substituting 3-fluorobenzaldehyde for 4-chloro-3-fluorobenzaldehyde in Step A) in dioxane (2 mL) was added. The mixture was heated at 95° C. overnight. The reaction mixture was diluted with water and extracted with EtOAc. The EtOAc was washed with water, brine, dried over MgSO$_4$, filtered, and evaporated to yield a crude product (0.45 g) as an oil. The crude product was chromatographed on a 50 g Biotage SNAP column with 4:1 EtOAc/hexane. Fractions 42-84 contained the desired (S)-1-(2-(tert-butyldimethylsilyloxy)-1-(3-fluorophenyl)ethyl)-4-(2-((tetrahydro-2H-pyran-4-yl)amino)pyrimidin-4-yl)pyridin-2(1H)-one (0.14 g, 0.267 mmol, 39.3% yield) as a glass.

Step B: 1M Tetrabutylammonium fluoride in THF (0.800 mL, 0.800 mmol) to (S)-1-(2-(tert-butyldimethylsilyloxy)-1-(3-fluorophenyl)ethyl)-4-(2-((tetrahydro-2H-pyran-4-yl)amino)pyrimidin-4-yl)pyridin-2(1H)-one (0.14 g, 0.267 mmol) in THF (10 mL). The mixture was stirred at room temperature for 20 minutes. The reaction mixture was evaporated, and the residue was partitioned between dilute aqueous NaCl and EtOAc. The EtOAc was washed with water, brine, dried over MgSO$_4$, filtered, and evaporated to yield a crude product (0.17 g) as a film. The crude product was purified by chromatography on a 10 g Biotage SNAP column with 10:1 EtOAc/MeOH. Fractions 7-11 contained the desired (S)-1-(1-(3-fluorophenyl)-2-hydroxyethyl)-4-(2-((tetrahydro-2H-pyran-4-yl)amino)pyrimidin-4-yl)pyridin-2(1H)-one (0.100 g, 0.244 mmol, 91.3% yield) as a film. $^1$H NMR (400 MHz, CDCl$_3$) δ 8.31 (d, 1H), 7.47 (d, 1H), 7.32-7.28 (m, 1H), 7.20-7.06 (m, 3H), 6.80 (d, 1H), 6.78-6.76 (m, 1H), 6.38-6.34 (m, 1H), 5.34-5.31 (m, 1H), 4.35-4.28 (m, 3H), 4.15-4.09 (m, 2H), 4.08-3.96 (m, 2H), 3.58-3.50 (m, 2H), 2.07-2.00 (m, 2H), 1.62-1.51 (m, 2H); m/z (APCI-pos) M+1=411.1; 86% e.e. by chiral HPLC (Chiral Tech, column OD-H, 4.6 mm×250 mm, 5 u, 20% ethanol/80% hexanes, 1 mL/minute).

Example 19

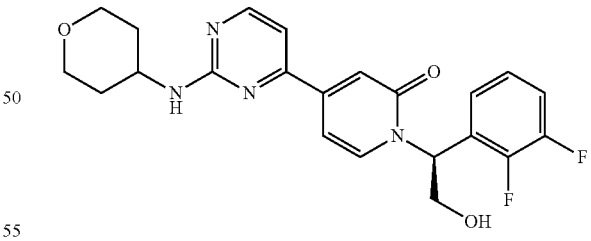

(S)-1-(1-(2,3-difluorophenyl-2-hydroxyethyl)-4-(2-((tetrahydro-2H-pyran-4-yl)amino)pyrimidin-4-yl)pyridin-2(1H)-one Step A: 1M Potassium 2-methylpropan-2-olate in THF (0.815 mL, 0.815 mmol; solution) and tetrabutylammonium iodide (0.0251 g, 0.0679 mmol) were added to 4-(2-(tetrahydro-2H-pyran-4-ylamino)pyrimidin-4-yl)pyridin-2(1H)-one (0.185 g, 0.679 mmol) suspended in dioxane (10 mL) in a sealed vial. After 10 minutes stirring, a solution of (R)-2-

(tert-butyldimethylsilyloxy)-1-(2,3-difluorophenyl)ethyl methanesulfonate (0.355 g, 1.02 mmol; prepared as described in Intermediate Example B substituting 2,3-difluorobenzaldehyde for 4-chloro-3-fluorobenzaldehyde in Step A) in dioxane (2 mL) was added. The mixture was heated at 95° C. overnight. The reaction mixture was diluted with water and extracted with EtOAc. The EtOAc was washed with water, brine, dried over MgSO$_4$, filtered, and evaporated to yield a crude product (0.45 g) as an oil. The crude product was chromatographed on a 50 g Biotage SNAP column with 4:1 EtOAc/hexane. Fractions 42-84 contained the desired (S)-1-(2-(tert-butyldimethylsilyloxy)-1-(2,3-difluorophenyl)ethyl)-4-(2-((tetrahydro-2H-pyran-4-yl)amino)pyrimidin-4-yl)pyridin-2(1H)-one (0.14 g, 0.267 mmol, 39.3% yield) as a glass.

Step B: 1M Tetrabutylammonium fluoride in THF (1.00 mL, 1.00 mmol) was added to (S)-1-(2-(tert-butyldimethylsilyloxy)-1-(2,3-difluorophenyl)ethyl)-4-(2-((tetrahydro-2H-pyran-4-yl)amino)pyrimidin-4-yl)pyridin-2(1H)-one (0.18 g, 0.33 mmol) in THF (10 mL). The mixture was stirred at room temperature for 20 minutes. The reaction mixture was evaporated, and the residue was partitioned between dilute aqueous NaCl and EtOAc. The EtOAc was washed with water, brine, dried over MgSO$_4$, filtered, and evaporated to yield a crude product (0.15 g) as a film. The crude product was purified by chromatography on a 10 g Biotage SNAP column with 10:1 EtOAc/MeOH. Fractions 7-11 contained the desired (S)-1-(1-(2,3-difluorophenyl)-2-hydroxyethyl)-4-(2-((tetrahydro-2H-pyran-4-yl)amino)pyrimidin-4-yl)pyridin-2(1H)-one (0.091 g, 0.21 mmol, 64% yield) as a film. $^1$H NMR (400 MHz, CDCl$_3$) δ 8.31 (d, 1H), 7.43 (d, 1H), 7.36-7.28 (m, 1H), 7.15-7.08 (m, 3H), 7.04-6.98 (m, 1H), 6.80 (d, 1H), 6.77-6.74 (m, 1H), 6.30-6.26 (m, 1H), 5.46-5.43 (m, 1H), 4.41 (br s, 1H), 4.32-4.23 (m, 2H), 4.25-4.19 (m, 2H), 4.18-4.02 (m, 1H), 4.02-3.96 (m, 1H), 3.57-3.50 (m, 2H), 2.06-2.00 (m, 2H), 1.62-1.51 (m, 2H); m/z (APCI-pos) M+1=429.1; 83% e.e. by chiral HPLC (Chiral Tech, column OD-H, 4.6 mm×250 mm, 5 u, 20% ethanol/80% hexanes, 1 mL/minute).

Example 20

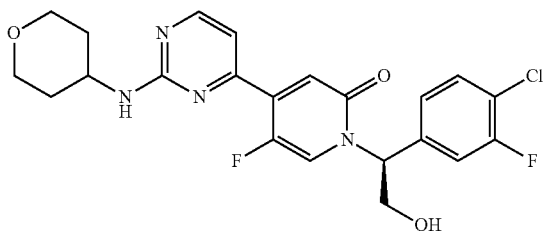 [SMILES: O=c1cc(-c2ccnc(NC3CCOCC3)n2)c(F)cn1[C@H](CO)c1ccc(Cl)c(F)c1]

(S)-1-(1-(4-chloro-3-fluorophenyl)-2-hydroxyethyl)-5-fluoro-4-(2-((tetrahydro-2H-pyran-4-yl)amino)pyrimidin-4-yl)pyridin-2(1H)-one Step A: Sodium carbonate (1.6 g, 15 mmol) was added to 5-fluoro-2-methoxypyridin-4-ylboronic acid (1.0 g, 6.0 mmol) and 2,4-dichloropyrimidine (0.75 g, 5.0 mmol) in 4:1 dioxane/water (25 mL), and the suspension was purged with argon. PdCl$_2$(dppf)*DCM (0.21 g, 0.25 mmol) was added, and the mixture was heated at 80° C. under argon overnight. The reaction mixture was diluted with water, and the resulting solid was collected by vacuum filtration, washed with water, and dried to provide the desired 2-chloro-4-(5-fluoro-2-methoxypyridin-4-yl)pyrimidine (1.2 g, 5.0 mmol, 99% yield) as a solid.

Step B: Tetrahydro-2H-pyran-4-amine (0.101 g, 1.00 mmol) and N-ethyl-N-isopropylpropan-2-amine (0.188 mL, 1.08 mmol) were added to 2-chloro-4-(5-fluoro-2-methoxypyridin-4-yl)pyrimidine (0.20 g, 0.835 mmol) dissolved in 2-butanol (5 mL) in a vial. The vial was sealed and heated at 100° C. overnight. The mixture was evaporated, and the dark residue was partitioned between EtOAc and water. The EtOAc was washed with brine, dried over MgSO$_4$, filtered, and evaporated to yield a crude product (0.25 g) as an oil. This was chromatographed on a 50 g Biotage SNAP column with 2:1 EtOAc/hexane. Fractions 22-48 contained the desired 4-(5-fluoro-2-methoxypyridin-4-yl)-N-(tetrahydro-2H-pyran-4-yl)pyrimidin-2-amine (0.0992 g, 0.326 mmol, 39.1% yield) as a solid.

Step C: Iodotrimethylsilane (0.186 mL, 1.30 mmol) was added dropwise to a solution of 4-(5-fluoro-2-methoxypyridin-4-yl)-N-(tetrahydro-2H-pyran-4-yl)pyrimidin-2-amine (0.0992 g, 0.3260 mmol) in acetonitrile (6 mL) in a vial at room temperature. The sealed vial was heated at 80° C. overnight. The reaction mixture was treated with MeOH (about 2 mL) and some saturated aqueous NaHCO$_3$. The mixture was concentrated, and the aqueous residue was treated dropwise with 1M HCl until a tan precipitate formed (pH 2). This was extracted with 2 portions 10% isopropyl alcohol ("IPA") in DCM. The combined organics were dried over MgSO$_4$, filtered, and evaporated to yield 5-fluoro-4-(2-((tetrahydro-2H-pyran-4-yl)amino)pyrimidin-4-yl)pyridin-2(1H)-one (0.0293 g, 0.1009 mmol, 30.96% yield) as a solid.

Step D: Tetrabutylammonium iodide (0.00186 g, 0.00505 mmol) and 1M potassium 2-methylpropan-2-olate in THF (0.121 mL, 0.121 mmol) were added to 5-fluoro-4-(2-((tetrahydro-2H-pyran-4-yl)amino)pyrimidin-4-yl)pyridin-2(1H)-one (0.0293 g, 0.101 mmol) in THF (3 mL). After 10 minutes stirring at room temperature, a solution of (R)-2-(tert-butyldimethylsilyloxy)-1-(4-chloro-3-fluorophenyl)ethyl methanesulfonate (0.0541 g, 0.141 mmol) in THF (2 mL) was added. The mixture was heated at reflux for 2 hours. The reaction mixture was partitioned between water and EtOAc. The EtOAc was washed with brine, dried over MgSO$_4$, filtered, and evaporated to yield a crude product (0.12 g) as a film. This was chromatographed on a 1 g Sep-pack column with 1:1 hexane/EtOAc. Fractions 8-16 contained the desired (S)-1-(2-(tert-butyldimethylsilyloxy)-1-(4-chloro-3-fluorophenyl)ethyl)-5-fluoro-4-(2-((tetrahydro-2H-pyran-4-yl)amino)pyrimidin-4-yl)pyridin-2(1H)-one (0.0036 g, 0.00624 mmol, 6.18% yield).

Step E: 1M Tetrabutylammonium fluoride in THF (0.019 mL, 0.019 mmol) was added to (S)-1-(2-(tert-butyldimethylsilyloxy)-1-(4-chloro-3-fluorophenyl)ethyl)-5-fluoro-4-(2-((tetrahydro-2H-pyran-4-yl)amino)pyrimidin-4-yl)pyridin-2(1H)-one (0.0036 g, 0.0062 mmol) in THF (1 mL). After 10 minutes, the reaction mixture was evaporated, and the residue was partitioned between EtOAc and dilute NaCl. The EtOAc was washed with brine, dried over MgSO$_4$, filtered, and evaporated to yield a crude product (0.0092 g) as a film. This was chromatographed on a 1 g silica Sep-pack with 10:1 EtOAc/MeOH. Fractions 2-4 contained the desired (S)-1-(1-(4-chloro-3-fluorophenyl)-2-hydroxyethyl)-5-fluoro-4-(2-((tetrahydro-2H-pyran-4-yl)amino)pyrimidin-4-yl)pyridin-2(1H)-one (0.0018 g, 0.0039 mmol, 62% yield) as a film. $^1$H NMR (400 MHz, CDCl$_3$) δ 8.38 (d, 1H), 7.46-7.42 (m, 1H), 7.34 (d, 1H), 7.27-7.20 (m, 2H), 7.14-7.11 (m, 1H), 6.93-6.90 (m, 1H), 6.20-6.12 (m, 1H), 5.22-5.19 (m, 1H), 4.31 (d, 2H), 4.15-4.09 (m, 2H), 4.03-3.97 (m, 2H), 3.60-3.53 (m, 2H), 2.09-2.03 (m, 2H), 1.63-1.55 (m, 2H); m/z (APCI-pos) M+1=463.1.

Example 21

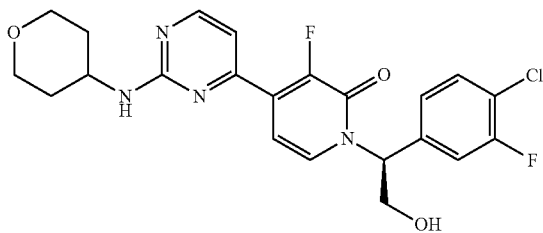 [SMILES: O=c1c(F)c(-c2ccnc(NC3CCOCC3)n2)ccn1[C@H](CO)c1ccc(Cl)c(F)c1]

(S)-1-(1-(4-chloro-3-fluorophenyl)-2-hydroxyethyl)-3-fluoro-4-(2-((tetrahydro-2H-pyran-4-yl)amino)pyrimidin-4-yl)pyridin-2(1H)-one Step A: Sodium carbonate (2.13 g, 20.1 mmol) was added to 2-chloro-3-fluoropyridin-4-ylboronic acid (1.41 g, 8.05 mmol) and 2,4-dichloropyrimidine (1.0 g, 6.71 mmol) in 4:1 dioxane/water (50 mL), and the mixture was sparged with argon. PdCl$_2$(dppf)*DCM (0.274 g, 0.336 mmol) was added, and the mixture was heated at 80° C. under argon. After 4.5 hours, more boronic acid (approximately 0.2 g) was added and heating continued for a total of 8.5 hours. The reaction mixture was diluted with water, and the resulting solid was collected by vacuum filtration to afford the desired 2-chloro-4-(2-chloro-3-fluoropyridin-4-yl)pyrimidine (1.18 g, 4.84 mmol, 72.0% yield) with minor impurities.

Step B: N-Ethyl-N-isopropylpropan-2-amine (0.185 mL, 1.07 mmol) and tetrahydro-2H-pyran-4-amine (0.0912 g, 0.901 mmol) were added to 2-chloro-4-(2-chloro-3-fluoropyridin-4-yl)pyrimidine (0.200 g, 0.819 mmol) in 2-butanol (7 mL) in a vial. The vial was sealed and heated at 80° C. overnight. The reaction mixture was evaporated, and the residue was partitioned between EtOAc and water. The EtOAc was washed with brine, dried over MgSO$_4$, filtered, and evaporated to yield a crude product (0.25 g) as a film. This was chromatographed on a 10 g Biotage SNAP column with EtOAc. Fractions 8-13 contained the desired 4-(2-chloro-3-fluoropyridin-4-yl)-N-(tetrahydro-2H-pyran-4-yl)pyrimidin-2-amine (0.08 g, 0.259 mmol, 31.6% yield) as a solid.

Step C: 4-(2-Chloro-3-fluoropyridin-4-yl)-N-(tetrahydro-2H-pyran-4-yl)pyrimidin-2-amine (0.08 g, 0.259 mmol) and 1M HCl (3.89 mL, 3.89 mmol) were added to a microwave vial. The vial was heated in a microwave at 140° C. for a total of 10 hours in 2 hour segments. The reaction mixture was diluted with water, and the desired 3-fluoro-4-(2-((tetrahydro-2H-pyran-4-yl)amino)pyrimidin-4-yl)pyridin-2(1H)-one (0.0565 g, 0.195 mmol, 75.1% yield) was collected by vacuum filtration.

Step D: 1M KHMDS in THF (0.234 mL, 0.234 mmol) was added to 3-fluoro-4-(2-((tetrahydro-2H-pyran-4-yl)amino)pyrimidin-4-yl)pyridin-2(1H)-one (0.0565 g, 0.195 mmol) suspended in 2-methyltetrahydrofuran (5 mL) cooled in ice. The mixture was stirred for 10 minutes at room temperature. Then, a solution of (R)-2-(tert-butyldimethylsilyloxy)-1-(4-chloro-3-fluorophenyl)ethyl methanesulfonate (0.112 g, 0.292 mmol) in 2-methyltetrahydrofuran (2 mL) was added, and the mixture was heated at 80-90° C. for 2 days. The cooled reaction mixture was evaporated. The residue was treated with dilute NaCl and EtOAc, filtered to remove solids, and the layers were separated. The EtOAc was washed with brine, dried over MgSO$_4$, filtered, and evaporated to yield a crude product (0.09 g) as a film. This was chromatographed on a 10 g Biotage SNAP column with 2:1 EtOAc/hexane. Fractions 12-16 contained the desired (S)-1-(2-(tert-butyldimethylsilyloxy)-1-(4-chloro-3-fluorophenyl)ethyl)-3-fluoro-4-(2-((tetrahydro-2H-pyran-4-yl)amino)pyrimidin-4-yl)pyridin-2(1H)-one (0.02 g, 0.0347 mmol, 17.8% yield) as a glass.

Step E: 1M Tetrabutylammonium fluoride in THF (0.10 mL, 0.10 mmol) was added to (S)-1-(2-(tert-butyldimethylsilyloxy)-1-(4-chloro-3-fluorophenyl)ethyl)-3-fluoro-4-(2-((tetrahydro-2H-pyran-4-yl)amino)pyrimidin-4-yl)pyridin-2(1H)-one (0.02 g, 0.035 mmol) in THF (5 mL). After 30 minutes, the reaction mixture was evaporated, and the residue was partitioned between EtOAc and dilute NaCl. The EtOAc was washed with brine, dried over MgSO$_4$, filtered, and evaporated to yield a crude product (0.02 g) as a film. This was chromatographed on a Biotage 10 g SNAP column with EtOAc. Fractions 23-33 contained the desired (S)-1-(1-(4-chloro-3-fluorophenyl)-2-hydroxyethyl)-3-fluoro-4-(2-((tetrahydro-2H-pyran-4-yl)amino)pyrimidin-4-yl)pyridin-2(1H)-one (0.0018 g, 0.0039 mmol, 11% yield) as a film. $^1$H NMR (400 MHz, CDCl$_3$) δ 8.41 (d, 1H), 7.45-7.40 (m, 1H), 7.24-7.18 (m, 2H), 7.14-7.10 (m, 2H), 6.81-6.77 (m, 1H), 6.23-6.20 (m, 1H), 5.14-5.12 (m, 1H), 4.34-4.31 (m, 2H), 4.15-4.04 (m, 2H), 4.03-3.97 (m, 2H), 3.58-3.51 (m, 2H), 2.09-2.03 (m, 2H), 1.63-1.53 (m, 2H); m/z (APCI-pos) M+1=463.1.

Example 22

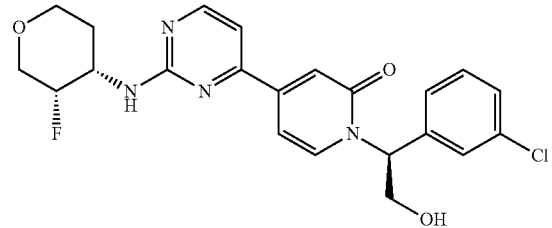 [SMILES: O=c1cc(-c2ccnc(N[C@H]3CCOC[C@H]3F)n2)ccn1[C@H](CO)c1cccc(Cl)c1]

1-((S)-1-(3-chlorophenyl)-2-hydroxyethyl)-4-(2-(((3S,4S)-3-fluorotetrahydro-2H-pyran-4-yl)amino)pyrimidin-4-yl)pyridin-2(1H)-one Step A: 1M KHMDS in THF (5.47 mL, 5.47 mmol) was added to a suspension of 4-(2-(methylthio)pyrimidin-4-yl)pyridin-2(1H)-one (1.00 g, 4.56 mmol) in 2-methyltetrahydrofuran (15 mL) cooled in ice. After stirring 15 minutes at room temperature, a solution of (R)-2-(tert-butyldimethylsilyloxy)-1-(3-chlorophenyl)ethyl methanesulfonate (2.33 g, 6.39 mmol; prepared as described in Intermediate Example B, substituting 1-chloro-3-vinylbenzene for 1-chloro-2-fluoro-4-vinylbenzene in Step B) in 2-methyltetrahydrofuran (5 mL) was added to the mixture and heated at 80° C. for 48 hours. The reaction mixture was evaporated, and the residue was partitioned between water and EtOAc. The EtOAc was washed with water, brine, dried over MgSO$_4$, filtered, and evaporated to yield a crude product (2.22 g) as a solid. This was chromatographed on a 50 g Biotage SNAP column with 1:1 hexane/EtOAc. Fractions 12-30 contained (S)-1-(2-(tert-butyldimethylsilyloxy)-1-(3-chlorophenyl) ethyl)-4-(2-(methylthio)pyrimidin-4-yl)pyridin-2(1H)-one (0.86 g, 1.76 mmol, 38.6% yield) as a solid foam.

Step B: 3-Chlorobenzoperoxoic acid (0.91 g, 5.3 mmol) was added to (S)-1-(2-(tert-butyldimethylsilyloxy)-1-(3-chlorophenyl)ethyl)-4-(2-(methylthio)pyrimidin-4-yl)pyridin-2(1H)-one (0.86 g, 1.8 mmol) in DCM (20 mL) cooled in ice. The mixture was stirred at room temperature for 2 hours. The reaction mixture was diluted with DCM, washed twice with a mixture of saturated aqueous NaHCO$_3$ and saturated aqueous Na$_2$S$_2$O$_3$, water, dried over MgSO$_4$, filtered, and evaporated to yield (S)-1-(2-(tert-butyldimethylsilyloxy)-1-(3-chlorophenyl)ethyl)-4-(2-(methylsulfonyl) pyrimidin-4-yl)pyridin-2(1H)-one (0.83 g, 1.6 mmol, 91% yield).

Step C: (S)-1-(2-(tert-Butyldimethylsilyloxy)-1-(3-chlorophenyl)ethyl)-4-(2-(methylsulfonyl)pyrimidin-4-yl)pyridin-2(1H)-one (0.200 g, 0.385 mmol) and 2-butanol (2 mL) were added to a vial. N-Ethyl-N-isopropylpropan-2-amine (0.0999 mL, 0.577 mmol) and (3S,4S)-3-fluorotetrahydro-2H-pyran-4-amine (0.0596 g, 0.500 mmol) were added to the solution. The vial was sealed and heated at 120° C. for 40 hours. The reaction mixture was evaporated, and the residue partitioned between water and EtOAc. The EtOAc was washed with brine, dried over MgSO$_4$, filtered, and evaporated to yield a crude product (0.20 g) as a film. This was chromatographed on a 10 g Biotage SNAP column with EtOAc. Fractions 9-18 contained 1-((S)-2-(tert-butyldimethylsilyloxy)-1-(3-chlorophenyl)ethyl)-4-(2-(((3S,4S)-3-fluorotetrahydro-2H-pyran-4-yl)amino)pyrimidin-4-yl)pyridin-2(1H)-one (0.105 g, 0.188 mmol, 48.8% yield) as a glass.

Step D: 4M HCl in dioxane (0.939 mL, 3.76 mmol) was added to 1-((S)-2-(tert-butyldimethylsilyloxy)-1-(3-chlorophenyl)ethyl)-4-(2-(((3S,4S)-3-fluorotetrahydro-2H-pyran-4-yl)amino)pyrimidin-4-yl)pyridin-2(1H)-one (0.105 g, 0.188 mmol) in MeOH (5 mL). After 30 minutes, the reaction mixture was evaporated, and the residue was partitioned between EtOAc and saturated aqueous NaHCO$_3$. The EtOAc was washed with brine, dried over MgSO$_4$, filtered, and evaporated to yield a crude product (0.08 g) as a film. This was chromatographed on a 10 g Biotage SNAP column with 10:1 EtOAc/i-PrOH. Fractions 9-16 contained 1-((S)-1-(3-chlorophenyl)-2-hydroxyethyl)-4-(2-(((3S,4S)-3-fluorotetrahydro-2H-pyran-4-yl)amino)pyrimidin-4-yl)pyridin-2(1H)-one as a solid foam. $^1$H NMR (400 MHz, CD$_3$OD) δ 8.38 (d, 1H), 7.80 (d, 1H), 7.41-7.39 (m, 1H), 7.38-7.28 (m, 2H), 7.22 (d, 1H), 7.09 (d, 1H), 7.00-6.97 (m, 1H), 6.15-6.11 (m, 1H), 4.83-4.70 (m, 1H), 4.34-4.25 (m, 2H), 4.20-4.15 (m, 1H), 4.01-3.98 (m, 1H), 3.94-3.88 (m, 1H), 3.70-3.54 (m, 2H), 2.08-1.95 (m, 1H), 1.83-1.77 (m, 1H) 1.13 (d, 1H); m/z (APCI-pos) M+1=445.1; 97.5% e.e. by chiral HPLC (Chiral Tech, column OD-H, 4.6 mm×250 mm, 5 u, 20% ethanol/80% hexanes, 1 mL/minute).

Example 23

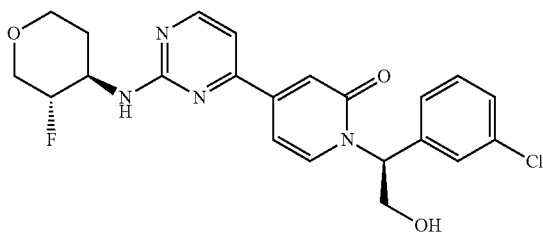 [SMILES: O=c1cc(-c2ccnc(N[C@@H]3CCOC[C@H]3F)n2)ccn1[C@H](CO)c1cccc(Cl)c1]

1-((S)-1-(3-chlorophenyl)-2-hydroxyethyl)-4-(2-(((3S,4R)-3-fluorotetrahydro-2H-pyran-4-yl)amino) pyrimidin-4-yl)pyridin-2(1H)-one 1-((S)-1-(3-Chlorophenyl)-2-hydroxyethyl)-4-(2-(((3S, 4R)-3-fluorotetrahydro-2H-pyran-4-yl)amino)pyrimidin-4-yl)pyridin-2(1H)-one was prepared as described in Example 22, substituting (3S,4R)-3-fluorotetrahydro-2H-pyran-4-amine for (3S,4S)-3-fluorotetrahydro-2H-pyran-4-amine in Step C. $^1$H NMR (400 MHz, CD$_3$OD) δ 8.39 (d, 1H), 7.83 (d, 1H), 7.43-7.41 (m, 1H), 7.38-7.27 (m, 3H), 7.26 (d, 1H), 7.10 (d, 1H), 7.02 (dd, 1H), 6.14 (dd, 1H), 4.62-4.44 (m, 1H), 4.36-4.26 (m, 2H), 4.22-4.17 (m, 1H), 4.07-3.86 (m, 1H), 3.60-3.44 (m, 2H), 2.22-2.14 (m, 1H), 1.73-1.63 (m, 1H) 1.15 (d, 1H); m/z (APCI-pos) M+1=445.1; 99% e.e. by chiral HPLC (Chiral Tech, column OD-H, 4.6 mm×250 mm, 5 u, 20% ethanol/80% hexanes, 1 mL/minute).

Example 24

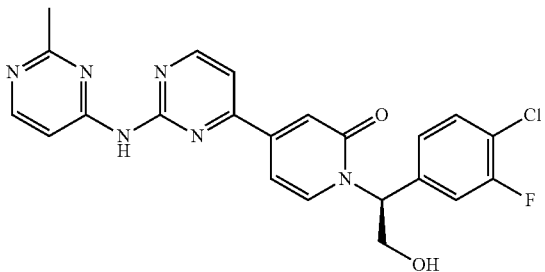 [SMILES: Cc1nccc(Nc2nccc(-c3ccn([C@H](CO)c4ccc(Cl)c(F)c4)c(=O)c3)n2)n1]

(S)-1-(1-(4-chloro-3-fluorophenyl)-2-hydroxyethyl)-4-(2-((2-methylpyrimidin-4-yl)amino)pyrimidin-4-yl)pyridin-2(1H)-one Step A: 2-Methylpyrimidin-4-amine (0.41 g, 3.7 mmol) and (S)-1-(2-(tert-butyldimethylsilyloxy)-1-(4-chloro-3-fluorophenyl)ethyl)-4-(2-(methylsulfonyl)pyrimidin-4-yl) pyridin-2(1H)-one (0.10 g, 0.19 mmol) were placed in sec-BuOH (1 mL), heated to 110° C. in a sealed tube for 18 hours, then poured into water, and extracted with DCM. The combined organic fractions were dried (MgSO$_4$), filtered, and concentrated to give the crude product, which was purified by column chromatography (500:5 DCM/MeOH to remove impurity, then 500:15 for product) to give (S)-1-(2-(tert-butyldimethylsilyloxy)-1-(4-chloro-3-fluorophenyl) ethyl)-4-(2-((2-methylpyrimidin-4-yl)amino)pyrimidin-4-yl)pyridin-2(1H)-one (0.034 g, 32% yield).

Step B: (S)-1-(2-(tert-Butyldimethylsilyloxy)-1-(4-chloro-3-fluorophenyl)ethyl)-4-(2-((2-methylpyrimidin-4-yl)amino)pyrimidin-4-yl)pyridin-2(1H)-one (0.034 g, 0.060 mmol) was placed in THF (5 mL) at room temperature. Tetra-n-butylammonium fluoride ("TBAF") (0.18 mL, 0.18 mmol) was added to the mixture. The mixture was stirred for 1 hour, then poured into water, and extracted with DCM. The combined organic fractions were dried (MgSO$_4$), filtered, and concentrated to give the crude product, which was purified by column chromatography (0-5.5% MeOH in DCM) to give the product (S)-1-(1-(4-chloro-3-fluorophenyl)-2-hydroxyethyl)-4-(2-((2-methylpyrimidin-4-yl) amino)pyrimidin-4-yl)pyridin-2(1H)-one (0.005 g, 18% yield). m/z (APCI-pos) M+1=453.

Example 25

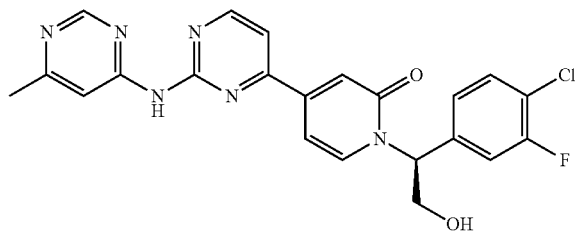 [SMILES: Cc1cc(Nc2nccc(-c3ccn([C@H](CO)c4ccc(Cl)c(F)c4)c(=O)c3)n2)ncn1]

(S)-1-(1-(4-chloro-3-fluorophenyl)-2-hydroxyethyl)-4-(2-((6-methylpyrimidin-4-yl)amino)pyrimidin-4-yl)pyridin-2(1H)-one (S)-1-(1-(4-Chloro-3-fluorophenyl)-2-hydroxyethyl)-4-(2-((6-methylpyrimidin-4-yl)amino)pyrimidin-4-yl)pyridin-2(1H)-one was prepared according to Example 24, substituting 6-methylpyrimidin-4-amine for 2-methylpyrimidin-4-amine in Step A. m/z (APCI-pos) M+1=453.

Example 26

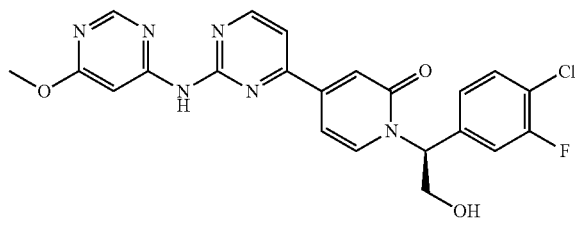 [SMILES: COc1cc(Nc2nccc(-c3ccn([C@H](CO)c4ccc(Cl)c(F)c4)c(=O)c3)n2)ncn1]

(S)-1-(1-(4-chloro-3-fluorophenyl)-2-hydroxyethyl)-4-(2-((6-methoxypyrimidin-4-yl)amino)pyrimidin-4-yl)pyridin-2(1H)-one (S)-1-(1-(4-Chloro-3-fluorophenyl)-2-hydroxyethyl)-4-(2-((6-methoxypyrimidin-4-yl)amino)pyrimidin-4-yl)pyridin-2(1H)-one was prepared according to Example 24, substituting 6-methoxypyrimidin-4-amine for 2-methylpyrimidin-4-amine in Step A. m/z (APCI-pos) M+1=469.

Example 27

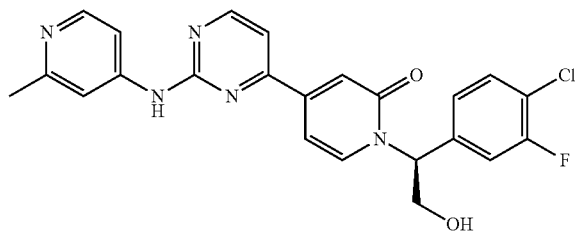 [SMILES: Cc1cc(Nc2nccc(-c3ccn([C@H](CO)c4ccc(Cl)c(F)c4)c(=O)c3)n2)ccn1]

(S)-1-(1-(4-chloro-3-fluorophenyl)-2-hydroxyethyl)-4-(2-((2-methylpyridin-4-yl)amino)pyrimidin-4-yl)pyridin-2(1H)-one Step A: 2-Methylpyridin-4-amine (0.28 g, 2.6 mmol) was placed in THF (5 mL) and cooled to −78° C. t-BuLi (1.5 mL, 2.6 mmol) was added dropwise, and the solution was warmed to 0° C. for 30 minutes. This solution was then added dropwise to a −78° C. THF solution (5 mL) of (S)-1-(2-(tert-butyldimethylsilyloxy)-1-(4-chloro-3-fluorophenyl)ethyl)-4-(2-(methylsulfonyl)pyrimidin-4-yl)pyridin-2(1H)-one (0.070 g, 0.13 mmol). The reaction was stirred for an additional 30 minutes at −78° C., then poured into water, and extracted with DCM. The combined organic fractions were dried (MgSO$_4$), filtered, and concentrated to give the crude product, which was purified by column chromatography (500:10-500:20 DCM/MeOH) to give the product (S)-1-(2-(tert-butyldimethylsilyloxy)-1-(4-chloro-3-fluorophenyl)ethyl)-4-(2-((2-methylpyridin-4-yl)amino)pyrimidin-4-yl)pyridin-2(1H)-one (0.028 g, 38% yield).

Step B: (S)-1-(2-(tert-Butyldimethylsilyloxy)-1-(4-chloro-3-fluorophenyl)ethyl)-4-(2-((2-methylpyridin-4-yl)amino)pyrimidin-4-yl)pyridin-2(1H)-one (0.028 g, 0.049 mmol) was placed in THF (5 mL). TBAF (0.054 mL, 0.054 mmol) was then added, and the reaction was stirred for 1 hour, then poured into water, and extracted with DCM. The combined organic fractions were dried (MgSO$_4$), filtered, and concentrated to give the crude product, which was purified by column chromatography (500:40-500:50 DCM/MeOH) to give the product (S)-1-(1-(4-chloro-3-fluorophenyl)-2-hydroxyethyl)-4-(2-((2-methylpyridin-4-yl)amino)pyrimidin-4-yl)pyridin-2(1H)-one (0.005 g, 22% yield). m/z (APCI-pos) M+1=452.

Example 28

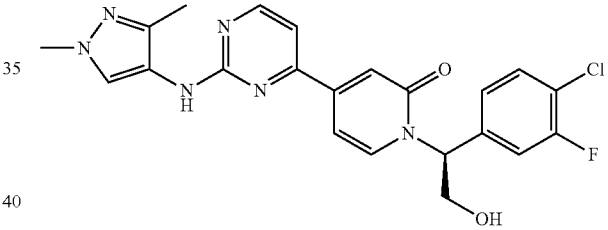

(S)-1-(1-(4-chloro-3-fluorophenyl)-2-hydroxyethyl)-4-(2-((1,3-dimethyl-1H-pyrazol-4-yl)amino)pyrimidin-4-yl)pyridin-2(1H)-one Step A: (S)-1-(2-(tert-Butyldimethylsilyloxy)-1-(4-chloro-3-fluorophenyl)ethyl)-4-(2-(methylsulfonyl)pyrimidin-4-yl)pyridin-2(1H)-one (0.100 g, 0.186 mmol) and 1,3-dimethyl-1H-pyrazol-4-amine (0.413 g, 3.72 mmol) were placed in s-BuOH (2 mL), heated to 110° C. overnight, then poured into water and extracted with DCM. The combined organic fractions were dried (MgSO$_4$), filtered, and concentrated to give the crude product, which was purified by column chromatography (500:10 DCM/MeOH) to give the product (S)-1-(2-(tert-butyldimethylsilyloxy)-1-(4-chloro-3-fluorophenyl)ethyl)-4-(2-((1,3-dimethyl-1H-pyrazol-4-yl)amino)pyrimidin-4-yl)pyridin-2(1H)-one (0.070 g, 66.2% yield).

Step B: (S)-1-(2-(tert-Butyldimethylsilyloxy)-1-(4-chloro-3-fluorophenyl)ethyl)-4-(2-((1,3-dimethyl-1H-pyrazol-4-yl)amino)pyrimidin-4-yl)pyridin-2(1H)-one (0.070 g, 0.12 mmol) was placed in THF (3 mL). TBAF (0.14 mL, 0.14 mmol) was added, and the mixture was stirred for 1 hour, then poured into water, and extracted with DCM. The combined organic fractions were dried (MgSO$_4$), filtered, and concentrated to give the crude product, which was purified by column chromatography (500:20-500:30 DCM/MeOH) to give the product (S)-1-(1-(4-chloro-3-fluorophenyl)-2-hydroxyethyl)-4-(2-((1,3-dimethyl-1H-pyrazol-4-yl) amino)pyrimidin-4-yl)pyridin-2(1H)-one (0.040 g, 71% yield). m/z (APCI-pos) M+1=455.

Example 29

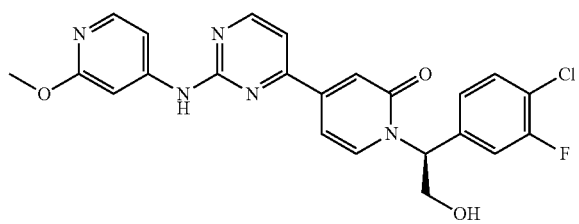 [SMILES: COc1cc(Nc2nccc(-c3ccn([C@H](CO)c4ccc(Cl)c(F)c4)c(=O)c3)n2)ccn1]

(S)-1-(1-(4-chloro-3-fluorophenyl)-2-hydroxyethyl)-4-(2-((2-methoxypyridin-4-yl)amino)pyrimidin-4-yl) pyridin-2(1H)-one (S)-1-(1-(4-Chloro-3-fluorophenyl)-2-hydroxyethyl)-4-(2-((2-methoxypyridin-4-yl)amino)pyrimidin-4-yl)pyridin-2(1H)-one was prepared according to Example 27, substituting 2-methoxypyridin-4-amine for 2-methylpyridin-4-amine in Step A. m/z (APCI-pos) M+1=468.

Example 30

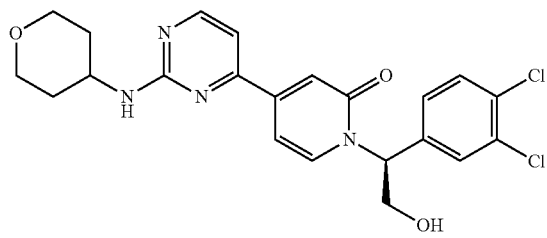

(S)-1-(1-(3,4-dichlorophenyl)-2-hydroxyethyl)-4-(2-((tetrahydro-2H-pyran-4-yl)amino)pyrimidin-4-yl) pyridin-2(1H)-one Step A: (S)-1-(2-(tert-Butyldimethylsilyloxy)-1-(3,4-dichlorophenyl)ethyl)-4-(2-((tetrahydro-2H-pyran-4-yl) amino)pyrimidin-4-yl)pyridin-2(1H)-one was prepared according to the general procedure of Example 1, Step A substituting (S)-1-(2-(tert-butyldimethylsilyloxy)-1-(3,4-dichlorophenyl)ethyl)-4-(2-(methylsulfonyl)pyrimidin-4-yl) pyridin-2(1H)-one for 1-(2-(tert-butyldimethylsilyloxy)-1-(4-chloro-3-fluorophenyl)ethyl)-4-(2-(methylsulfonyl) pyrimidin-4-yl)pyridin-2(1H)-one. m/z (APCI-pos) M+1=575.2, 577.2.

Step B: (S)-1-(1-(3,4-Dichlorophenyl)-2-hydroxyethyl)-4-(2-((tetrahydro-2H-pyran-4-yl)amino)pyrimidin-4-yl)pyridin-2(1H)-one (43%, 2 steps) was prepared according to the general procedure of Example 1, Step B, substituting (S)-1-(2-(tert-butyldimethylsilyloxy)-1-(3,4-dichlorophenyl)ethyl)-4-(2-((tetrahydro-2H-pyran-4-yl)amino)pyrimidin-4-yl)pyridin-2(1H)-one for (S)-1-(2-(tert-butyldimethylsilyloxy)-1-(4-chloro-3-fluorophenyl)ethyl)-4-(2-((tetrahydro-2H-pyran-4-yl)amino)pyrimidin-4-yl)pyridin-2 (1H)-one. $^1$H NMR (400 MHz, (CD$_3$)$_2$SO) δ 8.42-8.41 (d, J=5.1 Hz, 1H), 7.92-7.90 (d, J=7.4 Hz, 1H), 7.64-7.62 (m, 2H), 7.36-7.34 (d, J=6.9 Hz, 1H), 7.31-7.28 (d, J=10.6 Hz, 1H), 7.16-7.14 (d, J=5.1 Hz, 1H), 7.10 (s, 1H), 6.89-6.87 (d, J=5.9 Hz, 1H), 5.97-5.93 (t, 1H), 5.34-5.31 (t, 1H), 4.19-4.13 (m, 1H), 4.08-3.96 (m, 2H), 3.89-3.86 (m, 2H), 3.43-3.37 (t, 2H), 1.87-1.84 (m, 2H), 1.59-1.48 (m, 2H); m/z (APCI-pos) M+1=461.1, 463.1.

Example 31

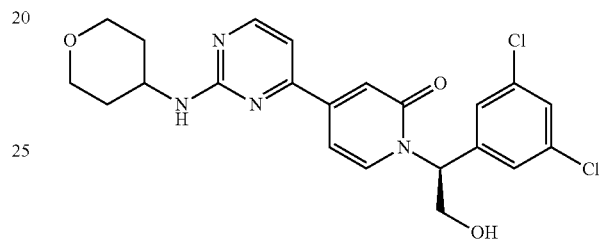

(S)-1-(1-(3,5-dichlorophenyl)-2-hydroxyethyl)-4-(2-((tetrahydro-2H-pyran-4-yl)amino)pyrimidin-4-yl) pyridin-2(1H)-one Step A: (S)-1-(2-(tert-Butyldimethylsilyloxy)-1-(3,5-dichlorophenyl)ethyl)-4-(2-((tetrahydro-2H-pyran-4-yl) amino)pyrimidin-4-yl)pyridin-2(1H)-one was prepared according to the general procedure of Example 1, Step A, substituting (S)-1-(2-(tert-butyldimethylsilyloxy)-1-(3,5-dichlorophenyl)ethyl)-4-(2-(methylsulfonyl)pyrimidin-4-yl) pyridin-2(1H)-one for 1-(2-(tert-butyldimethylsilyloxy)-1-(4-chloro-3-fluorophenyl)ethyl)-4-(2-(methylsulfonyl) pyrimidin-4-yl)pyridin-2(1H)-one. m/z (APCI-pos) M+1=575.2, 577.2.

Step B: (S)-1-(1-(3,5-Dichlorophenyl)-2-hydroxyethyl)-4-(2-((tetrahydro-2H-pyran-4-yl)amino)pyrimidin-4-yl)pyridin-2(1H)-one (60%, 2 steps) was prepared according to the general procedure of Example 1, Step B, substituting (S)-1-(2-(tert-butyldimethylsilyloxy)-1-(3,5-dichlorophenyl)ethyl)-4-(2-((tetrahydro-2H-pyran-4-yl)amino)pyrimidin-4-yl)pyridin-2(1H)-one for (S)-1-(2-(tert-butyldimethylsilyloxy)-1-(4-chloro-3-fluorophenyl)ethyl)-4-(2-((tetrahydro-2H-pyran-4-yl)amino)pyrimidin-4-yl)pyridin-2 (1H)-one. $^1$H NMR (400 MHz, (CD$_3$)$_2$SO) δ 8.43-8.41 (d, J=5.1 Hz, 1H), 7.96-7.94 (d, J=7.5 Hz, 1H), 7.57 (s, 1H), 7.39-7.38 (d, J=1.7 Hz, 2H), 7.36-7.34 (d, J=7.5 Hz, 1H), 7.17-7.15 (d, J=5.1 Hz, 1H), 7.11-7.10 (d, J=1.5 Hz, 1H), 5.94-5.91 (t, 1H), 5.36-5.33 (t, 1H), 4.21-4.14 (m, 1H), 4.09-3.95 (m, 2H), 3.89-3.86 (m, 2H), 3.43-3.37 (t, 2H), 1.88-1.84 (m, 2H), 1.58-1.49 (m, 2H); m/z (APCI-pos) M+1=461.1, 463.1.

Example 32

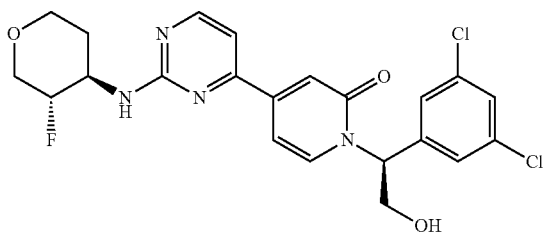 [SMILES: O=c1cc(-c2ccnc(N[C@@H]3CCOC[C@H]3F)n2)ccn1[C@H](CO)c1cc(Cl)cc(Cl)c1]

1-((S)-1-(3,5-dichlorophenyl)-2-hydroxyethyl)-4-(2-(((3S,4R)-3-fluorotetrahydro-2H-pyran-4-yl)amino)pyrimidin-4-yl)pyridin-2(1H)-one Step A: 1-((S)-2-(tert-Butyldimethylsilyloxy)-1-(3,5-dichlorophenyl)ethyl)-4-(2-(((3S,4R)-3-fluorotetrahydro-2H-pyran-4-yl)amino)pyrimidin-4-yl)pyridin-2(1H)-one was prepared according to the general procedure of Example 3, Step A, substituting (S)-1-(2-(tert-butyldimethylsilyloxy)-1-(3,5-dichlorophenyl)ethyl)-4-(2-(methylsulfonyl)pyrimidin-4-yl)pyridin-2(1H)-one for (S)-1-(2-(tert-butyldimethylsilyloxy)-1-(4-chloro-3-fluorophenyl)ethyl)-4-(2-(methylsulfonyl)pyrimidin-4-yl)pyridin-2(1H)-one. m/z (APCI-pos) M+1=593.2, 595.2.

Step B: 1-((S)-1-(3,5-Dichlorophenyl)-2-hydroxyethyl)-4-(2-(((3S,4R)-3-fluorotetrahydro-2H-pyran-4-yl)amino)pyrimidin-4-yl)pyridin-2(1H)-one (52%, 2 steps) was prepared according to the general procedure of Example 3, Step B, substituting 1-((S)-2-(tert-butyldimethylsilyloxy)-1-(3,5-dichlorophenyl)ethyl)-4-(2-(((3S,4R)-3-fluorotetrahydro-2H-pyran-4-yl)amino)pyrimidin-4-yl)pyridin-2(1H)-one for 1-((S)-2-(tert-butyldimethylsilyloxy)-1-(4-chloro-3-fluorophenyl)ethyl)-4-(2-(((3S,4S)-3-fluorotetrahydro-2H-pyran-4-yl)amino)pyrimidin-4-yl)pyridin-2(1H)-one. $^1$H NMR (400 MHz, (CD$_3$)$_2$SO) δ 8.45-8.44 (d, J=5.0 Hz, 1H), 7.97-7.95 (d, J=7.3 Hz, 1H), 7.63-7.61 (d, J=7.9 Hz, 1H), 7.58-7.57 (t, 1H), 7.39-7.38 (d, J=1.9 Hz, 2H), 7.22-7.21 (d, J=5.0 Hz, 1H), 7.13-7.12 (d, J=1.9 Hz, 1H), 6.92-6.90 (m, 1H), 5.95-5.91 (t, 1H), 5.36-5.33 (t, 1H), 4.66-4.49 (m, 1H), 4.31-4.15 (m, 2H) 4.09-3.97 (m, 2H), 3.85-3.81 (m, 1H), 3.51-3.40 (m, 2H), 2.04-2.01 (m, 1H), 1.63-1.57 (m, 1H); m/z (APCI-pos) M+1=479.0, 481.1.

Example 33

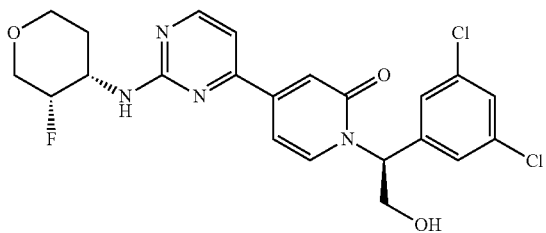 [SMILES: O=c1cc(-c2ccnc(N[C@H]3CCOC[C@H]3F)n2)ccn1[C@H](CO)c1cc(Cl)cc(Cl)c1]

1-((S)-1-(3,5-dichlorophenyl-2-hydroxyethyl)-4-(2-(((3S,4S)-3-fluorotetrahydro-2H-pyran-4-yl)amino)pyrimidin-4-yl)pyridin-2(1H)-one Step A: 1-((S)-2-(tert-Butyldimethylsilyloxy)-1-(3,5-dichlorophenyl)ethyl)-4-(2-(((3S,4S)-3-fluorotetrahydro-2H-pyran-4-yl)amino)pyrimidin-4-yl)pyridin-2(1H)-one was prepared according to the general procedure of Example 2, Step A, substituting (S)-1-(2-(tert-butyldimethylsilyloxy)-1-(3,5-dichlorophenyl)ethyl)-4-(2-(methylsulfonyl)pyrimidin-4-yl)pyridin-2(1H)-one for (S)-1-(2-(tert-butyldimethylsilyloxy)-1-(4-chloro-3-fluorophenyl)ethyl)-4-(2-(methylsulfonyl)pyrimidin-4-yl)pyridin-2(1H)-one. m/z (APCI-pos) M+1=593.1, 595.1.

Step B: 1-((S)-1-(3,5-Dichlorophenyl)-2-hydroxyethyl)-4-(2-(((3S,4S)-3-fluorotetrahydro-2H-pyran-4-yl)amino)pyrimidin-4-yl)pyridin-2(1H)-one (59%, 2 steps) was prepared according to the general procedure of Example 2, Step B, substituting 1-((S)-2-(tert-butyldimethylsilyloxy)-1-(3,5-dichlorophenyl)ethyl)-4-(2-(((3S,4S)-3-fluorotetrahydro-2H-pyran-4-yl)amino)pyrimidin-4-yl)pyridin-2(1H)-one for 1-((S)-2-(tert-butyldimethylsilyloxy)-1-(4-chloro-3-fluorophenyl)ethyl)-4-(2-(((3S,4S)-3-fluorotetrahydro-2H-pyran-4-yl)amino)pyrimidin-4-yl)pyridin-2(1H)-one. $^1$H NMR (400 MHz, (CD$_3$)$_2$SO) δ 8.46-8.45 (d, J=5.1 Hz, 1H), 7.96-7.94 (d, J=7.4 Hz, 1H), 7.58-7.57 (t, 1H), 7.41-7.38 (m, 3H), 7.24-7.23 (d, J=5.0 Hz, 1H), 7.13-7.12 (d, J=2.1 Hz, 1H), 6.93-6.91 (m, 1H), 5.95-5.91 (t, 1H), 5.36-5.33 (t, 1H), 4.86-4.73 (d, J=51.7 Hz, 1H), 4.25-4.15 (m, 2H), 4.09-3.89 (m, 3H), 3.66-3.48 (m, 2H), 2.02-1.92 (m, 1H), 1.69-1.65 (m, 1H); m/z (APCI-pos) M+1=479.0, 481.0.

Example 34

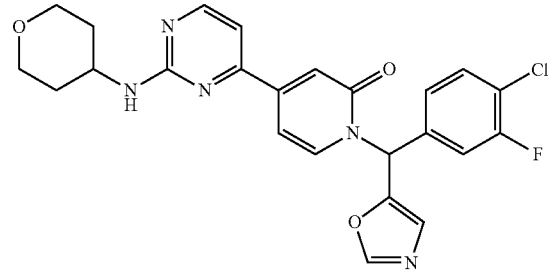 [SMILES: O=c1cc(-c2ccnc(NC3CCOCC3)n2)ccn1C(c1ccc(Cl)c(F)c1)c1cnco1]

1-((4-chloro-3-fluorophenyl)(oxazol-5-yl)methyl)-4-(2-((tetrahydro-2H-pyran-4-yl)amino)pyrimidin-4-yl)pyridin-2(1H)-one Step A: (4-Chloro-3-fluorophenyl)magnesium bromide (40.6 mL, 20.3 mmol; 0.5M in THF) was added dropwise by syringe to a stirred solution of oxazole-5-carbaldehyde (1.97 g, 20.3 mmol) in THF (40 mL) at 0° C. under nitrogen. The reaction was allowed to warm to room temperature and then stirred for 30 minutes at room temperature. TLC in 1/1 ethyl acetate/hexanes showed near complete consumption of starting material, and a new slightly lower rf spot as major. The reaction was quenched by careful addition of saturated ammonium chloride solution by pipet with stirring. An ammonium chloride (50 mL) solution was added. The majority of the THF was then removed by rotovap. The residual aqueous suspension was diluted with ethyl acetate (100 mL) and water (50 mL), transferred to a separatory funnel and shaken. The layers were separated, and the organics were isolated and washed with brine (100 mL), dried (MgSO$_4$), filtered and concentrated to an oil. The crude product was loaded onto a Biotage 40M column with 2/3 ethyl acetate/hexanes and eluted. Product containing fractions were pooled and concentrated to a solid, (4-chloro-3-fluorophenyl)(oxazol-5-yl)methanol (4 g, 86%).

Step B: N,N-Diisopropylethylamine ("DIEA") (174 μL, 0.997 mmol; d 0.742) was added neat by syringe to a stirred solution of (4-chloro-3-fluorophenyl)(oxazol-5-yl)methanol (227 mg, 0.997 mmol) in dichloromethane (3 mL) at 0° C. under nitrogen, followed by addition of methane sulfonyl chloride (77.5 μL, 0.997 mmol) neat by syringe. After 1 hour, TLC in 2/3 ethyl acetate/hexanes showed the reaction was complete. The reaction was diluted to 30 mL with dichloromethane and washed with 2N HCl (2×30 mL) and with saturated sodium bicarbonate solution (2×30 mL). The organics were isolated, dried (MgSO$_4$), filtered and concentrated to a foam, 5-(chloro(4-chloro-3-fluorophenyl)methyl)oxazole (240 mg, 90%). $^1$H-NMR shows no mesylate methyl signal. The chloride is the assumed product.

Step C: NaH (13.2 mg, 0.331 mmol; 60 wt % oil dispersion) neat as a solid was added to a stirred suspension of 4-(2-(methylthio)pyrimidin-4-yl)pyridin-2(1H)-one (65.9 mg, 0.301 mmol) in DMF (600 μL) at room temperature under nitrogen. After 30 minutes, the suspension had become a solution. A solution of 5-(chloro(4-chloro-3-fluorophenyl)methyl)oxazole (111 mg, 0.451 mmol) was then added as a solution in DMF (300 μL) dropwise by syringe. After stirring at room temperature overnight, TLC in ethyl acetate showed a new high rf spot, as well as a new mid rf spot (both bright blue under UV). The reaction was quenched with water (1 mL) and then partitioned between ethyl acetate (30 mL) and water with a little brine (30 mL). The organics were isolated and washed with water/brine (3×30 mL). The organics were isolated, dried (MgSO$_4$), filtered and concentrated to an oil. The mixture was loaded onto a Biotage 12M column with 7/3 ethyl acetate/hexanes and eluted. Two main spots eluted and corresponding fractions were pooled and concentrated. The least polar fraction appears to be alkylated on the pyridone oxygen. The second eluting spot appears to be the desired N-alkylated pyridone, which was isolated as a foam, 1-((4-chloro-3-fluorophenyl)(oxazol-5-yl)methyl)-4-(2-(methylthio)pyrimidin-4-yl)pyridin-2(1H)-one (50 mg, 39%).

Step D: mCPBA (80.5 mg, 0.350 mmol) neat as a solid was added to a stirred solution of 1-((4-chloro-3-fluorophenyl)(oxazol-5-yl)methyl)-4-(2-(methylthio)pyrimidin-4-yl)pyridin-2(1H)-one (50 mg, 0.117 mmol) in dichloromethane (2 mL) at room temperature under nitrogen. After 1 hour, TLC in ethyl acetate showed complete consumption of starting material and a new lower rf spot (bright blue under UV visualization). The reaction was quenched with 10% Na$_2$S$_2$O$_3$ (1 mL) and stirred for 5 minutes. The reaction was diluted with dichloromethane (20 mL) and washed with 10% Na$_2$S$_2$O$_3$ (2×20 mL) and with saturated sodium bicarbonate solution (2×20 mL). The organics were isolated, dried (MgSO$_4$), filtered and concentrated to an oil, 1-((4-chloro-3-fluorophenyl)(oxazol-5-yl)methyl)-4-(2-(methylsulfonyl)pyrimidin-4-yl)pyridin-2(1H)-one (53 mg, 99%).

Step E: A microwave tube was charged with a solution of 1-((4-chloro-3-fluorophenyl)(oxazol-5-yl)methyl)-4-(2-(methylsulfonyl)pyrimidin-4-yl)pyridin-2(1H)-one (53 mg, 0.12 mmol) in DMA (1.2 mL). Tetrahydro-2H-pyran-4-amine (35 mg, 0.35 mmol) was added neat by syringe. The reaction was put into a microwave apparatus and heated to 120° C. After 1 hour, the solution was diluted to 30 mL with ethyl acetate and washed with a water/brine mixture (4×30 mL). The organics were isolated, dried (MgSO$_4$), filtered and concentrated. TLC in ethyl acetate showed complete loss of starting material and a new spot of nearly the same rf. The crude product was loaded onto a Biotage 12M column with ethyl acetate and eluted. Product containing fractions were pooled and concentrated to an oil, 1-((4-chloro-3-fluorophenyl)(oxazol-5-yl)methyl)-4-(2-((tetrahydro-2H-pyran-4-yl)amino)pyrimidin-4-yl)pyridin-2(1H)-one (20 mg, 36%). $^1$H NMR (400 MHz, CDCl$_3$) δ 8.40 (d, 1H), 7.98 (s, 1H), 7.56 (s, 1H), 7.43 (dd, 1H), 7.31 (d, 1H), 7.22 (br s, 1H), 7.08 (s, 1H), 7.00 (m, 2H), 6.90 (s, 1H), 6.83 (dd, 1H), 5.20 (br d, 1H), 4.11 (m, 1H), 4.01 (m 2H), 3.55 (m, 2H), 2.06 (m, 2H), 1.58 (m, 2H); m/z (APCI-pos) M+1=483.0.

Example 35

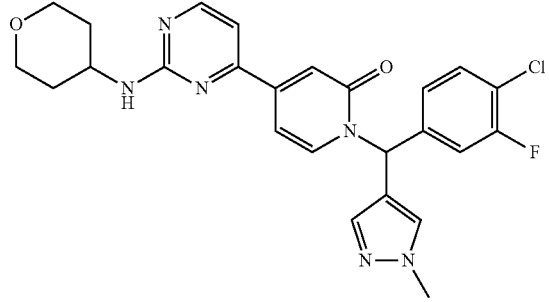 [SMILES: Cn1cc(C(c2ccc(Cl)c(F)c2)n2ccc(-c3ccnc(NC4CCOCC4)n3)cc2=O)cn1]

1-((4-chloro-3-fluorophenyl)(1-methyl-1H-pyrazol-4-yl)methyl)-4-(2-((tetrahydro-2H-pyran-4-yl)amino)pyrimidin-4-yl)pyridin-2(1H)-one Step A: Boc$_2$O (2183 mg, 10.0 mmol) was added to a stirred solution of 1H-pyrazole-4-carbaldehyde (961 mg, 10.0 mmol) in acetonitrile (30 mL) at room temperature, followed by 4-dimethylaminopyridine ("DMAP") (61.1 mg, 0.500 mmol). After stirring overnight, the reaction was concentrated to dryness and partitioned between ethyl acetate (30 mL) and water (30 mL). The organics were isolated and washed with 0.5N HCL (30 mL) and with brine (30 mL). The organics were isolated, dried (MgSO$_4$), filtered and concentrated to an oil, which was loaded onto a Biotage 40M column with 4/1 hexanes/ethyl acetate and eluted with the same solvent. Product containing fractions were pooled and concentrated to an oil, which eventually solidified to a solid, tert-butyl 4-formyl-1H-pyrazole-1-carboxylate (1.4 g, 71%).

Step B: (4-Chloro-3-fluorophenyl)magnesium bromide (7400 μL, 3.70 mmol) (0.5M in THF) was added dropwise by syringe to a stirred solution of tert-butyl 4-formyl-1H-pyrazole-1-carboxylate (605 mg, 3.08 mmol) in THF (24 mL) at −78° C. under nitrogen. After 10 minutes, TLC in 2/3 ethyl acetate/hexanes showed a new spot of lower rf than starting material in an approximate 1:1 ratio. After 1 hour, the reaction was quenched at −78° C. with saturated ammonium chloride solution (10 mL) and allowed to warm to 0° C. The reaction was then partially concentrated to remove THF, and the residual mixture was partitioned between ethyl acetate (50 mL) and water (50 mL). The organics were isolated and washed with brine (30 mL). The organics were again isolated, dried (MgSO$_4$), filtered and concentrated. The crude material was loaded onto a Biotage 40S column with 35/65 ethyl acetate/hexanes and eluted. Product containing fractions were pooled and concentrated to an oil, tert-butyl 4-((4-chloro-3-fluorophenyl)(hydroxy)methyl)-1H-pyrazole-1-carboxylate (400 mg, 40%).

Step C: DIEA (646 μL, 3.71 mmol; d 0.742) neat was added by syringe to a stirred solution of tert-butyl 4-((4-chloro-3-fluorophenyl)(hydroxy)methyl)-1H-pyrazole-1-carboxylate (808 mg, 2.47 mmol) in dichloromethane (25 mL) at 0° C. under nitrogen, followed by methane sulfonyl chloride (191 μL, 2.47 mmol) neat by syringe. After 1 hour, TLC in 1/1 ethyl acetate/hexanes showed the reaction was complete with a new high rf spot dominant. The reaction was diluted to 50 mL with dichloromethane and washed with 2N HCl (2×50 mL) and with saturated sodium bicarbonate solution (2×50 mL). The organics were isolated, dried (MgSO$_4$), filtered and concentrated to a foam, tert-butyl 4-(chloro(4-chloro-3-fluorophenyl)methyl)-1H-pyrazole-1-carboxylate (850 mg, 100%). The chloride is the assumed product.

Step D: NaH (92.0 mg, 2.30 mmol; 60% oil dispersion) neat as a solid was added to a stirred suspension of 4-(2-(methylthio)pyrimidin-4-yl)pyridin-2(1H)-one (504 mg, 2.30 mmol) in DMF (15 mL) at room temperature under nitrogen. After 15 minutes, a solution had formed. tert-Butyl 4-(chloro(4-chloro-3-fluorophenyl)methyl)-1H-pyrazole-1-carboxylate (794 mg, 2.30 mmol) was then added dropwise by syringe as a solution in DMF (7 mL). After stirring overnight, the reaction was quenched by addition of saturated ammonium chloride solution (10 mL). The mixture was partitioned between ethyl acetate (50 mL) and water (50 mL). The organics were isolated and washed with water (3×50 mL) and with brine (50 mL). The organics were isolated, dried (MgSO$_4$), filtered and concentrated. The crude product was loaded onto a Biotage 40M column with 3/2 ethyl acetate/hexanes and eluted with the same solvent. Product containing fractions were pooled and concentrated to a foam, tert-butyl 4-((4-chloro-3-fluorophenyl)(4-(2-(methylthio)pyrimidin-4-yl)-2-oxopyridin-1(2H)-yl)methyl)-1H-pyrazole-1-carboxylate (565 mg, 46%).

Step E: Trifluoroacetic acid ("TFA") (5 mL) was added by pipet to a stirred solution of tert-butyl 4-((4-chloro-3-fluorophenyl)(4-(2-(methylthio)pyrimidin-4-yl)-2-oxopyridin-1(2H)-yl)methyl)-1H-pyrazole-1-carboxylate (562 mg, 1.06 mmol) in dichloromethane (5 mL) at room temperature under nitrogen. After 3 hours, the reaction was concentrated by rotovap. The residue was redissolved in dichloromethane (10 mL), carefully treated with saturated sodium bicarbonate solution (10 mL) and stirred rapidly for 10 minutes. The layers were separated, and the aqueous phase was extracted with dichloromethane (20 mL). The combined organics were dried (MgSO$_4$), filtered and concentrated to a foam, 1-((4-chloro-3-fluorophenyl)(1H-pyrazol-4-yl)methyl)-4-(2-(methylthio)pyrimidin-4-yl)pyridin-2(1H)-one (455 mg, 100%).

Step F: NaH (51.0 mg, 1.28 mmol; 60% oil dispersion) neat as a solid was added to a stirred solution of 1-((4-chloro-3-fluorophenyl)(1H-pyrazol-4-yl)methyl)-4-(2-(methylthio)pyrimidin-4-yl)pyridin-2(1H)-one (455 mg, 1.06 mmol) in DMF (5 mL) at room temperature under nitrogen. After 30 minutes, methyl iodide (86.1 μL, 1.38 mmol) was added neat by syringe. After stirring overnight, the reaction was quenched by addition of saturated ammonium chloride solution (5 mL). The mixture was partitioned between ethyl acetate (30 mL) and saturated sodium bicarbonate (30 mL). The organics were isolated and washed with water (3×30 mL) and with brine (30 mL). TLC in 98/2 ethyl acetate/methanol showed very little residual starting material with a major new spot of slightly higher rf. The organics were isolated, dried (MgSO$_4$), filtered and concentrated. The crude product was loaded onto a Biotage 40S column with 98/2 ethyl acetate/methanol and eluted with the same solvent. Product containing fractions were pooled and concentrated to a foam, 1-((4-chloro-3-fluorophenyl)(1-methyl-1H-pyrazol-4-yl)methyl)-4-(2-(methylthio)pyrimidin-4-yl)pyridin-2(1H)-one (340 mg, 72%).

Step G: mCPBA (523 mg, 2.27 mmol) neat as a solid was added to a stirred solution of 1-((4-chloro-3-fluorophenyl)(1-methyl-1H-pyrazol-4-yl)methyl)-4-(2-(methylthio)pyrimidin-4-yl)pyridin-2(1H)-one (335 mg, 0.758 mmol) in dichloromethane (7.6 mL) at room temperature under nitrogen. After 1 hour, TLC in ethyl acetate showed complete consumption of starting material and a new lower rf spot (bright blue under UV visualization). The reaction was quenched with 10% Na$_2$S$_2$O$_3$ (10 mL) and stirred for 5 minutes. The reaction was diluted with dichloromethane (40 mL) and washed with 10% Na$_2$S$_2$CO$_3$ (2×50 mL) and saturated sodium bicarbonate solution (2×50 mL). The organics were isolated, dried (MgSO$_4$), filtered and concentrated to an oil, 1-((4-chloro-3-fluorophenyl)(1-methyl-1H-pyrazol-4-yl)methyl)-4-(2-(methylsulfonyl)pyrimidin-4-yl)pyridin-2(1H)-one (343 mg, 95%).

Step H: 1-((4-Chloro-3-fluorophenyl)(1-methyl-1H-pyrazol-4-yl)methyl)-4-(2-(methylsulfonyl)pyrimidin-4-yl)pyridin-2(1H)-one (343 mg, 0.724 mmol) as a solution in DMA (5 mL) was added to a microwave tube equipped with a stir bar. Tetrahydro-2H-pyran-4-amine (366 mg, 3.62 mmol) was then added neat by syringe. The solution was heated in a microwave apparatus with stirring to 120° C. for 1 hour. After 1 hour, the solution was diluted to 30 mL with ethyl acetate and washed with a water/brine mixture (4×30 mL). The organics were isolated, dried (MgSO$_4$), filtered and concentrated. TLC in 5/95 methanol/ethyl acetate showed complete loss of starting material and a new spot of nearly the same rf. The crude product was loaded onto a Biotage 40S column with 2.5/97.5 methanol/ethyl acetate and eluted. Product containing fractions were pooled and concentrated to a foam, 1-((4-chloro-3-fluorophenyl)(1-methyl-1H-pyrazol-4-yl)methyl)-4-(2-((tetrahydro-2H-pyran-4-yl)amino)pyrimidin-4-yl)pyridin-2(1H)-one (225 mg, 63%). $^1$H NMR (400 MHz, CDCl$_3$) δ 8.39 (d, 1H), 7.37 (m, 4H), 7.23 (s, 1H), 7.18 (br s, 1H), 7.00 (m, 2H), 6.90 (d, 1H), 6.79 (dd, 1H), 5.15 (br d, 1H), 4.11 (m, 1H), 4.00 (m, 2H), 3.91 (s, 3H), 3.56 (m, 2H), 2.06 (m, 2H), 1.57 (m, 2H); m/z (APCI-pos) M+1=496.1.

Example 36

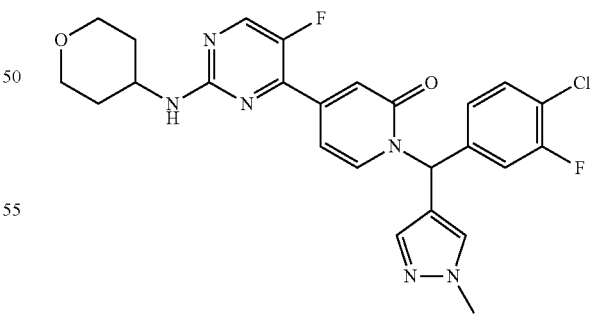

1-((4-chloro-3-fluorophenyl)(1-methyl-1H-pyrazol-4-yl)methyl)-4-(5-fluoro-2-((tetrahydro-2H-pyran-4-yl)amino)pyrimidin-4-yl)pyridin-2(1H)-one Step A: NaH (8.1 mg, 0.20 mmol; 60% oil dispersion) neat as a solid was added to a stirred suspension of 4-(5- fluoro-2-((tetrahydro-2H-pyran-4-yl)amino)pyrimidin-4-yl)pyridin-2(1H)-one (59 mg, 0.20 mmol) in DMF (1.5 mL) at room temperature under nitrogen. After 15 minutes, a solution had formed. tert-Butyl 4-(chloro(4-chloro-3-fluorophenyl)methyl)-1H-pyrazole-1-carboxylate (70 mg, 0.20 mmol) was then added dropwise by syringe as a solution in DMF (500 µL). After stirring overnight, the reaction was quenched by addition of saturated ammonium chloride solution (1 mL). The mixture was partitioned between ethyl acetate (30 mL) and water (30 mL). The organics were isolated and washed with water (3×30 mL) and with brine (30 mL). The organics were isolated, dried (MgSO$_4$), filtered and concentrated. The crude product was dissolved in a minimum of dichloromethane and filtered to remove insoluble unreacted pyridone. The filtrate was re-concentrated and loaded onto a Biotage 12M column with 1/1 ethyl acetate/hexanes and eluted. Product containing fractions were pooled and concentrated to a foam, tert-butyl 4-((4-chloro-3-fluorophenyl)(4-(5-fluoro-2-((tetrahydro-2H-pyran-4-yl)amino)pyrimidin-4-yl)-2-oxopyridin-1(2H)-yl)methyl)-1H-pyrazole-1-carboxylate (46 mg, 38%).

Step B: TFA (1 mL) was added to a stirred solution of tert-butyl 4-((4-chloro-3-fluorophenyl)(4-(5-fluoro-2-((tetrahydro-2H-pyran-4-yl)amino)pyrimidin-4-yl)-2-oxopyridin-1(2H)-yl)methyl)-1H-pyrazole-1-carboxylate (46 mg, 0.077 mmol) in dichloromethane (1 mL) at room temperature under a nitrogen balloon. After 3 hours, the reaction was concentrated by rotovap. The residue was redissolved in dichloromethane (10 mL) and carefully treated with saturated sodium bicarbonate solution (10 mL) and stirred rapidly for 10 minutes. The layers were separated, and the aqueous phase was extracted with dichloromethane (10 mL). The combined organics were dried (MgSO$_4$), filtered and concentrated to a foam, 1-((4-chloro-3-fluorophenyl)(1H-pyrazol-4-yl)methyl)-4-(5-fluoro-2-((tetrahydro-2H-pyran-4-yl)amino)pyrimidin-4-yl)pyridin-2(1H)-one (38 mg, 100%).

Step C: NaH (3.05 mg, 0.0762 mmol; 60% oil dispersion) neat as a solid was added to a stirred solution of 1-((4-chloro-3-fluorophenyl)(1H-pyrazol-4-yl)methyl)-4-(5-fluoro-2-((tetrahydro-2H-pyran-4-yl)amino)pyrimidin-4-yl)pyridin-2(1H)-one (38 mg, 0.0762 mmol) in DMF (1 mL) at room temperature under nitrogen. After 15 minutes, a red solution had formed. Methyl iodide (4.75 µL, 0.0762 mmol) was then added neat by syringe. After stirring overnight, the reaction was quenched by addition of saturated ammonium chloride solution (1 mL). The mixture was partitioned between ethyl acetate (15 mL) and saturated sodium bicarbonate (15 mL). The organics were isolated and washed with water (3×15 mL) and with brine (15 mL). TLC in 95/5 ethyl acetate/methanol showed complete consumption of starting material with two new major spots of higher rf. The organics were isolated, dried (MgSO$_4$), filtered and concentrated. The crude product was loaded onto a 20 cm×20 cm×0.5 mm prep plate and eluted with 95/5 ethyl acetate/methanol. Three bands were scraped off the plate. Compound was freed from the silica gel by stirring for 15 minutes with ethyl acetate (50 mL) and filtration. The high rf material shows two methyl signals by $^1$H-NMR and is presumed to be dimethylated byproduct. The lower rf material was isolated as a clear oil, 1-((4-chloro-3-fluorophenyl)(1-methyl-1H-pyrazol-4-yl)methyl)-4-(5-fluoro-2-((tetrahydro-2H-pyran-4-yl)amino)pyrimidin-4-yl)pyridin-2(1H)-one (9 mg, 23%) and appears to be the desired product by comparison to the non-fluoro analog (see Example 35). $^1$H NMR (400 MHz, CDCl$_3$) δ 8.27 (d, 1H), 7.36 (m, 3H), 7.30 (br s, 1H), 7.23 (s, 1H), 7.01 (m, 2H), 6.80 (d, 1H), 5.09 (d, 1H), 4.00 (m, 3H), 3.91 (s, 3H), 3.54 (m, 2H), 2.04 (m, 2H), 1.57 (m, 2H).

Example 37

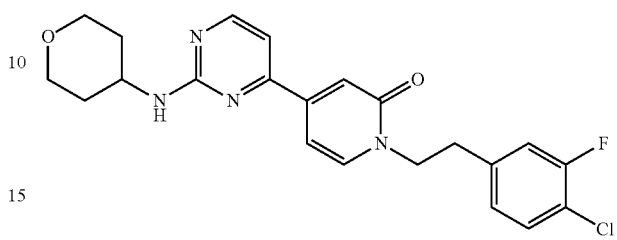

1-(4-chloro-3-fluorophenethyl)-4-(2-((tetrahydro-2H-pyran-4-yl)amino)pyrimidin-4-yl)pyridin-2(1H)-one Step A: DIEA (172 µL, 0.985 mmol; d 0.742) neat was added by syringe to a stirred solution of 2-(4-chloro-3-fluorophenyl)ethanol (172 mg, 0.985 mmol) in dichloromethane (3 mL) at 0° C. under nitrogen, followed by methanesulfonyl chloride (76.2 µL, 0.985 mmol) neat by syringe. After 15 minutes, TLC in 1/1 ethyl acetate/hexanes showed a new high rf spot. Starting material was completely consumed. The reaction was diluted to 30 mL with dichloromethane and washed with 2N HCl (2×30 mL) and with saturated sodium bicarbonate solution (2×30 mL). The organics were isolated, dried (MgSO$_4$), filtered and concentrated to an oil, 4-chloro-3-fluorophenethyl methanesulfonate (240 mg, 96%).

Step B: NaH (11.1 mg, 0.277 mmol; 60% oil dispersion) neat as a solid was added to a stirred suspension of 4-(2-((tetrahydro-2H-pyran-4-yl)amino)pyrimidin-4-yl)pyridin-2(1H)-one (75.4 mg, 0.277 mmol) in DMF (700 µL) at room temperature under nitrogen. After 15 minutes, a clear solution had formed. A solution of 4-chloro-3-fluorophenethyl methanesulfonate (105 mg, 0.416 mmol) in of DMF (700 µL) was then added dropwise. After stirring overnight, the reaction was quenched by addition of saturated ammonium chloride solution (1 mL). The mixture was partitioned between ethyl acetate (30 mL) and water (30 mL). The organics were isolated and washed with water (3×30 mL) and with brine (30 mL). The organics were isolated, dried (MgSO$_4$), filtered and concentrated. The crude product was loaded onto a Biotage 12M column with 2.5/97.5 methanol/ethyl acetate and eluted. The undesired O-alkylated product eluted first and was not collected. Product containing fractions then eluted and were pooled and concentrated to an oil that eventually solidified, 1-(4-chloro-3-fluorophenethyl)-4-(2-((tetrahydro-2H-pyran-4-yl)amino)pyrimidin-4-yl)pyridin-2(1H)-one (20 mg, 17%). $^1$H NMR (400 MHz, CDCl$_3$) δ 8.38 (d, 1H), 7.30 (dd, 1H), 7.18 (br s, 1H), 7.02 (d, 1H), 6.98 (dd, 1H), 6.90 (m, 2H), 6.66 (dd, 1H), 5.17 (br d, 1H), 4.16 (t, 2H), 4.12 (m, 1H), 4.00 (m, 2H), 3.57 (m, 2H), 3.08 (t, 2H), 2.06 (m, 2H), 1.58 (m, 2H); m/z (APCI-pos) M+1=430.1.

Example 38

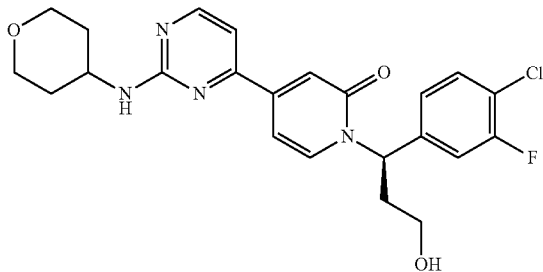 [SMILES: O=c1cc(-c2ccnc(NC3CCOCC3)n2)ccn1[C@H](CCO)c1ccc(Cl)c(F)c1]

(R)-1-(1-(4-chloro-3-fluorophenyl)-3-hydroxypropyl)-4-(2-((tetrahydro-2H-pyran-4-yl)amino)pyrimidin-4-yl)pyridin-2(1H)-one Step A: Potassium bis(trimethylsilyl)amide (0.91M in THF, 0.202 mL) was added to a cooled to 0° C. suspension of 4-(2-((tetrahydro-2H-pyran-4-yl)amino)pyrimidin-4-yl)pyridin-2(1H)-one (40 mg, 0.147 mmol) in 2-methyltetrahydrofuran (4 mL). The mixture was agitated 15 minutes, and (S)-3-(tert-butyldimethylsilyloxy)-1-(4-chloro-3-fluorophenyl)propyl methanesulfonate (81.6 mg, 0.206 mmol) in 2-methyltetrahydrofuran (1 mL) was added. The mixture was then heated to 75° C. and agitated overnight. The reaction was quenched with saturated sodium bicarbonate solution and diluted with ethyl acetate (5 mL). The organic layer was washed with water (2×) and evaporated. Purified by chromatography on silica gel, eluted with 50-75% ethyl acetate/hexanes to give (R)-1-(3-(tert-butyldimethylsilyloxy)-1-(4-chloro-3-fluorophenyl)propyl)-4-(2-((tetrahydro-2H-pyran-4-yl)amino)pyrimidin-4-yl)pyridin-2(1H)-one (0.056 g, 0.0977 mmol, 66.5% yield) as thick oil.

Step B: (R)-1-(3-(tert-Butyldimethylsilyloxy)-1-(4-chloro-3-fluorophenyl)propyl)-4-(2-((tetrahydro-2H-pyran-4-yl)amino)pyrimidin-4-yl)pyridin-2(1H)-one (0.056 g, 0.098 mmol) was dissolved in chloroform (1 mL), and 4M HCl in dioxane was added. After agitating for 30 minutes, the mixture was evaporated and dried in vacuo to give (R)-1-(1-(4-chloro-3-fluorophenyl)-3-hydroxypropyl)-4-(2-((tetrahydro-2H-pyran-4-yl)amino)pyrimidin-4-yl)pyridin-2(1H)-one (0.045 g, 0.098 mmol, quantitative yield) as a solid. $^1$H NMR (400 MHz, CDCl$_3$) δ 9.22 (d, J=5.0 Hz, 1H), 8.37 (d, J=5.0 Hz, 1H), 7.42 (t, J=5.0 Hz, 1H), 7.36 (s, 1H), 7.28-7.10 (m, 4H), 6.77 (d, J=5.0 Hz, 1H), 6.45 (m, 1H), 4.25 (br s, 1H), 4.20-4.00 (m, 2H), 3.80-3.42 (m, 9H), 2.55 (m, 1H), 2.20 (m, 1H), 2.02 (m, 2H), 1.82 (m, 2H); m/z (APCI-pos) M+1=459.0.

Example 39

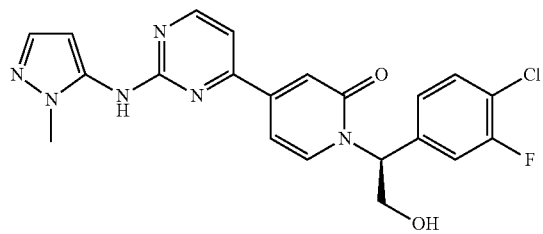 [SMILES: Cn1nccc1Nc1nccc(-c2ccn([C@H](CO)c3ccc(Cl)c(F)c3)c(=O)c2)n1]

(S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one Step A: (S)-1-(2-(tert-Butyldimethylsiloxy)-1-(4-chloro-3-fluorophenyl)ethyl)-4-(2-(methylsulfonyl)pyrimidin-4-yl)pyridine-2(1H)-one (47 mg, 0.087 mmol), 2-methyl pyrazole-3-amine (0.175 mmol, 2.0 equivalents) and anhydrous DMF (3.0 mL) were added to a 25 mL round bottomed flask equipped with a stirring bar. The flask was capped with a rubber septum and flushed with nitrogen. Under a blanket of nitrogen, sodium hydride (8.5 mg, 60% dispersion in mineral oil) was added in one portion. The flask was flushed with nitrogen, capped and stirred at room temperature. The reaction progress was monitored by LCMS, and after 30 minutes, the starting material was consumed. The reaction mixture was quenched by the addition of water (0.5 mL) and ethyl acetate (15 mL). The contents of the round bottomed flask were transferred to a 125 mL separatory funnel, and the reaction flask was rinsed several times with additional ethyl acetate. Crude (S)-1-(2-((tert-butyldimethylsilyl)oxy)-1-(4-chloro-3-fluorophenyl)ethyl)-4-(2-((1-methyl-1H-pyrazol-5-yl)amino)pyrimidin-4-yl)pyridin-2(1H)-one was partitioned between ethyl acetate and water (80 mL/30 mL). The ethyl acetate layer was washed once with brine, dried (MgSO$_4$), filtered and concentrated to give crude (S)-1-(2-((tert-butyldimethylsilyl)oxy)-1-(4-chloro-3-fluorophenyl)ethyl)-4-(2-((1-methyl-1H-pyrazol-5-yl)amino)pyrimidin-4-yl)pyridin-2(1H)-one. The crude was taken directly into the deprotection step.

Step B: Crude (S)-1-(2-((tert-butyldimethylsilyl)oxy)-1-(4-chloro-3-fluorophenyl)ethyl)-4-(2-((1-methyl-1H-pyrazol-5-yl)amino)pyrimidin-4-yl)pyridin-2(1H)-one (48 mg) was dissolved in ethyl acetate (4 mL) and treated dropwise slowly (over 2 minutes) with an ethyl acetate solution (1.0 mL, which had been saturated with HCl gas). The reaction stirred at room temperature for 15 minutes, after which time LCMS indicated complete consumption of the starting material. The reaction mixture was concentrated to an oily residue and purified by prep RP HPLC to yield (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one (20.8 mg, 54.6% yield) as a lyophilized powder. $^1$H NMR (400 MHz, (CD$_3$)$_2$SO) δ 9.58 (s, 1H), 8.60 (d, J=5.1 Hz, 1H), 7.91 (t, J=9.0 Hz, 1H), 7.58 (t, J=8.1 Hz, 1H), 7.52-7.41 (m, 2H), 7.37 (d, J=1.8 Hz, 1H), 7.14 (dd, J=10.7, 5.1 Hz, 2H), 6.86 (dd, J=7.3, 1.8 Hz, 1H), 6.27 (d, J=1.7 Hz, 1H), 5.97 (dd, J=7.7, 5.7 Hz, 1H), 5.31 (t, J=5.2 Hz, 1H), 4.15 (m, 1H), 4.10-3.95 (m, 1H), 3.69 (s, 3H); LCMS m/z 441 (M+H)+.

Example 40

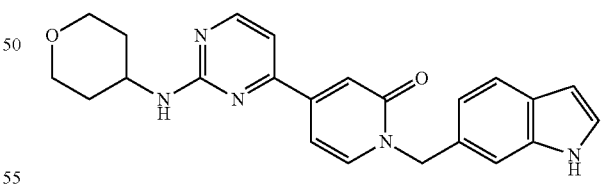

1-((1H-indol-6-yl)methyl)-4-(2-((tetrahydro-2H-pyran-4-yl)amino)pyrimidin-4-yl)pyridin-2(1H)-one Step A: N,N-Dimethylpyridin-4-amine (460 mg, 3.76 mmol) and di-tert-butyl dicarbonate (6.17 g, 28.3 mmol) were added to a solution of methyl 1H-indole-1,6-dicarboxylate (3.30 g, 18.8 mmol) in acetonitrile (60 mL) at room temperature. The reaction mixture was stirred at room temperature overnight. After removal of the solvent, the residue was purified by silica gel chromatography, eluting with petroleum ether/ethyl acetate (10:1) to afford 1-tert-butyl 6-methyl 1H-indole-1,6-dicarboxylate (4.9 g, 95% yield) as a solid. LCMS (ESI) m/z 220.1 [M+H-56]$^+$, 276.1 [M+H]$^+$.

Step B: Diisobutylaluminum hydride (1M in toluene, 12 mL, 12 mmol) was added to a solution of 1-tert-butyl 6-methyl 1H-indole-1,6-dicarboxylate (1.38 g, 5.00 mmol) in toluene (15 mL) at −50° C. over 10 minutes. After being stirred at −50° C. for 30 minutes, the reaction was quenched with methanol (2.5 mL) and water (2.5 mL). The resulting precipitate was filtered off, and the filtrate was evaporated. The residue was purified by silica gel chromatography, eluting with petroleum ether/ethyl acetate (5:1 to 1:1) to afford tert-butyl 6-(hydroxymethyl)-1H-indole-1-carboxylate (815 mg, 55% yield) as an oil. LCMS (ESI) m/z 174.3 [M+H-18-56]$^+$, 230.3 [M+H-18]$^+$.

Step C: Triethylamine (122 mg, 1.20 mmol) and methanesulfonyl chloride (138 mg, 1.20 mmol) were added to a solution of tert-butyl 6-(hydroxymethyl)-1H-indole-1-carboxylate (198 mg, 0.800 mmol) in dichloromethane (10 mL) at room temperature. The reaction mixture was stirred at room temperature overnight. After being diluted with dichloromethane (15 mL), the mixture was washed with water (15 mL), dried with anhydrous Na$_2$SO$_4$, and filtered. After removal of the solvent, the residue (tert-butyl 6-((methylsulfonyloxy)methyl)-1H-indole-1-carboxylate) was used directly in the next step.

Step D: KOt-Bu (180 mg, 1.6 mmol) and n-Bu$_4$NI (37 mg, 0.1 mmol) were added to a mixture of tert-butyl 6-((methylsulfonyloxy)methyl)-1H-indole-1-carboxylate (0.8 mmol) and 4-(2-((tetrahydro-2H-pyran-4-yl)amino)pyrimidin-4-yl)pyridin-2(1H)-one (164 mg, 0.6 mmol) in anhydrous THF (15 mL). The resulting mixture was stirred at 70° C. under microwave irradiation for 2 hours. LC-MS showed the tert-butyl 6-(((methylsulfonyl)oxy)methyl)-1H-indole-1-carboxylate had disappeared. The reaction mixture was treated with water (20 mL) and diluted with dichloromethane. After removal of the insolubles by filtration, the filtrate was extracted with dichloromethane. The combined organic phase was dried with Na$_2$SO$_4$ and concentrated. The residue was purified with Combiflash (A: H$_2$O including 0.5% NH$_3$HCO$_3$, B: CH$_3$CN) to afford tert-butyl 6-((2-oxo-4-(2-((tetrahydro-2H-pyran-4-yl)amino)pyrimidin-4-yl)pyridin-1(2H)-yl)methyl)-1H-indole-1-carboxylate (70 mg, 23% yield).

Step E: TFA (2 mL) was added to a solution of tert-butyl 6-((2-oxo-4-(2-((tetrahydro-2H-pyran-4-yl)amino)pyrimidin-4-yl)pyridin-1(2H)-yl)methyl)-1H-indole-1-carboxylate (70 mg, 0.14 mmol) in dichloromethane (3 mL) at 20° C. The mixture was stirred at room temperature for 2 hours. LC-MS showed the tert-butyl 6-((2-oxo-4-(2-((tetrahydro-2H-pyran-4-yl)amino)pyrimidin-4-yl)pyridin-1(2H)-yl)methyl)-1H-indole-1-carboxylate had disappeared. The reaction mixture was adjusted with a saturated NaHCO$_3$ solution to a pH of around 8-9, then extracted with dichloromethane, and dried with Na$_2$SO$_4$. The organic phase was evaporated, and the residue was purified with prep-HPLC (A: H$_2$O including 0.5% NH$_3$HCO$_3$, B: CH$_3$CN) to afford 1-((1H-indol-6-yl)methyl)-4-(2-(tetrahydro-2H-pyran-4-ylamino)pyrimidin-4-yl)pyridin-2(1H)-one (11 mg, 20% yield). $^1$H NMR (500 MHz, (CD$_3$)$_2$SO) δ 11.10 (s, 1H), 8.41 (d, J=5.0 Hz, 1H), 7.92 (d, J=7.0 Hz, 1H), 7.50 (d, J=8 Hz, 1H), 7.40-7.32 (m, 3H), 7.15-7.11 (m, 2H), 7.03 (d, J=8 Hz, 1H), 6.85 (d, J=7 Hz, 1H), 6.39 (s, 1H), 5.22 (s, 2H), 3.98 (m, 1H), 3.89-3.85 (m, 2H), 3.45-3.36 (m, 2H), 1.86-1.83 (m, 2H), 1.60-1.45 (m, 2H); LCMS (ESI) m/z: 402.2 [M+H+].

Example 41

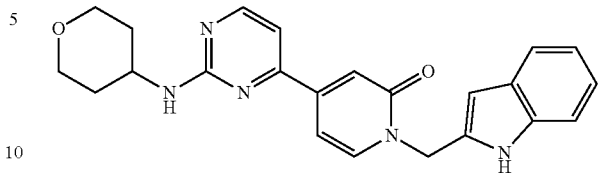

1-((1H-indol-2-yl)methyl)-4-(2-((tetrahydro-2H-pyran-4-yl)amino)pyrimidin-4-yl)pyridin-2(1H)-one Step A: N,N-Dimethylpyridin-4-amine (460 mg, 3.76 mmol) and di-tert-butyl dicarbonate (4.46 g, 40 mmol) were added to a solution of methyl 1H-indole-1,6-dicarboxylate (3.5 g, 20.0 mmol) in acetonitrile (60 mL) at room temperature. The reaction mixture was stirred at room temperature overnight. After removal of the solvent, the residue was purified by silica gel chromatography, eluting with petroleum ether/ethyl acetate (10:1) to afford 1-tert-butyl 2-methyl 1H-indole-1,6-dicarboxylate (5.1 g, 92% yield) as a solid.

Step B: Diisobutylaluminum hydride (1M in toluene, 29 mL, 29 mmol) was added to a solution of 1-tert-butyl 2-methyl 1H-indole-1,6-dicarboxylate (3.28 g, 12.0 mmol) in toluene (25 mL) at −50° C. over 10 minutes. After being stirred at −50° C. for 30 minutes, the reaction was quenched with methanol (10 mL) and water (10 mL). The resulting precipitate was filtered off, and the filtrate was evaporated. The residue was purified by silica gel chromatography, eluting with petroleum ether/ethyl acetate (5:1 to 1:1) to afford tert-butyl 2-(hydroxymethyl)-1H-indole-1-carboxylate (1.5 g, 51% yield) as an oil. LCMS (ESI) m/z 174.3 [M+H-18-56]$^+$.

Step C: Triethylamine (194 mg, 1.7 mmol) and methanesulfonyl chloride (171 mg, 1.7 mmol) were added to a solution of tert-butyl 2-(hydroxymethyl)-1H-indole-1-carboxylate (300 mg, 1.20 mmol) in dichloromethane (10 mL) at room temperature. The reaction mixture was stirred at room temperature overnight. After being diluted with dichloromethane (15 mL), the mixture was washed with water (15 mL), dried over anhydrous Na$_2$SO$_4$, and filtered. After removal of the solvent, the residue (tert-butyl 2-((methylsulfonyloxy)methyl)-1H-indole-1-carboxylate) was used directly in the next step.

Step D: KOt-Bu (224 mg, 2 mmol) and n-Bu$_4$NI (37 mg, 0.1 mmol) were added to a mixture of tert-butyl 2-((methylsulfonyloxy)methyl)-1H-indole-1-carboxylate (350 mg, 1.07 mmol) and 4-(2-((tetrahydro-2H-pyran-4-yl)amino)pyrimidin-4-yl)pyridin-2(1H)-one (272 mg, 1 mmol) in anhydrous THF (15 mL). The resulting mixture was stirred at 70° C. under microwave irradiation for 2 hours. LC-MS showed the tert-butyl 2-(((methylsulfonyl)oxy)methyl)-1H-indole-1-carboxylate had disappeared. The reaction mixture was treated with water (20 mL) and diluted with dichloromethane. After removal of the insolubles by filtration, the filtrate was extracted with dichloromethane. The combined organic phase was dried with Na$_2$SO$_4$ and concentrated. The residue was purified with Combiflash (A: H$_2$O including 0.5% NH$_3$HCO$_3$, B: CH$_3$CN) to afford tert-butyl 2-((2-oxo-4-(2-((tetrahydro-2H-pyran-4-yl)amino)pyrimidin-4-yl)pyridin-1(2H)-yl)methyl)-1H-indole-1-carboxylate (130 mg, 26% yield).

Step E: TFA (2 mL) was added to a solution of tert-butyl 2-((2-oxo-4-(2-((tetrahydro-2H-pyran-4-yl)amino)pyrimidin-4-yl)pyridin-1 (2H)-yl)methyl)-1H-indole-1-carboxylate (130 mg, 0.32 mmol) in dichloromethane (3 mL) at 20° C. The mixture was stirred at room temperature for 2 hours. LC-MS showed the tert-butyl 2-((2-oxo-4-(2-((tetrahydro-2H-pyran-4-yl)amino)pyrimidin-4-yl)pyridin-1(2H)-yl)methyl)-1H-indole-1-carboxylate had disappeared. The reaction mixture was adjusted to a pH of around 8-9 with saturated NaHCO$_3$ solution, extracted with dichloromethane, and dried with Na$_2$SO$_4$. The organic phase was evaporated, and the residue was purified with prep-HPLC (A: H$_2$O including 0.5% NH$_3$HCO$_3$, B: CH$_3$CN) to afford 1-((1H-indol-2-yl)methyl)-4-(2-(tetrahydro-2H-pyran-4-ylamino)pyrimidin-4-yl)pyridin-2(1H)-one (60 mg, 60% yield). $^1$H NMR (500 MHz, (CD$_3$)$_2$SO) δ 11.07 (s, 1H), 8.41 (d, J=4.5 Hz, 1H), 7.88 (d, J=7.5 Hz, 1H), 7.47 (d, J=8 Hz, 1H), 7.37-7.36 (m, 2H), 7.15-7.14 (m, 2H), 7.06 (m 1H), 6.96 (m, 1H), 6.88 (d, J=6 Hz, 1H), 6.35 (s, 1H), 5.26 (s, 2H), 3.97 (m, 1H), 3.88-3.86 (m, 2H), 3.42-3.37 (m, 2H), 1.85-1.83 (m, 2H), 1.56-1.48 (m, 2H); LCMS (ESI) m/z 402.3 [M+H+].

Example 42

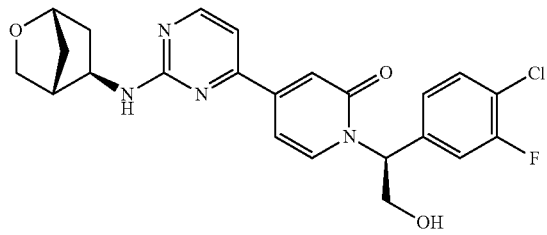 [SMILES: O=c1cc(-c2ccnc(N[C@@H]3C[C@@H]4C[C@H]3CO4)n2)ccn1[C@H](CO)c1ccc(Cl)c(F)c1]

4-(2-((1S,4R,5R)-2-oxabicyclo[2.2.1]heptan-5-ylamino)pyrimidin-4-yl)-1-((S)-1-(4-chloro-3-fluorophenyl)-2-hydroxyethyl)pyridin-2(1H)-one Step A: Diphenylphosphoryl azide ("DPPA") (0.97 g, 3.5 mmol) and triethylamine (384 mg, 3.80 mmol) were added to a solution of 3-oxo-2-oxa-bicyclo[2.2.1]heptane-5-carboxylic acid (0.50 g, 3.2 mmol; prepared according to WO 2008/092955) in dry toluene (5.0 mL). The resulting mixture was stirred at 100° C. under nitrogen atmosphere. After adding phenylmethanol (354 mg, 3.50 mmol), the mixture was stirred at 130° C. for another 2 hours. After being quenched with water (1 mL), the mixture was diluted with ethyl acetate (300 mL), washed with saturated brine (3×50 mL), dried over anhydrous sodium sulfate, and then concentrated. The residue was purified by silica gel chromatography eluting with petroleum ether/ethyl acetate (4:1) to give benzyl 3-oxo-2-oxa-bicyclo[2.2.1]heptan-5-ylcarbamate (600 mg, 72% yield) as a solid. $^1$H NMR (500 MHz, CDCl$_3$) δ 7.80-7.74 (m, 1H), 7.39-7.31 (m, 5H), 5.08-5.00 (m, 3H), 3.87 (s, 1H), 2.78 (s, 1H), 2.24-2.15 (m, 1H), 2.14 (d, J=9.0 Hz, 1H), 1.97 (t, J=20.5 Hz, 1H), 1.71 (d, J=14.0 Hz, 1H).

Step B: NaBH$_4$ (0.580 g, 15.2 mmol) was added to a solution of benzyl 3-oxo-2-oxa-bicyclo[2.2.1]heptan-5-ylcarbamate (1.0 g, 3.8 mmol) and CaCl$_2$ (0.85 g, 7.6 mmol) in ethanol (50 mL) at 0° C. After being stirred at room temperature for 12 hours, the reaction mixture was treated with concentrated HCl. The volatiles were removed, and the residue was extracted with CHCl$_3$ (3×100 mL), washed with water (50 mL) and brine (50 mL), dried over anhydrous sodium sulfate and concentrated. The residue was re-crystallized from petroleum ether to afford benzyl 4-hydroxy-2-(hydroxymethyl)cyclopentylcarbamate (750 mg, 75% yield) as a solid. $^1$H NMR (500 MHz, (CD$_3$)$_2$SO) δ 7.38-7.31 (m, 5H), 7.25 (d, J=13.5 Hz, 1H), 4.99 (s, 2H), 4.53 (d, J=4 Hz, 1H), 4.48 (t, J=10 Hz, 1H), 4.09 (d, J=4 Hz, 1H), 3.73 (t, J=15.5 Hz, 1H), 3.46-3.43 (m, 1H), 3.31-3.28 (m, 1H), 1.99 (d, J=7 Hz, 1H), 1.80-1.74 (m, 2H), 1.57 (t, J=12.5 Hz, 1H), 1.26 (s, 1H).

Step C: A solution of TsCl (290 mg, 1.52 mmol) in dry toluene (3.0 mL) was added dropwise to a solution of benzyl 4-hydroxy-2-(hydroxymethyl)cyclopentylcarbamate (100 mg, 0.380 mmol) and dry pyridine (3.0 mL) in dry toluene (6.0 mL) at 0° C. The mixture was then warmed to room temperature and stirred for 2 days. The reaction mixture was heated to 120° C. and stirred for another 16 hours. After concentration, the residue was purified by reverse phase Combi-flash (0.3% NH$_4$HCO$_3$/CH$_3$CN) to afford benzyl 2-oxa-bicyclo[2.2.1]heptan-5-ylcarbamate as a solid (58 mg, 62% yield). $^1$H NMR (500 MHz, CD$_3$OD) δ 7.37-7.31 (m, 5H), 5.09 (s, 2H), 4.33 (s, 1H), 3.73 (d, J=5.5 Hz, 1H), 3.63-3.61 (m, 1H), 3.48 (d, J=7.5 Hz, 1H), 2.53 (s, 1H), 2.07-2.04 (m, 1H), 1.72 (d, J=10.5 Hz, 1H), 1.61 (d, J=11.0 Hz, 1H), 1.42 (d, J=14.0 Hz, 1H).

Step D: A mixture of benzyl 2-oxa-bicyclo[2.2.1]heptan-5-ylcarbamate (0.50 g, 2.0 mmol) and Pd/C (10%, 50 mg) in methanol (20 mL) was stirred under hydrogen atmosphere (1 atm) at room temperature for 16 hours. After completion of the reaction, the reaction mixture was adjusted to pH around 4 by 1M HCl in methanol. The mixture was filtered through Celite® and concentrated under reduced pressure to give 2-oxa-bicyclo[2.2.1]heptan-5-amine hydrochloride (300 mg, 100% yield) as a solid. $^1$H NMR (500 MHz, CD$_3$OD) δ 4.43 (s, 1H), 3.72-3.70 (m, 1H), 3.54 (d, J=7.5 Hz, 1H), 3.50-3.48 (m, 1H), 2.76 (s, 1H), 2.20-2.15 (m, 1H), 1.96 (d, J=11.0 Hz, 1H), 1.78 (d, J=11.0 Hz, 1H), 1.61 (d, J=11.0 Hz, 1H).

Step E: A microwave vial was charged with (S)-1-(2-(tert-butyldimethylsilyloxy)-1-(4-chloro-3-fluorophenyl)ethyl)-4-(2-(methylsulfonyl)pyrimidin-4-yl)pyridin-2(1H)-one (100 mg, 0.190 mmol), 2-oxa-bicyclo[2.2.1]heptan-5-amine hydrochloride (53 mg, 0.47 mmol), TEA (0.50 mmol, 50 mg) and s-butanol (3.0 mL). The mixture was stirred at 130° C. under microwave irradiation for 3 hours. After completion of the reaction, the mixture was concentrated to give 4-(2-(2-oxabicyclo[2.2.1]heptan-5-ylamino)pyrimidin-4-yl)-1-((S)-2-(tert-butyldimethylsilyloxy)-1-(4-chloro-3-fluorophenyl)ethyl)pyridin-2(1H)-one as an oil, which was used in the next step without further purification. LCMS (ESI) m/z: 571.3 [M+H]+.

Step F: The crude 4-(2-(2-oxabicyclo[2.2.1]heptan-5-ylamino)pyrimidin-4-yl)-1-((S)-2-(tert-butyldimethylsilyloxy)-1-(4-chloro-3-fluorophenyl)ethyl)pyridin-2(1H)-one was dissolved in a solution of HCl in methanol (5 mL, 1M). After being stirred at room temperature for 2 hours, the reaction mixture was then adjusted to pH around 8 by saturated Na$_2$CO$_3$. The resulting mixture was extracted with ethyl acetate (3×20 mL). The combined organic layers were dried over Na$_2$SO$_4$ and concentrated. The residue was purified by prep-HPLC to afford 4-(2-(2-oxabicyclo[2.2.1]heptan-5-ylamino)pyrimidin-4-yl)-1-((S)-1-(4-chloro-3-fluorophenyl)-2-hydroxyethyl)pyridin-2(1H)-one (23 mg, 29% yield). $^1$H NMR (500 MHz, CD$_3$OD) δ 8.42 (d, J=5.0 Hz, 1H), 7.86 (d, J=8.5 Hz, 1H), 7.51 (t, J=16 Hz, 1H), 7.35☐7.33 (m, 1H), 7.29 (s, 1H), 7.20 (d, J=8.0 Hz, 1H), 7.14 (d, J=5.5 Hz, 1H), 7.08-7.06 (m, 1H), 6.15-6.13 (m, 1H), 4.40 (s, 1H), 4.32-4.28 (m, 1H), 4.22-4.19 (m, 1H), 4.09-4.07 (m, 1H), 3.71-3.69 (m, 1H), 3.61 (d, J=7.0 Hz, 1H), 2.69 (s, 1H), 2.19 (t, J=12.0 Hz, 1H), 1.86 (d, J=10.5 Hz, 1H), 1.66 (d, J=10.0 Hz, 1H), 1.58 (d, J=14.0 Hz, 1H); LCMS (ESI) m/z: 571.3 [M+H]+.

Example 43

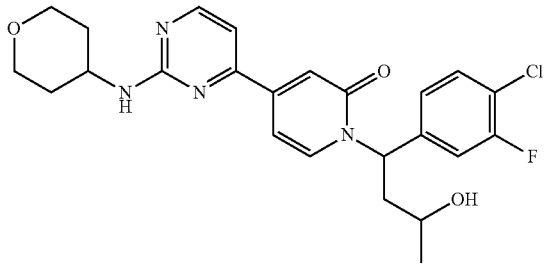 [SMILES: CC(O)CC(c1ccc(Cl)c(F)c1)n1ccc(-c2ccnc(NC3CCOCC3)n2)cc1=O]

1-(1-(4-chloro-3-fluorophenyl)-3-hydroxybutyl)-4-(2-((tetrahydro-2H-pyran-4-yl)amino)pyrimidin-4-yl)pyridin-2(1H)-one Step A: Proline (23 mg, 0.20 mmol) was added to a solution of 4-chloro-3-fluorobenzaldehyde (159 mg, 1.00 mmol) in acetone (2.5 mL). The resulting mixture was stirred at room temperature overnight. The reaction mixture was then treated with saturated ammonium chloride. After partitioning, the aqueous layer was extracted with ethyl acetate (3×25 mL). The combined organic layers were dried over anhydrous Na$_2$SO$_4$ and concentrated. The residue was purified by silica gel column chromatography eluting with ethyl acetate/petroleum ether (1:4) to afford 4-(4-chloro-3-fluorophenyl)-4-hydroxybutan-2-one (160 mg, 73% yield) as a solid. $^1$H NMR (500 MHz, CDCl$_3$) δ 7.36 (m, 1H), 7.19 (m, 1H), 7.06 (m, 1H), 5.13 (t, J=6.5 Hz, 1H), 3.43 (br s, 1H), 2.82 (d, J=6.5 Hz, 1H), 2.21 (s, 3H).

Step B: Sodium borohydride (112 mg, 2.95 mmol) was added in three portions to a solution of 4-(4-chloro-3-fluorophenyl)-4-hydroxybutan-2-one (160 mg, 0.73 mmol) in methanol (5 mL). The resulting mixture was stirred at room temperature overnight. The reaction mixture was then treated with saturated ammonium chloride. After removal of methanol, the aqueous layer was extracted with ethyl acetate (3×25 mL). The combined organic layers were dried and concentrated to give 1-(4-chloro-3-fluorophenyl)butane-1,3-diol (130 mg, 81% yield) as a solid. $^1$H NMR (500 MHz, CDCl$_3$) δ 7.36 (m, 1H), 7.17 (m, 1H), 7.04 (m, 1H), 5.07 (m, 1H), 3.48 (br s, 1H), 2.13 (m, 1H), 1.56 (m, 1H), 1.30 (d, J=6.0 Hz, 3H).

Step C: Imidazole (96.0 mg, 1.42 mmol) and tert-butylchlorodimethylsilane (107 mg, 0.710 mmol) were added to a solution of 1-(4-chloro-3-fluorophenyl)butane-1,3-diol (130 mg, 0.590 mmol) in DCM (10 mL). The resulting mixture was stirred at room temperature overnight. The reaction mixture was then diluted with DCM (15 mL), washed with brine and water, dried over anhydrous Na$_2$SO$_4$, and concentrated. The residue was purified by silica gel column chromatography eluting with ethyl acetate/petroleum ether (1:4) to afford 3-(tert-butyldimethylsilyloxy)-1-(4-chloro-3-fluorophenyl)butan-1-ol (130 mg, 66% yield) as oil.

Step D: Triethylamine (84 mg, 0.85 mmol) and methanesulfonyl chloride (94.6 mg, 0.850 mmol) were added at room temperature to a solution of 3-(tert-butyldimethylsilyloxy)-1-(4-chloro-3-fluorophenyl)butan-1-ol (250 mg, 0.75 mmol) in DCM (15 mL). After being stirred at room temperature overnight, the reaction mixture was diluted with dichloromethane (15 mL), washed with water (15 mL), dried over anhydrous Na$_2$SO$_4$, and concentrated. The product, 3-(tert-butyldimethylsilyloxy)-1-(4-chloro-3-fluorophenyl)butyl methanesulfonate, was used directly in the next step.

Step E: Potassium 2-methylpropan-2-olate (135 mg, 1.20 mmol), tetrabutylammonium iodide (67 mg, 0.18 mmol), and a solution of 3-(tert-butyldimethylsilyloxy)-1-(4-chloro-3-fluorophenyl)butyl methanesulfonate (0.75 mmol) in anhydrous THF (15 mL) were added to a suspension of 4-(2-((tetrahydro-2H-pyran-4-yl)amino)pyrimidin-4-yl)pyridin-2(1H)-one (163 mg, 0.600 mmol) in anhydrous THF (5.0 mL). The resulting mixture was stirred at 95° C. under microwave irradiation for 2 hours. The reaction was quenched with water (20 mL). The mixture was further diluted with DCM. After removal of the insoluble by filtration, the filtrate was extracted with DCM. The combined organic phases were dried over Na$_2$SO$_4$ and concentrated. The residue was purified by Combiflash (0.5% NH$_3$HCO$_3$/CH$_3$CN) to afford 1-(3-(tert-butyldimethylsilyloxy)-1-(4-chloro-3-fluorophenyl)butyl)-4-(2-((tetrahydro-2H-pyran-4-yl)amino)pyrimidin-4-yl)pyridin-2(1H)-one (80 mg, 26% yield). LCMS (ESI) m/z: 587.2 [M+H]$^+$.

Step F: HCl/methanol (3N, 1.0 mL) was added at 5° C. to a solution of 1-(3-(tert-butyldimethylsilyloxy)-1-(4-chloro-3-fluorophenyl)butyl)-4-(2-((tetrahydro-2H-pyran-4-yl)amino)pyrimidin-4-yl)pyridin-2(1H)-one (90.0 mg, 0.154 mmol) in methanol (3.0 mL). After being stirred at room temperature for 2 hours, the reaction mixture was adjusted to pH around 8-9 with saturated NaHCO$_3$, extracted with dichloromethane, dried over Na$_2$SO$_4$ and concentrated. The residue was purified with prep-HPLC to afford 1-(1-(4-chloro-3-fluorophenyl)-3-hydroxybutyl)-4-(2-((tetrahydro-2H-pyran-4-yl)amino)pyrimidin-4-yl)pyridin-2(1H)-one (36 mg, 50% yield) as a solid. $^1$H NMR (500 MHz, (CD$_3$)$_2$SO) δ 10.92 (s, 1H), 8.41 (d, J=5.0 Hz, 1H), 7.95 (m, 1H), 7.58 (m, 1H), 7.46 (m, 1H), 7.30 (m, 1H), 7.23 (m, 1H), 7.10 (m, 1H), 7.07 (m, 1H), 6.87 (m, 1H), 6.14 (m, 1H), 4.70 (m, 1H), 3.97 (m, 1H), 3.89-3.87 (m, 2H), 3.41-3.33 (m, 2H), 2.47 (m, 1H), 2.06 (m, 1H), 1.86-1.84 (m, 2H), 1.56-1.52 (m, 2H), 1.12-1.09 (m, 3H); LCMS (ESI) m/z: 473.2 [M+H]$^+$.

Example 44

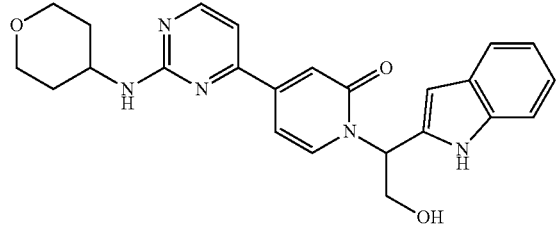 [SMILES: O=c1cc(-c2ccnc(NC3CCOCC3)n2)ccn1C(CO)c1cc2ccccc2[nH]1]

1-(2-hydroxy-1-(1H-indol-2-yl)ethyl)-4-(2-((tetrahydro-2H-pyran-4-yl)amino)pyrimidin-4-yl)pyridin-2(1H)-one Step A: Diisobutylaluminum hydride (159 mL, 159 mmol) was added dropwise at −60° C. to a solution of methyl 1H-indole-2-carboxylate (10.0 g, 52.9 mmol) in THF (100 mL). After being stirred for 1 hour, the reaction was quenched with saturated NH$_4$Cl. The resulting mixture was extracted with ethyl acetate (2×100 mL) and washed with brine, dried, and concentrated to give (1H-indol-2-yl)methanol (8.0 g, 100% yield) as a solid. LCMS (ESI) m/z: 148.1 [M+H]$^+$.

Step B: A mixture of (1H-indol-2-yl)methanol (8.00 g, 54.4 mmol) and 2-iodoxybenzoic acid ("IBX") (40.0 g, 0.163 mol) in ethyl acetate (200 mL) was stirred at 80° C. for 16 hours. The solid was filtered off, and the filtrate was concentrated. The residue was purified by silica gel column chromatography eluting with petroleum ether/ethyl acetate (50:1) to give 1H-indole-2-carbaldehyde (4.0 g, 50% yield) as a solid. LCMS (ESI) m/z: 146.1 [M+H]$^+$.

Step C: NaH (2.6 g, 66.2 mmol) at 0° C. was added to a mixture of 1H-indole-2-carbaldehyde (4.00 g, 27.6 mmol) and PPh$_3$CH$_3$Br (19.7 g, 55.2 mmol) in dry THF (100 mL). After being stirred at room temperature for 16 hours, the reaction was quenched with water. After partition, the aqueous layer was extracted with ethyl acetate (2×50 mL). The combined organic layers were washed with brine, dried, and concentrated. The residue was purified by silica gel column chromatography eluting with petroleum ether/ethyl acetate (50:1) to give 2-vinyl-1H-indole (4.0 g, 83% yield) as a solid.

Step D: N,N-Dimethylpyridin-4-amine (100 mg) and triethylamine (7.0 mL, 69 mmol) at room temperature were added to a mixture of 2-vinyl-1H-indole (4.0 g, 28 mmol) and Boc$_2$O (7.26 g, 33.6 mmol) in DCM (50 mL). After being stirred for 1 hour, the mixture was concentrated. The residue was purified by silica gel column chromatography eluting with petroleum ether/ethyl acetate (200:1) to give tert-butyl 2-vinyl-1H-indole-1-carboxylate (5.2 g, 76% yield) as an oil.

Step E: 4-Methoxy-4-methylmorpholin-4-ium (1.5 g, 12.8 mmol), water (10 mL), and OsO$_4$ (250 mg, 1 mmol) in water (10 mL) were added to a mixture of tert-butyl 2-vinyl-1H-indole-1-carboxylate (2.60 g, 10.7 mmol) in acetone (15 mL) and THF (15 mL). After being stirred at room temperature for 16 hours, saturated Na$_2$SO$_3$ was added, and the resulting mixture was stirred for 30 minutes. The insoluble material was filtered off. The filtrate was extracted with ethyl acetate (2×100 mL), washed with brine, dried, and concentrated to give tert-butyl 2-(1,2-dihydroxyethyl)-1H-indole-1-carboxylate (2.0 g, 69% yield) as an oil.

Step F: TBSCl (1.3 g, 8.9 mmol) in dichloromethane (20 mL) was added dropwise at 0° C. over 10 minutes to a solution of tert-butyl 2-(1,2-dihydroxyethyl)-1H-indole-1-carboxylate (2.0 g, 7.2 mmol) and imidazole (1.20 g, 17.4 mmol) in DCM (30 mL). After being stirred at room temperature for 1 hour, the mixture was washed with water (2×50 mL) and brine, dried, and concentrated. The residue was purified by silica gel column chromatography eluting with petroleum ether/ethyl acetate (50:1) to give an oil, which was further purified by prep-HPLC to afford tert-butyl 2-(2-(tert-butyldimethylsilyloxy)-1-hydroxyethyl)-1H-indole-1-carboxylate (500 mg, 18% yield) as an oil. LCMS (ESI) m/z: 318.3 [M-56-17]$^+$.

Step G: Triethylamine (68 mg, 0.67 mmol) and methanesulfonyl chloride (71 mg, 0.67 mmol) were added at room temperature to a solution of tert-butyl 2-(2-(tert-butyldimethylsilyloxy)-1-hydroxyethyl)-1H-indole-1-carboxylate (240 mg, 0.610 mmol) in DCM (20 mL). After being stirred at room temperature overnight, the reaction mixture was diluted with dichloromethane (15 mL). The resulting mixture was further washed with water (15 mL) and dried over anhydrous Na$_2$SO$_4$. After removal of the solvent, the residue tert-butyl 2-(2-(tert-butyldimethylsilyloxy)-1-methylsulfonyloxyethyl)-1H-indole-1-carboxylate was used directly in the next step.

Step H: Potassium 2-methylpropan-2-olate (114 mg, 1.02 mmol), tetrabutylammonium iodide (57 mg, 0.15 mmol), and a solution of tert-butyl 2-(2-(tert-butyldimethylsilyloxy)-1-methylsulfonyloxyethyl)-1H-indole-1-carboxylate (0.61 mmol) in anhydrous THF (15 mL) were added to a suspension of 4-(2-(tetrahydro-2H-pyran-4-ylamino)pyrimidin-4-yl)pyridin-2(1H)-one (139 mg, 0.510 mmol) in anhydrous THF (5.0 mL). The resulting mixture was stirred at 95° C. under microwave irradiation for 2 hours. The reaction mixture was then treated with water (20 mL) and diluted with DCM. After removal of the insoluble by filtration, the filtrate was extracted with DCM. The combined organic phase was dried over Na$_2$SO$_4$ and concentrated. The residue was purified with prep-HPLC to afford 1-(2-hydroxy-1-(1H-indol-2-yl)ethyl)-4-(2-((tetrahydro-2H-pyran-4-yl)amino)pyrimidin-4-yl)pyridin-2(1H)-one formate (4.6 mg, 1.1% yield) as a solid. $^1$H NMR (500 MHz, (CD$_3$)$_2$SO) δ 11.20 (s, 1H), 8.46-8.40 (m, 2H), 7.64 (d, J=7.0 Hz, 1H), 7.50 (d, J=8.5 Hz, 1H), 7.35-7.31 (m, 2H), 7.14-7.12 (m, 2H), 7.06 (m, 1H), 6.97 (m, 1H), 6.81 (d, J=7.0 Hz, 1H), 6.54 (s, 1H), 6.24 (m, 1H), 5.30 (m, 1H), 4.13-4.07 (m, 2H), 3.97 (m, 1H), 3.88-3.86 (m, 2H), 3.41-3.36 (m, 2H), 1.85-1.83 (m, 2H), 1.56-1.49 (m, 2H); LCMS (ESI) m/z: 432.2 [M+H]$^+$.

Example 45

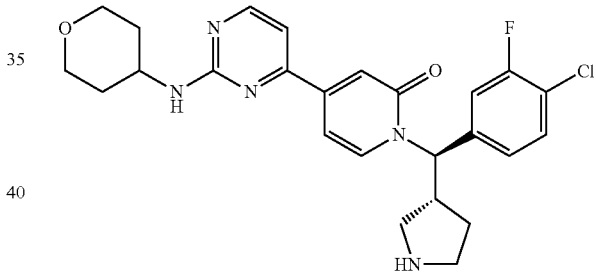

1-((R)-(4-chloro-3-fluorophenyl)((R)-pyrrolidin-3-yl)methyl)-4-(2-((tetrahydro-2H-pyran-4-yl)amino)pyrimidin-4-yl)pyridin-2(1H)-one Step A: (R)-1-(tert-Butoxycarbonyl)pyrrolidine-3-carboxylic acid (922.3 mg, 4.285 mmol) was dissolved in dichloromethane (42.8 mL, 0.1M) at room temperature under nitrogen and was treated with N,O-dimethylhydroxylamine hydrochloride (501.6 mg, 5.142 mmol), O-(7-azabenzotriazol-1-yl)-N,N,N',N'-tetramethylurea (1955 mg, 5.142 mmol), and N,N-diisopropylethylamine (1493 μL, 8.570 mmol). The mixture was stirred at room temperature for 2 hours. The reaction was then diluted to 100 mL with dichloromethane and washed with water (100 mL). The water layer was back extracted with 4/1 dichloromethane/isopropanol (2×50 mL). The combined organics were washed with water (100 mL), were isolated, dried over sodium sulfate, filtered and concentrated to an oil. The crude product was loaded onto an SP1 samplet and purified by silica gel chromatography using a gradient from 10% to 70% acetone in hexanes. Product containing fractions (ninhydrin visualization) were pooled and concentrated to afford (R)- tert-butyl 3-(methoxy(methyl)carbamoyl)pyrrolidine-1-carboxylate as an oil (1.1 gram, 100% yield).

Step B: (R)-tert-Butyl 3-(methoxy(methyl)carbamoyl) pyrrolidine-1-carboxylate (1.107 g, 4.285 mmol) was dissolved in THF (21.4 mL, 0.2M), cooled to 0° C., and degassed with N₂. 4-Chloro-3-fluorophenylmagnesium bromide (0.5M in THF; 17.14 mL, 8.571 mmol) was added drop wise by syringe, and the reaction was then stirred at 0° C. for 1.5 hours. Water (10 mL) was then added to quench the reaction. The mixture was concentrated by rotovap to remove the bulk of the THF. The remaining mixture was diluted to 50 mL with water and extracted with 4/1 dichloromethane/isopropyl alcohol (2×50 mL). The combined organics were washed with water (100 mL), were isolated, dried over sodium sulfate, filtered and concentrated. The crude product was loaded onto an SP1 samplet and purified by silica gel chromatography using a gradient from 2% to 50% ethyl acetate in hexanes. Product containing fractions were pooled and concentrated to afford (R)-tert-butyl 3-(4-chloro-3-fluorobenzoyl)pyrrolidine-1-carboxylate as an oil (920 mg, 65% yield).

Step C: (R)-tert-Butyl 3-(4-chloro-3-fluorobenzoyl)pyrrolidine-1-carboxylate (920 mg, 2.806 mmol) was dissolved in THF (14.0 mL, 0.2M), degassed with N₂, and cooled to −78° C. Lithium tri-sec-butylborohydride (1M in THF; 4210 µL, 4.210 mmol) was added slowly drop wise by syringe. The reaction was then stirred at −78° C. for 30 minutes. Water (5 mL) was then added to quench the reaction. The mixture was concentrated by rotovap to remove the bulk of the THF. The remaining mixture was diluted to 50 mL with water and extracted with 4/1 dichloromethane/isopropyl alcohol (2×50 mL). The combined organics were washed with water (100 mL), were isolated, dried over sodium sulfate, filtered and concentrated. The crude product was loaded onto an SP1 samplet and purified by silica gel chromatography using a gradient from 1% to 55% ethyl acetate in hexanes. Product containing fractions were pooled and concentrated to afford (3R)-tert-butyl 3-((4-chloro-3-fluorophenyl)(hydroxy)methyl)pyrrolidine-1-carboxylate as an oil and as a 1:1 mixture of diastereomers (640 mg, 69% yield).

Step D: (3R)-tert-Butyl 3-((4-chloro-3-fluorophenyl)(hydroxy)methyl)pyrrolidine-1-carboxylate (640 mg, 1.943 mmol) was dissolved in DCM (4.9 mL, 0.2M) under nitrogen, treated with triphenylphosphine (637.0 mg, 2.429 mmol) and cooled to 0° C. Diisopropyl azodicarboxylate (478.2 µL, 2.429 mmol) was added by syringe. After 5 minutes, the mixture was warmed to room temperature and stirred for 10 minutes prior to being treated with 4-(2-(methylthio)pyrimidin-4-yl)pyridin-2(1H)-one (213 mg, 0.9714 mmol). The mixture was then stirred at room temperature for 16 hours. After concentration by rotovap and high vacuum, the mixture was loaded onto a C18 reverse phase column and eluted with a gradient of 5% acetonitrile to 100% acetonitrile in water. The mixture of diastereomers isolated were then loaded onto an SP1 samplet and purified by silica gel chromatography using a 20% to 80% gradient of MTBE in dichloromethane. Fractions containing each diastereomer were isolated and concentrated to afford (R)-tert-butyl 3-((R)-(4-chloro-3-fluorophenyl)(4-(2-(methylthio)pyrimidin-4-yl)-2-oxopyridin-1(2H)-yl)methyl)pyrrolidine-1-carboxylate from the higher rf spot and (R)-tert-butyl 3-((S)-(4-chloro-3-fluorophenyl)(4-(2-(methylthio)pyrimidin-4-yl)-2-oxopyridin-1(2H)-yl)methyl)pyrrolidine-1-carboxylate as the lower rf spot, both as oils (54 mg, 10% yield and 48 mg, 9% yield respectively).

Step E: (R)-tert-Butyl 3-((R)-(4-chloro-3-fluorophenyl) (4-(2-(methylthio)pyrimidin-4-yl)-2-oxopyridin-1(2H)-yl) methyl)pyrrolidine-1-carboxylate (54.5 mg, 0.103 mmol) was dissolved in DCM (1.0 mL, 0.1 M) at room temperature under nitrogen and treated with 3-chloroperoxybenzoic acid (75.9 mg, 0.308 mmol). After stirring for 1 hour, the mixture was diluted with EtOAc (15 mL) and washed with 10% sodium thiosulfate (15 mL) and brine (15 mL). The isolated organics were then dried over sodium sulfate, filtered and concentrated. The crude product was loaded onto an SP1 samplet and purified by silica gel chromatography using a 2% to 50% gradient of acetone in dichloromethane to afford (R)-tert-butyl 3-((R)-(4-chloro-3-fluorophenyl)(4-(2-(methylsulfonyl)pyrimidin-4-yl)-2-oxopyridin-1(2H)-yl)methyl) pyrrolidine-1-carboxylate as a solid (45 mg, 78% yield).

Step F: (R)-tert-Butyl 3-((R)-(4-chloro-3-fluorophenyl) (4-(2-(methylsulfonyl)pyrimidin-4-yl)-2-oxopyridin-1(2H)-yl)methyl)pyrrolidine-1-carboxylate (45.1 mg, 0.0801 mmol) was dissolved in DMA (1.0 mL, 0.1M) at room temperature under nitrogen and treated with tetrahydro-2H-pyran-4-amine (40.5 mg, 0.401 mmol). The solution was heated to 120° C. for 1 hour in the microwave. The reaction was then diluted with EtOAc (15 mL) and washed with water (3×15 mL) and brine (15 mL). The organics were isolated, dried over sodium sulfate, filtered and concentrated. The crude product was loaded onto an SP1 samplet and purified by silica gel chromatography using a 10% to 80% gradient of acetone in hexanes. Product containing fractions were pooled, concentrated and then redissolved in dichloromethane (2 mL) and treated with 1:1 TFA/DCM (1.0 mL) and stirred at room temperature for 1 hour. The reaction was diluted to 15 mL with additional DCM and washed with NaHCO₃ (2×15 mL). The organics were isolated, dried over sodium sulfate, filtered and concentrated to afford 1-((R)-(4-chloro-3-fluorophenyl)((R)-pyrrolidin-3-yl)methyl)-4-(2-((tetrahydro-2H-pyran-4-yl)amino)pyrimidin-4-yl)pyridin-2(1H)-one as an oil. ¹H NMR (400 MHz, ((CD₃)₂SO) δ 8.40 (d, 1H), 8.04 (d, 1H), 7.62 (m, 2H), 7.37 (d, 1H), 7.34 (br s, 1H), 7.13 (d, 1H), 7.08 (s, 1H), 6.86 (d, 1H), 5.84 (br s, 1H), 3.97 (m, 1H), 3.87 (m, 2H), 3.38 (m, 2H), 2.86 (m, 1H), 2.79 (m, 2H), 2.34 (m, 1H), 1.84 (br d, 2H), 1.74 (m, 1H), 1.52 (m, 3H), 1.27 (m, 2H); LCMS (ESI) m/z 484.1 [M+H+].

Example 46

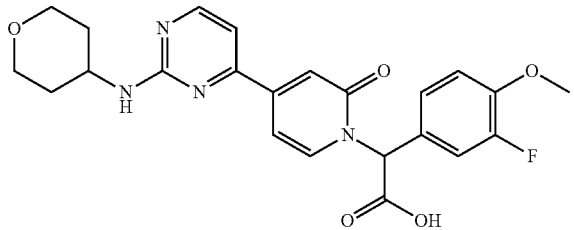 [SMILES: COc1ccc(C(C(=O)O)n2ccc(-c3ccnc(NC4CCOCC4)n3)cc2=O)cc1F]

2-(3-fluoro-4-methoxyphenyl)-2-(2-oxo-4-(2-((tetrahydro-2H-pyran-4-yl)amino)pyrimidin-4-yl)pyridin-1(2H)-yl)acetic acid Step A: A 500 mL 24/40 round bottomed flask equipped with a stirring bar was charged with (3-fluoro-4-methoxyphenyl)acetic acid methyl ester (4.17 g) and dissolved in anhydrous carbon tetrachloride (200 mL). N-Bromosuccinimide ("NBS") (4.89 g) was added, followed by benzoyl peroxide ("BPO") (550 mg). The flask was equipped with a water cooled condenser and placed in a pre-heated 100° C. oil bath. After refluxing for 17.5 hours, the flask was removed from the oil bath, cooled to room temperature and filtered. The filtrate was analyzed by LCMS and TLC. Since the starting material and both products did not ionize well, TLC (40% ethyl acetate/heptane) was used to determine conversion of starting material to product. TLC indicated the starting material had been completely consumed. The filtrate was concentrated to a residue, dissolved in a minimal amount of DCM and adsorbed onto a silica pre-column. After ISCO purification (80 g column, 0-100% ethyl acetate/heptane over 25 column volumes) fractions for the major uv product (30-40% ethyl acetate) were combined and concentrated to yield methyl 2-bromo-2-(3-fluoro-4-methoxyphenyl)acetate (4.73 g). The NMR in CDCl$_3$ was consistent with methyl 2-bromo-2-(3-fluoro-4-methoxyphenyl)acetate and matched that reported in WO 2007/024945. The fractions for a second minor uv active product (50-60% ethyl acetate) were combined and concentrated. NMR indicated the di-brominated compound methyl 2,2-dibromo-2-(3-fluoro-4-methoxyphenyl)acetate (0.539 g, 6.7%).

Step B: A 25 mL oven dried round bottom flask equipped with a stirring bar that had been cooled under nitrogen was charged with 4-[2-(tetrahydropyran-4-ylamino)pyrimidin-4-yl]-1H-pyridin-2-one (553 mg, 2.031 mmol). The solid was dissolved in anhydrous THF (10 mL, 0.203M), cooled to 0° C. and treated with 1M lithium hexamethyldisilazide in tetrahydrofuran (3.6 mL, 1.8 equivalents, 3.66 mmol). The ice bath was removed, and the reaction mixture warmed to room temperature. With vigorous stirring at room temperature, a THF solution (2.0 mL) of methyl 2-bromo-2-(3-fluoro-4-methoxy-phenyl)acetate (563 mg, 1.0 equivalent, 2.031 mmol) was added drop wise over 2 minutes. The reaction mixture was stirred at room temperature for 16 hours and concentrated to a residue. LCMS indicated the major new product was the acid resulting from hydrolysis of the methyl ester. The residue was dissolved in methanol (15 mL) and purified by preparative RP HPLC (5 injections×3 mL/per inject, 0-80% CH$_3$CN/H$_2$O with 0.1% FA over 14 minutes). Fractions containing the desired M+H+ and >90% purity from all runs were combined and lyophilized to yield 2-(3-fluoro-4-methoxyphenyl)-2-(2-oxo-4-(2-((tetrahydro-2H-pyran-4-yl)amino)pyrimidin-4-yl)pyridin-1(2H)-yl)acetic acid (89 mg, 10% yield, 94.2% purity uv, 254 nm). $^1$H NMR (400 MHz, (CD$_3$)$_2$SO) δ 8.41 (d, J=5.1 Hz, 1H), 7.44 (d, J=7.3 Hz, 1H), 7.34 (m, 2H), 7.25 (m, 2H), 7.12 (br s, 2H), 6.81 (d, J=7.0 Hz, 1H), 6.32 (s, 1H), 4.13-3.91 (m, 1H), 3.90-3.83 (m, 2H), 3.89 (s, 3H), 3.38 (m and H$_2$O 2H), 1.85 (m, 2H), 1.53 (dq, J=12.0, 4.4 Hz, 2H); LC-MS: m/z=+455.17 (M+H)$^+$.

Example 47

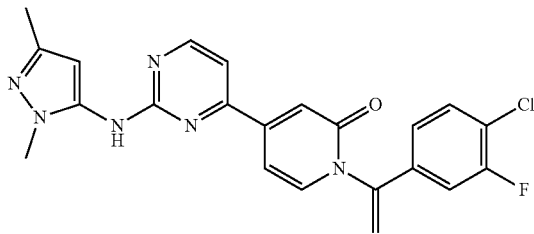 [SMILES: C=C(c1ccc(Cl)c(F)c1)n1ccc(-c2ccnc(Nc3cc(C)nn3C)n2)cc1=O]

1-(1-(4-chloro-3-fluorophenyl)vinyl)-4-(2-((1,3-dimethyl-1H-pyrazol-5-ylamino)pyrimidin-4-yl)pyridin-2(1H)-one A 2-5 mL microwave vial equipped with a stirring bar was charged with 1-[(1S)-2-[tert-butyl(dimethyl)silyl]oxy-1-(4-chloro-3-fluoro-phenyl)ethyl]-4-(2-methylsulfonylpyrimidin-4-yl)pyridin-2-one (100 mg, 0.1858 mmol, 1.0 equivalent) and 2,5-dimethylpyrazol-3-amine (41.31 mg, 0.3717 mmol, 2.0 equivalents). The solids were dissolved in dimethyl formamide (3.0 mL), and sodium hydride (14.08 mg, 0.5575 mmol, 3.0 equivalents, 60% dispersion in mineral oil) was added at room temperature. The microwave vial was capped, placed in a microwave reactor and heated at 160° C. for 10 minutes. The vial was cooled to room temperature, uncapped and analyzed by LCMS. The major uv active product exhibited an a M+H+ consistent with 1-(1-(4-chloro-3-fluorophenyl)vinyl)-4-(2-((1,3-dimethyl-1H-pyrazol-5-yl)amino)pyrimidin-4-yl)pyridin-2(1H)-one. The reaction mixture was partitioned between water/EtOAc. The ethyl acetate layer was washed with brine, dried (Na$_2$SO$_4$), filtered and concentrated to a crude semi-solid residue. The residue was purified by RP HPLC to yield 1-(1-(4-chloro-3-fluorophenyl)vinyl)-4-(2-((1,3-dimethyl-1H-pyrazol-5-yl)amino)pyrimidin-4-yl)pyridin-2(1H)-one (11.7 mg, 14% yield, 99.5% purity, uv 254 nm). $^1$H NMR (400 MHz, (CD$_3$)$_2$SO) δ 9.53 (s, 1H), 8.61 (d, J=5.1 Hz, 1H), 7.79 (d, J=7.2 Hz 1H), 7.58 (t, J=8.2 Hz 1H), 7.53-7.44 (m, 2H), 7.15 (d, J=1.6 Hz, 1H), 7.07 (dd, J=8.5, 2.0 Hz, 1H), 6.96 (dd, J=7.1, 1.8 Hz 1H), 6.22 (d, J=1.5 Hz 1H), 6.05 (s, 1H), 5.63 (d, J=1.4 Hz, 1H), 3.61 (s, 3H), 2.12 (s, 3H); LCMS: m/z=+437.12 (M+H)$^+$.

Example 48

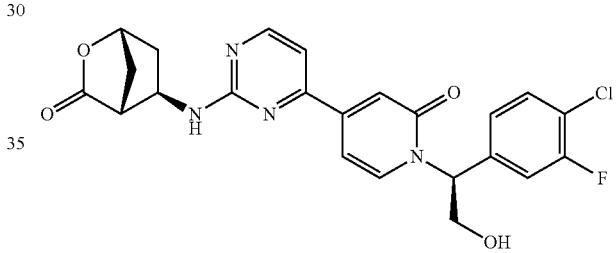

1-((S)-1-(4-chloro-3-fluorophenyl)-2-hydroxyethyl)-4-(2-(3-oxo-2-oxabicyclo[2.2.1]heptan-5-yl)amino)pyrimidin-4-yl)pyridin-2(1H)-one Step A: A mixture of benzyl 2-oxa-bicyclo[2.2.1]heptan-5-ylcarbamate (0.05 g, 2.0 mmol) and Pd/C (10%, 50 mg) in methanol (20 mL) was stirred under hydrogen atmosphere (1 atm) at room temperature for 16 hours. After completion of the reaction, the mixture was filtered through Celite®. The filtrate was concentrated under reduced pressure to afford 5-amino-2-oxa-bicyclo[2.2.1]heptan-3-one (360 mg, over 100%), which was used in the next step without further purification. LCMS (ESI) m/z: 128.1 [M+H]$^+$.

Step B: A microwave vial was charged with 1-(2-(tert-butyldimethylsilyloxy)-1-(4-chloro-3-fluorophenyl)ethyl)-4-(2-(methylsulfonyl)pyrimidin-4-yl)pyridin-2(1H)-one (150 mg, 0.280 mmol), 5-amino-2-oxa-bicyclo[2.2.1]heptan-3-one (89 mg, 0.70 mmol), a drop of concentrated HCl, and s-butanol (2.0 mL). The mixture was stirred at 130° C. under microwave irradiation for 3 hours. After completion of the reaction, the mixture was concentrated to give 1-((S)-2-(tert-butyldimethylsilyloxy)-1-(4-chloro-3-fluorophenyl)ethyl)-4-(2-(3-oxo-2-oxa-bicyclo[2.2.1]heptan-5-ylamino)pyrimidin-4-yl)pyridin-2(1H)-one (164 mg, 100% yield), which was used in the next step without further purification. LCMS (ESI) m/z: 285.2 [M+H]$^+$.

Step C: TBAF (80 mg, 0.31 mmol) was added to a solution of 1-((S)-2-(tert-butyldimethylsilyloxy)-1-(4-chloro-3-fluorophenyl)ethyl)-4-(2-(3-oxo-2-oxa-bicyclo[2.2.1]heptan-5-ylamino)pyrimidin-4-yl)pyridin-2(1H)-one (164 mg, 0.280 mmol) in THF (10 mL). After being stirred at room temperature for 16 hours, the reaction mixture was diluted with ethyl acetate (100 mL), washed with water (5×30 mL). The organic layer was dried over $Na_2SO_4$ and concentrated. The residue was purified by prep-HPLC to afford 1-((S)-1-(4-chloro-3-fluorophenyl)-2-hydroxyethyl)-4-(2-(3-oxo-2-oxabicyclo[2.2.1]heptan-5-yl)amino)pyrimidin-4-yl)pyridin-2(1H)-one (6 mg, 5% yield). $^1$H NMR (500 MHz, CDCl$_3$) δ 8.45 (d, J=3 Hz, 1H), 7.43 (t, J=13.5 Hz, 2H), 7.20 (d, J=10 Hz, 1H), 5.27 (d, J=5.5, 1H), 5.03 (s, 1H), 4.16 (s, 1H), 4.33 (d, J=5 Hz, 2H), 3.21 (s, 1H), 2.62 (s, 3H), 2.32 (t, J=13.5 Hz, 1H), 2.02 (d, J=10.5 Hz, 1H), 1.69 (d, J=4.5 Hz, 1H); LCMS (ESI) m/z: 471.1 [M+H]$^+$.

Example 49

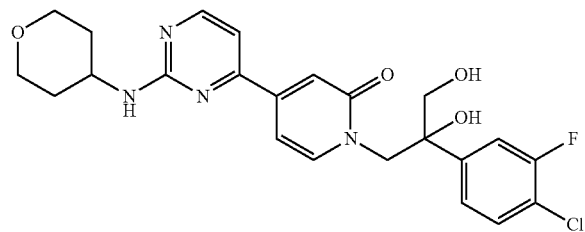 [SMILES: O=c1cc(-c2ccnc(NC3CCOCC3)n2)ccn1CC(O)(CO)c1ccc(Cl)c(F)c1]

1-(2-(4-chloro-3-fluorophenyl)-2,3-dihydroxypropyl)-4-(2-((tetrahydro-2H-pyran-4-yl)amino)pyrimidin-4-yl)pyridin-2(1H)-one Step A: n-BuLi (2.5N, 8.0 mL) was added at −78° C. to a mixture of methyltriphenylphosphonium bromide (5.6 g, 0.15 mol) in THF (50 mL). After being stirred for 0.5 hours, 2-(tert-butyldimethylsilyloxy)-1-(4-chloro-3-fluorophenyl)ethanone (3.9 g, 0.013 mol) was added to the reaction mixture. The mixture was then stirred for 2 hours at 25° C. After quenching with saturated NH$_4$Cl (100 mL), the reaction mixture was extracted with ethyl acetate (3×50 mL). The combined organic layers were dried and concentrated. The residue was purified by silica gel column chromatography eluting with petroleum ether to give tert-butyl (2-(4-chloro-3-fluorophenyl)allyloxy)dimethylsilane (1.6 g, 40% yield).

Step B: mCPBA (372 mg, 2.20 mmol) was added to a solution of tert-butyl (2-(4-chloro-3-fluorophenyl)allyloxy)dimethylsilane (450 mg, 1.50 mmol) in CH$_2$Cl$_2$ (10 mL). After being stirred at room temperature overnight, the reaction was quenched with Na$_2$S$_2$O$_3$ (10%, 2×10 mL). The organic layer was washed with saturated Na$_2$CO$_3$ (3×10 mL), dried over Na$_2$SO$_4$, and concentrated to give tert-butyl (2-(4-chloro-3-fluorophenyl)oxiran-2-yloxy)dimethylsilane (490 mg, over 100% yield).

Step C: 4-(2-(Tetrahydro-2H-pyran-4-ylamino)pyrimidin-4-yl)pyridin-2(1H)-one (136 mg, 0.500 mmol) and K$_2$CO$_3$ (248 mg, 1.80 mmol) were added to a solution of tert-butyl (2-(4-chloro-3-fluorophenyl)oxiran-2-yloxy)dimethylsilane (200 mg, 0.600 mmol) in DMF (5.0 mL). After being heated at 80° C. overnight, the mixture was diluted with H$_2$O (50 mL) and extracted with EtOAc (3×100 mL). The organic phases were washed with brine (3×30 mL), dried, and concentrated. The residue was dissolved in CH$_2$Cl$_2$, followed by addition of TFA (5.0 mL). The mixture was stirred at room temperature overnight. The solvent was removed under vacuum, and the residue was purified by prep-HPLC to give 1-(2-(4-chloro-3-fluorophenyl)-2,3-dihydroxypropyl)-4-(2-((tetrahydro-2H-pyran-4-yl)amino)pyrimidin-4-yl)pyridine-2(1H)-one (70 mg, 30% yield). $^1$H NMR (500 MHz, CD$_3$OD) δ 8.39 (m, 1H), 7.67-7.66 (m, 1H), 7.51-7.49 (m, 1H), 7.45-7.38 (m, 1H), 7.22 (s, 2H), 7.08-7.07 (m, 1H), 6.97-6.95 (m, 1H), 4.69-4.66 (m, 1H), 4.31-4.28 (m, 1H), 4.10 (s, 1H), 4.01-3.99 (m, 2H), 3.72-3.66 (m, 2H), 3.60-3.56 (m, 2H), 2.03-2.00 (m, 2H), 1.67-1.59 (m, 2H); LCMS (ESI) m/z: 475.1 [M+H]$^+$.

The following compounds in Table 2 were prepared according to the above procedures using appropriate starting materials and intermediates.

TABLE 2

| Ex. # | Structure | Name | MS |
|---|---|---|---|
| 50 | 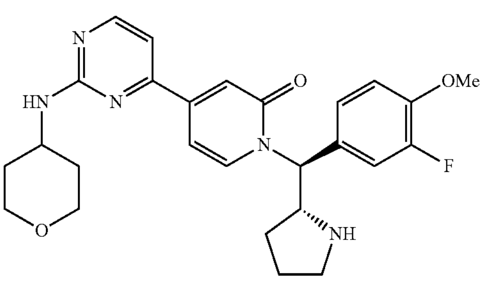 [SMILES: COc1ccc([C@@H]([C@H]2CCCN2)n2ccc(-c3ccnc(NC4CCOCC4)n3)cc2=O)cc1F] | 1-((S)-(3-fluoro-4-methoxyphenyl)((R)-pyrrolidin-2-yl)methyl)-4-(2-((tetrahydro-2H-pyran-4-yl)amino)pyrimidin-4-yl)pyridin-2(1H)-one | m/z (APCI-pos) M +1 = 480.2, 482.2 |
| 51 | 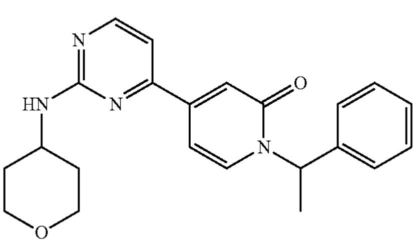 [SMILES: CC(c1ccccc1)n1ccc(-c2ccnc(NC3CCOCC3)n2)cc1=O] | 1-(1-phenylethyl)-4-(2-((tetrahydro-2H-pyran-4-yl)amino)pyrimidin-4-yl)pyridin-2(1H)-one | m/z (APCI-pos) M + 1 = 377.2 |

| Ex. # | Structure | Name | MS |
|---|---|---|---|
| 52 | 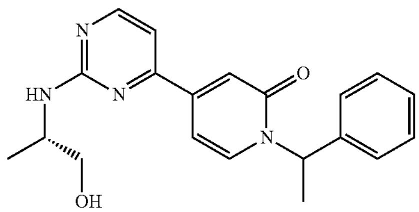 [SMILES: CC(c1ccccc1)n1ccc(-c2ccnc(N[C@@H](C)CO)n2)cc1=O] | 4-(2-(((S)-1-hydroxypropan-2-yl)amino)pyrimidin-4-yl)-1-(1-phenylethyl)pyridin-2(1H)-one | m/z (APCI-pos) M + 1 = 351.2 |
| 53 | 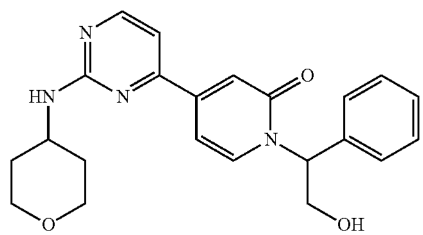 [SMILES: O=c1cc(-c2ccnc(NC3CCOCC3)n2)ccn1C(CO)c1ccccc1] | 1-(2-hydroxy-1-phenylethyl)-4-(2-((tetrahydro-2H-pyran-4-yl)amino)pyrimidin-4-yl)pyridin-2(1H)-one | m/z (APCI-pos) M + 1 = 393.2 |
| 54 | 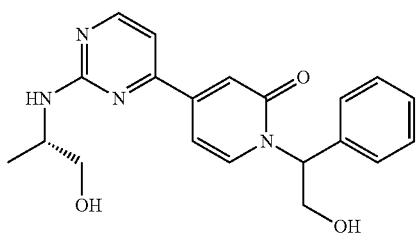 [SMILES: C[C@@H](CO)Nc1nccc(-c2ccn(C(CO)c3ccccc3)c(=O)c2)n1] | 1-(2-hydroxy-1-phenylethyl)-4-(2-(((S)-1-hydroxypropan-2-yl)amino)pyrimidin-4-yl)pyridin-2(1H)-one | m/z (APCI-pos) M + 1 = 367.1 |
| 55 | 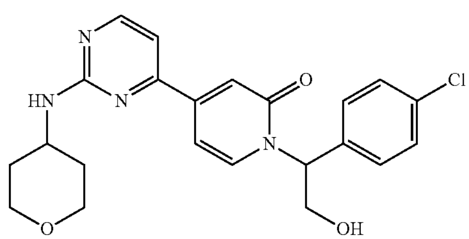 [SMILES: O=c1cc(-c2ccnc(NC3CCOCC3)n2)ccn1C(CO)c1ccc(Cl)cc1] | 1-(1-(4-chlorophenyl)-2-hydroxyethyl)-4-(2-((tetrahydro-2H-pyran-4-yl)amino)pyrimidin-4-yl)pyridin-2(1H)-one | m/z (APCI-pos) M + 1 = 427.1, 429.1 |
| 56 | 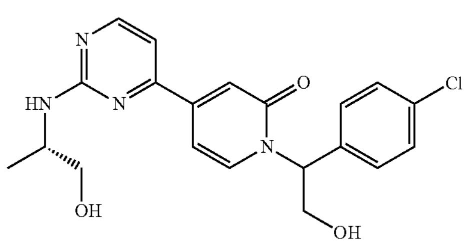 [SMILES: C[C@@H](CO)Nc1nccc(-c2ccn(C(CO)c3ccc(Cl)cc3)c(=O)c2)n1] | 1-(1-(4-chlorophenyl)-2-hydroxyethyl)-4-(2-(((S)-1-hydroxypropan-2-yl)amino)pyrimidin-4-yl)pyridin-2(1H)-one | m/z (APCI-pos) M + 1 = 401.1, 403.1 |
| 57 | 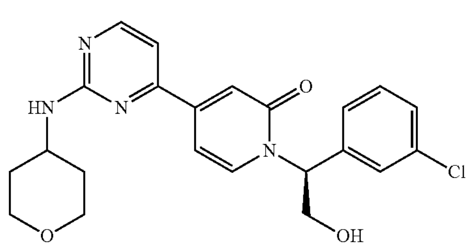 [SMILES: O=c1cc(-c2ccnc(NC3CCOCC3)n2)ccn1[C@H](CO)c1cccc(Cl)c1] | (S)-1-(1-(3-chlorophenyl)-2-hydroxyethyl)-4-(2-((tetrahydro-2H-pyran-4-yl)amino)pyrimidin-4-yl)pyridin-2(1H)-one | m/z (APCI-pos) M + 1 = 427.1, 429.1 |

TABLE 2-continued

| Ex. # | Structure | Name | MS |
|---|---|---|---|
| 58 | 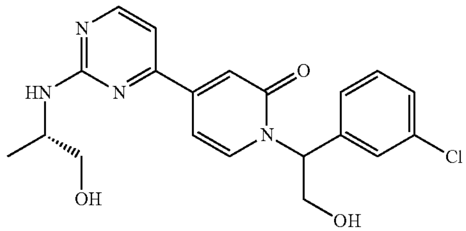 [SMILES: C[C@@H](CO)Nc1nccc(-c2ccn(C(CO)c3cccc(Cl)c3)c(=O)c2)n1] | 1-(1-(3-chlorophenyl)-2-hydroxyethyl)-4-(2-(((S)-1-hydroxypropan-2-yl)amino)pyrimidin-4-yl)pyridin-2(1H)-one | m/z (APCI-pos) M + 1 = 401.1, 403.1 |
| 59 | 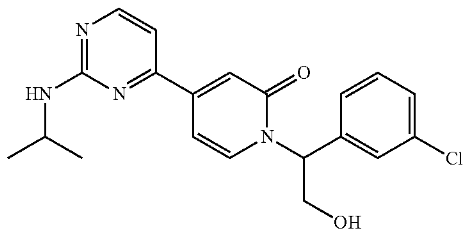 [SMILES: CC(C)Nc1nccc(-c2ccn(C(CO)c3cccc(Cl)c3)c(=O)c2)n1] | 1-(1-(3-chlorophenyl)-2-hydroxyethyl)-4-(2-(isopropylamino)pyrimidin-4-yl)pyridin-2(1H)-one | m/z (APCI-pos) M + 1 = 385.1, 387.1 |
| 60 | 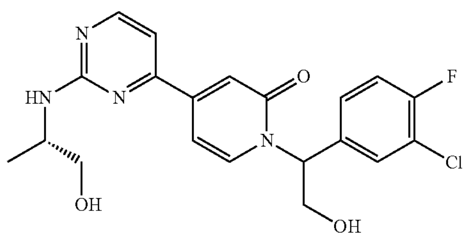 [SMILES: C[C@@H](CO)Nc1nccc(-c2ccn(C(CO)c3ccc(F)c(Cl)c3)c(=O)c2)n1] | 1-(1-(3-chloro-4-fluorophenyl)-2-hydroxyethyl)-4-(2-(((S-1-hydroxypropan-2-yl)amino)pyrimidin-4-yl)pyridin-2(1H)-one | m/z (APCI-pos) M + 1 = 419.1, 421.1 |
| 61 | 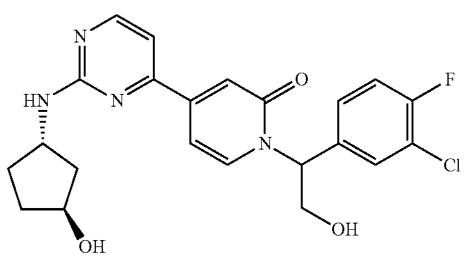 [SMILES: O=c1cc(-c2ccnc(N[C@H]3CC[C@H](O)C3)n2)ccn1C(CO)c1ccc(F)c(Cl)c1] | 1-(1-(3-chloro-4-fluorophenyl)-2-hydroxyethyl)-4-(2-(((1S,3S)-3-hydroxycyclopentyl)amino)pyrimidin-4-yl)pyridin-2(1H)-one | m/z (APCI-pos) M + 1 = 445.1, 447.1 |
| 62 | 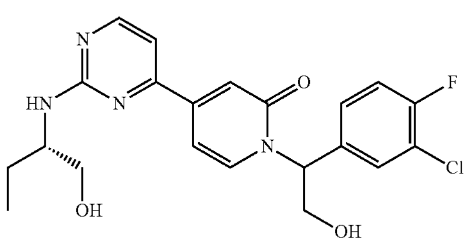 [SMILES: CC[C@@H](CO)Nc1nccc(-c2ccn(C(CO)c3ccc(F)c(Cl)c3)c(=O)c2)n1] | 1-(1-(3-chloro-4-fluorophenyl)-2-hydroxyethyl)-4-(2-(((S)-1-hydroxybutan-2-yl)amino)pyrimidin-4-yl)pyridin-2(1H)-one | m/z (APCI-pos) M + 1 = 433.1, 435.1 |
| 63 | 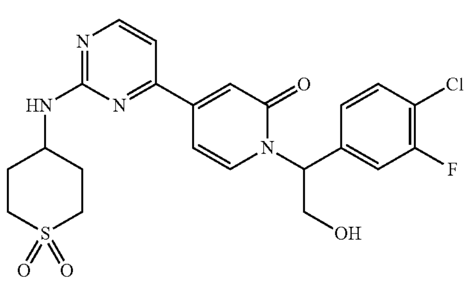 [SMILES: O=c1cc(-c2ccnc(NC3CCS(=O)(=O)CC3)n2)ccn1C(CO)c1ccc(Cl)c(F)c1] | 1-(1-(4-chloro-3-fluorophenyl)-2-hydroxyethyl)-4-(2-((tetrahydro-2H-dioxo-thiopyran-4-yl)amino)pyrimidin-4-yl)pyridin-2(1H)-one | m/z (APCI-neg) M − 1 = 491.1, 493.0 |

TABLE 2-continued

| Ex. # | Structure | Name | MS |
|---|---|---|---|
| 64 | 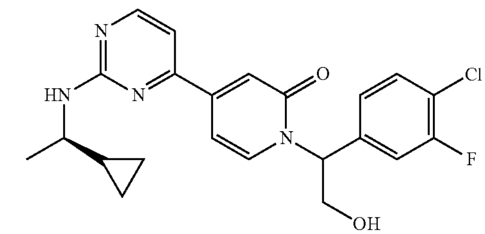 [SMILES: C[C@@H](Nc1nccc(-c2ccn(C(CO)c3ccc(Cl)c(F)c3)c(=O)c2)n1)C1CC1] | 1-(1-(4-chloro-3-fluorophenyl)-2-hydroxyethyl)-4-(2-(((R)-1-cyclopropylethyl)amino)pyrimidinyl)pyridin-2(1H)-one | m/z (APCI-pos) M + 1 = 429.1, 431.1 |
| 65 | 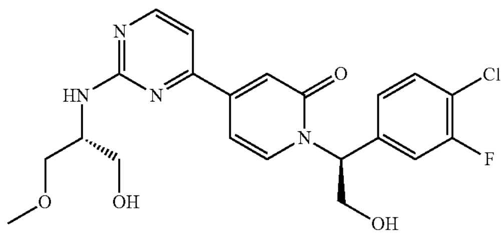 [SMILES: COC[C@@H](CO)Nc1nccc(-c2ccn([C@H](CO)c3ccc(Cl)c(F)c3)c(=O)c2)n1] | 1-((S)-1-(4-chloro-3-fluorophenyl)-2-hydroxyethyl)-4-(2-(((R)-1-hydroxy-3-methoxypropan-2-yl)amino)pyrimidin-4-yl)pyridin-2(1H)-one | m/z (APCI-pos) M + 1 = 449.1, 451.1 |
| 66 | 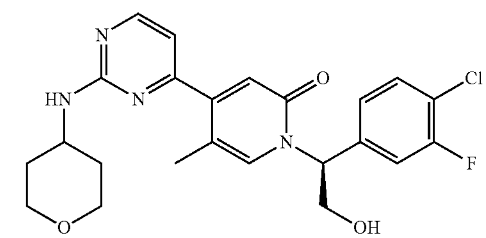 [SMILES: Cc1cn([C@H](CO)c2ccc(Cl)c(F)c2)c(=O)cc1-c1ccnc(NC2CCOCC2)n1] | (S)-1-(1-(4-chloro-3-fluorophenyl)-2-hydroxyethyl)-5-methyl-4-(2-((tetrahydro-2H-pyran-4-yl)amino)pyrimidin-4-yl)pyridin-2(1H)-one | m/z (APCI-pos) M + 1 = 459.1, 461.1 |
| 67 | 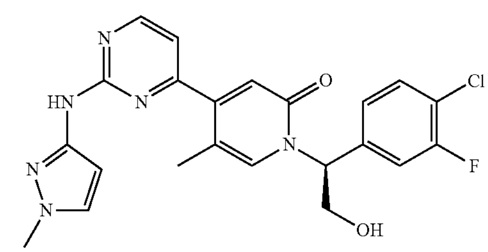 | (S)-1-(1-(4-chloro-3-fluorophenyl)-2-hydroxyethyl)-4-(2-((1-methyl-1H-pyrazol-3-yl)amino)pyrimidin-4-yl)pyridin-2(1H)-one | m/z (APCI-pos) M + 1 = 441.1, 443.1 |
| 68 | 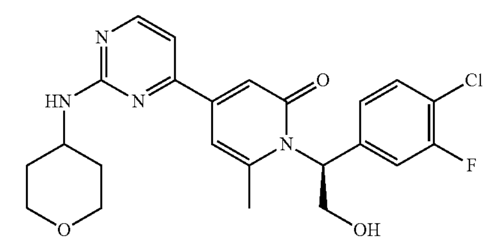 [SMILES: Cc1cc(-c2ccnc(NC3CCOCC3)n2)cc(=O)n1[C@H](CO)c1ccc(Cl)c(F)c1] | (S)-1-(1-(4-chloro-3-fluorophenyl)-2-hydroxyethyl)-6-methyl-4-(2-((tetrahydro-2H-pyran-4-yl)amino)pyrimidin-4-yl)pyridin-2(1H)-one | m/z (APCI-pos) M + 1 = 459.1, 461.1 |
| 69 | 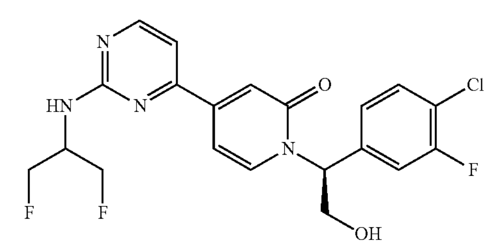 [SMILES: O=c1cc(-c2ccnc(NC(CF)CF)n2)ccn1[C@H](CO)c1ccc(Cl)c(F)c1] | (S)-1-(1-(4-chloro-3-fluorophenyl)-2-hydroxyethyl)-4-(2-(((1,3-difluoropropan-2-yl)amino)pyrimidin-4-yl)pyridin-2(1H)-one | m/z (APCI-pos) M + 1 = 439.1, 441.1 |

TABLE 2-continued

| Ex. # | Structure | Name | MS |
|---|---|---|---|
| 70 | 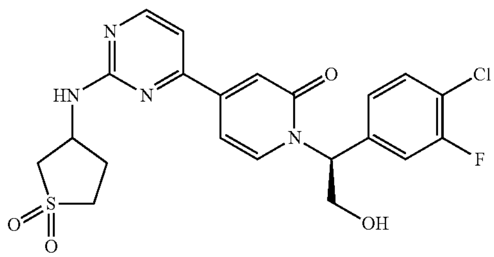 [SMILES: O=c1cc(-c2ccnc(NC3CCS(=O)(=O)C3)n2)ccn1[C@H](CO)c1ccc(Cl)c(F)c1] | 1-((S)-1-(4-chloro-3-fluorophenyl)-2-hydroxyethyl)-4-(2-((1,1-dioxidotetrahydrothiophen-3-yl)amino)pyrimidin-4-yl)pyridin-2(1H)-one | m/z (APCI-neg) M − 1 = 479.0, 481.0 |
| 71 | 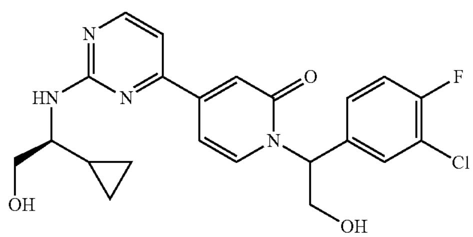 [SMILES: O=c1cc(-c2ccnc(N[C@H](CO)C3CC3)n2)ccn1C(CO)c1ccc(F)c(Cl)c1] | 1-(1-(3-chloro-4-fluorophenyl)-2-hydroxyethyl)-4-(2-(((S)-1-cyclopropyl-2-hydroxyethyl)amino)pyrimidin-4-yl)pyridin-2(1H)-one | m/z (APCI-neg) M − 1 = 445.1, 447.1 |
| 72 | 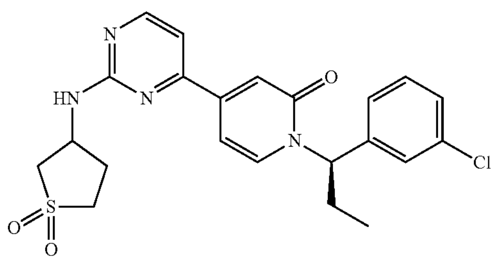 [SMILES: CC[C@H](c1cccc(Cl)c1)n1ccc(-c2ccnc(NC3CCS(=O)(=O)C3)n2)cc1=O] | 1-((R)-1-(3-chlorophenyl)propyl)-4-(2-((1,1-dioxidotetrahydrothiophen-3-yl)amino)pyrimidin-4-yl)pyridin-2(1H)-one | m/z (APCI-neg) M − 1 = 459.1, 460.0 |
| 73 | 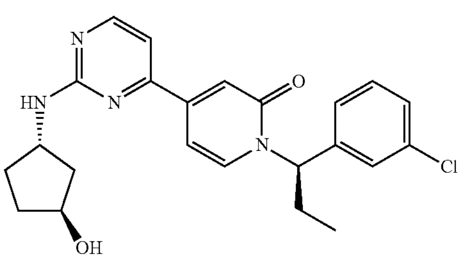 [SMILES: CC[C@H](c1cccc(Cl)c1)n1ccc(-c2ccnc(N[C@H]3CC[C@H](O)C3)n2)cc1=O] | 1-((R)-1-(3-chlorophenyl)propyl)-4-(2-(((1S,3S)-3-hydroxycyclopentyl)amino)pyrimidin-4-yl)pyridin-2(1H)-one | m/z (APCI-neg) M − 1 = 425.1, 427.1 |
| 74 | 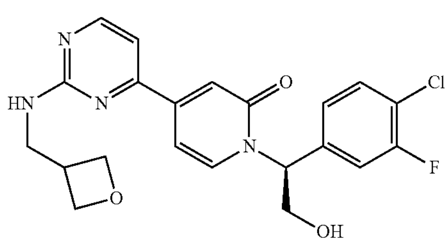 [SMILES: O=c1cc(-c2ccnc(NCC3COC3)n2)ccn1[C@H](CO)c1ccc(Cl)c(F)c1] | (S)-1-(1-(4-chloro-3-fluorophenyl)-2-hydroxyethyl)-4-(2-((oxetan-3-ylmethyl)amino)pyrimidin-4-yl)pyridin-2(1H)-one | m/z (APCI-pos) M + 1 = 431.1 |
| 75 | 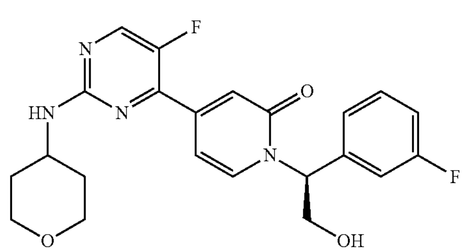 [SMILES: O=c1cc(-c2nc(NC3CCOCC3)ncc2F)ccn1[C@H](CO)c1cccc(F)c1] | (S)-4-(5-fluoro-2-((tetrahydro-2H-pyran-4-yl)amino)pyrimidin-4-yl)-1-(1-(3-fluorophenyl)-2-hydroxyethyl)pyridin-2(1H)-one | m/z (APCI-pos) M + 1 = 429.1 |

TABLE 2-continued

| Ex. # | Structure | Name | MS |
|---|---|---|---|
| 76 | 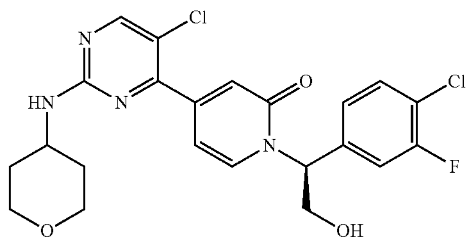 [SMILES: O=c1cc(-c2nc(NC3CCOCC3)ncc2Cl)ccn1[C@H](CO)c1ccc(Cl)c(F)c1] | (S)-4-(5-chloro-2-((tetrahydro-2H-pyran-4-yl)amino)pyrimidin-4-yl)-1-(1-(4-chloro-3-fluorophenyl)-2-hydroxyethyl)pyridin-2(1H)-one | m/z (APCI-pos) M + 1 = 479.0, 481 (73%) |
| 77 | 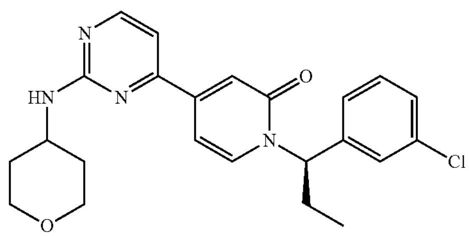 [SMILES: CC[C@H](c1cccc(Cl)c1)n1ccc(-c2ccnc(NC3CCOCC3)n2)cc1=O] | (R)-1-(1-3-chlorophenyl)propyl)-4-(2-((tetrahydro-2H-pyran-4-yl)amino)pyrimidin-4-yl)pyridin-2(1H)-one | m/z (APCI-pos) M + 1 = 425.1, 426.1 |
| 78 | 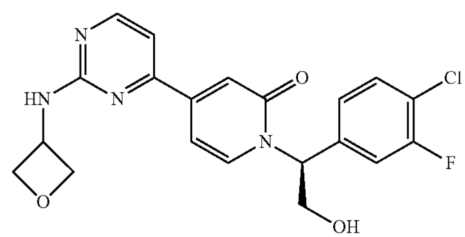 | (S)-1-(1-(4-chloro-3-fluorophenyl)-2-hydroxyethyl)-4-(2-((oxetan-3-yl)amino)pyrimidin-4-yl)pyridin-2(1H)-one | m/z (APCI-pos) M + 1 = 417.1, 419.1 |
| 79 | 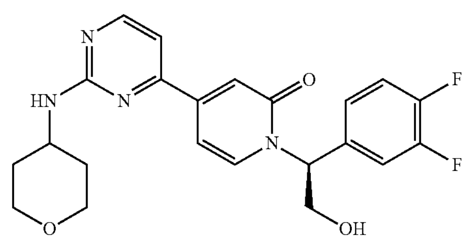 [SMILES: O=c1cc(-c2ccnc(NC3CCOCC3)n2)ccn1[C@H](CO)c1ccc(F)c(F)c1] | (S)-1-(1-(3,4-difluorophenyl)-2-hydroxyethyl)-4-(2-((tetrahydro-pyran-4-yl)amino)pyrimidin-4-yl)pyridin-2(1H)-one | m/z (APCI-pos) M + 1 = 429.1 |
| 80 | 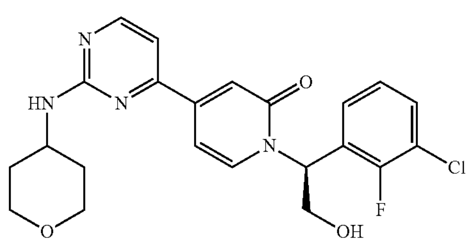 [SMILES: O=c1cc(-c2ccnc(NC3CCOCC3)n2)ccn1[C@H](CO)c1cccc(Cl)c1F] | (S)-1-(1-(3-chloro-2-fluorophenyl)-2-hydroxyethyl)-4-(2-((tetrahydro-2H-pyran-4-yl)amino)pyrimidin-4-yl)pyridin-2(1H)-one | m/z (APCI-pos) M + 1 = 445.0, 447.1 |
| 81 | 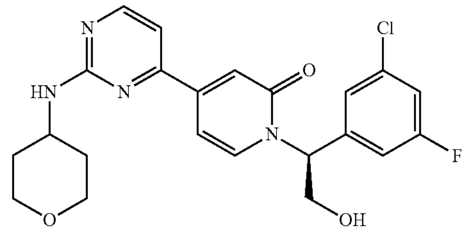 [SMILES: O=c1cc(-c2ccnc(NC3CCOCC3)n2)ccn1[C@H](CO)c1cc(F)cc(Cl)c1] | (S)-1-(1-(3-chloro-5-fluorophenyl)-2-hydroxyethyl)-4-(2-((tetrahydro-2H-pyran-4-yl)amino)pyrimidin-4-yl)pyridin-2(1H)-one | m/z (APCI-pos) M + 1 = 445.1, 447.1 |

| Ex. # | Structure | Name | MS |
|---|---|---|---|
| 82 | 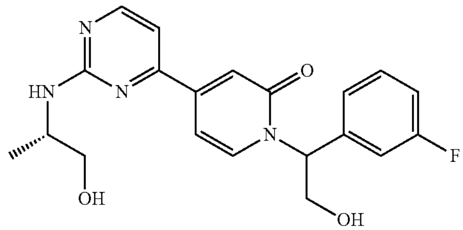 [SMILES: C[C@@H](CO)Nc1nccc(-c2ccn(C(CO)c3cccc(F)c3)c(=O)c2)n1] | 1-(1-(3-fluorophenyl)-2-hydroxyethyl)-4-(2-(((S)-1-hydroxypropan-2-yl)amino)pyrimidin-4-yl)pyridin-2(1H)-one | m/z (APCI-pos) M + 1 = 385.1 |
| 83 | 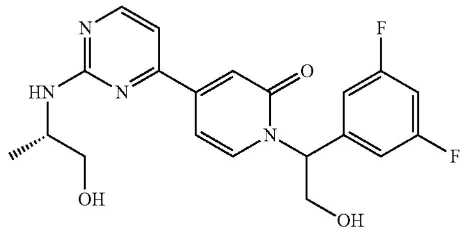 [SMILES: C[C@@H](CO)Nc1nccc(-c2ccn(C(CO)c3cc(F)cc(F)c3)c(=O)c2)n1] | 1-(1-(3,5-difluorophenyl)-2-hydroxyethyl)-4-(2-(((S)-1-hydroxypropan-2-yl)amino)pyrimidin-4-yl)pyridin-2(1H)-one | m/z (APCI-pos) M + 1 = 403.1 |
| 84 | 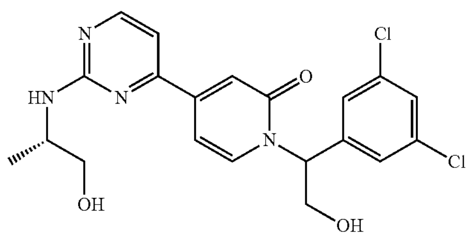 [SMILES: C[C@@H](CO)Nc1nccc(-c2ccn(C(CO)c3cc(Cl)cc(Cl)c3)c(=O)c2)n1] | 1-(1-(3,5-dichlorophenyl)-2-hydroxyethyl)-4-(2-(((S)-1-hydroxypropan-2-yl)amino)pyrimidin-4-yl)pyridin-2(1H)-one | (APCI-pos) M + 1 = 435.1, 437.0 |
| 85 | 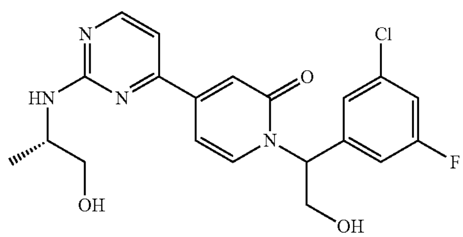 [SMILES: C[C@@H](CO)Nc1nccc(-c2ccn(C(CO)c3cc(F)cc(Cl)c3)c(=O)c2)n1] | 1-(1-(3-chloro-5-fluorophenyl)-2-hydroxyethyl)-4-(2-(((S)-1-hydroxypropan-2-yl)amino)pyrimidin-4-yl)pyridin-2(1H)-one | m/z (APCI-pos) M + 1 = 419.1, 421.1 |
| 86 | 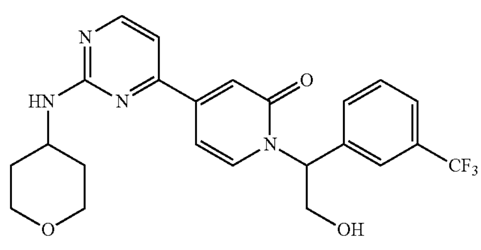 [SMILES: O=c1cc(-c2ccnc(NC3CCOCC3)n2)ccn1C(CO)c1cccc(C(F)(F)F)c1] | 1-(2-hydroxy-1-(3-(trifluoromethyl)phenyl)ethyl)-4-(2-((tetrahydro-2H-pyran-4-yl)amino)pyrimidin-4-yl)pyridin-2(1H)-one | m/z (APCI-pos) M + 1 = 461.1 |
| 87 | 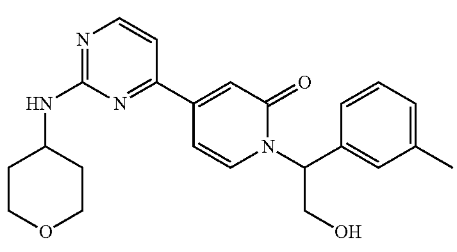 [SMILES: Cc1cccc(C(CO)n2ccc(-c3ccnc(NC4CCOCC4)n3)cc2=O)c1] | 1-(2-hydroxy-1-m-tolylethyl)-4-(2-((tetrahydro-2H-pyran-4-yl)amino)pyrimidin-4-yl)pyridin-2(1H)-one | m/z (APCI-pos) M + 1 = 407.1 |

TABLE 2-continued

| Ex. # | Structure | Name | MS |
|---|---|---|---|
| 88 | 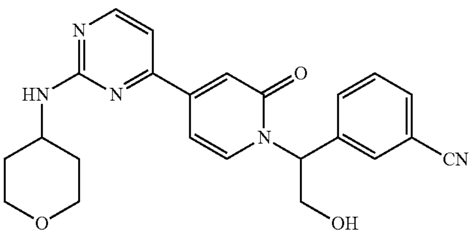 [SMILES: N#Cc1cccc(C(CO)n2ccc(-c3ccnc(NC4CCOCC4)n3)cc2=O)c1] | 3-(2-hydroxy-1-(2-oxo-4-(2-((tetrahydro-2H-pyran-4-yl)amino)pyrimidin-4-yl)pyridin-1(2H)-yl)ethyl)benzonitrile | m/z (APCI-pos) M + 1 = 418.1 |
| 89 | 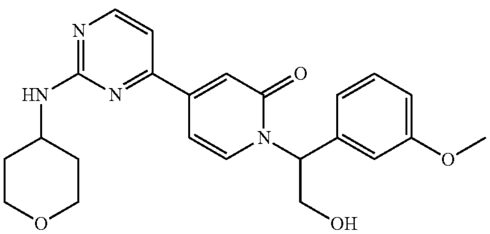 [SMILES: COc1cccc(C(CO)n2ccc(-c3ccnc(NC4CCOCC4)n3)cc2=O)c1] | 1-(2-hydroxy-1-(3-methoxyphenyl)ethyl)-4-(2-((tetrahydro-2H-pyran-4-yl)amino)pyrimidin-4-yl)pyridin-2(1H)-one | m/z (APCI-pos) M + 1 = 423.1 |
| 90 | 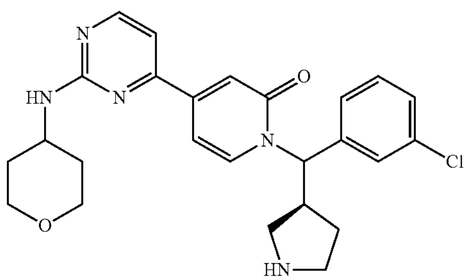 [SMILES: O=c1cc(-c2ccnc(NC3CCOCC3)n2)ccn1C(c1cccc(Cl)c1)[C@H]1CCNC1] | 1-((3-chlorophenyl)((S)-pyrrolidin-3-yl)methyl)-4-(2-((tetrahydro-2H-pyran-4-yl)amino)pyrimidin-4-yl)pyridin-2(1H)-one | m/z (APCI-pos) M + 1 = 466.1, 467.1 |
| 91 | 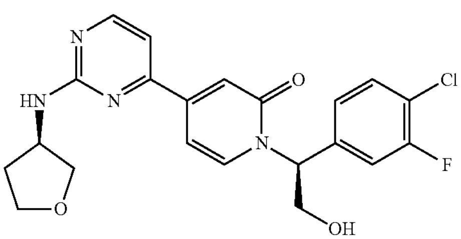 [SMILES: O=c1cc(-c2ccnc(N[C@@H]3CCOC3)n2)ccn1[C@H](CO)c1ccc(Cl)c(F)c1] | 1-((S)-1-(4-chloro-3-fluorophenyl)-2-hydroxyethyl)-4-(2-(((R)-tetrahydrofuran-3-yl)amino)pyrimidin-4-yl)pyridin-2(1H)-one | m/z (APCI-pos) M + 1 = 431.1, 433.1 |
| 92 | 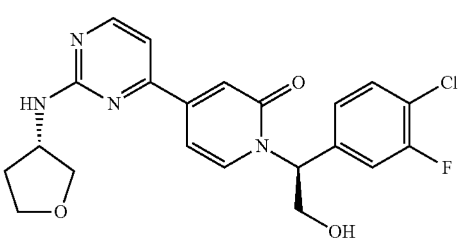 [SMILES: O=c1cc(-c2ccnc(N[C@H]3CCOC3)n2)ccn1[C@H](CO)c1ccc(Cl)c(F)c1] | 1-((S)-1-(4-chloro-3-fluorophenyl)-2-hydroxyethyl)-4-(2-(((S)-tetrahydrofuran-3-yl)amino)pyrimidin-4-yl)pyridin-2(1H)-one | m/z (APCI-pos) M + 1 = 431.1, 433.1 |
| 93 | 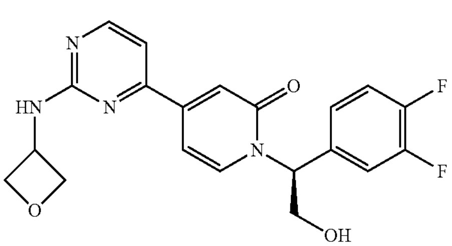 [SMILES: O=c1cc(-c2ccnc(NC3COC3)n2)ccn1[C@H](CO)c1ccc(F)c(F)c1] | (S)-1-(1-(3,4-difluorophenyl)-2-hydroxyethyl)-4-(2-((oxetan-3-yl)amino)pyrimidin-4-yl)pyridin-2(1H)-one | m/z (APCI-pos) M + 1 = 401.1 |

| Ex. # | Structure | Name | MS |
|---|---|---|---|
| 94 | 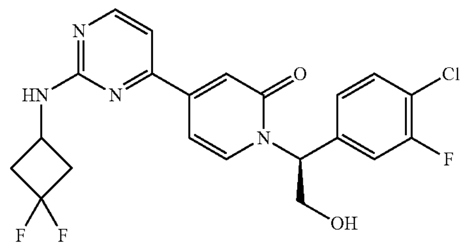 [SMILES: O=c1cc(-c2ccnc(NC3CC(F)(F)C3)n2)ccn1[C@H](CO)c1ccc(Cl)c(F)c1] | (S)-1-(1-(4-chloro-3-fluorophenyl)-2-hydroxyethyl)-4-(2-((3,3-difluorocyclobutyl)amino)pyrimidin-4-yl)pyridin-2(1H)-one | m/z (APCI-pos) M + 1 = 451.1, 453.1 |
| 95 | 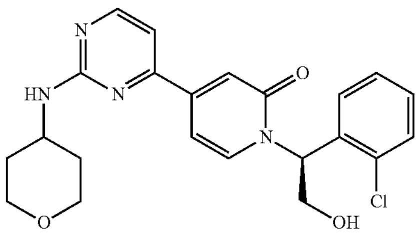 [SMILES: O=c1cc(-c2ccnc(NC3CCOCC3)n2)ccn1[C@H](CO)c1ccccc1Cl] | (S)-1-(1-(2-chlorophenyl)-2-hydroxyethyl)-4-(2-((tetrahydro-2H-pyran-4-yl)amino)pyrimidin-4-yl)pyridin-2(1H)-one | m/z (APCI-pos) M + 1 = 427.1, 429.1 |
| 96 | 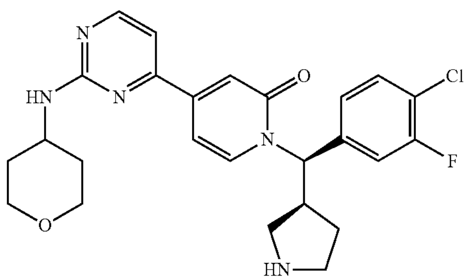 [SMILES: O=c1cc(-c2ccnc(NC3CCOCC3)n2)ccn1[C@@H](c1ccc(Cl)c(F)c1)[C@H]1CCNC1] | 1-((R-(4-chloro-3-fluorophenyl)((S)-pyrrolidin-3-yl)methyl)-4-(2-((tetrahydro-2H-pyran-4-yl)amino)pyrimidin-4-yl)pyridin-2(1H)-one | m/z (APCI-pos) M + 1 = 484.1, 485.1 |
| 97 | 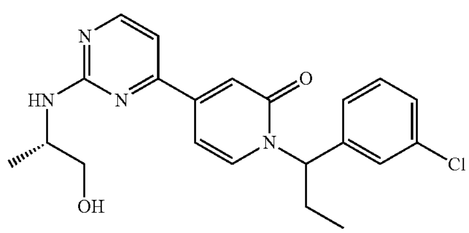 [SMILES: CCC(c1cccc(Cl)c1)n1ccc(-c2ccnc(N[C@@H](C)CO)n2)cc1=O] | 1-(1-(3-chlorophenyl)propyl)-4-(2-(((S)-1-hydroxypropan-2-yl)amino)pyrimidin-4-yl)pyridin-2(1H)-one | m/z (APCI-pos) M + 1 = 399.1, 401.1 |
| 98 | 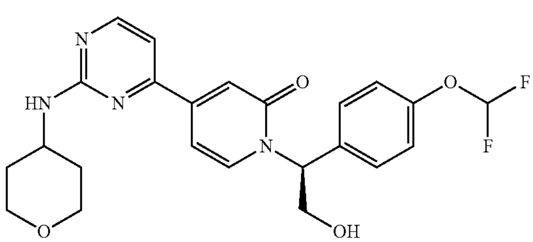 [SMILES: O=c1cc(-c2ccnc(NC3CCOCC3)n2)ccn1[C@H](CO)c1ccc(OC(F)F)cc1] | (S)-1-(1-(4-(difluoromethoxy)phenyl)-2-hydroxyethyl)-4-(2-((tetrahydro-2H-pyran-4-yl)amino)pyrimidin-4-yl)pyridin-2(1H)-one | m/z (APCI-pos) M + 1 = 459.1 |
| 99 | 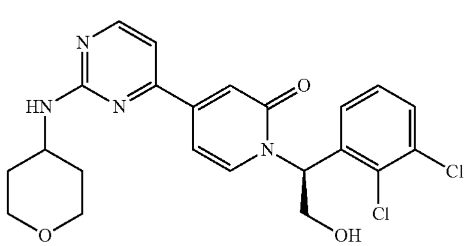 [SMILES: O=c1cc(-c2ccnc(NC3CCOCC3)n2)ccn1[C@H](CO)c1cccc(Cl)c1Cl] | (S)-1-(1-(2,3-dichlorophenyl)-2-hydroxyethyl)-4-(2-((tetrahydro-2H-pyran-4-yl)amino)pyrimidin-4-yl)pyridin-2(1H)-one | m/z (APCI-pos) M + 1 = 461.1, 463.1 |

TABLE 2-continued

| Ex. # | Structure | Name | MS |
|---|---|---|---|
| 100 | 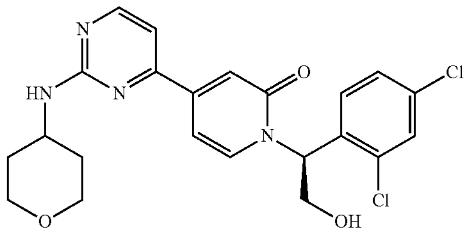 [SMILES: O=c1cc(-c2ccnc(NC3CCOCC3)n2)ccn1[C@H](CO)c1ccc(Cl)cc1Cl] | (S)-1-(1-(2,4-dichlorophenyl)-2-hydroxyethyl)-4-(2-((tetrahydro-2H-pyran-4-yl)amino)pyrimidin-4-yl)pyridin-2(1H)-one | m/z (APCI-pos) M + 1 = 461.1, 463.0 |
| 101 | 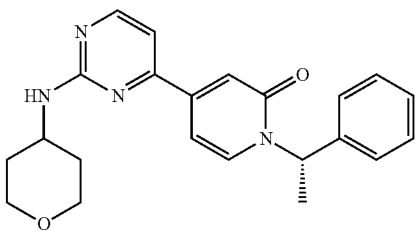 [SMILES: C[C@@H](c1ccccc1)n1ccc(-c2ccnc(NC3CCOCC3)n2)cc1=O] | (S)-1-(1-phenylethyl)-4-(2-((tetrahydro-2H-pyran-4-yl)amino)pyrimidin-4-yl)pyridin-2(1H)-one | m/z (APCI-pos) M +1 = 377.2 |
| 102 | 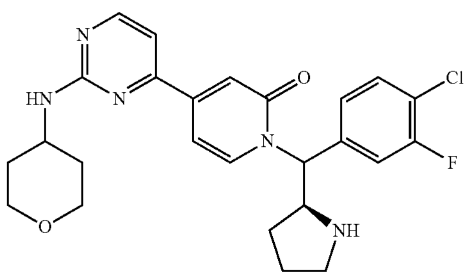 [SMILES: O=c1cc(-c2ccnc(NC3CCOCC3)n2)ccn1C(c1ccc(Cl)c(F)c1)[C@@H]1CCCN1] | 1-((4-chloro-3-fluorophenyl)((S)-pyrrolidin-2-yl)methyl)-4-(2-((tetrahydro-2H-pyran-4-yl)amino)pyrimidin-4-yl)pyridin-2(1H)-one | m/z (APCI-pos) M + 1 = 484.1, 485.1 |
| 103 | 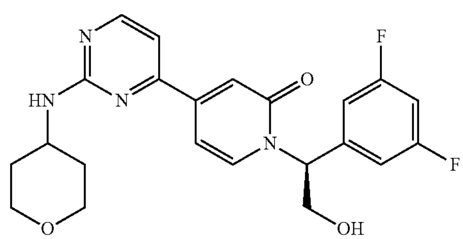 [SMILES: O=c1cc(-c2ccnc(NC3CCOCC3)n2)ccn1[C@H](CO)c1cc(F)cc(F)c1] | (S)-1-(1-(3,5-difluorophenyl)-2-hydroxyethyl)-4-(2-((tetrahydro-2H-pyran-4-yl)amino)pyrimidin-4-yl)pyridin-2(1H)-one | m/z (APCI-pos) M + 1 = 429.1 |
| 104 | 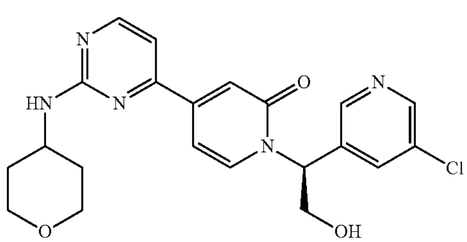 [SMILES: O=c1cc(-c2ccnc(NC3CCOCC3)n2)ccn1[C@H](CO)c1cncc(Cl)c1] | (S)-1-(1-(5-chloropyridin-3-yl)-2-hydroxyethyl)-4-(2-((tetrahydro-2H-pyran-4-yl)amino)pyrimidin-4-yl)pyridin-2(1H)-one | m/z (APCI-pos) M + 1 = 428.1, 430.1 |
| 105 | 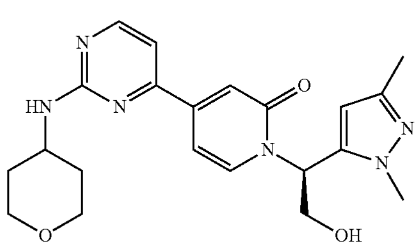 [SMILES: Cc1cc([C@@H](CO)n2ccc(-c3ccnc(NC4CCOCC4)n3)cc2=O)n(C)n1] | (S)-(1-(1,3-dimethyl-1H-pyrazol-5-yl)-2-hydroxyethyl)-4-(2-((tetrahydro-2H-pyran-4-yl)amino)pyrimidin-4-yl)pyridin-2(1H)-one | m/z (APCI-pos) M + 1 = 411.2 |

TABLE 2-continued

| Ex. # | Structure | Name | MS |
|---|---|---|---|
| 106 | 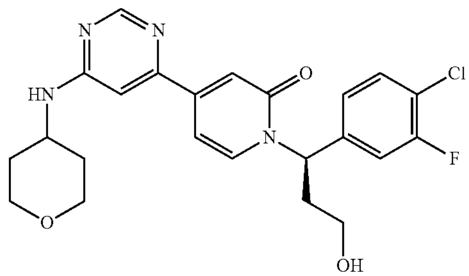 [SMILES: O=c1cc(-c2cc(NC3CCOCC3)ncn2)ccn1[C@H](CCO)c1ccc(Cl)c(F)c1] | (R)-1-(1-(4-chloro-3-fluorophenyl)-3-hydroxypropyl)-4-(6-((tetrahydro-2H-pyran-4-yl)amino)pyrimidin-4-yl)pyridin-2(1H)-one | m/z (APCI-pos) M + 1 = 459.0 |
| 107 | 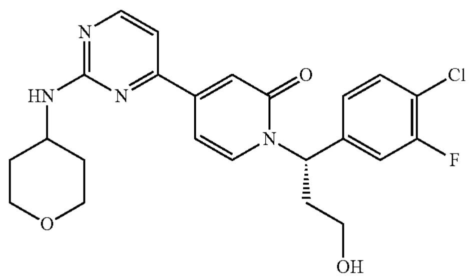 [SMILES: O=c1cc(-c2ccnc(NC3CCOCC3)n2)ccn1[C@@H](CCO)c1ccc(Cl)c(F)c1] | (S)-1-(1-(4-chloro-3-fluorophenyl)-3-hydroxypropyl)-4-(2-((tetrahydro-2H-pyran-4-yl)amino)pyrimidin-4-yl)pyridin-2(1H)-one | m/z (APCI-pos) M + 1 = 459.0 |
| 108 | 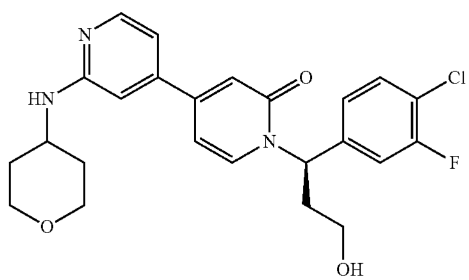 [SMILES: O=c1cc(-c2ccnc(NC3CCOCC3)c2)ccn1[C@H](CCO)c1ccc(Cl)c(F)c1] | (R)-1-(1-(4-chloro-3-fluorophenyl)-3-hydroxypropyl)-4-(2-((tetrahydro-2H-pyran-4-yl)amino)pyridin-4-yl)pyridin-2(1H)-one | m/z (APCI-pos) M + 1 = 458.0 |
| 109 | 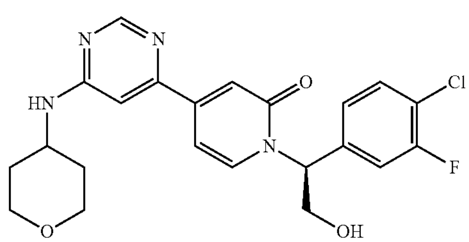 [SMILES: O=c1cc(-c2cc(NC3CCOCC3)ncn2)ccn1[C@H](CO)c1ccc(Cl)c(F)c1] | (S)-1-(1-(4-chloro-3-fluorophenyl)-2-hydroxyethyl)-4-(6-((tetrahydro-2H-pyran-4-yl)amino)pyrimidin-4-yl)pyridin-2(1H)-one | m/z (APCI-pos) M + 1 = 445.0 |
| 110 | 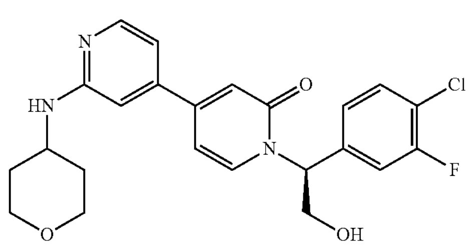 [SMILES: O=c1cc(-c2ccnc(NC3CCOCC3)c2)ccn1[C@H](CO)c1ccc(Cl)c(F)c1] | (S)-1-(1-(4-chloro-3-fluorophenyl)-2-hydroxyethyl)-4-(2-((tetrahydro-2H-pyran-4-yl)amino)pyridin-4-yl)pyridin-2(1H)-one | m/z (APCI-pos) M + 1 = 444.0 |

TABLE 2-continued

| Ex. # | Structure | Name | MS |
|---|---|---|---|
| 111 | 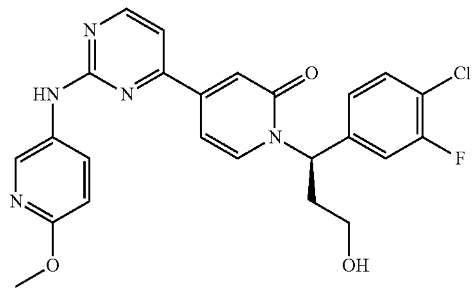 [SMILES: COc1ccc(Nc2nccc(-c3ccn([C@H](CCO)c4ccc(Cl)c(F)c4)c(=O)c3)n2)cn1] | (R)-1-(1-(4-chloro-3-fluorophenyl)-3-hydroxypropyl)-4-(2-((6-methoxypyridin-3-yl)amino)pyrimidin-4-yl)pyridin-2(1H)-one | m/z (APCI-pos) M + 1 = 482.1 |
| 112 | 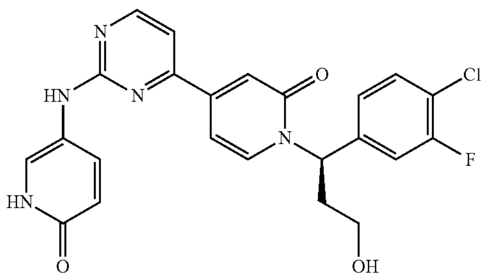 [SMILES: O=c1ccc(Nc2nccc(-c3ccn([C@H](CCO)c4ccc(Cl)c(F)c4)c(=O)c3)n2)c[nH]1] | (R)-1-(1-(4-chloro-3-fluorophenyl)-3-hydroxypropyl)-4-(2-)(6-oxo-1,6-dihydropyridin-3-yl)amino)pyrimidin-4-yl)pyridin-2(1H)-one | m/z (APCI-pos) M + 1 = 468.1 |
| 113 | 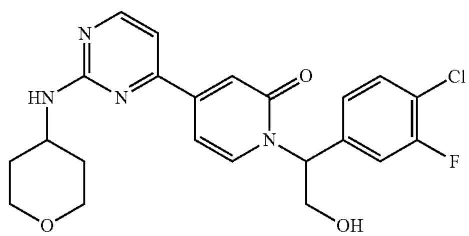 [SMILES: O=c1cc(-c2ccnc(NC3CCOCC3)n2)ccn1C(CO)c1ccc(Cl)c(F)c1] | 1-(1-(4-chloro-3-fluorophenyl)-2-hydroxyethyl)-4-(2-((tetrahydro-2H-pyran-4-yl)amino)pyrimidin-4-yl)pyridin-2(1H)-one | 445.1 |
| 114 | 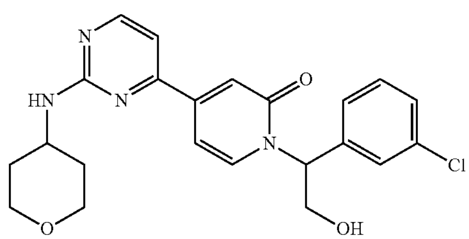 [SMILES: O=c1cc(-c2ccnc(NC3CCOCC3)n2)ccn1C(CO)c1cccc(Cl)c1] | 1-(1-(3-chlorophenyl)-2-hydroxyethyl)-4-(2-((tetrahydro-2H-pyran-4-yl)amino)pyrimidin-4-yl)pyridin-2(1H)-one | 427.1 |
| 115 | 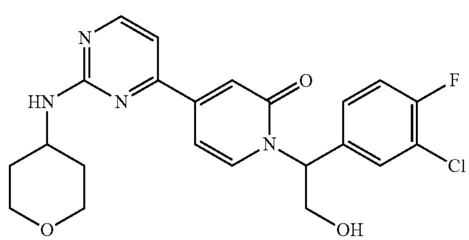 [SMILES: O=c1cc(-c2ccnc(NC3CCOCC3)n2)ccn1C(CO)c1ccc(F)c(Cl)c1] | 1-(1-(3-chloro-4-fluorophenyl)-2-hydroxyethyl)-4-(2-((tetrahydro-2H-pyran-4-yl)amino)pyrimidin-4-yl)pyridin-2(1H)-one | 445.1 |
| 116 | 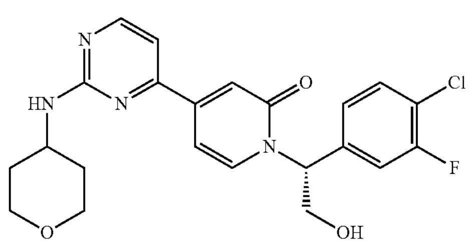 [SMILES: O=c1cc(-c2ccnc(NC3CCOCC3)n2)ccn1[C@@H](CO)c1ccc(Cl)c(F)c1] | (R)-1-(1-(4-chloro-3-fluorophenyl)-2-hydroxyethyl)-4-(2-((tetrahydro-2H-pyran-4-yl)amino)pyrimidin-4-yl)pyridin-2(1H)-one | 444.1 |

TABLE 2-continued

| Ex. # | Structure | Name | MS |
|---|---|---|---|
| 117 | 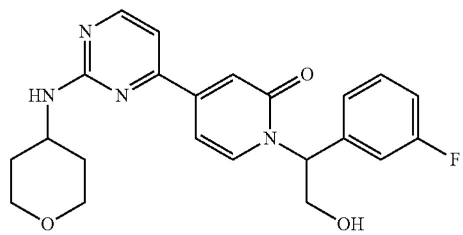 [SMILES: O=c1cc(-c2ccnc(NC3CCOCC3)n2)ccn1C(CO)c1cccc(F)c1] | 1-(1-(3-fluorophenyl)-2-hydroxyethyl)-4-(2-((tetrahydro-2H-pyran-4-yl)amino)pyrimidin-4-yl)pyridin-2(1H)-one | 411.1 |
| 118 | 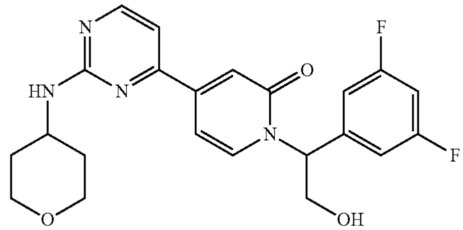 [SMILES: O=c1cc(-c2ccnc(NC3CCOCC3)n2)ccn1C(CO)c1cc(F)cc(F)c1] | 1-(1-(3,5-difluorophenyl)-2-hydroxyethyl)-4-(2-((tetrahydro-2H-pyran-4-yl)amino)pyrimidin-4-yl)pyridin-2(1H)-one | 429.1 |
| 119 | 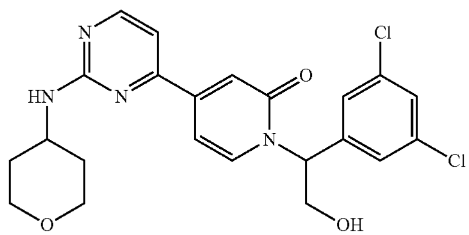 [SMILES: O=c1cc(-c2ccnc(NC3CCOCC3)n2)ccn1C(CO)c1cc(Cl)cc(Cl)c1] | 1-(1-(3,5-dichlorophenyl)-2-hydroxyethyl)-4-(2-((tetrahydro-2H-pyran-4-yl)amino)pyrimidin-4-yl)pyridin-2(1H)-one | 461.1 |
| 120 | 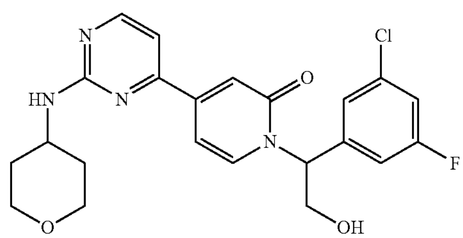 [SMILES: O=c1cc(-c2ccnc(NC3CCOCC3)n2)ccn1C(CO)c1cc(F)cc(Cl)c1] | 1-(1-(3-chloro-5-fluorophenyl)-2-hydroxyethyl)-4-(2-((tetrahydro-2H-pyran-4-yl)amino)pyrimidin-4-yl)pyridin-2(1H)-one | 445.1 |
| 121 | 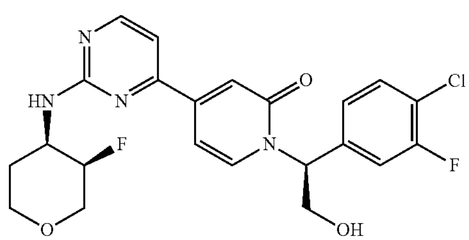 [SMILES: O=c1cc(-c2ccnc(N[C@@H]3CCOC[C@@H]3F)n2)ccn1[C@H](CO)c1ccc(Cl)c(F)c1] | 1-((S)-1-(4-chloro-3-fluorophenyl)-2-hydroxyethyl)-4-(2-(((3R,4R)-3-fluorotetrahydro-2H-pyran-4-yl)amino)pyrimidin-4-yl)pyridin-2(1H)-one | 463.1 |
| 122 | 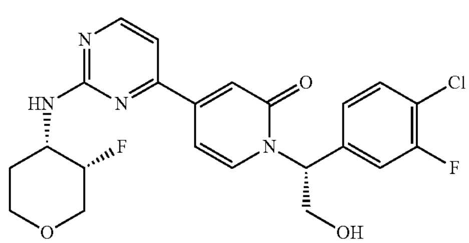 [SMILES: O=c1cc(-c2ccnc(N[C@H]3CCOC[C@H]3F)n2)ccn1[C@@H](CO)c1ccc(Cl)c(F)c1] | 1-((R)-1-(4-chloro-3-fluorophenyl)-2-hydroxyethyl)-4-(2-(((3S,4S)-3-fluorotetrahydro-2H-pyran-4-yl)amino)pyrimidin-4-yl)pyridin-2(1H)-one | 463.1 |

TABLE 2-continued

| Ex. # | Structure | Name | MS |
|---|---|---|---|
| 123 | 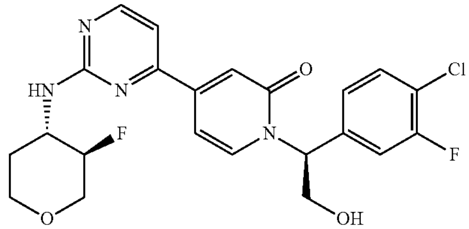 [SMILES: O=c1cc(-c2ccnc(N[C@H]3CCOC[C@@H]3F)n2)ccn1[C@H](CO)c1ccc(Cl)c(F)c1] | 1-((S)-1-(4-chloro-3-fluorophenyl)-2-hydroxyethyl)-4-(2-(((3R,4S)-3-fluorotetrahydro-2H-pyran-4-yl)amino)pyrimidin-4-yl)pyridin-2(1H)-one | 463.1 |
| 124 | 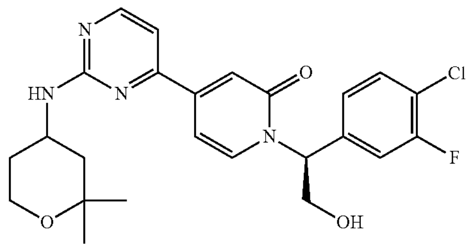 [SMILES: CC1(C)CC(Nc2nccc(-c3ccn([C@H](CO)c4ccc(Cl)c(F)c4)c(=O)c3)n2)CCO1] | 1-((S)-1-(4-chloro-3-fluorophenyl)-2-hydroxyethyl)-4-(2-((2,2-dimethyltetrahydro-2H-pyran-4-yl)amino)pyrimidin-4-yl)pyridin-2(1H)-one | 473.1 |
| 125 | 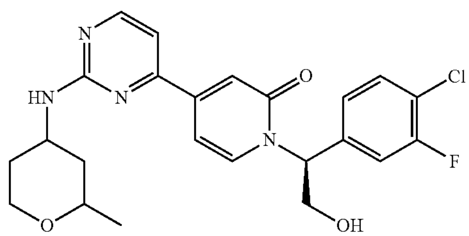 [SMILES: CC1CC(Nc2nccc(-c3ccn([C@H](CO)c4ccc(Cl)c(F)c4)c(=O)c3)n2)CCO1] | 1-((S)-1-(4-chloro-3-fluorophenyl)-2-hydroxyethyl)-4-(2-((2-methyltetrahydro-2H-pyran-4-yl)amino)pyrimidin-4-yl)pyridin-2(1H)-one | 459.1 |
| 126 | 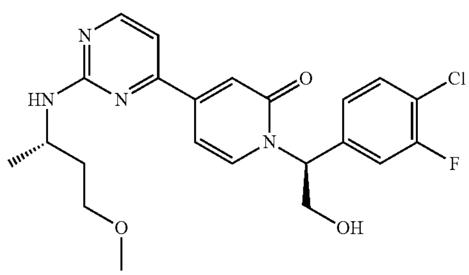 [SMILES: COCC[C@H](C)Nc1nccc(-c2ccn([C@H](CO)c3ccc(Cl)c(F)c3)c(=O)c2)n1] | 1-((S)-1-(4-chloro-3-fluorophenyl)-2-hydroxyethyl)-4-(2-(((S)-4-methoxybutan-2-yl)amino)pyrimidin-4-yl)pyridin-2(1H)-one | 447.1 |
| 127 | 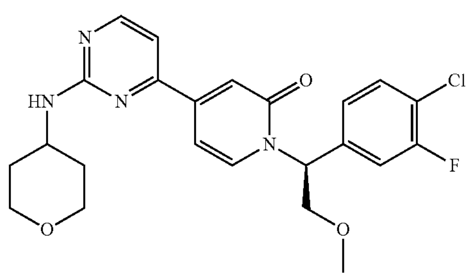 [SMILES: COC[C@H](c1ccc(Cl)c(F)c1)n1ccc(-c2ccnc(NC3CCOCC3)n2)cc1=O] | (S)-1-(1-(4-chloro-3-fluorophenyl)-2-methoxyethyl)-4-(2-((tetrahydro-2H-pyran-4-yl)amino)pyrimidin-4-yl)pyridin-2(1H)-one | 459.2 |
| 128 | 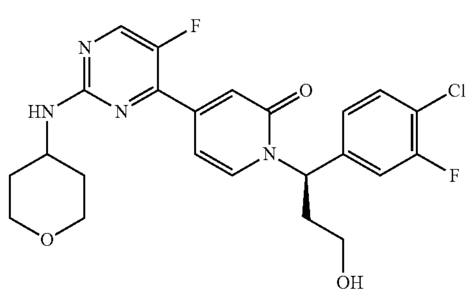 [SMILES: O=c1cc(-c2nc(NC3CCOCC3)ncc2F)ccn1[C@H](CCO)c1ccc(Cl)c(F)c1] | (R)-1-(1-(4-chloro-3-fluorophenyl)-3-hydroxypropyl)-4-(5-fluoro-2-((tetrahydro-2H-pyran-4-yl)amino)pyrimidin-4-yl)pyridin-2(1H)-one | 477.1 |

TABLE 2-continued

| Ex. # | Structure | Name | MS |
|---|---|---|---|
| 129 | 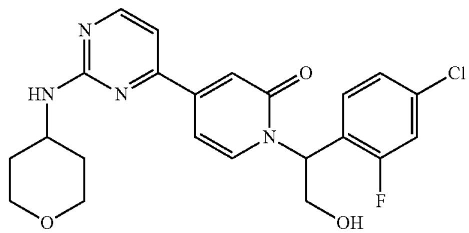 [SMILES: O=c1cc(-c2ccnc(NC3CCOCC3)n2)ccn1C(CO)c1ccc(Cl)cc1F] | 1-(1-(4-chloro-2-fluorophenyl)-2-hydroxyethyl)-4-(2-((tetrahydro-2H-pyran-4-yl)amino)pyrimidin-4-yl)pyridin-2(1H)-one | 445.1 |
| 130 | 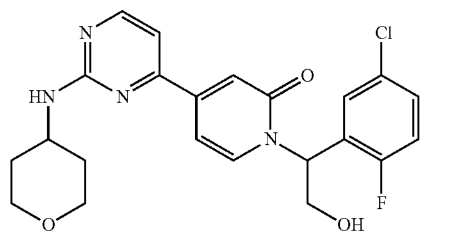 [SMILES: O=c1cc(-c2ccnc(NC3CCOCC3)n2)ccn1C(CO)c1cc(Cl)ccc1F] | 1-(1-(5-chloro-2-fluorophenyl)-2-hydroxyethyl)-4-(2-((tetrahydro-2H-pyran-4-yl)amino)pyrimidin-4-yl)pyridin-2(1H)-one | 445.1 |
| 131 | 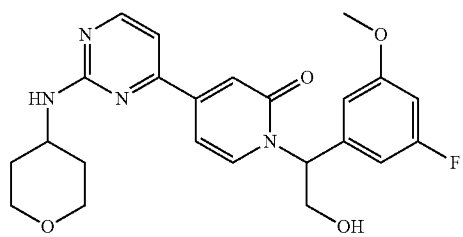 [SMILES: COc1cc(F)cc(C(CO)n2ccc(-c3ccnc(NC4CCOCC4)n3)cc2=O)c1] | 1-(1-(3-fluoro-5-methoxyphenyl)-2-hydroxyethyl)-4-(2-((tetrahydro-2H-pyran-4-yl)amino)pyrimidin-4-yl)pyridin-2(1H)-one | 441.2 |
| 132 | 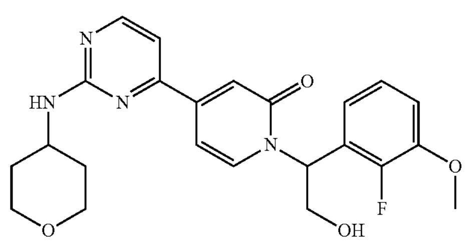 [SMILES: COc1cccc(C(CO)n2ccc(-c3ccnc(NC4CCOCC4)n3)cc2=O)c1F] | 1-(1-(2-fluoro-3-methoxyphenyl)-2-hydroxyethyl)-4-(2-((tetrahydro-2H-pyran-4-yl)amino)pyrimidin-4-yl)pyridin-2(1H)-one | 441.2 |
| 133 | 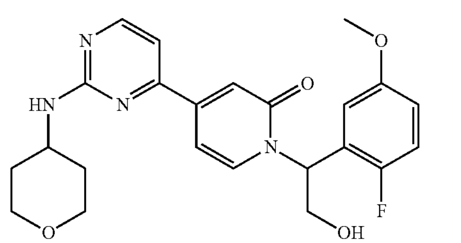 [SMILES: COc1ccc(F)c(C(CO)n2ccc(-c3ccnc(NC4CCOCC4)n3)cc2=O)c1] | 1-(1-(2-fluoro-5-methoxyphenyl)-2-hydroxyethyl)-4-(2-((tetrahydro-2H-pyran-4-yl)amino)pyrimidin-4-yl)pyridin-2(1H)-one | 441 |
| 134 | 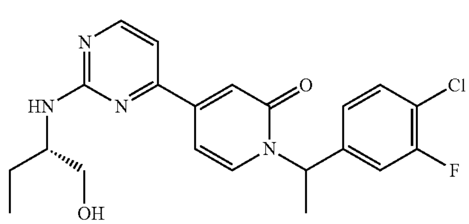 [SMILES: CC[C@@H](CO)Nc1nccc(-c2ccn(C(C)c3ccc(Cl)c(F)c3)c(=O)c2)n1] | 1-(1-(4-chloro-3-fluorophenyl)ethyl)-4-(2-(((S)-1-hydroxybutan-2-yl)amino)pyrimidin-4-yl)pyridin-2(1H)-one | 417.1 |

TABLE 2-continued

| Ex. # | Structure | Name | MS |
|---|---|---|---|
| 135 | 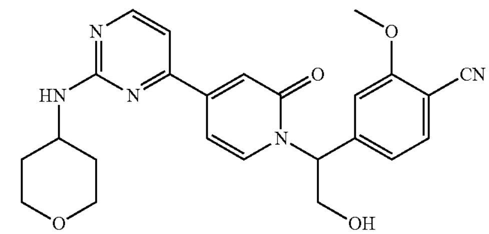 [SMILES: COc1cc(C(CO)n2ccc(-c3ccnc(NC4CCOCC4)n3)cc2=O)ccc1C#N] | 4-(2-hydroxy-1-(2-oxo-4-(2-((tetrahydro-2H-pyran-4-yl)amino)pyrimidin-4-yl)pyridin-1(2H)-yl)ethyl)-2-methoxybenzonitrile | 446.1 |
| 136 | 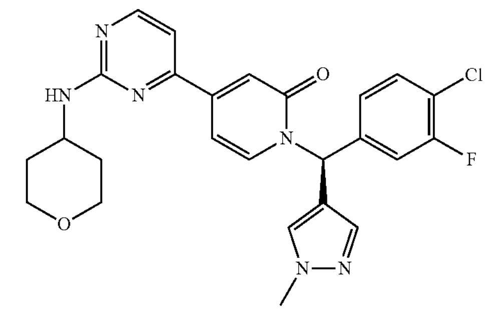 [SMILES: Cn1cc([C@H](c2ccc(Cl)c(F)c2)n2ccc(-c3ccnc(NC4CCOCC4)n3)cc2=O)cn1] | (S)-1-((4-chloro-3-fluorophenyl)(1-methyl-1H-pyrazol-4-yl)methyl)-4-(2-((tetrahydro-2H-pyran-4-yl)amino)pyrimidin-4-yl)pyridin-2(1H)-one | 495.2 |
| 137 | 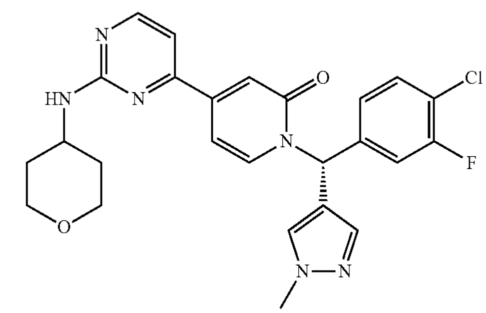 [SMILES: Cn1cc([C@@H](c2ccc(Cl)c(F)c2)n2ccc(-c3ccnc(NC4CCOCC4)n3)cc2=O)cn1] | (R)-1-((4-chloro-3-fluorophenyl)(1-methyl-1H-pyrazol-4-yl)methyl)-4-(2-((tetrahydro-2H-pyran-4-yl)amino)pyrimidin-4-yl)pyridin-2(1H)-one | 481.2 |
| 138 | 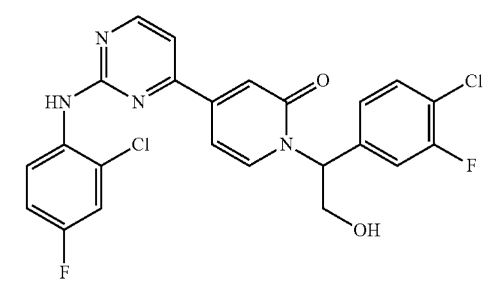 | 1-(1-(4-chloro-3-fluorophenyl)-2-hydroxyethyl)-4-(2-((2-chloro-4-fluorophenyl)amino)pyrimidin-4-yl)pyridin-2(1H)-one | 489 |
| 139 | 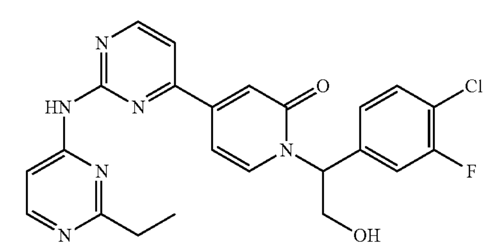 [SMILES: CCc1nccc(Nc2nccc(-c3ccn(C(CO)c4ccc(Cl)c(F)c4)c(=O)c3)n2)n1] | 1-(1-(4-chloro-3-fluorophenyl)-2-hydroxyethyl)-4-(2-((2-ethylpyrimidin-4-yl)amino)pyrimidin-4-yl)pyridin-2(1H)-one | 467.2 |

TABLE 2-continued

| Ex. # | Structure | Name | MS |
|---|---|---|---|
| 140 | 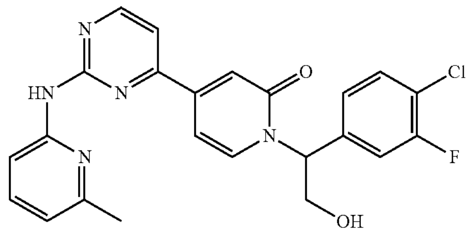 [SMILES: Cc1cccc(Nc2nccc(-c3ccn(C(CO)c4ccc(Cl)c(F)c4)c(=O)c3)n2)n1] | 1-(1-(4-chloro-3-fluorophenyl)-2-hydroxyethyl)-4-(2-((6-methylpyridin-2-yl)amino)pyrimidin-4-yl)pyridin-2(1H)-one | 452.1 |
| 141 | 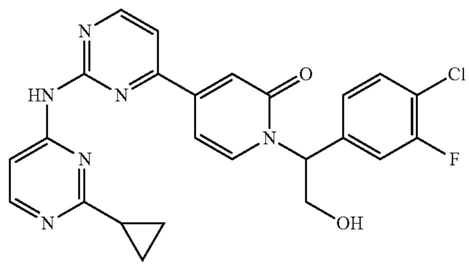 [SMILES: O=c1cc(-c2ccnc(Nc3ccnc(C4CC4)n3)n2)ccn1C(CO)c1ccc(Cl)c(F)c1] | 1-(1-(4-chloro-3-fluorophenyl)-2-hydroxyethyl)-4-(2-((2-cyclopropylpyrimidin-4-yl)amino)pyrimidin-4-yl)pyridin-2(1H)-one | 479.1 |
| 142 | 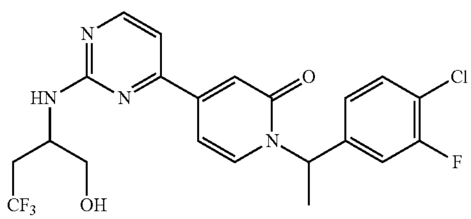 [SMILES: CC(c1ccc(Cl)c(F)c1)n1ccc(-c2ccnc(NC(CO)CC(F)(F)F)n2)cc1=O] | 1-(1-(4-chloro-3-fluorophenyl)ethyl)-4-(2-((4,4,4-trifluoro-1-hydroxybutan-2-yl)amino)pyrimidin-4-yl)pyridin-2(1H)-one | 471.1 |
| 143 | 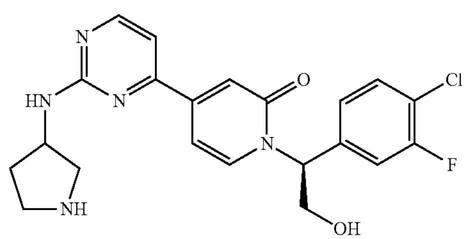 [SMILES: O=c1cc(-c2ccnc(NC3CCNC3)n2)ccn1[C@H](CO)c1ccc(Cl)c(F)c1] | 1-((S)-1-(4-chloro-3-fluorophenyl)-2-hydroxyethyl)-4-(2-(pyrrolidin-3-ylamino)pyrimidin-4-yl)pyridin-2(1H)-one | 430.3 |
| 144 | 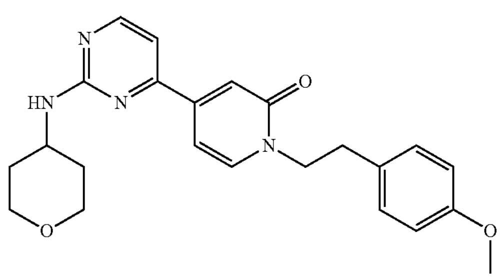 [SMILES: COc1ccc(CCn2ccc(-c3ccnc(NC4CCOCC4)n3)cc2=O)cc1] | 1-(4-methoxyphenethyl)-4-(2-((tetrahydro-2H-pyran-4-yl)amino)pyrimidin-4-yl)pyridin-2(1H)-one | 407.2 |
| 145 | 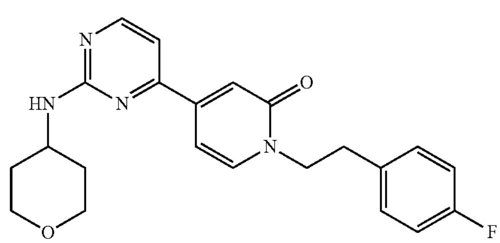 [SMILES: O=c1cc(-c2ccnc(NC3CCOCC3)n2)ccn1CCc1ccc(F)cc1] | 1-(4-fluorophenethyl)-4-(2-((tetrahydro-2H-pyran-4-yl)amino)pyrimidin-4-yl)pyridin-2(1H)-one | 395.2 |

TABLE 2-continued

| Ex. # | Structure | Name | MS |
|---|---|---|---|
| 146 | 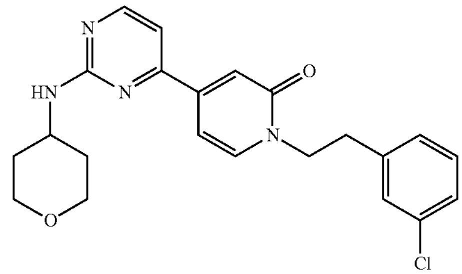 [SMILES: O=c1cc(-c2ccnc(NC3CCOCC3)n2)ccn1CCc1cccc(Cl)c1] | 1-(3-chlorophenethyl)-4-(2-((tetrahydro-2H-pyran-4-yl)amino)pyrimidin-4-yl)pyridin-2(1H)-one | 411.2 |
| 147 | 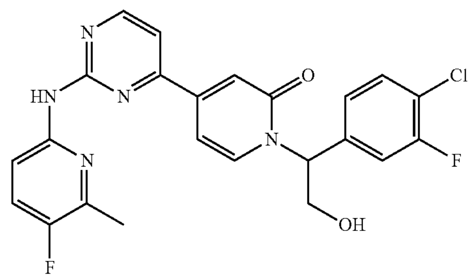 [SMILES: Cc1nc(Nc2nccc(-c3ccn(C(CO)c4ccc(Cl)c(F)c4)c(=O)c3)n2)ccc1F] | 1-(1-(4-chloro-3-fluorophenyl)-2-hydroxyethyl)-4-(2-((5-fluoro-6-methylpyridin-2-yl)amino)pyrimidin-4-yl)pyridin-2(1H)-one | 470.1 |
| 148 | 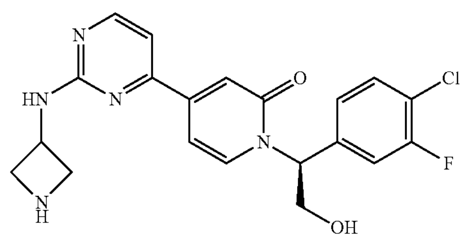 [SMILES: O=c1cc(-c2ccnc(NC3CNC3)n2)ccn1[C@H](CO)c1ccc(Cl)c(F)c1] | (S)-4-(2-(azetidin-3-ylamino)pyrimidin-4-yl)-1-(1-(4-chloro-3-fluorophenyl)-2-hydroxyethyl)pyridin-2(1H)-one | 416.2 |
| 149 | 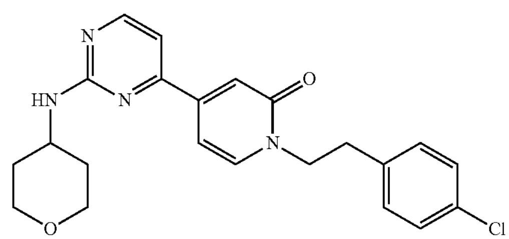 [SMILES: O=c1cc(-c2ccnc(NC3CCOCC3)n2)ccn1CCc1ccc(Cl)cc1] | 1-(4-chlorophenethyl)-4-(2-((tetrahydro-2H-pyran-4-yl)amino)pyrimidin-4-yl)pyridin-2(1H)-one | 411.2 |
| 150 | 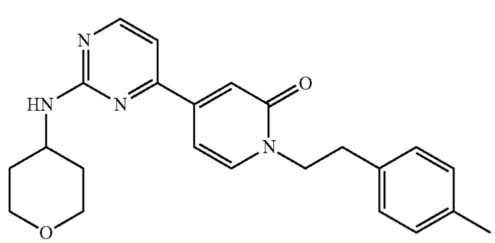 [SMILES: Cc1ccc(CCn2ccc(-c3ccnc(NC4CCOCC4)n3)cc2=O)cc1] | 1-(4-methylphenethyl)-4-(2-((tetrahydro-2H-pyran-4-yl)amino)pyrimidin-4-yl)pyridin-2(1H)-one | 391.2 |
| 151 | 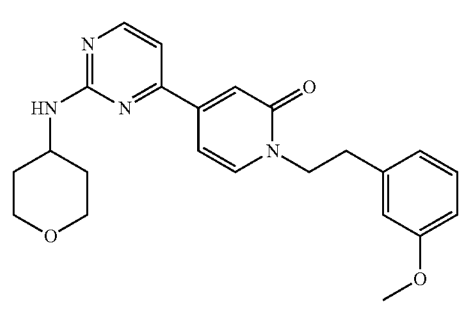 [SMILES: COc1cccc(CCn2ccc(-c3ccnc(NC4CCOCC4)n3)cc2=O)c1] | 1-(3-methoxyphenethyl)-4-(2-((tetrahydro-2H-pyran-4-yl)amino)pyrimidin-4-yl)pyridin-2(1H)-one | 407.3 |

TABLE 2-continued

| Ex. # | Structure | Name | MS |
|---|---|---|---|
| 152 | 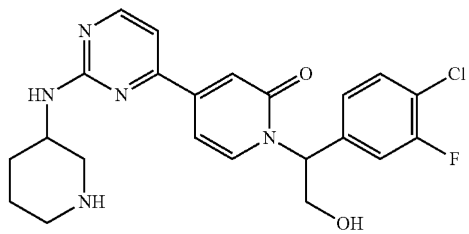 [SMILES: O=c1cc(-c2ccnc(NC3CCCNC3)n2)ccn1C(CO)c1ccc(Cl)c(F)c1] | 1-(1-(4-chloro-3-fluorophenyl)-2-hydroxyethyl)-4-(2-(piperidin-3-ylamino)pyrimidin-4-yl)pyridin-2(1H)-one | 444.2 |
| 153 | 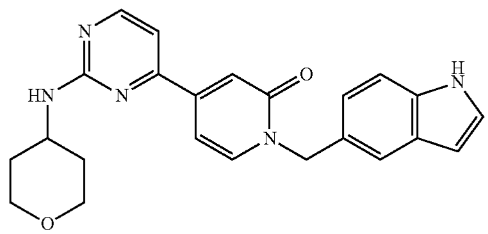 [SMILES: O=c1cc(-c2ccnc(NC3CCOCC3)n2)ccn1Cc1ccc2[nH]ccc2c1] | 1-((1H-indol-5-yl)methyl)-4-(2-((tetrahydro-2H-pyran-4-yl)amino)pyrimidin-4-yl)pyridin-2(1H)-one | 402.3 |
| 154 | 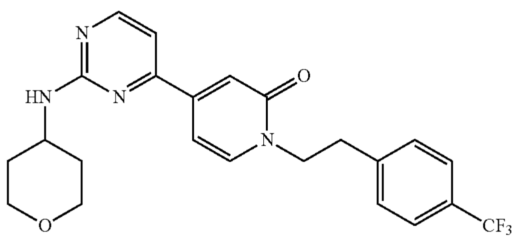 [SMILES: O=c1cc(-c2ccnc(NC3CCOCC3)n2)ccn1CCc1ccc(C(F)(F)F)cc1] | 4-(2-((tetrahydro-2H-pyran-4-yl)amino)pyrimidin-4-yl)-1-(4-(trifluoromethyl)phenethyl)pyridin-2(1H)-one | 445.2 |
| 155 | 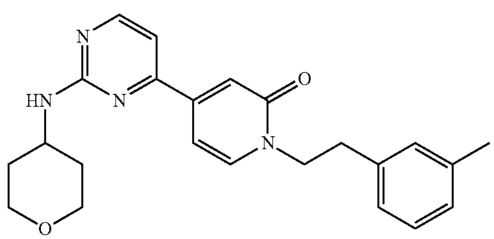 [SMILES: Cc1cccc(CCn2ccc(-c3ccnc(NC4CCOCC4)n3)cc2=O)c1] | 1-(3-methylphenethyl)-4-(2-((tetrahydro-2H-pyran-4-yl)amino)pyrimidin-4-yl)pyridin-2(1H)-one | 391.3 |
| 156 | 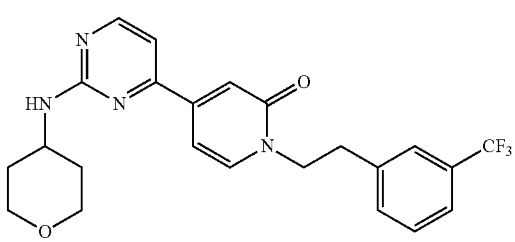 [SMILES: O=c1cc(-c2ccnc(NC3CCOCC3)n2)ccn1CCc1cccc(C(F)(F)F)c1] | 4-(2-((tetrahydro-2H-pyran-4-yl)amino)pyrimidin-4-yl)-1-(3-(trifluoromethyl)phenethyl)pyridin-2(1H)-one | 445.2 |
| 157 | 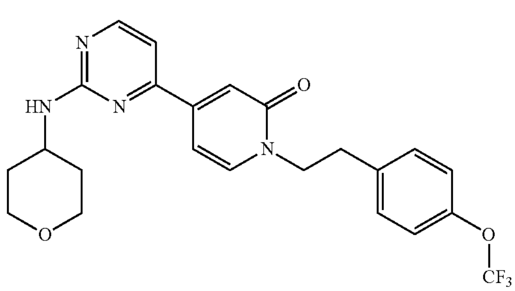 [SMILES: O=c1cc(-c2ccnc(NC3CCOCC3)n2)ccn1CCc1ccc(OC(F)(F)F)cc1] | 4-(2-((tetrahydro-2H-pyran-4-yl)amino)pyrimidin-4-yl)-1-(4-(trifluoromethoxy)phenethyl)pyridin-2(1H)-one | 461.2 |

TABLE 2-continued

| Ex. # | Structure | Name | MS |
|---|---|---|---|
| 158 | 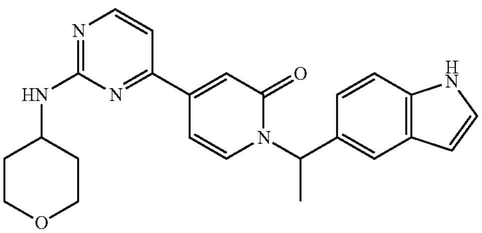 [SMILES: CC(c1ccc2[nH]ccc2c1)n1ccc(-c2ccnc(NC3CCOCC3)n2)cc1=O] | 1-(1-(1H-indol-5-yl)ethyl)-4-(2-((tetrahydro-2H-pyran-4-yl)amino)pyrimidin-4-yl)pyridin-2(1H)-one | 416.3 |
| 159 | 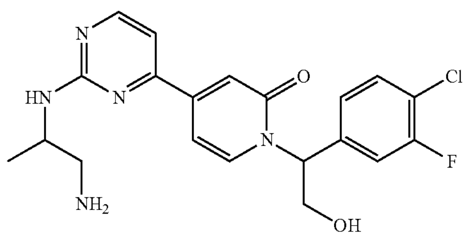 [SMILES: CC(CN)Nc1nccc(-c2ccn(C(CO)c3ccc(Cl)c(F)c3)c(=O)c2)n1] | 4-(2-((1-aminopropan-2-yl)amino)pyrimidin-4-yl)-1-(1-(4-chloro-3-fluorophenyl)-2-hydroxyethyl)pyridin-2(1H)-one | 418.2 |
| 160 | 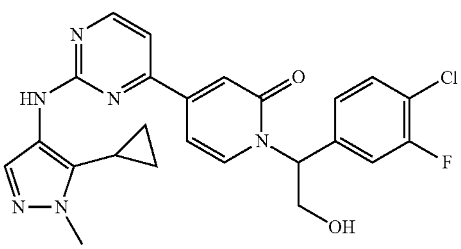 [SMILES: Cn1ncc(Nc2nccc(-c3ccn(C(CO)c4ccc(Cl)c(F)c4)c(=O)c3)n2)c1C1CC1] | 1-(1-(4-chloro-3-fluorophenyl)-2-hydroxyethyl)-4-(2-((5-cyclopropyl-1-methyl-1H-pyrazol-4-yl)amino)pyrimidin-4-yl)pyridin-2(1H)-one | 481.1 |
| 161 | 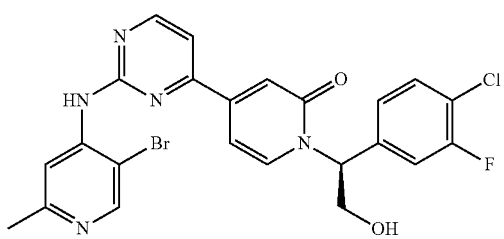 [SMILES: Cc1cc(Nc2nccc(-c3ccn([C@H](CO)c4ccc(Cl)c(F)c4)c(=O)c3)n2)c(Br)cn1] | (S)-4-(2-((5-bromo-2-methylpyridin-4-yl)amino)pyrimidin-4-yl)-1-(1-(4-chloro-3-fluorophenyl)-2-hydroxyethyl)pyridin-2(1H)-one | 529.93 |
| 162 | 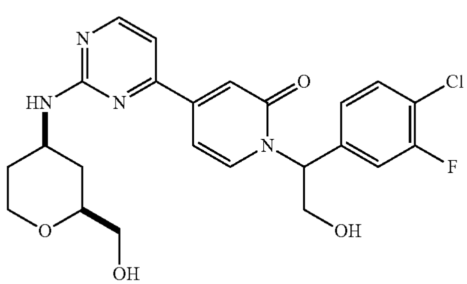 | 1-(1-(4-chloro-3-fluorophenyl)-2-hydroxyethyl)-4-(2-(((cis)-2-(hydroxymethyl)tetrahydro-2H-pyran-4-yl)amino)pyrimidin-4-yl)pyridin-2(1H)-one | 475.1 |
| 163 | 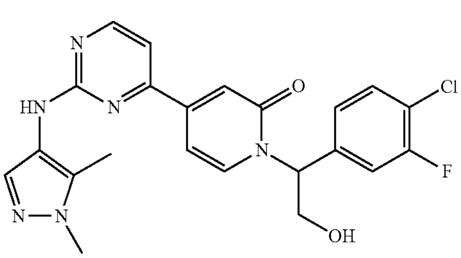 [SMILES: Cc1c(Nc2nccc(-c3ccn(C(CO)c4ccc(Cl)c(F)c4)c(=O)c3)n2)cnn1C] | 1-(1-(4-chloro-3-fluorophenyl)-2-hydroxyethyl)-4-(2-((1,5-dimethyl-1H-pyrazol-4-yl)amino)pyrimidin-4-yl)pyridin-2(1H)-one | 455.1 |

TABLE 2-continued

| Ex. # | Structure | Name | MS |
|---|---|---|---|
| 164 | 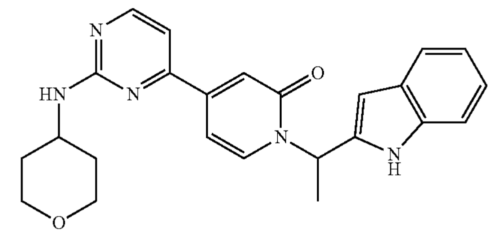 [SMILES: CC(c1cc2ccccc2[nH]1)n1ccc(-c2ccnc(NC3CCOCC3)n2)cc1=O] | 1-(1-(1H-indol-2-yl)ethyl)-4-(2-((tetrahydro-2H-pyran-4-yl)amino)pyrimidin-4-yl)pyridin-2(1H)-one | 416.2 |
| 165 | 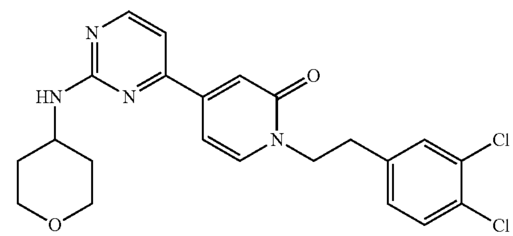 [SMILES: O=c1cc(-c2ccnc(NC3CCOCC3)n2)ccn1CCc1ccc(Cl)c(Cl)c1] | 1-(3,4-dichlorophenethyl)-4-(2-((tetrahydro-2H-pyran-4-yl)amino)pyrimidin-4-yl)pyridin-2(1H)-one | 445.1 |
| 166 | 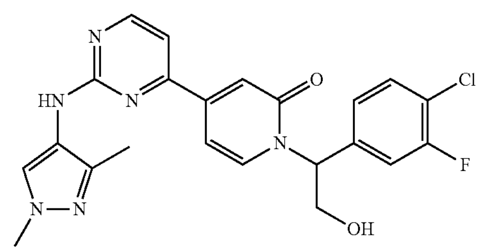 [SMILES: Cc1nn(C)cc1Nc1nccc(-c2ccn(C(CO)c3ccc(Cl)c(F)c3)c(=O)c2)n1] | 1-(1-(4-chloro-3-fluorophenyl)-2-hydroxyethyl)-4-(2-,3-dimethyl-1H-pyrazol-4-yl)amino)pyrimidin-4-yl)pyridin-2(1H)-one | 455.1 |
| 167 | 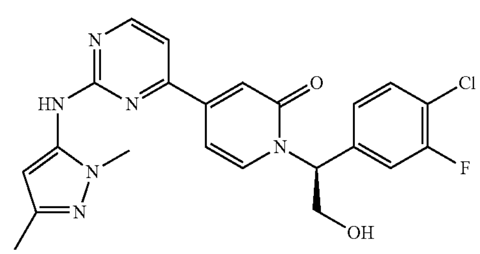 [SMILES: Cc1cc(Nc2nccc(-c3ccn([C@H](CO)c4ccc(Cl)c(F)c4)c(=O)c3)n2)n(C)n1] | (S)-1-(1-(4-chloro-3-fluorophenyl)-2-hydroxyethyl)-4-(2-((1,3-dimethyl-1H-pyrazol-5-yl)amino)pyrimidin-4-yl)pyridin-2(1H)-one | 455.13 |
| 168 | 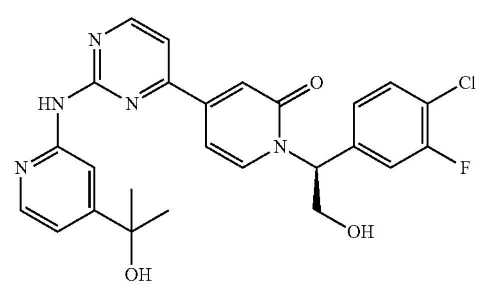 [SMILES: CC(C)(O)c1ccnc(Nc2nccc(-c3ccn([C@H](CO)c4ccc(Cl)c(F)c4)c(=O)c3)n2)c1] | (S)-1-(1-(4-chloro-3-fluorophenyl)-2-hydroxyethyl)-4-(2-((4-(2-hydroxypropan-2-yl)pyridin-2-yl)amino)pyrimidin-4-yl)pyridin-2(1H)-one | 496.15 |
| 169 | 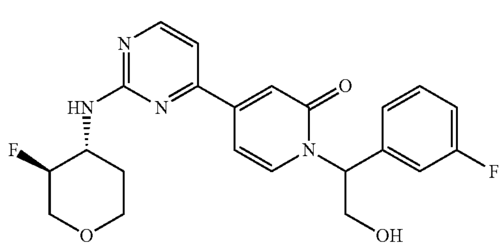 [SMILES: O=c1cc(-c2ccnc(N[C@@H]3CCOC[C@H]3F)n2)ccn1C(CO)c1cccc(F)c1] | 1-(1-(3-fluorophenyl)-2-hydroxyethyl)-4-(2-(((3S,4R)-3-fluorotetrahydro-2H-pyran-4-yl)amino)pyrimidin-4-yl)pyridin-2(1H)-one | 429.2 |

TABLE 2-continued

| Ex. # | Structure | Name | MS |
|---|---|---|---|
| 170 | 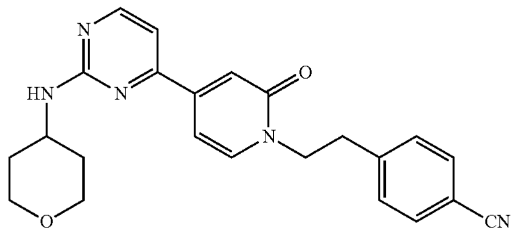 [SMILES: N#Cc1ccc(CCn2ccc(-c3ccnc(NC4CCOCC4)n3)cc2=O)cc1] | 4-(2-(2-oxo-4-(2-((tetrahydro-2H-pyran-4-yl)amino)pyrimidin-4-yl)pyridin-1(2H)-yl)ethyl)benzonitrile | 402.3 |
| 171 | 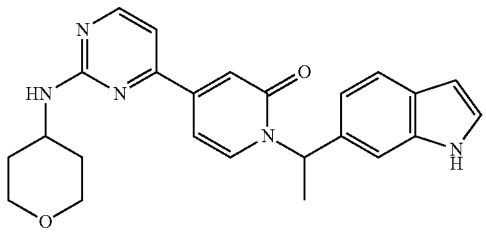 [SMILES: CC(c1ccc2cc[nH]c2c1)n1ccc(-c2ccnc(NC3CCOCC3)n2)cc1=O] | 1-(1-(1H-indol-6-yl)ethyl)-4-(2-((tetrahydro-2H-pyran-4-yl)amino)pyrimidin-4-yl)pyridin-2(1H)-one | 416.3 |
| 172 | 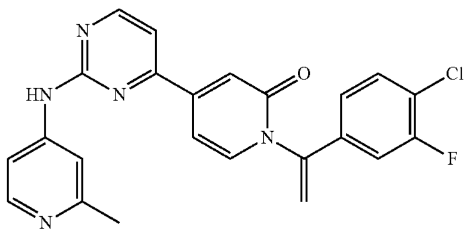 [SMILES: C=C(c1ccc(Cl)c(F)c1)n1ccc(-c2ccnc(Nc3ccnc(C)c3)n2)cc1=O] | 1-(1-(4-chloro-3-fluorophenyl)vinyl)-4-(2-((2-methylpyridin-4-yl)amino)pyrimidin-4-yl)pyridin-2(1H)-one | 434.1 |
| 173 | 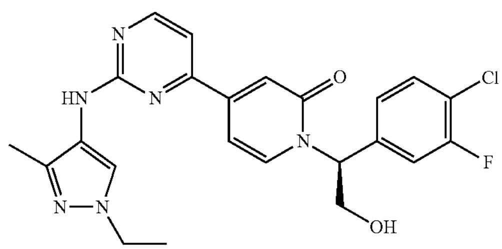 [SMILES: CCn1cc(Nc2nccc(-c3ccn([C@H](CO)c4ccc(Cl)c(F)c4)c(=O)c3)n2)c(C)n1] | (S)-1-(1-(4-chloro-3-fluorophenyl)-2-hydroxyethyl)-4-(2-((1-ethyl-3-methyl-1H-pyrazol-4-yl)amino)pyrimidin-4-yl)pyridin-2(1H)-one | 469.1 |
| 174 | 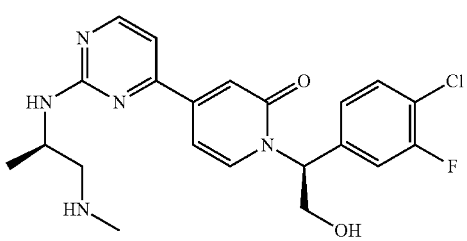 [SMILES: CNC[C@@H](C)Nc1nccc(-c2ccn([C@H](CO)c3ccc(Cl)c(F)c3)c(=O)c2)n1] | 1-((S)-1-(4-chloro-3-fluorophenyl)-2-hydroxyethyl)-4-(2-(((R)-1-(methylamino)propan-2-yl)amino)pyrimidin-4-yl)pyridin-2(1H)-one | 432.3 |
| 175 | 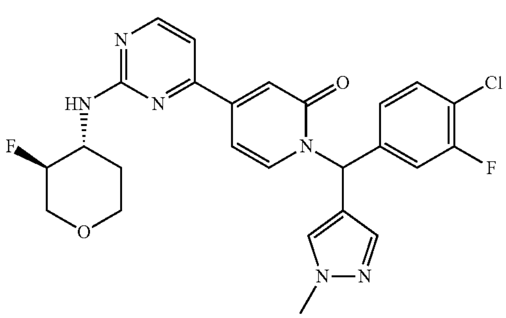 [SMILES: Cn1cc(C(c2ccc(Cl)c(F)c2)n2ccc(-c3ccnc(N[C@@H]4CCOC[C@H]4F)n3)cc2=O)cn1] | 1-((4-chloro-3-fluorophenyl)(1-methyl-1H-pyrazol-4-yl)methyl)-4-(2-(((3S,4R)-3-fluorotetrahydro-2H-pyran-4-yl)amino)pyrimidin-4-yl)pyridin-2(1H)-one | 513.2 |

| Ex. # | Structure | Name | MS |
|---|---|---|---|
| 176 | 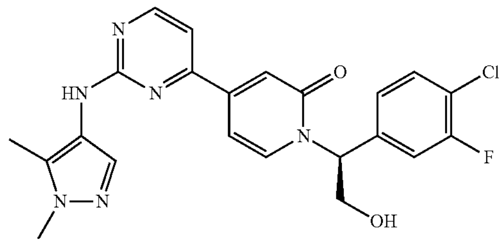 [SMILES: Cc1c(Nc2nccc(-c3ccn([C@H](CO)c4ccc(Cl)c(F)c4)c(=O)c3)n2)cnn1C] | (S)-1-(1-(4-chloro-3-fluorophenyl)-2-hydroxyethyl)-4-(2-((1,5-dimethyl-1H-pyrazol-4-yl)amino)pyrimidin-4-yl)pyridin-2(1H)-one | 455.1 |
| 177 | 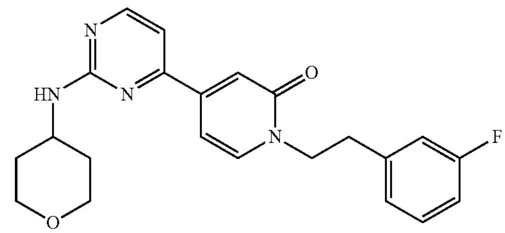 [SMILES: O=c1cc(-c2ccnc(NC3CCOCC3)n2)ccn1CCc1cccc(F)c1] | 1-(3-fluorophenethyl)-4-(2-((tetrahydro-2H-pyran-4-yl)amino)pyrimidin-4-yl)pyridin-2(1H)-one | 395.1 |
| 178 | 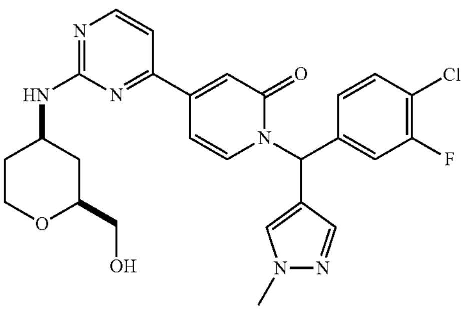 | 1-((4-chloro-3-fluorophenyl)(1-methyl-1H-pyrazol-4-yl)methyl)-4-(2-(((cis)-2-(hydroxymethyl)tetrahydro-2H-pyran-4-yl)amino)pyrimidin-4-yl)pyridin-2(1H)-one | 547.2 (+Na) |
| 179 | 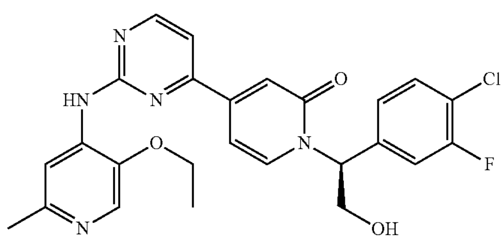 [SMILES: CCOc1cnc(C)cc1Nc1nccc(-c2ccn([C@H](CO)c3ccc(Cl)c(F)c3)c(=O)c2)n1] | (S)-1-(1-(4-chloro-3-fluorophenyl)-2-hydroxyethyl)-4-(2-((5-ethoxy-2-methylpyridin-4-yl)amino)pyrimidin-4-yl)pyridin-2(1H)-one | 496.2 |
| 180 | 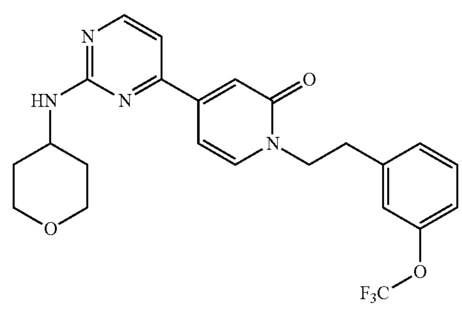 [SMILES: O=c1cc(-c2ccnc(NC3CCOCC3)n2)ccn1CCc1cccc(OC(F)(F)F)c1] | 4-(2-((tetrahydro-2H-pyran-4-yl)amino)pyrimidin-4-yl)-1-(3-(trifluoromethoxy)phenethyl)pyridin-2(1H)-one | 461.1 |
| 181 | 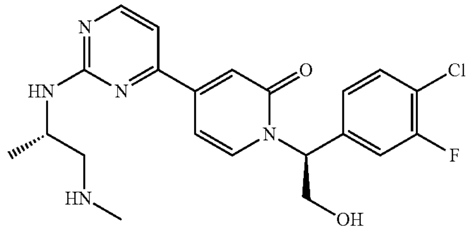 [SMILES: CNC[C@H](C)Nc1nccc(-c2ccn([C@H](CO)c3ccc(Cl)c(F)c3)c(=O)c2)n1] | 1-((S)-1-(4-chloro-3-fluorophenyl)-2-hydroxyethyl)-4-(2-(((S)-1-(methylamino)propan-2-yl)amino)pyrimidin-4-yl)pyridin-2(1H)-one | 432.2 |

TABLE 2-continued

| Ex. # | Structure | Name | MS |
|---|---|---|---|
| 182 | 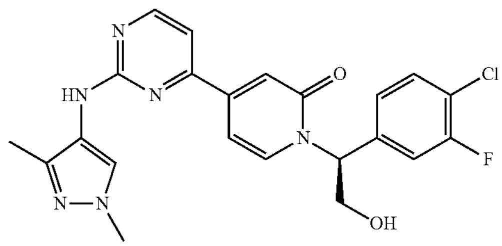 [SMILES: Cc1nn(C)cc1Nc1nccc(-c2ccn([C@H](CO)c3ccc(Cl)c(F)c3)c(=O)c2)n1] | (S)-1-(1-(4-chloro-3-fluorophenyl)-2-hydroxyethyl)-4-(2-((1,3-dimethyl-1H-pyrazol-4-yl)amino)pyrimidin-4-yl)pyridin-2(1H)-one | 455.13 |
| 183 | 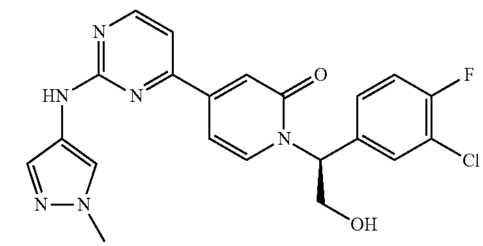 [SMILES: Cn1cc(Nc2nccc(-c3ccn([C@H](CO)c4ccc(F)c(Cl)c4)c(=O)c3)n2)cn1] | (S)-1-(1-(3-chloro-4-fluorophenyl)-2-hydroxyethyl)-4-(2-((1-methyl-1H-pyrazol-4-yl)amino)pyrimidin-4-yl)pyridin-2(1H)-one | 441.12 |
| 184 | 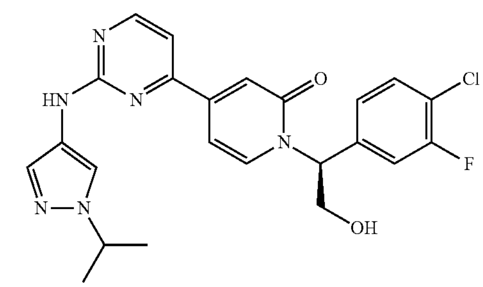 [SMILES: CC(C)n1cc(Nc2nccc(-c3ccn([C@H](CO)c4ccc(Cl)c(F)c4)c(=O)c3)n2)cn1] | (S)-1-(1-(4-chloro-3-fluorophenyl)-2-hydroxyethyl)-4-(2-((1-isopropyl-1H-pyrazol-4-yl)amino)pyrimidin-4-yl)pyridin-2(1H)-one | 469.1 |
| 185 | 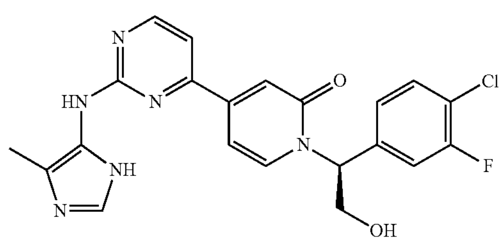 [SMILES: Cc1nc[nH]c1Nc1nccc(-c2ccn([C@H](CO)c3ccc(Cl)c(F)c3)c(=O)c2)n1] | (S)-1-(1-(4-chloro-3-fluorophenyl)-2-hydroxyethyl)-4-(2-((4-methyl-1H-imidazol-5-yl)amino)pyrimidin-4-yl)pyridin-2(1H)-one | 441.1 |
| 186 | 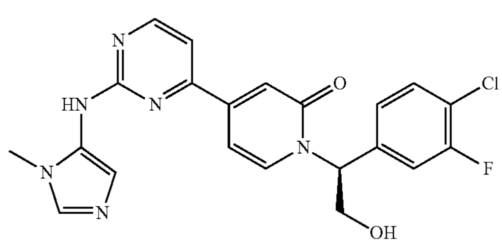 [SMILES: Cn1cncc1Nc1nccc(-c2ccn([C@H](CO)c3ccc(Cl)c(F)c3)c(=O)c2)n1] | (S)-1-(1-(4-chloro-3-fluorophenyl)-2-hydroxyethyl)-4-(2-((1-methyl-1H-imidazol-5-yl)amino)pyrimidin-4-yl)pyridin-2(1H)-one | 441.12 |
| 187 | 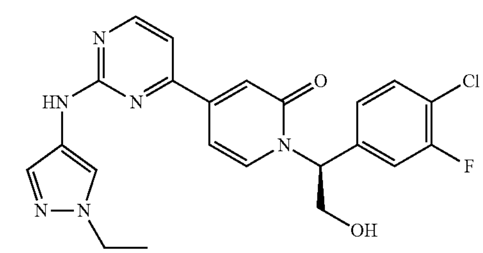 [SMILES: CCn1cc(Nc2nccc(-c3ccn([C@H](CO)c4ccc(Cl)c(F)c4)c(=O)c3)n2)cn1] | (S)-1-(1-(4-chloro-3-fluorophenyl)-2-hydroxyethyl)-4-(2-((1-ethyl-1H-pyrazol-4-yl)amino)pyrimidin-4-yl)pyridin-2(1H)-one | 455.13 |

TABLE 2-continued

| Ex. # | Structure | Name | MS |
|---|---|---|---|
| 188 | 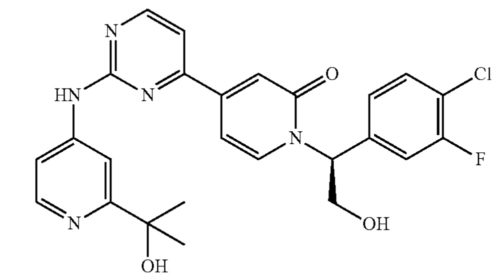 [SMILES: CC(C)(O)c1cc(Nc2nccc(-c3ccn([C@H](CO)c4ccc(Cl)c(F)c4)c(=O)c3)n2)ccn1] | (S)-1-(1-(4-chloro-3-fluorophenyl)-2-hydroxyethyl)-4-(2-((2-(2-hydroxypropan-2-yl)pyridin-4-yl)amino)pyrimidin-4-yl)pyridin-2(1H)-one | 496.2 |
| 189 | 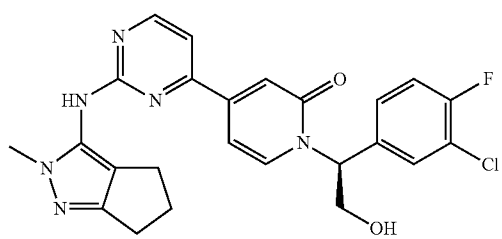 [SMILES: Cn1nc2c(c1Nc1nccc(-c3ccn([C@H](CO)c4ccc(F)c(Cl)c4)c(=O)c3)n1)CCC2] | (S)1-(1-(3-chloro-4-fluorophenyl)-2-hydroxyethyl)-4-(2-((2-methyl-2,4,5,6-tetrahydrocyclopenta[c]pyrazol-3-yl)amino)pyrimidin-4-yl)pyridin-2(1H)-one | 481.1 |
| 190 | 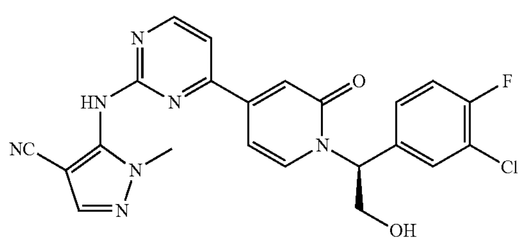 [SMILES: Cn1ncc(C#N)c1Nc1nccc(-c2ccn([C@H](CO)c3ccc(F)c(Cl)c3)c(=O)c2)n1] | (S)-5-((4-(1-(1-(3-chloro-4-fluorophenyl)-2-hydroxyethyl)-2-oxo-1,2-dihydropyridin-4-yl)pyrimidin-2-yl)amino)-1-methyl-1H-pyrazole-4-carbonitrile | 466 |
| 191 | 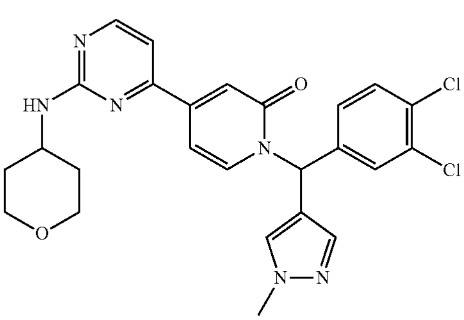 [SMILES: Cn1cc(C(c2ccc(Cl)c(Cl)c2)n2ccc(-c3ccnc(NC4CCOCC4)n3)cc2=O)cn1] | 1-((3,4-dichlorophenyl)(1-methyl-1H-pyrazol-4-yl)methyl)-4-(2-((tetrahydro-2H-pyran-4-yl)amino)pyrimidin-4-yl)pyridin-2(1H)-one | 513.2 |
| 192 | 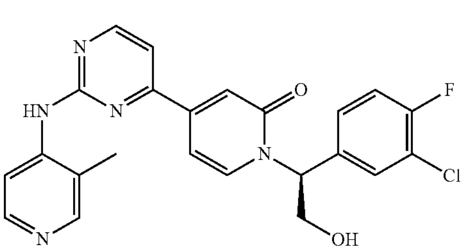 [SMILES: Cc1cnccc1Nc1nccc(-c2ccn([C@H](CO)c3ccc(F)c(Cl)c3)c(=O)c2)n1] | (S)-1-(1-(3-chloro-4-fluorophenyl)-2-hydroxyethyl)-4-(2-((3-methylpyridin-4-yl)amino)pyrimidin-4-yl)pyridin-2(1H)-one | 452.1 |

| Ex. # | Structure | Name | MS |
|---|---|---|---|
| 193 | 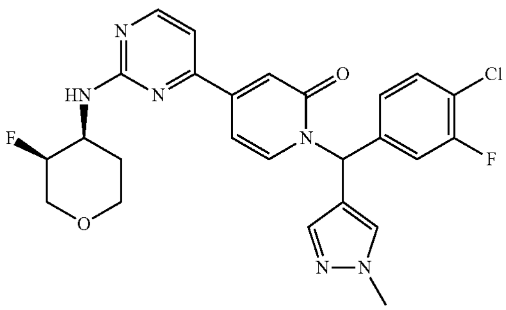 [SMILES: Cn1cc(C(c2ccc(Cl)c(F)c2)n2ccc(-c3ccnc(N[C@H]4CCOC[C@H]4F)n3)cc2=O)cn1] | 1-((4-chloro-3-fluorophenyl)(1-methyl-1H-pyrazol-4-yl)methyl)-4-(2-(((3S,4S)-3-fluorotetrahydro-2H-pyran-4-yl)amino)pyrimidin-4-yl)pyridin-2(1H)-one | 513.2 |
| 194 | 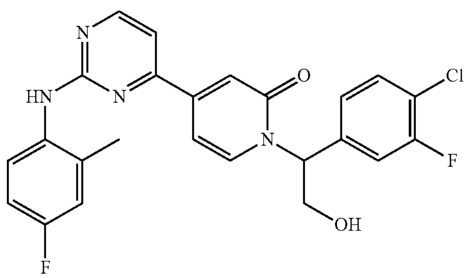 [SMILES: Cc1cc(F)ccc1Nc1nccc(-c2ccn(C(CO)c3ccc(Cl)c(F)c3)c(=O)c2)n1] | 1-(1-(4-chloro-3-fluorophenyl)-2-hydroxyethyl)-4-(2-((4-fluoro-2-methylphenyl)amino)pyrimidin-4-yl)pyridin-2(1H)-one | 469.1 |
| 195 | 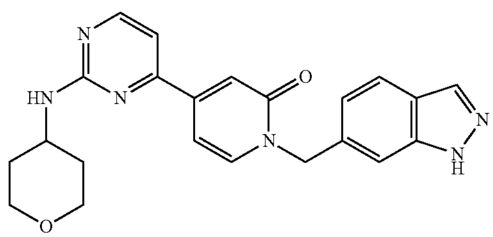 [SMILES: O=c1cc(-c2ccnc(NC3CCOCC3)n2)ccn1Cc1ccc2cn[nH]c2c1] | 1-((1H-indazol-6-yl)methyl)-4-(2-((tetrahydro-2H-pyran-4-yl)amino)pyrimidin-4-yl)pyridin-2(1H)-one | 403.1 |
| 196 | 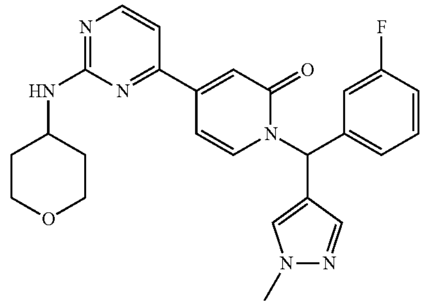 [SMILES: Cn1cc(C(c2cccc(F)c2)n2ccc(-c3ccnc(NC4CCOCC4)n3)cc2=O)cn1] | 1-((3-fluorophenyl)(1-methyl-1H-pyrazol-4-yl)methyl)-4-(2-((tetrahydro-2H-pyran-4-yl)amino)pyrimidin-4-yl)pyridin-2(1H)-one | 461.2 |
| 197 | 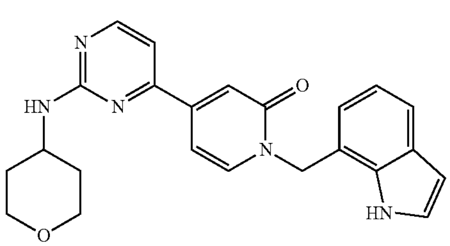 [SMILES: O=c1cc(-c2ccnc(NC3CCOCC3)n2)ccn1Cc1cccc2cc[nH]c12] | 1-((1H-indol-7-yl)methyl)-4-(2-((tetrahydro-2H-pyran-4-yl)amino)pyrimidin-4-yl)pyridin-2(1H)-one | 402.2 |

TABLE 2-continued

| Ex. # | Structure | Name | MS |
|---|---|---|---|
| 198 | 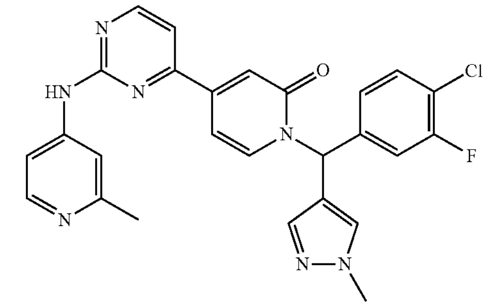 [SMILES: Cc1cc(Nc2nccc(-c3ccn(C(c4ccc(Cl)c(F)c4)c4cnn(C)c4)c(=O)c3)n2)ccn1] | 1-((4-chloro-3-fluorophenyl)(1-methyl-1H-pyrazol-4-yl)methyl)-4-(2-((2-methylpyridin-4-yl)amino)pyrimidin-4-yl)pyridin-2(1H)-one | 502.1 |
| 199 | 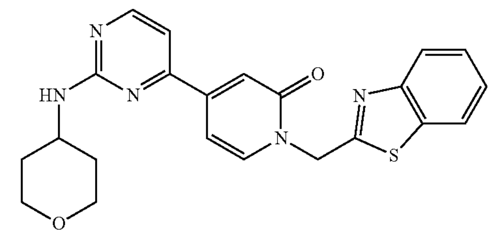 [SMILES: O=c1cc(-c2ccnc(NC3CCOCC3)n2)ccn1Cc1nc2ccccc2s1] | 1-(benzo[d]thiazol-2-ylmethyl)-4-(2-((tetrahydro-2H-pyran-4-yl)amino)pyrimidin-4-yl)pyridin-2(1H)-one | 420.1 |
| 200 | 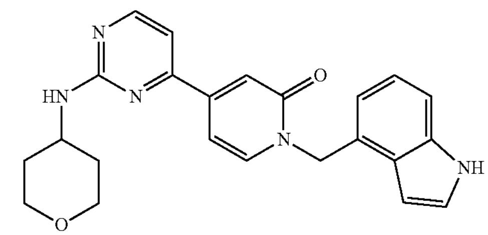 [SMILES: O=c1cc(-c2ccnc(NC3CCOCC3)n2)ccn1Cc1cccc2[nH]ccc12] | 1-((1H-indol-4-yl)methyl)-4-(2-((tetrahydro-2H-pyran-4-yl)amino)pyrimidin-4-yl)pyridin-2(1H)-one | 402.2 |
| 201 | 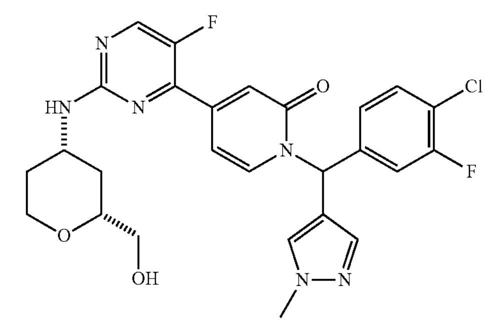 | 1-((4-chloro-3-fluorophenyl)(1-methyl-1H-pyrazol-4-yl)methyl)-4-(5-fluoro-2-(((cis)-2-(hydroxymethyl)tetrahydro-2H-pyran-4-yl)amino)pyrimidin-4-yl)pyridin-2(1H)-one | 565.2 (+Na) |
| 202 | 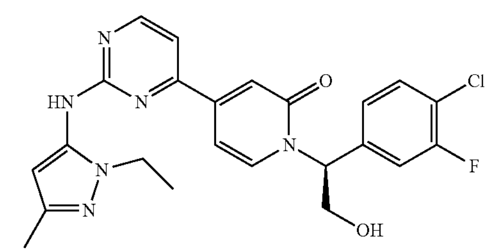 [SMILES: CCn1nc(C)cc1Nc1nccc(-c2ccn([C@H](CO)c3ccc(Cl)c(F)c3)c(=O)c2)n1] | (S)-1-(1-(4-chloro-3-fluorophenyl)-2-hydroxyethyl)-4-(2-((1-ethyl-3-methyl-1H-pyrazol-5-yl)amino)pyrimidin-4-yl)pyridin-2(1H)-one | 469.1 |
| 203 | 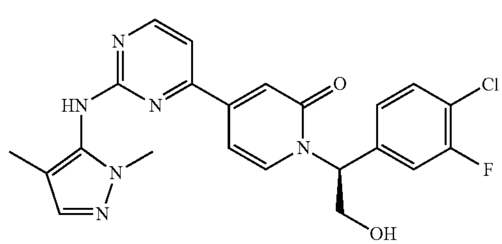 [SMILES: Cc1cnn(C)c1Nc1nccc(-c2ccn([C@H](CO)c3ccc(Cl)c(F)c3)c(=O)c2)n1] | (S)-1-(1-(4-chloro-3-fluorophenyl)-2-hydroxyethyl)-4-(2-((1,4-dimethyl-1H-pyrazol-5-yl)amino)pyrimidin-4-yl)pyridin-2(1H)-one | 455.1 |

TABLE 2-continued

| Ex. # | Structure | Name | MS |
|---|---|---|---|
| 204 | 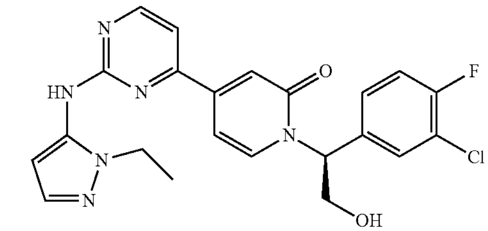 [SMILES: CCn1nccc1Nc1nccc(-c2ccn([C@H](CO)c3ccc(F)c(Cl)c3)c(=O)c2)n1] | (S)-1-(1-(3-chloro-4-fluorophenyl)-2-hydroxyethyl))-4-(2-((1-ethyl-1H-pyrazol-5-yl)amino)pyrimidin-4-yl)pyridin-2(1H)-one | 455.1 |
| 205 | 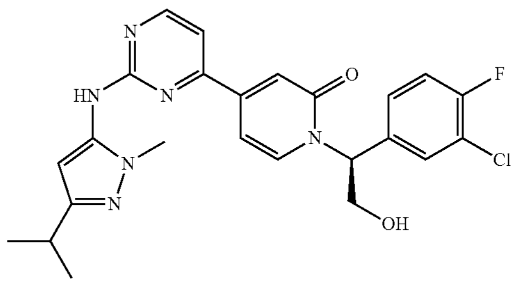 [SMILES: CC(C)c1cc(Nc2nccc(-c3ccn([C@H](CO)c4ccc(F)c(Cl)c4)c(=O)c3)n2)n(C)n1] | (S)-1-(1-(3-chloro-4-fluorophenyl)-2-hydroxyethyl)-4-(2-((3-isopropyl-1-methyl-1H-pyrazol-5-yl)amino)pyrimidin-4-yl)pyridin-2(1H)-one | 483.2 |
| 206 | 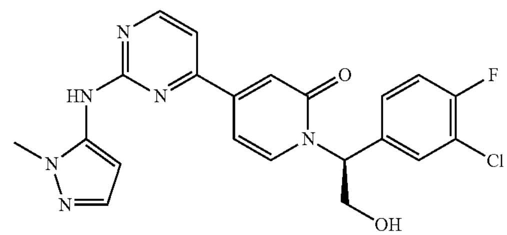 [SMILES: Cn1nccc1Nc1nccc(-c2ccn([C@H](CO)c3ccc(F)c(Cl)c3)c(=O)c2)n1] | (S)-1-(1-(3-chloro-4-fluorophenyl)-2-hydroxyethyl)-4-(2-((1-methyl-1H-pyrazol-5-yl)amino)pyrimidin-4-yl)pyridin-2(1H)-one | 441.1 |
| 207 | 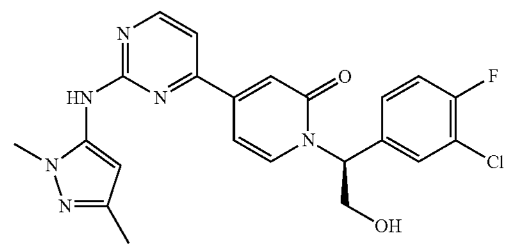 [SMILES: Cc1cc(Nc2nccc(-c3ccn([C@H](CO)c4ccc(F)c(Cl)c4)c(=O)c3)n2)n(C)n1] | (S)-1-(1-(3-chloro-4-fluorophenyl)-2-hydroxyethyl)-4-(2-((1,3-dimethyl-1H-pyrazol-5-yl)amino)pyrimidin-4-yl)pyridin-2(1H)-one | 455.1 |
| 208 | 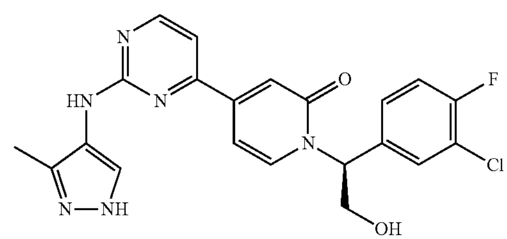 [SMILES: Cc1n[nH]cc1Nc1nccc(-c2ccn([C@H](CO)c3ccc(F)c(Cl)c3)c(=O)c2)n1] | (S)-1-(1-(3-chloro-4-fluorophenyl)-2-hydroxyethyl)-4-(2-((3-methyl-1H-pyrazol-4-yl)amino)pyrimidin-4-yl)pyridin-2(1H)-one | 441.12 |
| 209 | 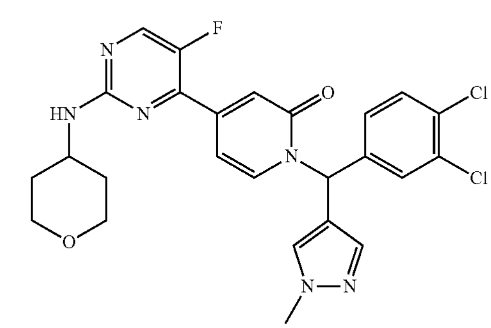 [SMILES: Cn1cc(C(c2ccc(Cl)c(Cl)c2)n2ccc(-c3nc(NC4CCOCC4)ncc3F)cc2=O)cn1] | 1-((3,4-dichlorophenyl)(1-methyl-1H-pyrazol-4-yl)methyl)-4-(5-fluoro-2-((tetrahydro-2H-pyran-4-yl)amino)pyrimidin-4-yl)pyridin-2(1H)-one | 531 |

TABLE 2-continued

| Ex. # | Structure | Name | MS |
|---|---|---|---|
| 210 | 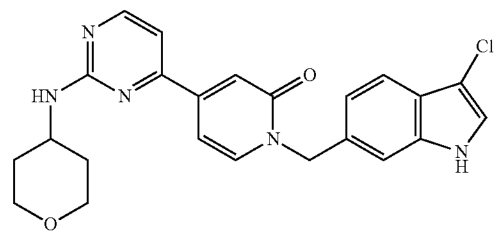 [SMILES: O=c1cc(-c2ccnc(NC3CCOCC3)n2)ccn1Cc1ccc2c(Cl)c[nH]c2c1] | 1-((3-chloro-1H-indol-6-yl)methyl)-4-(2-((tetrahydro-2H-pyran-4-yl)amino)pyrimidin-4-yl)pyridin-2(1H)-one | 436.2 |
| 211 | 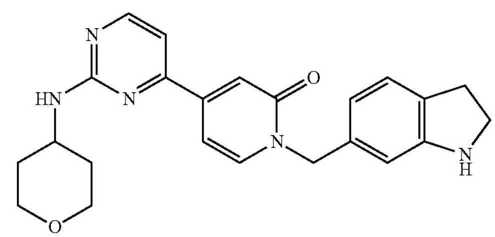 [SMILES: O=c1cc(-c2ccnc(NC3CCOCC3)n2)ccn1Cc1ccc2c(c1)NCC2] | 1-(indolin-6-ylmethyl)-4-(2-((tetrahydro-2H-pyran-4-yl)amino)pyrimidin-4-yl)pyridin-2(1H)-one | 404.2 |
| 212 | 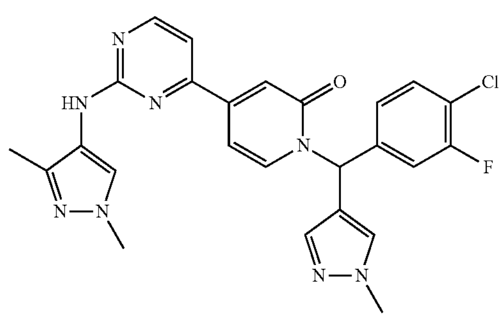 [SMILES: Cc1nn(C)cc1Nc1nccc(-c2ccn(C(c3ccc(Cl)c(F)c3)c3cnn(C)c3)c(=O)c2)n1] | 1-((4-chloro-3-fluorophenyl)(1-methyl-1H-pyrazol-4-yl)methyl)-4-(2-(((1,3-dimethyl-1H-pyrazol-4-yl)amino)pyrimidin-4-yl)pyridin-2(1H)-one | 505.2 |
| 213 | 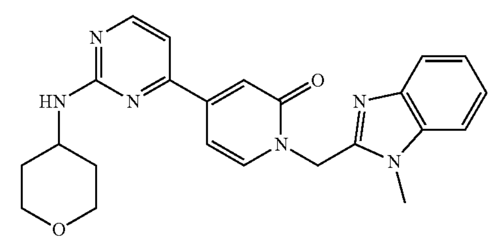 [SMILES: Cn1c(Cn2ccc(-c3ccnc(NC4CCOCC4)n3)cc2=O)nc2ccccc21] | 1-((1-methyl-1H-benzo[d]imidazol-2-yl)methyl)-4-(2-((tetrahydro-2H-pyran-4-yl)amino)pyrimidin-4-yl)pyridin-2(1H)-one | 417.2 |
| 214 | 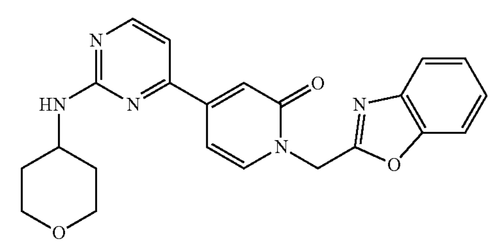 [SMILES: O=c1cc(-c2ccnc(NC3CCOCC3)n2)ccn1Cc1nc2ccccc2o1] | 1-(benzo[d]oxazol-2-ylmethyl)-4-(2-((tetrahydro-2H-pyran-4-yl)amino)pyrimidin-4-yl)pyridin-2(1H)-one | 404.2 |
| 215 | 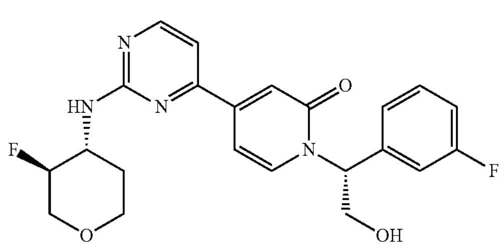 | 1-((R)-1-(3-fluorophenyl)-2-hydroxyethyl)-4-(2-(((3S,4R)-3-fluorotetrahydro-2H-pyran-4-yl)amino)pyrimidin-4-yl)pyridin-2(1H)-one | 429.2 |

TABLE 2-continued

| Ex. # | Structure | Name | MS |
|---|---|---|---|
| 216 | 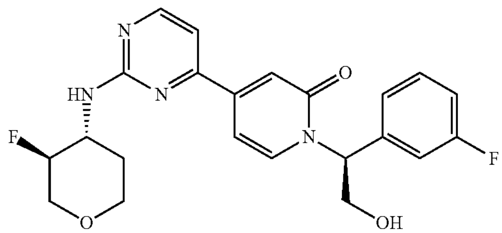 [SMILES: O=c1cc(-c2ccnc(N[C@@H]3CCOC[C@H]3F)n2)ccn1[C@H](CO)c1cccc(F)c1] | 1-((S)-1-3-fluorophenyl)-2-hydroxyethyl)-4-(2-(((3S,4R)-3-fluorotetrahydro-2H-pyran-4-yl)amino)pyrimidin-4-yl)pyridin-2(1H)-one | 429.2 |
| 217 | 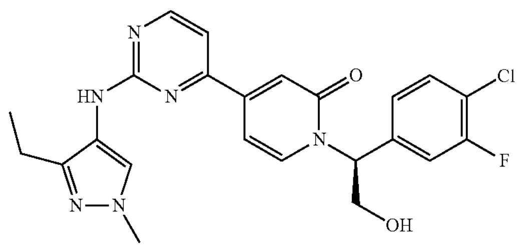 [SMILES: CCc1nn(C)cc1Nc1nccc(-c2ccn([C@H](CO)c3ccc(Cl)c(F)c3)c(=O)c2)n1] | (S)-1-(1-(4-chloro-3-fluorophenyl)-2-hydroxyethyl)-4-(2-((3-ethyl-1-methyl-1H-pyrazol-4-yl)amino)pyrimidin-4-yl)pyridin-2(1H)-one | 469.2 |
| 218 | 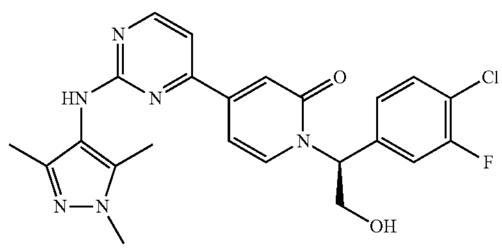 [SMILES: Cc1nn(C)c(C)c1Nc1nccc(-c2ccn([C@H](CO)c3ccc(Cl)c(F)c3)c(=O)c2)n1] | (S)-1-(1-(4-chloro-3-fluorophenyl)-2-hydroxyethyl)-4-(2-((1,3,5-trimethyl-1H-pyrazol-4-yl)amino)pyrimidin-4-yl)pyridin-2(1H)-one | 469.2 |
| 219 | 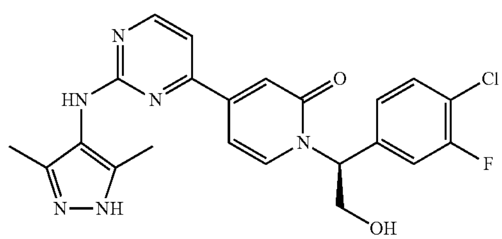 [SMILES: Cc1n[nH]c(C)c1Nc1nccc(-c2ccn([C@H](CO)c3ccc(Cl)c(F)c3)c(=O)c2)n1] | (S)-1-(1-(4-chloro-3-fluorophenyl)-2-hydroxyethyl)-4-(2-((3,5-dimethyl-1H-pyrazol-4-yl)amino)pyrimidin-4-yl)pyridin-2(1H)-one | 455.2 |
| 220 | 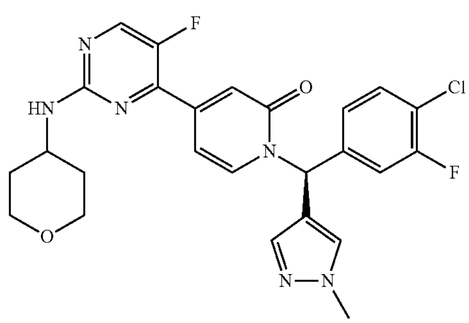 [SMILES: Cn1cc([C@H](c2ccc(Cl)c(F)c2)n2ccc(-c3nc(NC4CCOCC4)ncc3F)cc2=O)cn1] | (S)-1-((4-chloro-3-fluorophenyl)(1-methyl-1H-pyrazol-4-yl)methyl)-4-(5-fluoro-2-((tetrahydro-2H-pyran-4-yl)amino)pyrimidin-4-yl)pyridin-2(1H)-one | 513.1 |
| 221 | 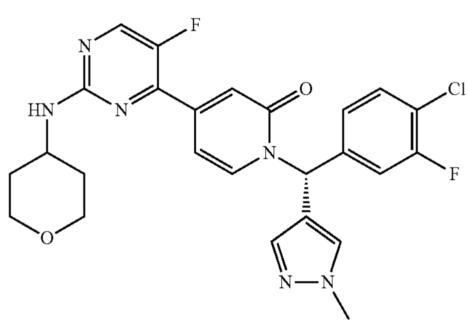 [SMILES: Cn1cc([C@@H](c2ccc(Cl)c(F)c2)n2ccc(-c3nc(NC4CCOCC4)ncc3F)cc2=O)cn1] | (R)-1-((4-chloro-3-fluorophenyl)(1-methyl-1H-pyrazol-4-yl)methyl)-4-(5-fluoro-2-((tetrahydro-2H-pyran-4-yl)amino)pyrimidin-4-yl)pyridin-2(1H)-one | 513.1 |

TABLE 2-continued

| Ex. # | Structure | Name | MS |
|---|---|---|---|
| 222 | 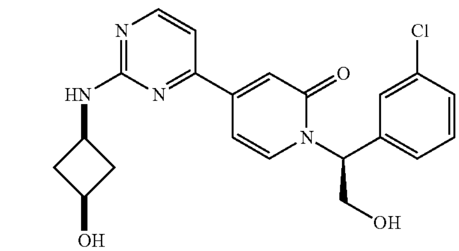 | 1-((S)-1-(3-chlorophenyl)-2-hydroxyethyl)-4-(2-(((cis)-3-hydroxycyclobutyl)amino)pyrimidin-4-yl)pyridin-2(1H)-one | 413.1 |
| 223 | 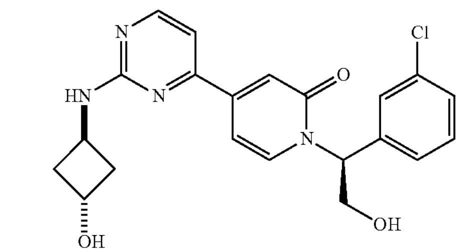 | 1-((S)-1-(3-chlorophenyl)-2-hydroxyethyl)-4-(2-(((trans)-3-hydroxycyclobutyl)amino)pyrimidin-4-yl)pyridin-2(1H)-one | 413.1 |
| 224 | 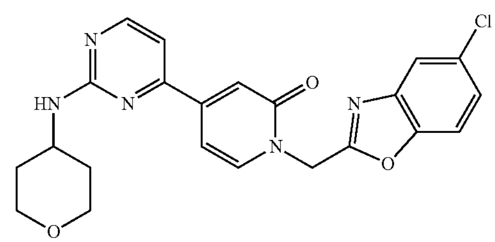 [SMILES: O=c1cc(-c2ccnc(NC3CCOCC3)n2)ccn1Cc1nc2cc(Cl)ccc2o1] | 1-((5-chlorobenzo[d]oxazol-2-yl)methyl)-4-(2-((tetrahydro-2H-pyran-4-yl)amino)pyrimidin-4-yl)pyridin-2(1H)-one | 438.1 |
| 225 | 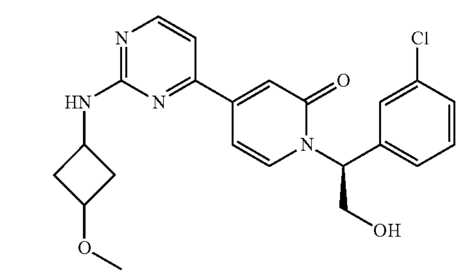 [SMILES: COC1CC(Nc2nccc(-c3ccn([C@H](CO)c4cccc(Cl)c4)c(=O)c3)n2)C1] | (S)-1-(1-(3-chlorophenyl)-2-hydroxyethyl)-4-(2-((3-methoxycyclobutyl)amino)pyrimidin-4-yl)pyridin-2(1H)-one | 427.1 |
| 226 | 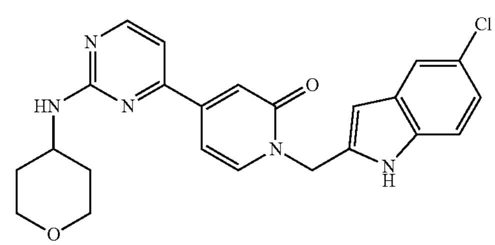 [SMILES: O=c1cc(-c2ccnc(NC3CCOCC3)n2)ccn1Cc1cc2cc(Cl)ccc2[nH]1] | 1-((5-chloro-1H-indol-2-yl)methyl)-4-(2-((tetrahydro-2H-pyran-4-yl)amino)pyrimidin-4-yl)pyridin-2(1H)-one | 436 |
| 227 | 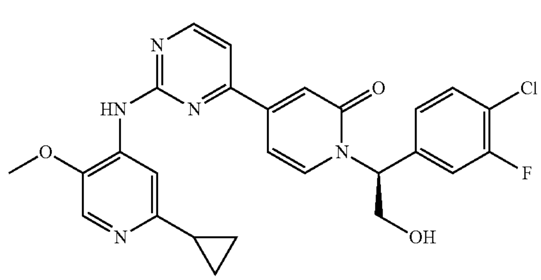 [SMILES: COc1cnc(C2CC2)cc1Nc1nccc(-c2ccn([C@H](CO)c3ccc(Cl)c(F)c3)c(=O)c2)n1] | (S)-1-(1-(4-chloro-3-fluorophenyl)-2-hydroxyethyl)-4-(2-((2-cyclopropyl-5-methoxypyridin-4-yl)amino)pyrimidin-4-yl)pyridin-2(1H)-one | 508.1 |

TABLE 2-continued

| Ex. # | Structure | Name | MS |
|---|---|---|---|
| 228 | 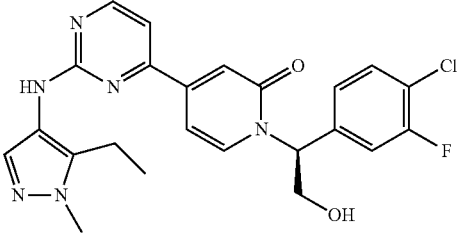 [SMILES: CCc1c(Nc2nccc(-c3ccn([C@H](CO)c4ccc(Cl)c(F)c4)c(=O)c3)n2)cnn1C] | (S)-1-(1-(4-chloro-3-fluorophenyl)-2-hydroxyethyl)-4-(2-((5-ethyl-1-methyl-1H-pyrazol-4-yl)amino)pyrimidin-4-yl)pyridin-2(1H)-one | 469.2 |
| 229 | 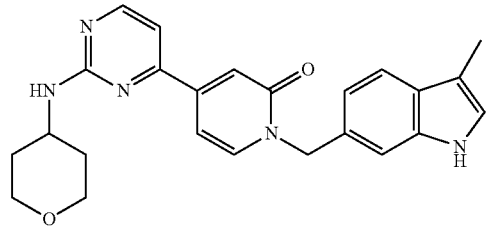 [SMILES: Cc1c[nH]c2cc(Cn3ccc(-c4ccnc(NC5CCOCC5)n4)cc3=O)ccc12] | 1-((3-methyl-1H-indol-6-yl)methyl)-4-(2-((tetrahydro-2H-pyran-4-yl)amino)pyrimidin-4-yl)pyridin-2(1H)-one | 416.3 |
| 230 | 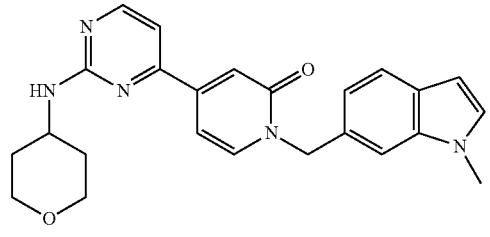 [SMILES: Cn1ccc2ccc(Cn3ccc(-c4ccnc(NC5CCOCC5)n4)cc3=O)cc21] | 1-((1-methyl-1H-indol-6-yl)methyl)-4-(2-((tetrahydro-2H-pyran-4-yl)amino)pyrimidin-4-yl)pyridin-2(1H)-one | 416.2 |
| 231 | 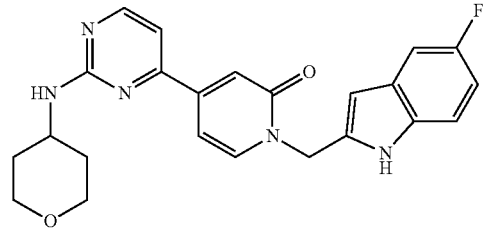 [SMILES: O=c1cc(-c2ccnc(NC3CCOCC3)n2)ccn1Cc1cc2cc(F)ccc2[nH]1] | 1-((5-fluoro-1H-indol-2-yl)methyl)-4-(2-((tetrahydro-2H-pyran-4-yl)amino)pyrimidin-4-yl)pyridin-2(1H)-one | 420.3 |
| 232 | 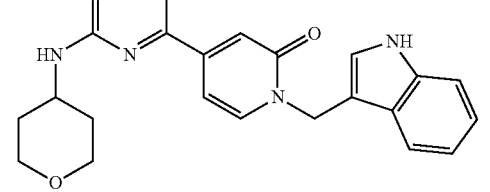 | 1-((1H-indol-3-yl)methyl)-4-(2-((tetrahydro-2H-pyran-4-yl)amino)pyrimidin-4-yl)pyridin-2(1H)-one | 402.3 |
| 233 | 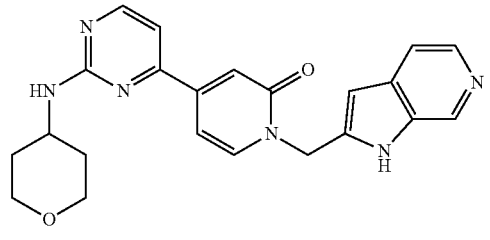 [SMILES: O=c1cc(-c2ccnc(NC3CCOCC3)n2)ccn1Cc1cc2ccncc2[nH]1] | 1-((1H-pyrrolo[2,3-c]pyridin-2-yl)methyl)-4-(2-((tetrahydro-2H-pyran-4-yl)amino)pyrimidin-4-yl)pyridin-2(1H)-one | 403.2 |

TABLE 2-continued

| Ex. # | Structure | Name | MS |
|---|---|---|---|
| 234 | 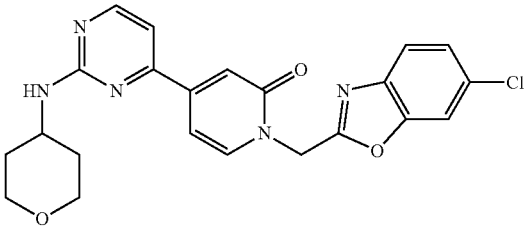 [SMILES: O=c1cc(-c2ccnc(NC3CCOCC3)n2)ccn1Cc1nc2ccc(Cl)cc2o1] | 1-((6-chlorobenzo[d]oxazol-2-yl)methyl)-4-(2-((tetrahydro-2H-pyran-4-yl)amino)pyrimidin-4-yl)pyridin-2(1H)-one | 438.1 |
| 235 | 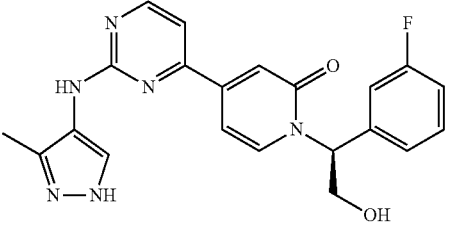 [SMILES: Cc1n[nH]cc1Nc1nccc(-c2ccn([C@H](CO)c3cccc(F)c3)c(=O)c2)n1] | (S)-1-(1-(3-fluorophenyl)-2-hydroxyethyl)-4-(2-((3-methyl-1H-pyrazol-4-yl)amino)pyrimidin-4-yl)pyridin-2(1H)-one | 407.3 |
| 236 | 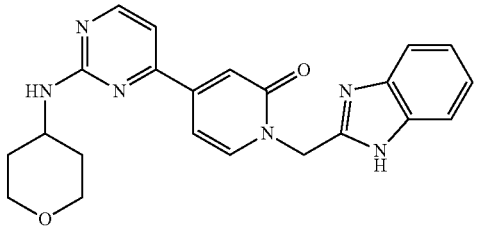 [SMILES: O=c1cc(-c2ccnc(NC3CCOCC3)n2)ccn1Cc1nc2ccccc2[nH]1] | 1-((1H-benzo[d]imidazol-2-yl)methyl)-4-(2-((tetrahydro-2H-pyran-4-yl)amino)pyrimidin-4-yl)pyridin-2(1H)-one | 403.2 |
| 237 | 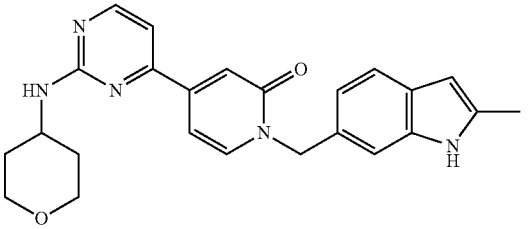 [SMILES: Cc1cc2ccc(Cn3ccc(-c4ccnc(NC5CCOCC5)n4)cc3=O)cc2[nH]1] | 1-((2-methyl-1H-indol-6-yl)methyl)-4-(2-((tetrahydro-2H-pyran-4-yl)amino)pyrimidin-4-yl)pyridin-2(1H)-one | 416.1 |
| 238 | 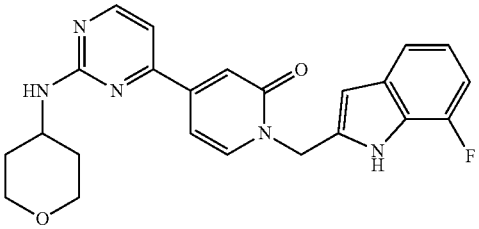 [SMILES: O=c1cc(-c2ccnc(NC3CCOCC3)n2)ccn1Cc1cc2cccc(F)c2[nH]1] | 1-((7-fluoro-1H-indol-2-yl)methyl)-4-(2-((tetrahydro-2H-pyran-4-yl)amino)pyrimidin-4-yl)pyridin-2(1H)-one | 420.1 |
| 239 | 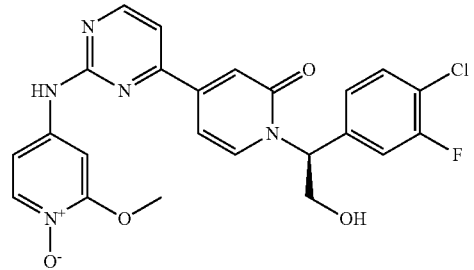 [SMILES: COc1cc(Nc2nccc(-c3ccn([C@H](CO)c4ccc(Cl)c(F)c4)c(=O)c3)n2)cc[n+]1[O-]] | (S)-4-((4-(1-(1-(4-chloro-3-fluorophenyl)-2-hydroxyethyl)-2-oxo-1,2-dihydropyridin-4-yl)pyrimidin-2-yl)amino)-2-methoxypyridine 1-oxide | 484.1 |

TABLE 2-continued

| Ex. # | Structure | Name | MS |
|---|---|---|---|
| 240 | 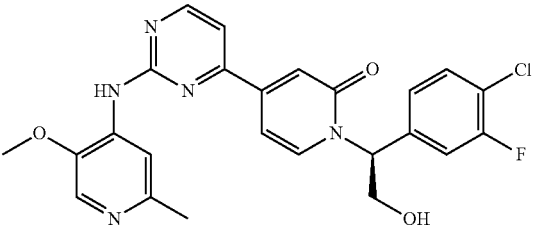 [SMILES: COc1cnc(C)cc1Nc1nccc(-c2ccn([C@H](CO)c3ccc(Cl)c(F)c3)c(=O)c2)n1] | (S)-1-(1-(4-chloro-3-fluorophenyl)-2-hydroxyethyl)-4-(2-((5-methoxy-2-methylpyridin-4-yl)amino)pyrimidin-4-yl)pyridin-2(1H)-one | 482.2 |
| 241 | 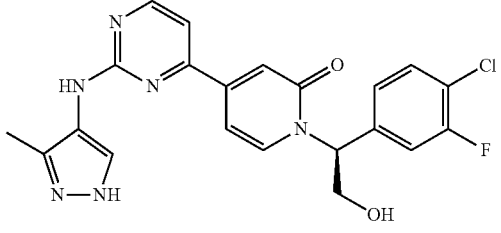 [SMILES: Cc1n[nH]cc1Nc1nccc(-c2ccn([C@H](CO)c3ccc(Cl)c(F)c3)c(=O)c2)n1] | (S)-1-(1-(4-chloro-3-fluorophenyl)-2-hydroxyethyl)-4-(2-((3-methyl-1H-pyrazol-4-yl)amino)pyrimidin-4-yl)pyridin-2(1H)-one | 441.2 |
| 242 | 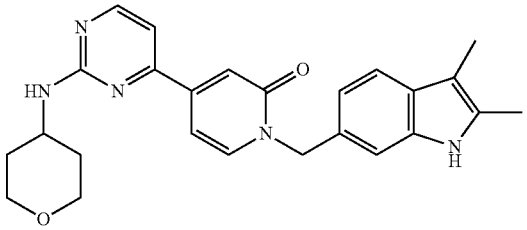 [SMILES: Cc1[nH]c2cc(Cn3ccc(-c4ccnc(NC5CCOCC5)n4)cc3=O)ccc2c1C] | 1-((2,3-dimethyl-1H-indol-6-yl)methyl)-4-(2-((tetrahydro-2H-pyran-4-yl)amino)pyrimidin-4-yl)pyridin-2(1H)-one | 430.1 |
| 243 | 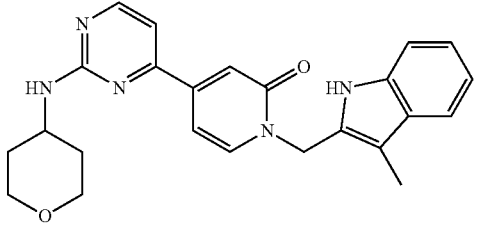 [SMILES: Cc1c(Cn2ccc(-c3ccnc(NC4CCOCC4)n3)cc2=O)[nH]c2ccccc12] | 1-((3-methyl-1H-indol-2-yl)methyl)-4-(2-((tetrahydro-2H-pyran-4-yl)amino)pyrimidin-4-yl)pyridin-2(1H)-one | 416.2 |
| 244 | 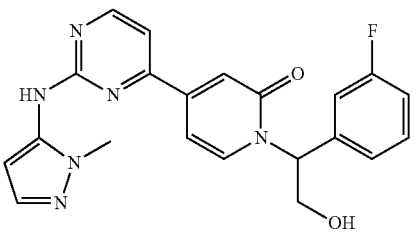 [SMILES: Cn1nccc1Nc1nccc(-c2ccn(C(CO)c3cccc(F)c3)c(=O)c2)n1] | 1-(1-(3-fluorophenyl)-2-hydroxyethyl)-4-(2-((1-methyl-1H-pyrazol-5-yl)amino)pyrimidin-4-yl)pyridin-2(1H)-one | 407.2 |
| 245 | 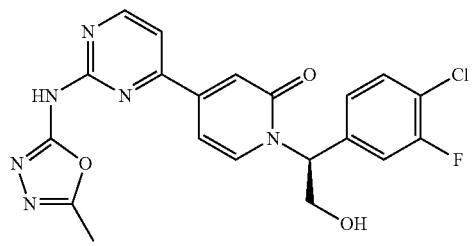 [SMILES: Cc1nnc(Nc2nccc(-c3ccn([C@H](CO)c4ccc(Cl)c(F)c4)c(=O)c3)n2)o1] | (S)-1-(1-(4-chloro-3-fluorophenyl)-2-hydroxyethyl)-4-(2-((5-methyl-1,3,4-oxadiazol-2-yl)amino)pyrimidin-4-yl)pyridin-2(1H)-one | 443.2 |

TABLE 2-continued

| Ex. # | Structure | Name | MS |
|---|---|---|---|
| 246 | 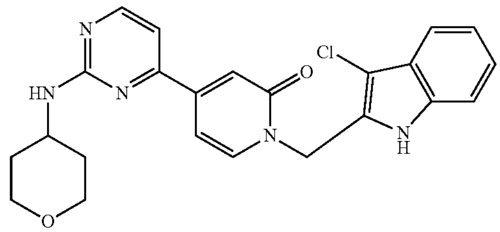 [SMILES: O=c1cc(-c2ccnc(NC3CCOCC3)n2)ccn1Cc1[nH]c2ccccc2c1Cl] | 1-((3-chloro-1H-indol-2-yl)methyl)-4-(2-((tetrahydro-2H-pyran-4-yl)amino)pyrimidin-4-yl)pyridin-2(1H)-one | 436.1 |
| 247 | 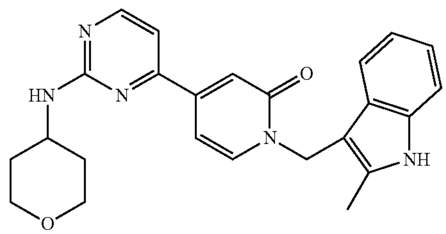 [SMILES: Cc1[nH]c2ccccc2c1Cn1ccc(-c2ccnc(NC3CCOCC3)n2)cc1=O] | 1-((2-methyl-1H-indol-3-yl)methyl)-4-(2-((tetrahydro-2H-pyran-4-yl)amino)pyrimidin-4-yl)pyridin-2(1H)-one | 416.2 |
| 248 | 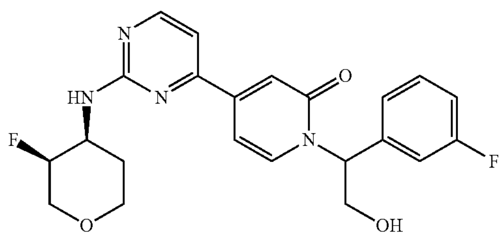 [SMILES: O=c1cc(-c2ccnc(N[C@H]3CCOC[C@H]3F)n2)ccn1C(CO)c1cccc(F)c1] | 1-(1-(3-fluorophenyl)-2-hydroxyethyl)-4-(2-(((3S,4S)-3-fluorotetrahydro-2H-pyran-4-yl)amino)pyrimidin-4-yl)pyridin-2(1H)-one | 429.3 |
| 249 | 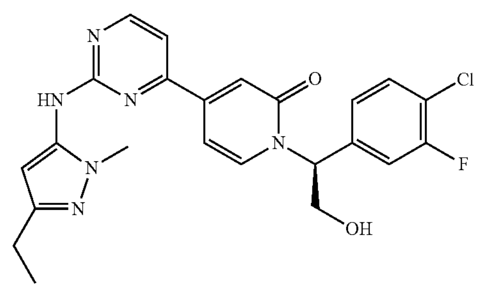 [SMILES: CCc1cc(Nc2nccc(-c3ccn([C@H](CO)c4ccc(Cl)c(F)c4)c(=O)c3)n2)n(C)n1] | (S)-1-(1-(4-chloro-3-fluorophenyl)-2-hydroxyethyl)-4-(2-((3-ethyl-1-methyl-1H-pyrazol-5-yl)amino)pyrimidin-4-yl)pyridin-2(1H)-one | 469.1 |
| 250 | 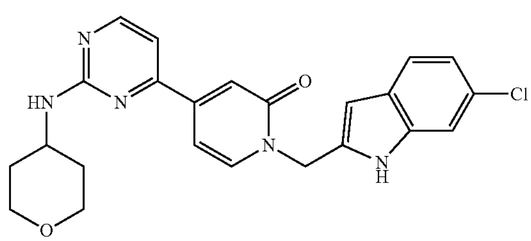 [SMILES: O=c1cc(-c2ccnc(NC3CCOCC3)n2)ccn1Cc1cc2ccc(Cl)cc2[nH]1] | 1-((6-chloro-1H-indol-2-yl)methyl)-4-(2-((tetrahydro-2H-pyran-4-yl)amino)pyrimidin-4-yl)pyridin-2(1H)-one | 436.1 |
| 251 | 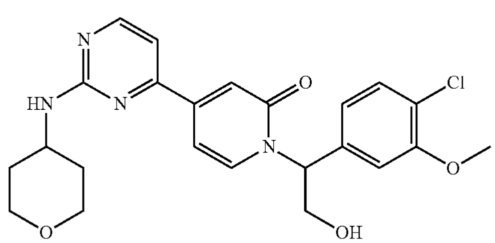 [SMILES: COc1cc(C(CO)n2ccc(-c3ccnc(NC4CCOCC4)n3)cc2=O)ccc1Cl] | 1-(1-(4-chloro-3-methoxyphenyl)-2-hydroxyethyl)-4-(2-((tetrahydro-2H-pyran-4-yl)amino)pyrimidin-4-yl)pyridin-2(1H)-one | 457.1 |

TABLE 2-continued

| Ex. # | Structure | Name | MS |
|---|---|---|---|
| 252 | 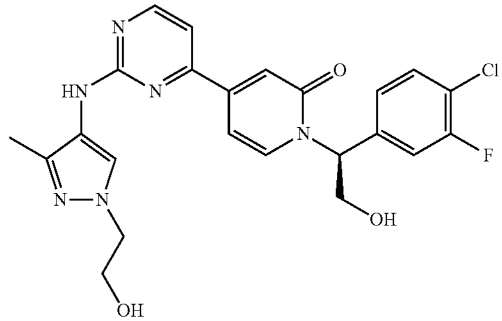 [SMILES: Cc1nn(CCO)cc1Nc1nccc(-c2ccn([C@H](CO)c3ccc(Cl)c(F)c3)c(=O)c2)n1] | (S)-1-(1-(4-chloro-3-fluorophenyl)-2-hydroxyethyl)-4-(2-((1-(2-hydroxyethyl)-3-methyl-1H-pyrazol-4-yl)amino)pyrimidin-4-yl)pyridin-2(1H)-one | 485.2 |
| 253 | 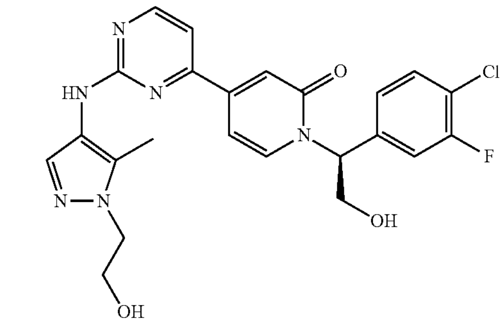 [SMILES: Cc1c(Nc2nccc(-c3ccn([C@H](CO)c4ccc(Cl)c(F)c4)c(=O)c3)n2)cnn1CCO] | (S)-1-(1-(4-chloro-3-fluorophenyl)-2-hydroxyethyl)-4-(2-((1-(2-hydroxyethyl)-5-methyl-1H-pyrazol-4-yl)amino)pyrimidin-4-yl)pyridin-2(1H)-one | 485.3 |
| 254 | 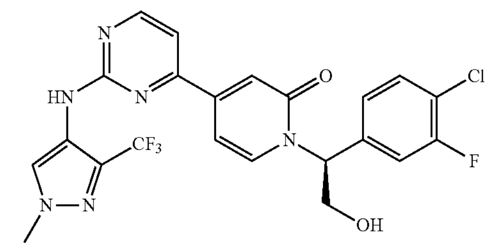 [SMILES: Cn1cc(Nc2nccc(-c3ccn([C@H](CO)c4ccc(Cl)c(F)c4)c(=O)c3)n2)c(C(F)(F)F)n1] | (S)-1-(1-(4-chloro-3-fluorophenyl)-2-hydroxyethyl)-4-(2-((1-methyl-3-(trifluoromelhyl)-1H-pyrazol-4-yl)amino)pyrimidin-4-yl)pyridin-2(1H)-one | 509.1 |
| 255 | 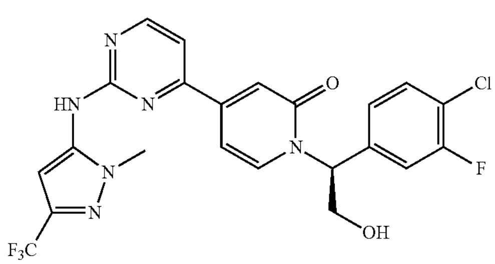 [SMILES: Cn1nc(C(F)(F)F)cc1Nc1nccc(-c2ccn([C@H](CO)c3ccc(Cl)c(F)c3)c(=O)c2)n1] | (S)-1-(1-(4-chloro-3-fluorophenyl)-2 hydroxyethyl)-4-(2-((1-methyl-3-(trifluoromethyl)-1H-pyrazol-5-yl)amino)pyrimidin-4-yl)pyridin-2(1H)-one | 509.1 |
| 256 | 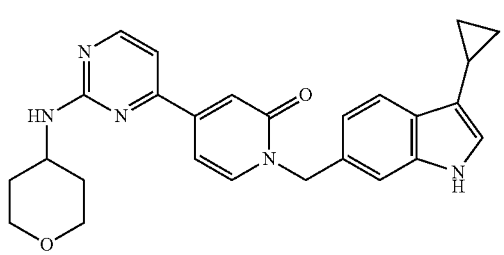 [SMILES: O=c1cc(-c2ccnc(NC3CCOCC3)n2)ccn1Cc1ccc2c(C3CC3)c[nH]c2c1] | 1-((3-cyclopropyl-1H-indol-6-yl)methyl)-4-(2-((tetrahydro-2H-pyran-4-yl)amino)pyrimidin-4-yl)pyridin-2(1H)-one | 442.2 |

TABLE 2-continued

| Ex. # | Structure | Name | MS |
|---|---|---|---|
| 257 | 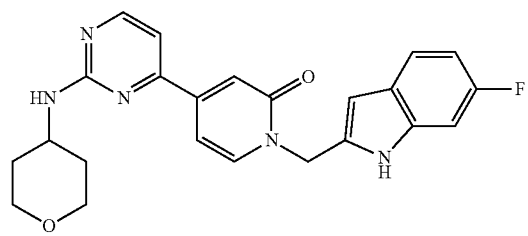 [SMILES: O=c1cc(-c2ccnc(NC3CCOCC3)n2)ccn1Cc1cc2ccc(F)cc2[nH]1] | 1-((6-fluoro-1H-indol-2-yl)methyl)-4-(2-((tetrahydro-2H-pyran-4-yl)amino)pyrimidin-4-yl)pyridin-2(1H)-one | 420.1 |
| 258 | 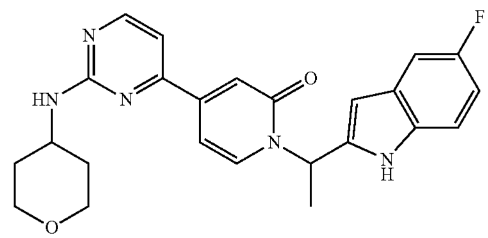 | 1-(1-(5-fluoro-1H-indol-2-yl)ethyl)-4-(2-((tetrahydro-2H-pyran-4-yl)amino)pyrimidin-4-yl)pyridin-2(1H)-one | 434.2 |
| 259 | 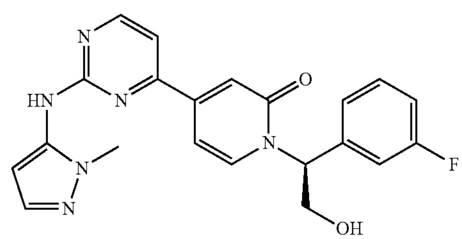 [SMILES: Cn1nccc1Nc1nccc(-c2ccn([C@H](CO)c3cccc(F)c3)c(=O)c2)n1] | (S)-1-(1-(3-fluorophenyl)-2-hydroxyethyl)-4-(2-((1-methyl-1H-pyrazol-5-yl)amino)pyrimidin-4-yl)pyridin-2(1H)-one | 407.1 |
| 260 | 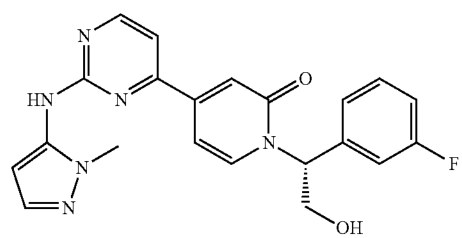 [SMILES: Cn1nccc1Nc1nccc(-c2ccn([C@@H](CO)c3cccc(F)c3)c(=O)c2)n1] | (R)-1-(1-(3-fluorophenyl)-2-hydroxyethyl)-4-(2-((1-methyl-1H-pyrazol-5-yl)amino)pyrimidin-4-yl)pyridin-2(1H)-one | 406 |
| 261 | 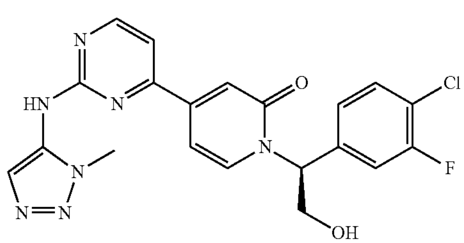 [SMILES: Cn1nncc1Nc1nccc(-c2ccn([C@H](CO)c3ccc(Cl)c(F)c3)c(=O)c2)n1] | (S)-1-(1-(4-chloro-3-fluorophenyl)-2-hydroxyethyl)-4-(2-((1-methyl-1H-1,2,3-triazol-5-yl)amino)pyrimidin-4-yl)pyridin-2(1H)-one | 442.2 |
| 262 | 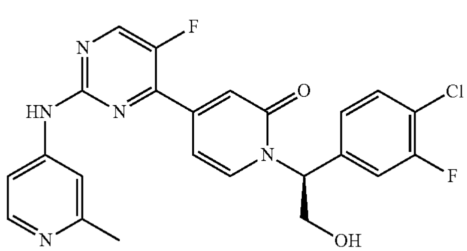 [SMILES: Cc1cc(Nc2ncc(F)c(-c3ccn([C@H](CO)c4ccc(Cl)c(F)c4)c(=O)c3)n2)ccn1] | (S)-1-(1-(4-chloro-3-fluorophenyl)-2-hydroxyethyl)-4-(5-fluoro-2-((2-methylpyridin-4-yl)amino)pyrimidin-4-yl)pyridin-2(1H)-one | 470.2 |

| Ex. # | Structure | Name | MS |
|---|---|---|---|
| 263 | 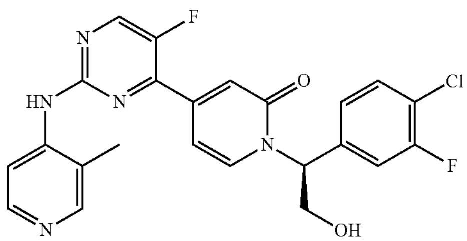 [SMILES: Cc1cnccc1Nc1ncc(F)c(-c2ccn([C@H](CO)c3ccc(Cl)c(F)c3)c(=O)c2)n1] | (S)-1-(1-(4-chloro-3-fluorophenyl)-2-hydroxyethyl)-4-(5-fluoro-2-((3-methylpyridin-4-yl)amino)pyrimidin-4-yl)pyridin-2(1H)-one | 470.1 |
| 264 | 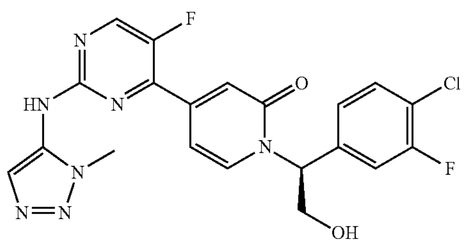 [SMILES: Cn1nncc1Nc1ncc(F)c(-c2ccn([C@H](CO)c3ccc(Cl)c(F)c3)c(=O)c2)n1] | (S)-1-(1-(4-chloro-3-fluorophenyl)-2-hydroxyethyl)-4-(5-fluoro-2-((1-methyl-1H-pyrazol-5-yl)amino)pyrimidin-4-yl)pyridin-2(1H)-one | 459.1 |
| 265 | 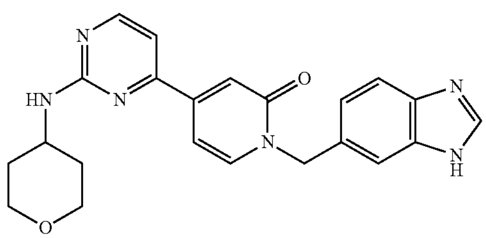 [SMILES: O=c1cc(-c2ccnc(NC3CCOCC3)n2)ccn1Cc1ccc2nc[nH]c2c1] | 1-((1H-benzo[d]imidazol-6-yl)methyl)-4-(2-((tetrahydro-2H-pyran-4-yl)amino)pyrimidin-4-yl)pyridin-2(1H)-one | 403.2 |
| 266 | 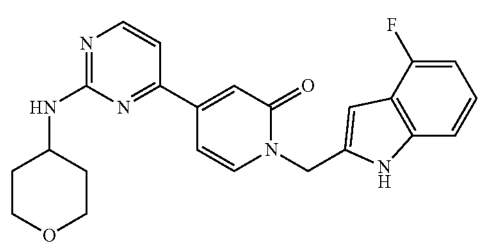 [SMILES: O=c1cc(-c2ccnc(NC3CCOCC3)n2)ccn1Cc1cc2c(F)cccc2[nH]1] | 1-((4-fluoro-1H-indol-2-yl)methyl)-4-(2-((tetrahydro-2H-pyran-4-yl)amino)pyrimidin-4-yl)pyridin-2(1H)-one | 420.1 |
| 267 | 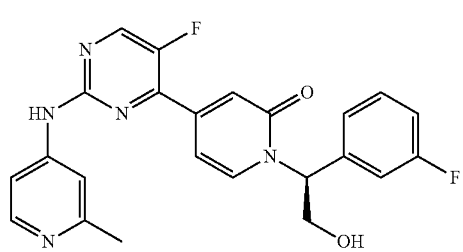 [SMILES: Cc1cc(Nc2ncc(F)c(-c3ccn([C@H](CO)c4cccc(F)c4)c(=O)c3)n2)ccn1] | (S)-4-(5-fluoro-2-((2-methylpyridin-4-yl)amino)pyrimidin-4-yl)-1-(1-(3-fluorophenyl)-2-hydroxyethyl)pyridin-2(1H)-one | 436.2 |
| 268 | 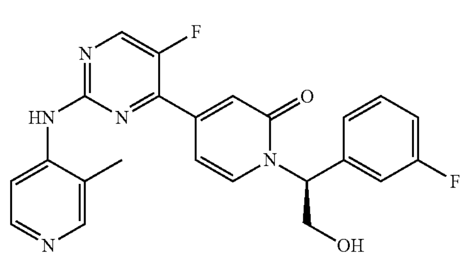 [SMILES: Cc1cnccc1Nc1ncc(F)c(-c2ccn([C@H](CO)c3cccc(F)c3)c(=O)c2)n1] | (S)-4-(5-fluoro-2-((3-methylpyridin-4-yl)amino)pyrimidin-4-yl)-1-(1-(3-fluorophenyl)-2-hydroxyethyl)pyridin-2(1H)-one | 436.2 |

TABLE 2-continued

| Ex. # | Structure | Name | MS |
|---|---|---|---|
| 269 | 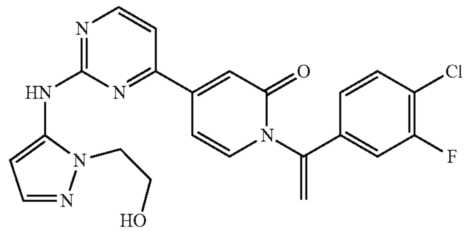 [SMILES: C=C(c1ccc(Cl)c(F)c1)n1ccc(-c2ccnc(Nc3ccnn3CCO)n2)cc1=O] | 1-(1-(4-chloro-3-fluorophenyl)vinyl)-4-(2-((1-(2-hydroxyethyl)-1H-pyrazol-5-yl)amino)pyrimidin-4-yl)pyridin-2(1H)-one | 453.1 |
| 270 | 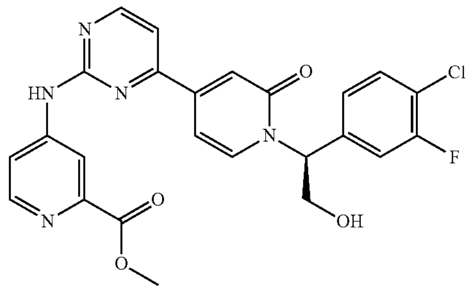 [SMILES: COC(=O)c1cc(Nc2nccc(-c3ccn([C@H](CO)c4ccc(Cl)c(F)c4)c(=O)c3)n2)ccn1] | (S)-methyl 4-((4-(1-(1-(4-chloro-3-fluorophenyl)-2-hydroxyethyl)-2-oxo-1,2-dihydropyridin-4-yl)pyrimidin-2-yl)amino)picolinate | 496.1 |
| 271 | 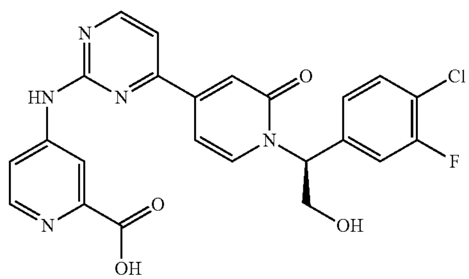 [SMILES: O=C(O)c1cc(Nc2nccc(-c3ccn([C@H](CO)c4ccc(Cl)c(F)c4)c(=O)c3)n2)ccn1] | (S)-4-((4-(1-(1-(4-chloro-3-fluorophenyl)-2-hydroxyethyl)-2-oxo-1,2-dihydropyridin-4-yl)pyrimidin-2-yl)amino)picolinic acid | 482.1 |
| 272 | 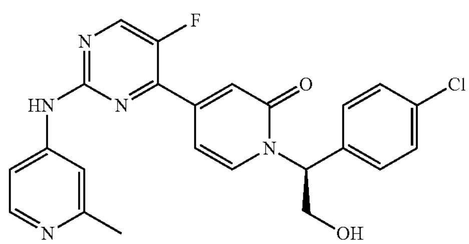 [SMILES: Cc1cc(Nc2ncc(F)c(-c3ccn([C@H](CO)c4ccc(Cl)cc4)c(=O)c3)n2)ccn1] | (S)-1-(1-(4-chlorophenyl)-2-hydroxyethyl)-4-(5-fluoro-2-((2-methylpyridin-4-yl)amino)pyrimidin-4-yl)pyridin-2(1H)-one | 445.1 |
| 273 | 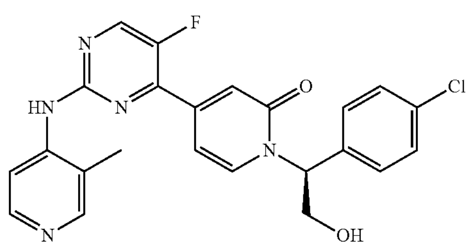 [SMILES: Cc1cnccc1Nc1ncc(F)c(-c2ccn([C@H](CO)c3ccc(Cl)cc3)c(=O)c2)n1] | (S)-1-(1-(4-chlorophenyl)-2-hydroxyethyl)-4-(5-fluoro-2-((3-methylpyridin-4-yl)amino)pyrimidin-4-yl)pyridin-2(1H)-one | 452.1 |
| 274 | 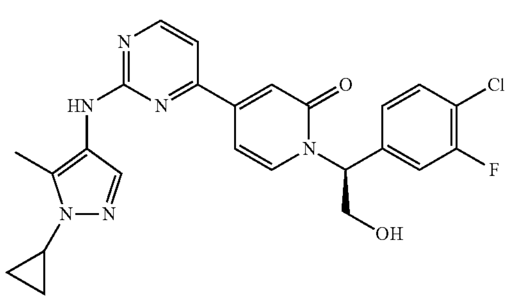 [SMILES: Cc1c(Nc2nccc(-c3ccn([C@H](CO)c4ccc(Cl)c(F)c4)c(=O)c3)n2)cnn1C1CC1] | (S)-1-(1-(4-chloro-3-fluorophenyl)-2-hydroxyethyl)-4-(2-((1-cyclopropyl-5-methyl-1H-pyrazol-4-yl)amino)pyrimidin-4-yl)pyridin-2(1H)-one | 481.1 |

TABLE 2-continued

| Ex. # | Structure | Name | MS |
|---|---|---|---|
| 275 | 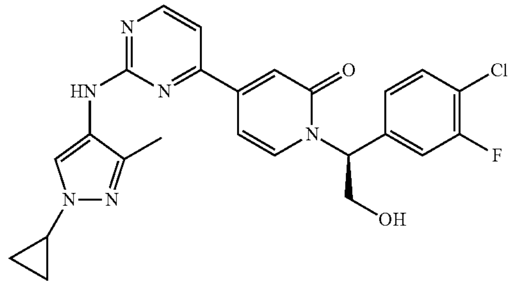 [SMILES: Cc1nn(C2CC2)cc1Nc1nccc(-c2ccn([C@H](CO)c3ccc(Cl)c(F)c3)c(=O)c2)n1] | (S)-1-(1-(4-chloro-3-fluorophenyl)-2-hydroxyethyl)-4-(2-((1-cyclopropyl-3-methyl-1H-pyrazol-4-yl)amino)pyrimidin-4-yl)pyridin-2(1H)-one | 481.1 |
| 276 | 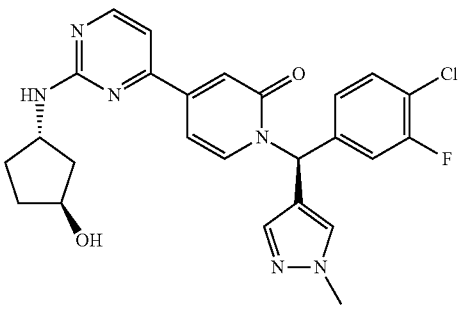 [SMILES: Cn1cc([C@H](c2ccc(Cl)c(F)c2)n2ccc(-c3ccnc(N[C@H]4CC[C@H](O)C4)n3)cc2=O)cn1] | 1-((S)-(4-chloro-3-fluorophenyl)(1-methyl-1H-pyrazol-4-yl)methyl)-4-(2-(((1S,3S)-3-hydroxycyclopentyl)amino)pyrimidin-4-yl)pyridin-2(1H)-one | 495.1 |
| 277 | 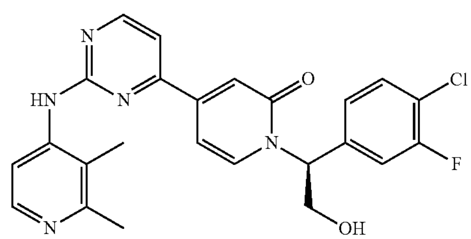 [SMILES: Cc1nccc(Nc2nccc(-c3ccn([C@H](CO)c4ccc(Cl)c(F)c4)c(=O)c3)n2)c1C] | (S)-1-(1-(4-chloro-3-fluorophenyl)-2-hydroxyethyl)-4-(2-((2,3-dimethylpyridin-4-yl)amino)pyrimidin-4-yl)pyridin-2(1H)-one | 466.1 |
| 278 | 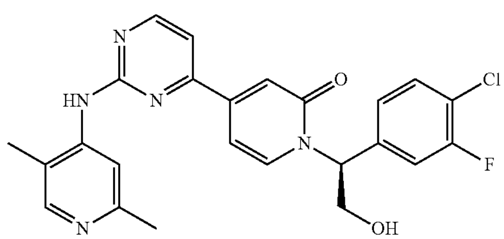 [SMILES: Cc1cc(Nc2nccc(-c3ccn([C@H](CO)c4ccc(Cl)c(F)c4)c(=O)c3)n2)c(C)cn1] | (S)-1-(1-(4-chloro-3-fluorophenyl)-2-hydroxyethyl)-4-(2-((2,5-dimethylpyridin-4-yl)amino)pyrimidin-4-yl)pyridin-2(1H)-one | 466.1 |
| 279 | 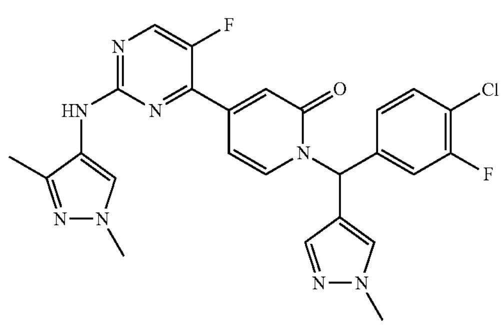 [SMILES: Cc1nn(C)cc1Nc1ncc(F)c(-c2ccn(C(c3ccc(Cl)c(F)c3)c3cnn(C)c3)c(=O)c2)n1] | 1-((4-chloro-3-fluorophenyl)(1-methyl-1H-pyrazol-4-yl)methyl)-4-(2-((1,3-dimethyl-1H-pyrazol-4-yl)amino)-5-fluoropyrimidin-4-yl)pyridin-2(1H)-one | 505.2 |

TABLE 2-continued

| Ex. # | Structure | Name | MS |
|---|---|---|---|
| 280 | 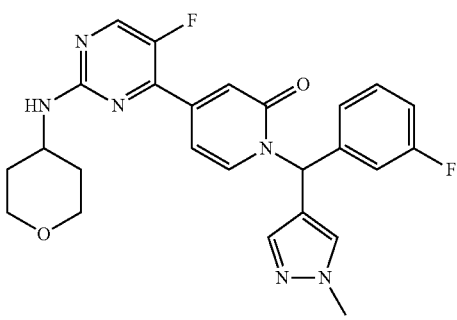 [SMILES: Cn1cc(C(c2cccc(F)c2)n2ccc(-c3nc(NC4CCOCC4)ncc3F)cc2=O)cn1] | 4-(5-fluoro-2-((tetrahydro-2H-pyran-4-yl)amino)pyrimidin-4-yl)-1-((3-fluorophenyl)(1-methyl-1H-pyrazol-4-yl)methyl)pyridin-2(1H)-one | 513.1 |
| 281 | 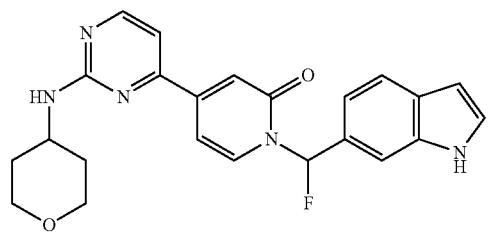 | 1-((7-fluoro-1H-indol-6-yl)methyl)-4-(2-((tetrahydro-2H-pyran-4-yl)amino)pyrimidin-4-yl)pyridin-2(1H)-one | 420.1 |
| 282 | 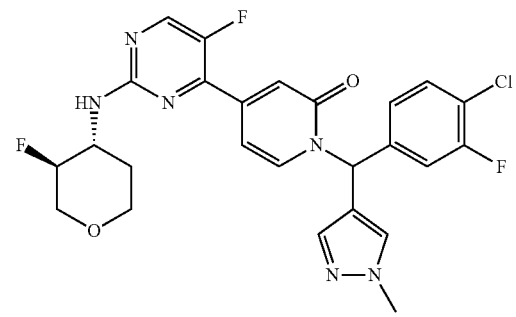 [SMILES: Cn1cc(C(c2ccc(Cl)c(F)c2)n2ccc(-c3nc(N[C@@H]4CCOC[C@H]4F)ncc3F)cc2=O)cn1] | 1-((4-chloro-3-fluorophenyl)(1-methyl-1H-pyrazol-4-yl)methyl)-4-(5-fluoro-2-(((3S,4R)-3-fluorotetrahydro-2H-pyran-4-yl)amino)pyrimidin-4-yl)pyridin-2(1H)-one | |
| 283 | 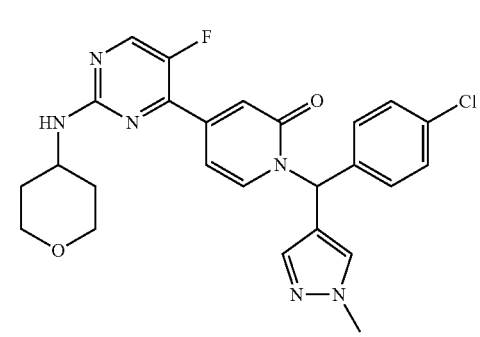 [SMILES: Cn1cc(C(c2ccc(Cl)cc2)n2ccc(-c3nc(NC4CCOCC4)ncc3F)cc2=O)cn1] | 1-((4-chlorophenyl)(1-methyl-1H-pyrazol-4-yl)methyl)-4-(5-fluoro-2-((tetrahydro-2H-pyran-4-yl)amino)pyrimidin-4-yl)pyridin-2(1H)-one | |
| 284 | 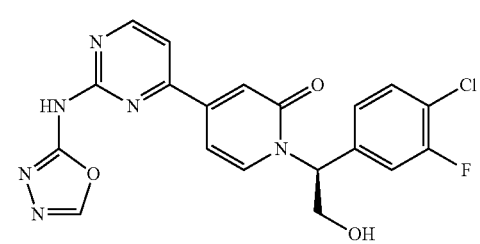 [SMILES: O=c1cc(-c2ccnc(Nc3nnco3)n2)ccn1[C@H](CO)c1ccc(Cl)c(F)c1] | (S)-4-(2-((1,3,4-oxadiazol-2-yl)amino)pyrimidin-4-yl)-1-(1-(4-chloro-3-fluorophenyl)-2-hydroxyethyl)pyridin-2(1H)-one | 429.1 |

TABLE 2-continued

| Ex. # | Structure | Name | MS |
|---|---|---|---|
| 285 | 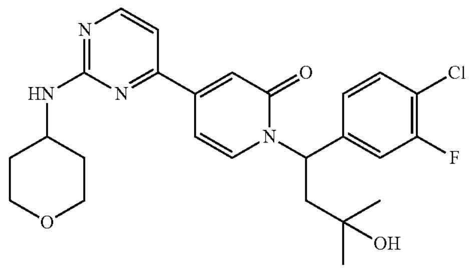 [SMILES: CC(C)(O)CC(c1ccc(Cl)c(F)c1)n1ccc(-c2ccnc(NC3CCOCC3)n2)cc1=O] | 1-(1-(4-chloro-3-fluorophenyl)-3-hydroxy-3-methylbutyl)-4-(2-((tetrahydro-2H-pyran-4-yl)amino)pyrimidin-4-yl)pyridin-2(1H)-one | 487.2 |
| 286 | 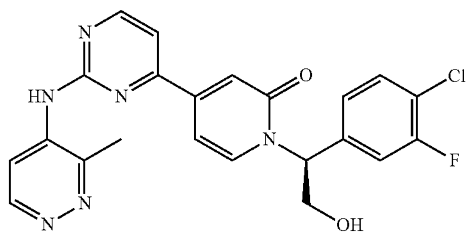 [SMILES: Cc1nnccc1Nc1nccc(-c2ccn([C@H](CO)c3ccc(Cl)c(F)c3)c(=O)c2)n1] | (S)-1-(1-(4-chloro-3-fluorophenyl)-2-hydroxyethyl)-4-(2-((3-methylpyridazin-4-yl)amino)pyrimidin-4-yl)pyridin-2(1H)-one | 453.1 |
| 287 | 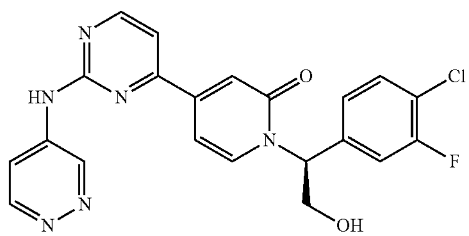 [SMILES: O=c1cc(-c2ccnc(Nc3ccnnc3)n2)ccn1[C@H](CO)c1ccc(Cl)c(F)c1] | (S)-1-(1-(4-chloro-3-fluorophenyl)-2-hydroxyethyl)-4-(2-(pyridazin-4-ylamino)pyrimidin-4-yl)pyridin-2(1H)-one | 439.0 |
| 288 | 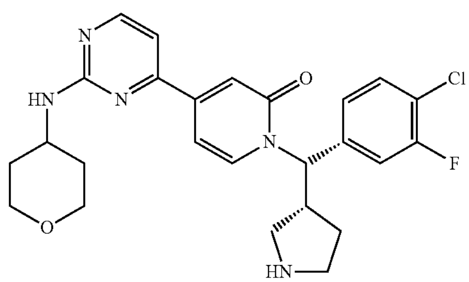 | 1-((S)-(4-chloro-3-fluorophenyl)((R)-pyrrolidin-3-yl)methyl)-4-(2-((tetrahydro-2H-pyran-4-yl)amino)pyrimidin-4-yl)pyridin-2(1H)-one | m/z (APCI-M + 1 = 484.2, 486.1 |
| 289 | 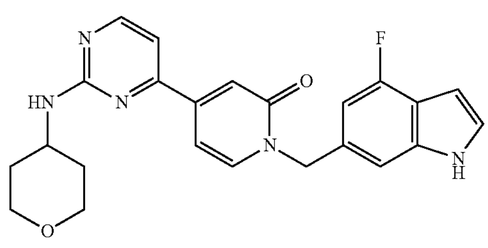 [SMILES: O=c1cc(-c2ccnc(NC3CCOCC3)n2)ccn1Cc1cc(F)c2cc[nH]c2c1] | 1-((4-fluoro-1H-indol-6-yl)methyl)-4-(2-((tetrahydro-2H-pyran-4-yl)amino)pyrimidin-4-yl)pyridin-2(1H)-one | 420.0 |
| 290 | 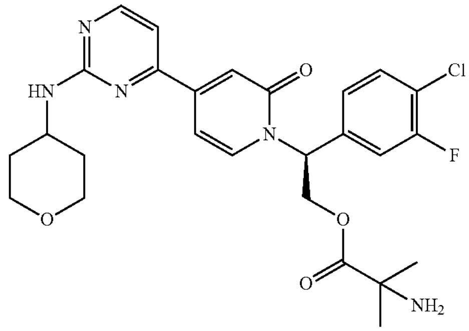 [SMILES: CC(C)(N)C(=O)OC[C@H](c1ccc(Cl)c(F)c1)n1ccc(-c2ccnc(NC3CCOCC3)n2)cc1=O] | (S)-2-(4-chloro-3-fluorophenyl)-2-(2-oxo-4-(2-((tetrahydro-2H-pyran-4-yl)amino)pyrimidin-4-yl)pyridin-1(2H)-yl)ethyl 2-amino-2-methylpropanoate | 530.2 |

TABLE 2-continued

| Ex. # | Structure | Name | MS |
|---|---|---|---|
| 291 | 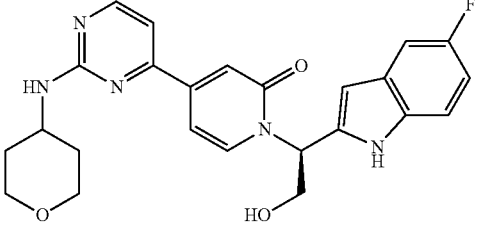 | (S)-1-(1-(5-fluoro-1H-indol-2-yl)-2-hydroxyethyl)-4-(2-((tetrahydro-2H-pyran-4-yl)amino)pyrimidin-4-yl)pyridin-2(1H)-one | 450.2 |
| 292 | 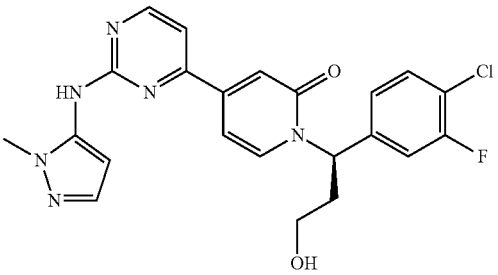 [SMILES: Cn1nccc1Nc1nccc(-c2ccn([C@H](CCO)c3ccc(Cl)c(F)c3)c(=O)c2)n1] | (R)-1-(1-(4-chloro-3-fluorophenyl)-3-hydroxypropyl)-4-(2-((1-methyl-1H-pyrazol-5-yl)amino)pyrimidin-4-yl)pyridin-2(1H)-one | 455.1 |
| 293 | 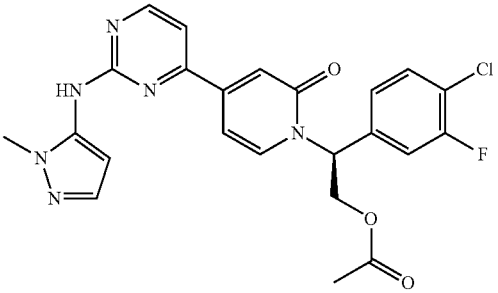 [SMILES: CC(=O)OC[C@H](c1ccc(Cl)c(F)c1)n1ccc(-c2ccnc(Nc3ccnn3C)n2)cc1=O] | (S)-2-(4-chloro-3-fluorophenyl)-2-(4-(2-((1-methyl-1H-pyrazol-5-yl)amino)pyrimidin-4-yl)-2-oxopyridin-1(2H)-yl)ethyl acetate | 483.1 |
| 294 | 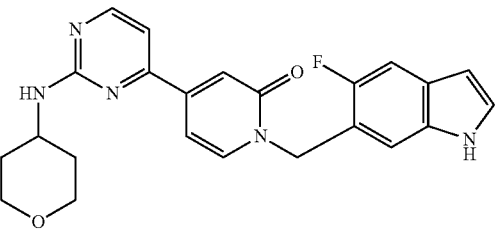 [SMILES: O=c1cc(-c2ccnc(NC3CCOCC3)n2)ccn1Cc1cc2[nH]ccc2cc1F] | 1-((5-fluoro-1H-indol-6-yl)methyl)-4-(2-((tetrahydro-2H-pyran-4-yl)amino)pyrimidin-4-yl)pyridin-2(1H)-one | 420.3 |
| 295 | 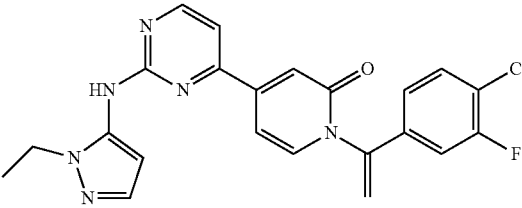 | 1-(1-(4-chloro-3-fluorophenyl)vinyl)-4-(2-((1-ethyl-1H-pyrazol-5-yl)amino)pyrimidin-4-yl)pyridin-2(1H)-one | 437.1 |
| 296 | 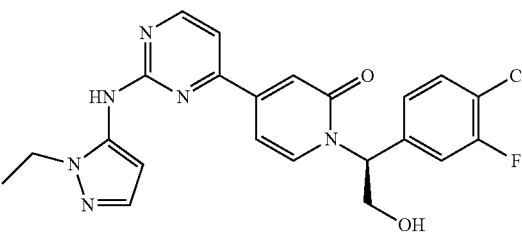 | (S)-1-(1-(4-chloro-3-fluorophenyl)-2-hydroxyethyl)-4-(2-((1-ethyl-1H-pyrazol-5-yl)amino)pyrimidin-4-yl)pyridin-2(1H)-one | 455.1 |

TABLE 2-continued

| Ex. # | Structure | Name | MS |
|---|---|---|---|
| 297 | 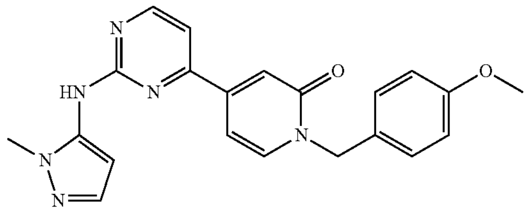 | 1-(4-methoxybenzyl)-4-(2-((1-methyl-1H-pyrazol-5-yl)amino)pyrimidin-4-yl)pyridin-2(1H)-one | 389.2 |
| 298 | 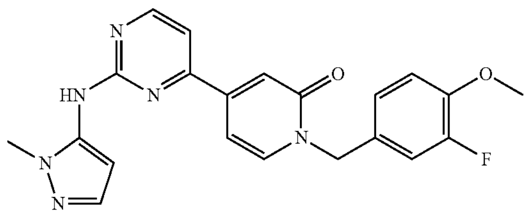 | 1-(3-fluoro-4-methoxybenzyl)-4-(2-((1-methyl-1H-pyrazol-5-yl)amino)pyrimidin-4-yl)pyridin-2(1H)-one | 407.2 |
| 299 | 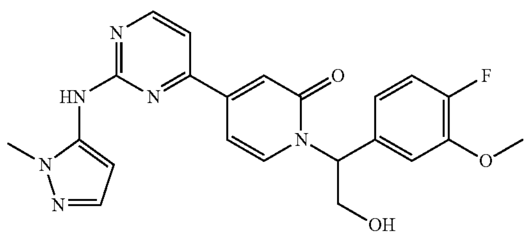 | 1-(1-(4-fluoro-3-methoxyphenyl)-2-hydroxyethyl)-4-(2-((1-methyl-1H-pyrazol-5-yl)amino)pyrimidin-4-yl)pyridin-2(1H)-one | 437.3 |
| 300 | 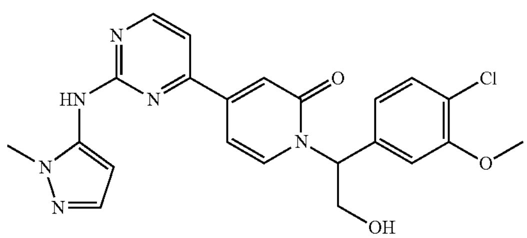 | 1-(1-(4-chloro-3-methoxyphenyl)-2-hydroxyethyl)-4-(2-((1-methyl-1H-pyrazol-5-yl)amino)pyrimidin-4-yl)pyridin-2(1H)-one | 453.3 |
| 301 | 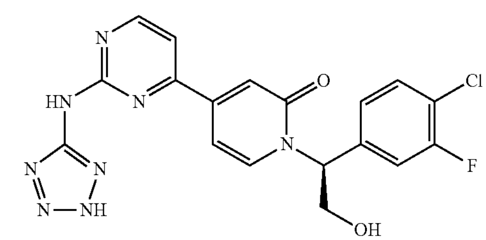 [SMILES: O=c1cc(-c2ccnc(Nc3nn[nH]n3)n2)ccn1[C@H](CO)c1ccc(Cl)c(F)c1] | (S)-4-(2-((2H-tetrazol-5-yl)amino)pyrimidin-4-yl)-1-(1-(4-chloro-3-fluorophenyl)-2-hydroxyethyl)pyridin-2(1H)-one | 429.2 |
| 302 | 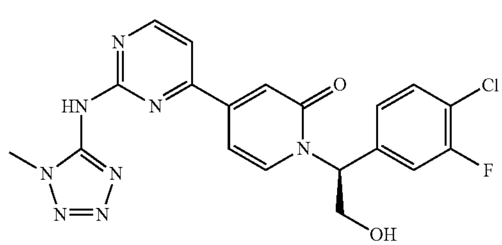 [SMILES: Cn1nnnc1Nc1nccc(-c2ccn([C@H](CO)c3ccc(Cl)c(F)c3)c(=O)c2)n1] | (S)-1-(1-(4-chloro-3-fluorophenyl)-2-hydroxyethyl)-4-(2-((1-methyl-1H-tetrazol-5-yl)amino)pyrimidin-4-yl)pyridin-2(1H)-one | 443.1 |

TABLE 2-continued

| Ex. # | Structure | Name | MS |
|---|---|---|---|
| 303 | 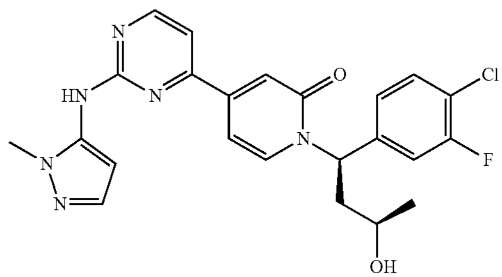 [SMILES: C[C@@H](O)C[C@H](c1ccc(Cl)c(F)c1)n1ccc(-c2ccnc(Nc3ccnn3C)n2)cc1=O] | 1-((1R,3R)-1-(4-chloro-3-fluorophenyl)-3-hydroxybutyl)-4-(2-((1-methyl-1H-pyrazol-5-yl)amino)pyrimidin-4-yl)pyridin-2(1H)-one | 469.3 |
| 304 | 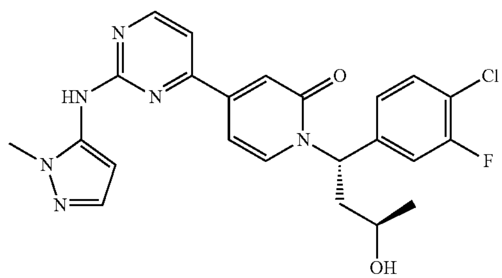 [SMILES: C[C@@H](O)C[C@@H](c1ccc(Cl)c(F)c1)n1ccc(-c2ccnc(Nc3ccnn3C)n2)cc1=O] | 1-((1S,3R)-1-(4-chloro-3-fluorophenyl)-3-hydroxybutyl)-4-(2-((1-methyl-1H-pyrazol-5-yl)amino)pyrimidin-4-yl)pyridin-2(1H)-one | 469.3 |
| 305 | 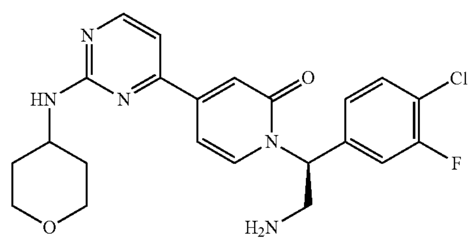 [SMILES: NC[C@H](c1ccc(Cl)c(F)c1)n1ccc(-c2ccnc(NC3CCOCC3)n2)cc1=O] | (S)-1-(2-amino-1-(4-chloro-3-fluorophenyl)ethyl)-4-(2-((tetrahydro-2H-pyran-4-yl)amino)pyrimidin-4-yl)pyridin-2(1H)-one | 444.2 |
| 306 | 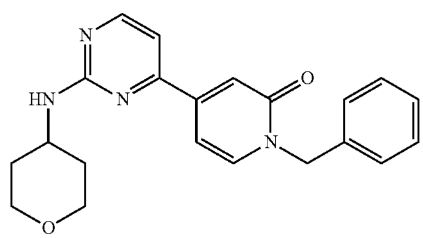 [SMILES: O=c1cc(-c2ccnc(NC3CCOCC3)n2)ccn1Cc1ccccc1] | 1-benzyl-4-(2-((tetrahydro-2H-pyran-4-yl)amino)pyrimidin-4-yl)pyridin-2(1H)-one | 363.2 |
| 307 | 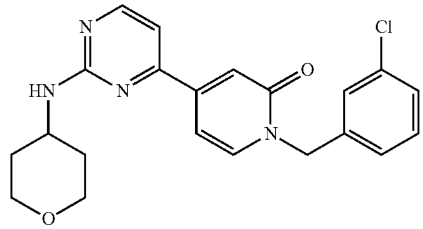 [SMILES: O=c1cc(-c2ccnc(NC3CCOCC3)n2)ccn1Cc1cccc(Cl)c1] | 1-(3-chlorobenzyl)-4-(2-((tetrahydro-2H-pyran-4-yl)amino)pyrimidin-4-yl)pyridin-2(1H)-one | 397.2 |
| 308 | 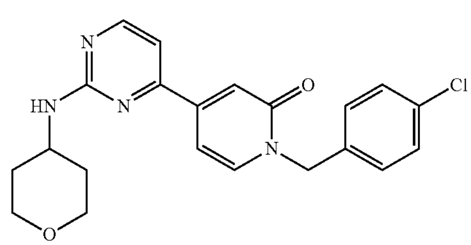 [SMILES: O=c1cc(-c2ccnc(NC3CCOCC3)n2)ccn1Cc1ccc(Cl)cc1] | 1-(4-chlorobenzyl)-4-(2-((tetrahydro-2H-pyran-4-yl)amino)pyrimidin-4-yl)pyridin-2(1H)-one | 397.2 |

US 9,708,290 B2

TABLE 2-continued

| Ex. # | Structure | Name | MS |
|---|---|---|---|
| 309 | 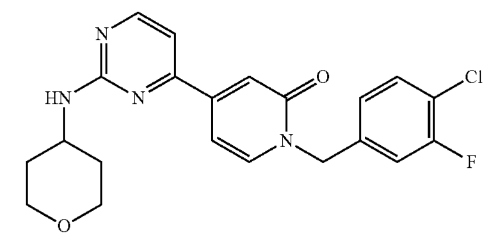 [SMILES: O=c1cc(-c2ccnc(NC3CCOCC3)n2)ccn1Cc1ccc(Cl)c(F)c1] | 1-(4-chloro-3-fluorobenzyl)-4-(2-((tetrahydro-2H-pyran-4-yl)amino)pyrimidin-4-yl)pyridin-2(1H)-one | 415.2 |
| 310 | 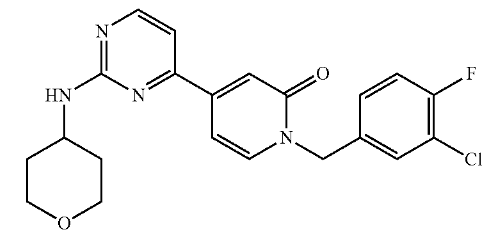 [SMILES: O=c1cc(-c2ccnc(NC3CCOCC3)n2)ccn1Cc1ccc(F)c(Cl)c1] | 1-(3-chloro-4-fluorobenzyl)-4-(2-((tetrahydro-2H-pyran-4-yl)amino)pyrimidin-4-yl)pyridin-2(1H)-one | 415.2 |
| 311 | 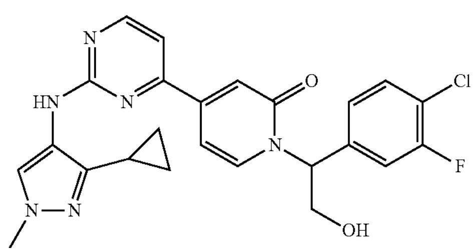 [SMILES: Cn1cc(Nc2nccc(-c3ccn(C(CO)c4ccc(Cl)c(F)c4)c(=O)c3)n2)c(C2CC2)n1] | 1-(1-(4-chloro-3-fluorophenyl)-2-hydroxyethyl)-4-(2-((3-cyclopropyl-1-methyl-1H-pyrazol-4-yl)amino)pyrimidin-4-yl)pyridin-2(1H)-one | 481.1 |
| 312 | 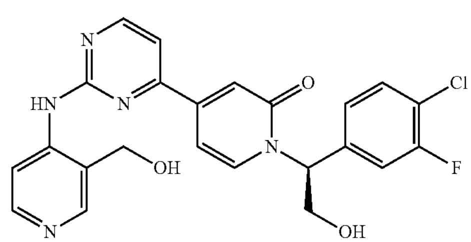 [SMILES: O=c1cc(-c2ccnc(Nc3ccncc3CO)n2)ccn1[C@H](CO)c1ccc(Cl)c(F)c1] | (S)-1-(1-(4-chloro-3-fluorophenyl)-2-hydroxyethyl)-4-(2-((3-(hydroxymethyl)pyridin-4-yl)amino)pyrimidin-4-yl)pyridin-2(1H)-one | 468.1 |
| 313 | 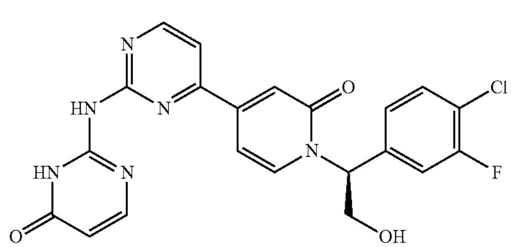 [SMILES: O=c1ccnc(Nc2nccc(-c3ccn([C@H](CO)c4ccc(Cl)c(F)c4)c(=O)c3)n2)[nH]1] | (S)-2-((4-(1-(1-(4-chloro-3-fluorophenyl)-2-hydroxyethyl)-2-oxo-1,2-dihydropyridin-4-yl)pyrimidin-2-yl)amino)pyrimidin-4(3H)-one | 455 |
| 314 | 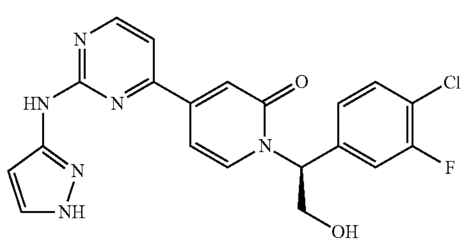 [SMILES: O=c1cc(-c2ccnc(Nc3cc[nH]n3)n2)ccn1[C@H](CO)c1ccc(Cl)c(F)c1] | (S)-4-(2-((1H-pyrazol-3-yl)amino)pyrimidin-4-yl)-1-(1-(4-chloro-3-fluorophenyl)-2-hydroxyethyl)pyridin-2(1H)-one | 427.1 |

TABLE 2-continued

| Ex. # | Structure | Name | MS |
|---|---|---|---|
| 315 | 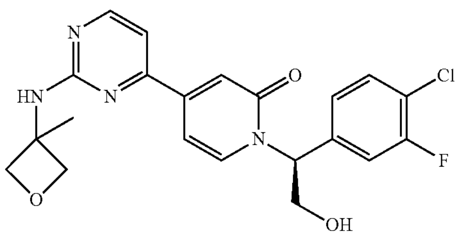 [SMILES: CC1(Nc2nccc(-c3ccn([C@H](CO)c4ccc(Cl)c(F)c4)c(=O)c3)n2)COC1] | (S)-1-(1-(4-chloro-3-fluorophenyl)-2-hydroxyethyl)-4-(2-((3-methyloxetan-3-yl)amino)pyrimidin-4-yl)pyridin-2(1H)-one | 431.1 |
| 316 | 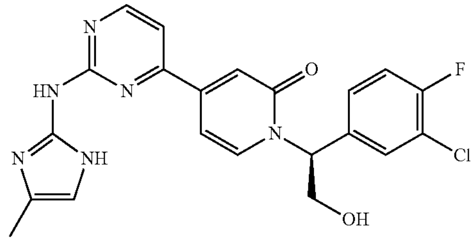 [SMILES: Cc1c[nH]c(Nc2nccc(-c3ccn([C@H](CO)c4ccc(F)c(Cl)c4)c(=O)c3)n2)n1] | (S)-1-(1-(3-chloro-4-fluorophenyl)-2-hydroxyethyl)-4-(2-((4-methyl-1H-imidazol-2-yl)amino)pyrimidin-4-yl)pyridin-2(1H)-one | 441.1 |
| 317 | 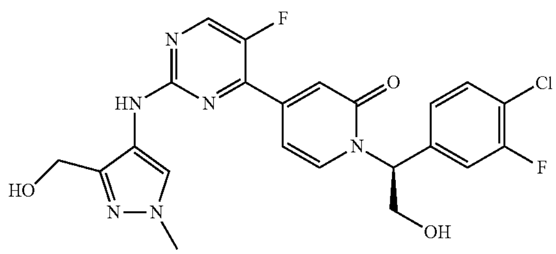 [SMILES: Cn1cc(Nc2ncc(F)c(-c3ccn([C@H](CO)c4ccc(Cl)c(F)c4)c(=O)c3)n2)c(CO)n1] | (S)-1-(1-(4-chloro-3-fluorophenyl)-2-hydroxyethyl)-4-(2-((3-(hydroxymethyl)-1-methyl-1H-pyrazol-4-yl)amino)pyrimidin-4-yl)pyridin-2(1H)-one | 471.1 |
| 318 | 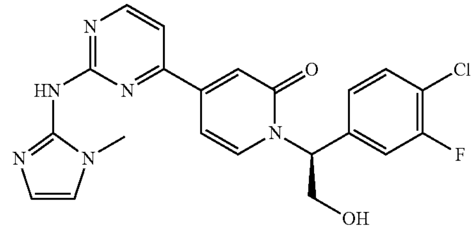 [SMILES: Cn1ccnc1Nc1nccc(-c2ccn([C@H](CO)c3ccc(Cl)c(F)c3)c(=O)c2)n1] | (S)-1-(1-(4-chloro-3-fluorophenyl)-2-hydroxyethyl)-4-(2-((1-methyl-1H-imidazol-2-yl)amino)pyrimidin-4-yl)pyridin-2(1H)-one | 441.1 |
| 319 | 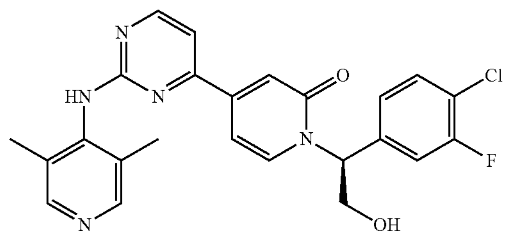 [SMILES: Cc1cncc(C)c1Nc1nccc(-c2ccn([C@H](CO)c3ccc(Cl)c(F)c3)c(=O)c2)n1] | (S)-1-(1-(4-chloro-3-fluorophenyl)-2-hydroxyethyl)-4-(2-((3,5-dimethylpyridin-4-yl)amino)pyrimidin-4-yl)pyridin-2(1H)-one | 466.1 |
| 320 | 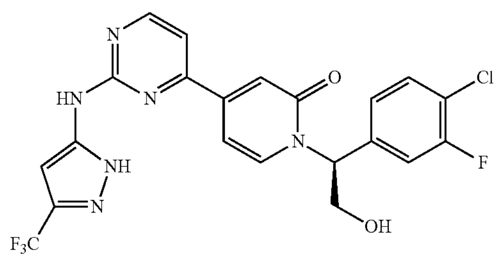 [SMILES: O=c1cc(-c2ccnc(Nc3cc(C(F)(F)F)n[nH]3)n2)ccn1[C@H](CO)c1ccc(Cl)c(F)c1] | (S)-1-(1-(4-chloro-3-fluorophenyl)-2-hydroxyethyl)-4-(2-((3-(trifluoromethyl)-1H-pyrazol-5-yl)amino)pyrimidin-4-yl)pyridin-2(1H)-one | 495.1 |

TABLE 2-continued

| Ex. # | Structure | Name | MS |
|---|---|---|---|
| 321 | 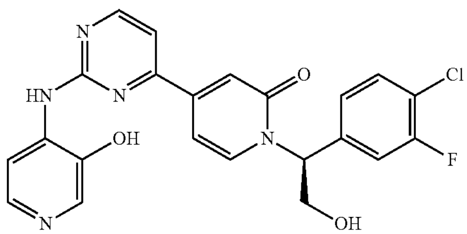 [SMILES: O=c1cc(-c2ccnc(Nc3ccncc3O)n2)ccn1[C@H](CO)c1ccc(Cl)c(F)c1] | (S)-1-(1-(4-chloro-3-fluorophenyl)-2-hydroxyethyl)-4-(2-((3-hydroxypyridin-4-yl)amino)pyrimidin-4-yl)pyridin-2(1H)-one | 454.1 |
| 322 | 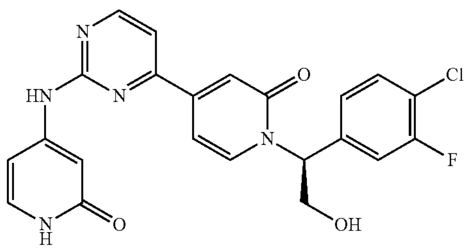 [SMILES: O=c1cc(Nc2nccc(-c3ccn([C@H](CO)c4ccc(Cl)c(F)c4)c(=O)c3)n2)cc[nH]1] | (S)-1-(1-(4-chloro-3-fluorophenyl)-2-hydroxyethyl)-4-(2-((2-oxo-1,2-dihydropyridin-4-yl)amino)pyrimidin-4-yl)pyridin-2(1H)-one | 454.1 |
| 323 | 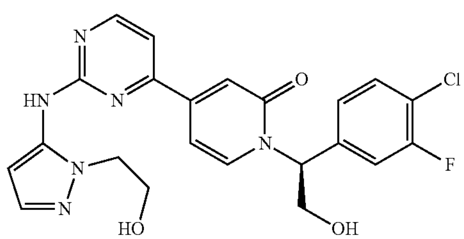 [SMILES: O=c1cc(-c2ccnc(Nc3ccnn3CCO)n2)ccn1[C@H](CO)c1ccc(Cl)c(F)c1] | (S)-1-(1-(4-chloro-3-fluorophenyl)-2-hydroxyethyl)-4-(2-((1-(2-hydroxyethyl)-1H-pyrazol-5-yl)amino)pyrimidin-4-yl)pyridin-2(1H)-one | 471.1 |

Example α

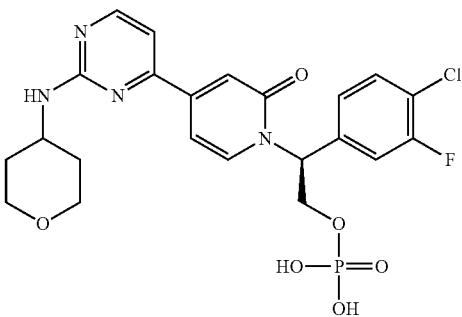 [SMILES: O=c1cc(-c2ccnc(NC3CCOCC3)n2)ccn1[C@H](COP(=O)(O)O)c1ccc(Cl)c(F)c1]

(S)-2-(4-chloro-3-fluorophenyl)-2-(2-oxo-4-(2-((tetrahydro-2H-pyran-4-yl)amino)pyrimidin-4-yl)pyridin-1(2H)-yl)ethyl dihydrogen phosphate Step A: 1-[(1S)-1-(4-Chloro-3-fluoro-phenyl)-2-hydroxyethyl]-4-[2-(tetrahydropyran-4-ylamino)pyrimidin-4-yl]pyridin-2-one (0.62 g, 1.39 mmol) was transferred to a dry 100 mL round bottom flask in THF (50 mL). Cesium carbonate (2.26 g, 6.93 mmol) was added. The mixture was stirred at room temperature for 20 minutes before adding dibenzylphosphoryl chloride (0.91 g, 3.05 mmol) in toluene. The mixture was left to stir overnight at room temperature. The mixture was diluted with ethyl acetate and washed with water (2×30 mL), saturated sodium bicarbonate (2×30 mL) and brine (2×30 mL), and then dried over sodium sulfate. The solvent was removed to leave an oil. The oil was purified by CombiFlash (24 g column; 0-5% methanol/DCM over 15 minutes). LCMS confirmed product to be (S)-dibenzyl (2-(4-chloro-3-fluorophenyl)-2-(2-oxo-4-(2-((tetrahydro-2H-pyran-4-yl)amino)pyrimidin-4-yl)pyridin-1(2H)-yl)ethyl)phosphate (978 mg). (M+1=705).

Step B: 5% Pd/C (0.15 g) was added to (S)-dibenzyl (2-(4-chloro-3-fluorophenyl)-2-(2-oxo-4-(2-((tetrahydro-2H-pyran-4-yl)amino)pyrimidin-4-yl)pyridin-1(2H)-yl)ethyl)phosphate (978 mg) under nitrogen. MeOH (8 mL) was added, and the mixture was purged with a hydrogen balloon. The mixture was left under hydrogen overnight. The mixture was filtered through Celite®, and the solvent was removed to leave a solid. The solid was purified by HPLC to obtain (S)-2-(4-chloro-3-fluorophenyl)-2-(2-oxo-4-(2-((tetrahydro-2H-pyran-4-yl)amino)pyrimidin-4-yl)pyridin-1(2H)-yl)ethyl dihydrogen phosphate (3.8 mg). MS=525.0.

Example β

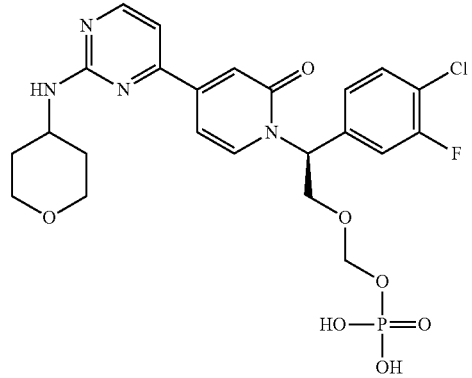 [SMILES: O=c1cc(-c2ccnc(NC3CCOCC3)n2)ccn1[C@H](COCOP(=O)(O)O)c1ccc(Cl)c(F)c1]

(S)-(2-(4-chloro-3-fluorophenyl)-2-(2-oxo-4-(2-((tetrahydro-2H-pyran-4-yl)amino)pyrimidin-4-yl)pyridin-1(2H)-yl)ethoxy)methyl dihydrogen phosphate Step A: Sodium hydride (44 mg, 1.10 mmol) was added to 1-[(1S)-1-(4-chloro-3-fluorophenyl)-2-hydroxyethyl]-4-

[2-(tetrahydropyran-4-ylamino)pyrimidin-4-yl]pyridine-2-one (0.49 g, 1.10 mmol) in DMF (10 mL) at 0° C., which was left to stir at 0° C. In a separate vial, sodium iodide (0.17 g, 1.10 mmol) and chlorodimethyl sulfide (0.11 g, 1.10 mmol) were transferred, which was then added to the reaction mixture. The reaction mixture was stirred overnight at room temperature. The mixture was quenched carefully with water before diluting with ethyl acetate. The phases were separated. The organic phase was washed with saturated sodium bicarbonate, water, and followed by brine. The mixture was dried over sodium sulfate before removing the solvent to leave an oil. The oil was purified by CombiFlash (24 g column, 0-10% MeOH/DCM over 20 minutes) to furnish (S)-1-(1-(4-chloro-3-fluorophenyl)-2-((methylthio)methoxy)ethyl)-4-(2-((tetrahydro-2H-pyran-4-yl)amino)pyrimidin-4-yl)pyridin-2(1H)-one (555 mg) as a solid (M+1=506).

Step B: Phosphoric acid (0.40 g, 3.98 mmol), 4 Å molecular sieves (5 g) and N-iodosuccinimide (0.46 g, 1.99 mmol) were added to (S)-1-(1-(4-chloro-3-fluorophenyl)-2-((methylthio)methoxy)ethyl)-4-(2-((tetrahydro-2H-pyran-4-yl)amino)pyrimidin-4-yl)pyridin-2(1H)-one (0.50 g, 1.00 mmol) in DMF (5 mL). The mixture was stirred at room temperature for 2 hours. The mixture was quenched with sodium thiosulfate. Sodium carbonate was added to bring pH to 10, and the solvent was removed. The resultant was purified by HPLC to afford (S)-(2-(4-chloro-3-fluorophenyl)-2-(2-oxo-4-(2-((tetrahydro-2H-pyran-4-yl)amino)pyrimidin-4-yl)pyridin-1(2H)-yl)ethoxy)methyl dihydrogen phosphate (13 mg). M+1=555.1.

It will be understood that the enumerated embodiments are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

What is claimed is:

1. A process for preparing a compound of Formula 10.1, comprising:

(a) coupling a compound having the structure:

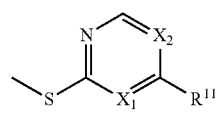

with a compound having the structure:

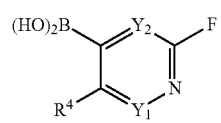

to prepare a compound having the structure:

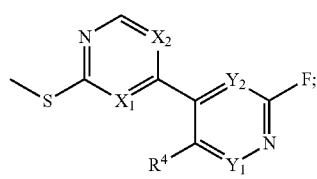

and (b) hydrolyzing the compound having the structure:

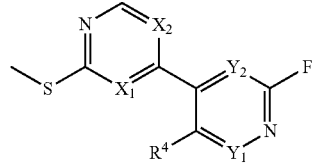

to prepare a compound of Formula 10.1:

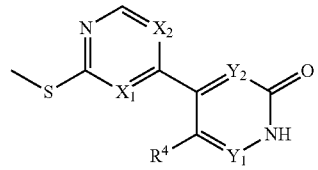

10.1 wherein:
$X_1$ is selected from CH and N;
$X_2$ is selected from $CR^5$ and N;
$Y_1$ is selected from $CR^6$ and N;
$Y_2$ is selected from $CR^7$ and N;
each $R^4$, $R^5$, $R^6$ and $R^7$ is independently selected from hydrogen, halogen and $C_1$-$C_3$ alkyl; and
$R^{11}$ is selected from Cl, Br and I.

2. The process of claim 1 wherein a compound of Formula 1.4 is prepared, comprising:

(a) coupling a compound of Formula 1.1:

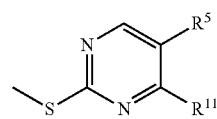

1.1 with a compound of Formula 1.2:

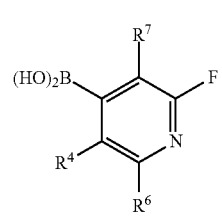

1.2 to prepare a compound of Formula 1.3:

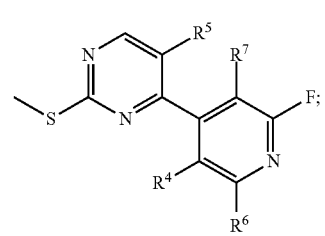

1.3 and
(b) hydrolyzing the compound of Formula 1.3 to prepare a compound of Formula 1.4:

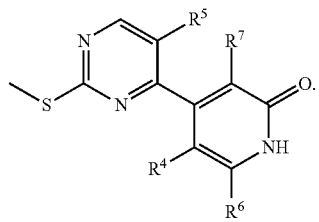

1.4

3. A process for preparing a compound of Formula 10.2, comprising:
reacting a compound of Formula 10.1:

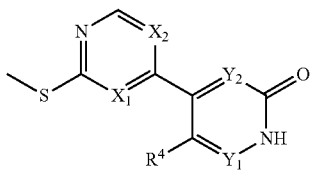

10.1 with a compound having the structure:

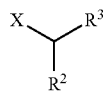

to prepare a compound of Formula 10.2:

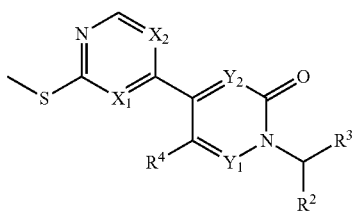

10.2 wherein:
$X_1$ is selected from CH and N;
$X_2$ is selected from $CR^5$ and N;
$Y_1$ is selected from $CR^6$ and N;
$Y_2$ is selected from $CR^7$ and N;
$R^2$ is selected from (a) hydrogen, (b) $C_1$-$C_6$ alkyl optionally substituted with one or more groups selected from $OR^f$, oxo, $NH_2$, $NH(C_1$-$C_3$ alkyl) and $N(C_1$-$C_3$ alkyl)$_2$, (c) $C_1$-$C_6$ alkenyl optionally substituted with one or more groups selected from $OR^f$, oxo, $NH_2$, $NH(C_1$-$C_3$ alkyl) and $N(C_1$-$C_3$ alkyl)$_2$, (d) $C_1$-$C_6$ alkynyl optionally substituted with one or more groups selected from $OR^f$, oxo, $NH_2$, $NH(C_1$-$C_3$ alkyl) and $N(C_1$-$C_3$ alkyl)$_2$, (e) $C_3$-$C_6$ cycloalkyl optionally substituted with one or more groups selected from $OR^f$ and $R^g$, (f) phenyl optionally substituted with one or more groups selected from $OR^f$ and $R^g$, (g) a 3 to 7 membered heterocycle optionally substituted with one or more groups selected from $OR^f$ and $R^g$, and (h) a 5 to 6 membered heteroaryl optionally substituted with one or more groups selected from $OR^f$ and $R^g$;
$R^3$ is selected from (a) $(CR^hR^i)_x$-phenyl, wherein the phenyl may be optionally substituted with one or more $R^j$ groups, (b) $(CR^hR^i)_x$-(5 to 6 membered heteroaryl), wherein the heteroaryl may be optionally substituted with one or more $R^j$ groups, (c) $(CR^hR^i)_x$-(9 to 10 membered bicyclic heterocycle), wherein the heterocycle may be optionally substituted with one or more $R^j$ groups, and (d) $(CR^hR^i)_x$-(9 to 10 membered bicyclic heteroaryl), wherein the heteroaryl may be optionally substituted with one or more $R^j$ groups;
each $R^4$, $R^5$, $R^6$ and $R^7$ is independently selected from hydrogen, halogen and $C_1$-$C_3$ alkyl;
each $R^f$ is independently selected from hydrogen and $C_1$-$C_6$ alkyl optionally substituted with one or more groups selected from oxo, $NH_2$, $NH(C_1$-$C_3$ alkyl) and $N(C_1$-$C_3$ alkyl)$_2$;
each $R^g$ is $C_1$-$C_6$ alkyl;
$R^h$ and $R^i$ are independently selected from hydrogen, $OR^k$ and $C_1$-$C_6$ alkyl optionally substituted with $OR^m$;
each $R^j$ is independently selected from halogen, CN, cyclopropyl, $C_1$-$C_6$ alkyl optionally substituted with halogen, and $C_1$-$C_6$ alkoxy optionally substituted with halogen;
$R^k$ and $R^m$ are independently hydrogen or $C_1$-$C_3$ alkyl;
x is 0 or 1; and
X is Cl, Br, I, OMs or OTf.

4. The process of claim 3, wherein a compound of Formula 3.2 is prepared, comprising:
reacting a compound of Formula 1.4:

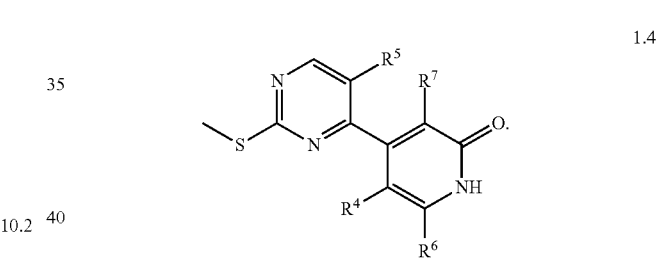

1.4 with a compound of Formula 3.1:

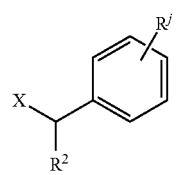

3.1 to prepare a compound of Formula 3.2:

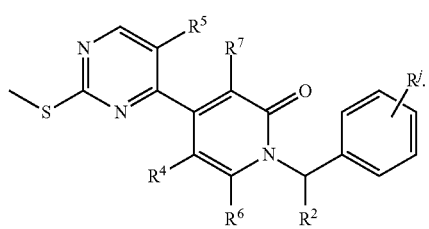

3.2

5. A process for preparing a compound of Formula 10.2, comprising:
reacting a compound of Formula 10.1:

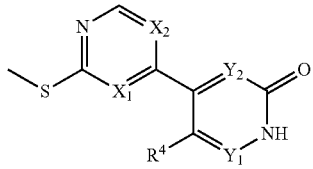

10.1 with a compound having the structure:

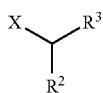

to prepare a compound of Formula 10.2:

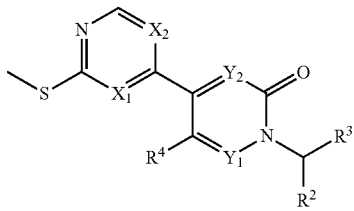

10.2 wherein:
$X_1$ is selected from CH and N;
$X_2$ is selected from $CR^5$ and N;
$Y_1$ is selected from $CR^6$ and N;
$Y_2$ is selected from $CR^7$ and N;
$R^2$ is selected from (a) hydrogen, (b) $C_1$-$C_6$ alkyl optionally substituted with one or more groups selected from $OR^f$, oxo, $NH_2$, $NH(C_1$-$C_3$ alkyl) and $N(C_1$-$C_3$ alkyl)$_2$, (c) $C_1$-$C_6$ alkenyl optionally substituted with one or more groups selected from $OR^f$, oxo, $NH_2$, $NH(C_1$-$C_3$ alkyl) and $N(C_1$-$C_3$ alkyl)$_2$, (d) $C_1$-$C_6$ alkynyl optionally substituted with one or more groups selected from $OR^f$, oxo, $NH_2$, $NH(C_1$-$C_3$ alkyl) and $N(C_1$-$C_3$ alkyl)$_2$, (e) $C_3$-$C_6$ cycloalkyl optionally substituted with one or more groups selected from $OR^f$ and $R^g$, (f) phenyl optionally substituted with one or more groups selected from $OR^f$ and $R^g$, (g) a 3 to 7 membered heterocycle optionally substituted with one or more groups selected from $OR^f$ and $R^g$, and (h) a 5 to 6 membered heteroaryl optionally substituted with one or more groups selected from $OR^f$ and $R^g$;
$R^3$ is selected from (a) $(CR^hR^i)_x$-phenyl, wherein the phenyl may be optionally substituted with one or more $R^j$ groups, (b) $(CR^hR^i)_x$-(5 to 6 membered heteroaryl), wherein the heteroaryl may be optionally substituted with one or more $R^j$ groups, (c) $(CR^hR^i)_x$-(9 to 10 membered bicyclic heterocycle), wherein the heterocycle may be optionally substituted with one or more $R^j$ groups, and (d) $(CR^hR^i)_x$-(9 to 10 membered bicyclic heteroaryl), wherein the heteroaryl may be optionally substituted with one or more $R^j$ groups;
each $R^4$, $R^5$, $R^6$ and $R^7$ is independently selected from hydrogen, halogen and $C_1$-$C_3$ alkyl;
each $R^f$ is independently selected from hydrogen and $C_1$-$C_6$ alkyl optionally substituted with one or more groups selected from oxo, $NH_2$, $NH(C_1$-$C_3$ alkyl) and $N(C_1$-$C_3$ alkyl)$_2$;

each $R^g$ is $C_1$-$C_6$ alkyl;
$R^h$ and $R^i$ are independently selected from hydrogen, $OR^k$ and $C_1$-$C_6$ alkyl optionally substituted with $OR^m$;
each $R^j$ is independently selected from halogen, CN, cyclopropyl, $C_1$-$C_6$ alkyl optionally substituted with halogen, and $C_1$-$C_6$ alkoxy optionally substituted with halogen;
$R^k$ and $R^m$ are independently hydrogen or $C_1$-$C_3$ alkyl; and
x is 0 or 1.

6. The process of claim 5, wherein a compound of Formula 3.2 is prepared, comprising:
reacting a compound of Formula 1.4:

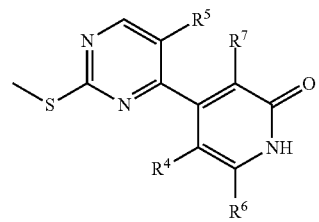

1.4 with a compound of Formula 4.1:

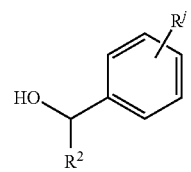

4.1 to prepare a compound of Formula 3.2:

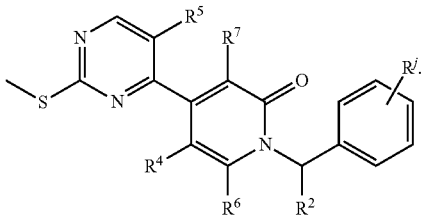

3.2

7. A process for preparing a compound of Formula 10.6, comprising:
oxidizing a compound of Formula 10.2:

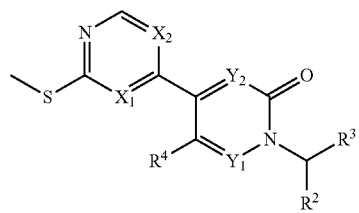

10.2 to prepare a compound of Formula 10.6:

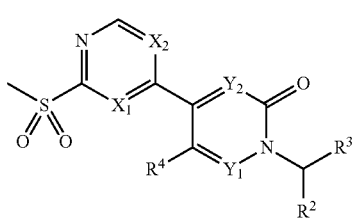

wherein:

$X_1$ is selected from CH and N;

$X_2$ is selected from $CR^5$ and N;

$Y_1$ is selected from $CR^6$ and N;

$Y_2$ is selected from $CR^7$ and N;

$R^2$ is selected from (a) hydrogen, (b) $C_1$-$C_6$ alkyl optionally substituted with one or more groups selected from $OR^f$, oxo, $NH_2$, $NH(C_1$-$C_3$ alkyl) and $N(C_1$-$C_3$ alkyl)$_2$, (c) $C_1$-$C_6$ alkenyl optionally substituted with one or more groups selected from $OR^f$, oxo, $NH_2$, $NH(C_1$-$C_3$ alkyl) and $N(C_1$-$C_3$ alkyl)$_2$, (d) $C_1$-$C_6$ alkynyl optionally substituted with one or more groups selected from $OR^f$, oxo, $NH_2$, $NH(C_1$-$C_3$ alkyl) and $N(C_1$-$C_3$ alkyl)$_2$, (e) $C_3$-$C_6$ cycloalkyl optionally substituted with one or more groups selected from $OR^f$ and $R^g$, (f) phenyl optionally substituted with one or more groups selected from $OR^f$ and $R^g$, (g) a 3 to 7 membered heterocycle optionally substituted with one or more groups selected from $OR^f$ and $R^g$, and (h) a 5 to 6 membered heteroaryl optionally substituted with one or more groups selected from $OR^f$ and $R^g$;

$R^3$ is selected from (a) $(CR^hR^i)_x$-phenyl, wherein the phenyl may be optionally substituted with one or more $R^j$ groups, (b) $(CR^hR^i)_x$-(5 to 6 membered heteroaryl), wherein the heteroaryl may be optionally substituted with one or more $R^j$ groups, (c) $(CR^hR^i)_x$-(9 to 10 membered bicyclic heterocycle), wherein the heterocycle may be optionally substituted with one or more $R^j$ groups, and (d) $(CR^hR^i)_x$-(9 to 10 membered bicyclic heteroaryl), wherein the heteroaryl may be optionally substituted with one or more $R^j$ groups;

each $R^4$, $R^5$, $R^6$ and $R^7$ is independently selected from hydrogen, halogen and $C_1$-$C_3$ alkyl;

each $R^f$ is independently selected from hydrogen and $C_1$-$C_6$ alkyl optionally substituted with one or more groups selected from oxo, $NH_2$, $NH(C_1$-$C_3$ alkyl) and $N(C_1$-$C_3$ alkyl)$_2$;

each $R^g$ is $C_1$-$C_6$ alkyl;

$R^h$ and $R^i$ are independently selected from hydrogen, $OR^k$ and $C_1$-$C_6$ alkyl optionally substituted with $OR^m$;

each $R^j$ is independently selected from halogen, CN, cyclopropyl, $C_1$-$C_6$ alkyl optionally substituted with halogen, and $C_1$-$C_6$ alkoxy optionally substituted with halogen;

$R^k$ and $R^m$ are independently hydrogen or $C_1$-$C_3$ alkyl; and x is 0 or 1.

8. The process of claim 7, wherein a compound of Formula 8.1 is prepared, comprising:

oxidizing a compound of Formula 3.2:

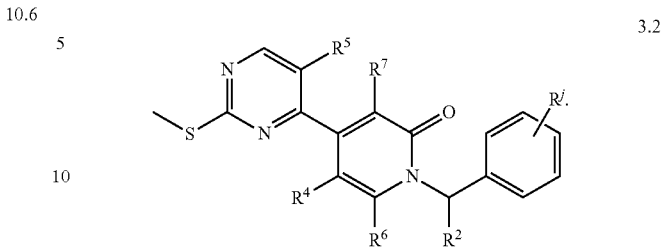

to prepare a compound of Formula 8.1:

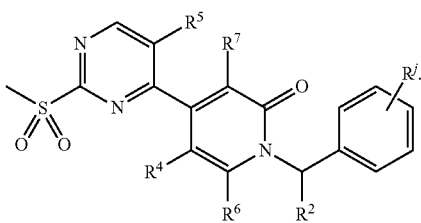

9. A process for preparing a compound of Formula 10.8, comprising:

(a) coupling a compound having the structure:

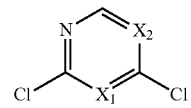

with a compound having the structure:

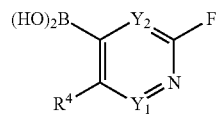

to prepare a compound having the structure:

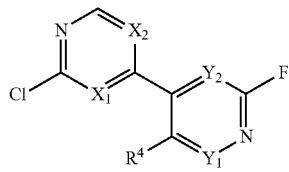

(b) reacting the compound having the structure:

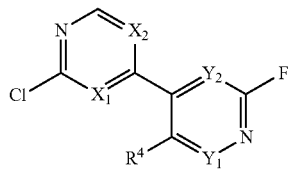

with NH$_2$R$^1$ to prepare a compound having the structure:

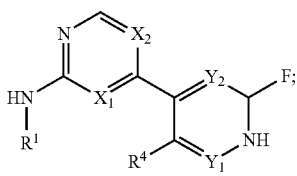

and (c) hydrolyzing the compound having the structure:

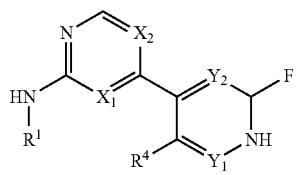

to prepare a compound of Formula 10.8:

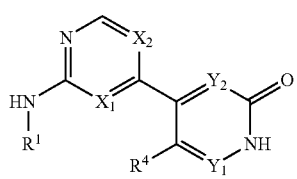

10.8 wherein:
X$_1$ is selected from CH and N;
X$_2$ is selected from CR$^5$ and N;
Y$_1$ is selected from CR$^6$ and N;
Y$_2$ is selected from CR$^7$ and N;
R$^1$ is selected from (a) C$_1$-C$_6$ alkyl optionally substituted with one or more groups independently selected from halogen, OR$^a$, NR$^b$R$^c$, oxo, CN, C$_3$-C$_6$ cycloalkyl and a 3 to 7 membered heterocycle, (b) C$_3$-C$_7$ cycloalkyl optionally substituted with one or more groups independently selected from halogen, OR$^a$, CN and C$_1$-C$_3$ alkyl optionally substituted with one or more groups independently selected from halogen and OR$^d$, (c) phenyl optionally substituted with one or more groups independently selected from halogen, OR$^a$, CN, C$_3$-C$_6$ cycloalkyl and C$_1$-C$_3$ alkyl optionally substituted with one or more groups independently selected from halogen and OR$^d$, (d) a 3 to 7 membered saturated or partially unsaturated heterocycle optionally substituted with one or more groups independently selected from halogen, OR$^a$, oxo, CN, C$_3$-C$_6$ cycloalkyl and C$_1$-C$_3$ alkyl optionally substituted with one or more groups independently selected from halogen and OR$^d$, (e) a 5 to 6 membered heteroaryl optionally substituted with one or more groups independently selected from halogen, OR$^e$, oxide, CN, C$_3$-C$_6$ cycloalkyl and C$_1$-C$_3$ alkyl optionally substituted with one or more groups independently selected from halogen, oxo and OR$^d$, and (f) a 7 to 10 membered bicyclic heterocycle optionally substituted with one or more groups independently selected from halogen, OR$^a$, oxo, CN, C$_3$-C$_6$ cycloalkyl and C$_1$-C$_3$ alkyl optionally substituted with one or more groups independently selected from halogen and OR$^d$;
each R$^4$, R$^5$, R$^6$ and R$^7$ is independently selected from hydrogen, halogen and C$_1$-C$_3$ alkyl; and
each R$^a$, R$^b$, R$^c$, R$^d$, and R$^e$ is independently selected from hydrogen and C$_1$-C$_6$ alkyl.

10. The process of claim 9, wherein a compound of Formula 9.4 is prepared, comprising:

(a) coupling a compound of Formula 9.1:

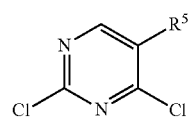

9.1 with a compound of Formula 1.2:

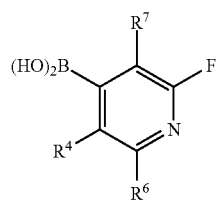

1.2 to prepare a compound of Formula 9.2:

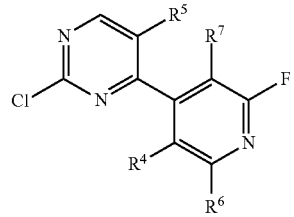

9.2

(b) reacting the compound of Formula 9.2 with NH$_2$R$^1$ to prepare a compound of Formula 9.3:

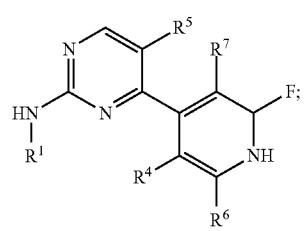

9.3 and (c) hydrolyzing the compound of Formula 9.3 to prepare a compound of Formula 9.4:

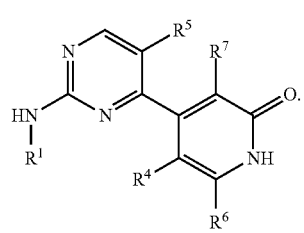

9.4

11. A process for preparing a compound of Formula I, comprising:
reacting a compound of Formula 10.6:

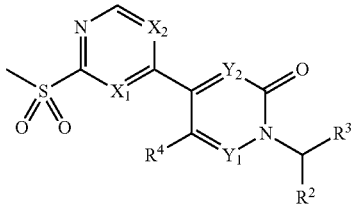

10.6 with $NH_2R^1$ to prepare a compound of Formula I:

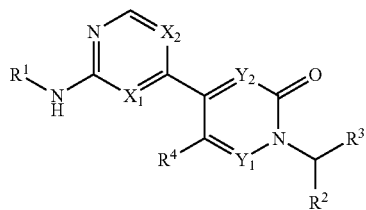

I wherein:
$X_1$ is selected from CH and N;
$X_2$ is selected from $CR^5$ and N;
$Y_1$ is selected from $CR^6$ and N;
$Y_2$ is selected from $CR^7$ and N;
$R^1$ is selected from (a) $C_1$-$C_6$ alkyl optionally substituted with one or more groups independently selected from halogen, $OR^a$, $NR^bR^c$, oxo, CN, $C_3$-$C_6$ cycloalkyl and a 3 to 7 membered heterocycle, (b) $C_3$-$C_7$ cycloalkyl optionally substituted with one or more groups independently selected from halogen, $OR^a$, CN and $C_1$-$C_3$ alkyl optionally substituted with one or more groups independently selected from halogen and $OR^d$, (c) phenyl optionally substituted with one or more groups independently selected from halogen, $OR^a$, CN, $C_3$-$C_6$ cycloalkyl and $C_1$-$C_3$ alkyl optionally substituted with one or more groups independently selected from halogen and $OR^d$, (d) a 3 to 7 membered saturated or partially unsaturated heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$, (e) a 5 to 6 membered heteroaryl optionally substituted with one or more groups independently selected from halogen, $OR^e$, oxide, CN, $C_3$-$C_6$ cycloalkyl and $C_1$-$C_3$ alkyl optionally substituted with one or more groups independently selected from halogen, oxo and $OR^d$, and (f) a 7 to 10 membered bicyclic heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$;
$R^2$ is selected from (a) hydrogen, (b) $C_1$-$C_6$ alkyl optionally substituted with one or more groups selected from $OR^f$, oxo, $NH_2$, $NH(C_1$-$C_3$ alkyl) and $N(C_1$-$C_3$ alkyl)$_2$, (c) $C_1$-$C_6$ alkenyl optionally substituted with one or more groups selected from $OR^f$, oxo, $NH_2$, $NH(C_1$-$C_3$ alkyl) and $N(C_1$-$C_3$ alkyl)$_2$, (d) $C_1$-$C_6$ alkynyl optionally substituted with one or more groups selected from $OR^f$, oxo, $NH_2$, $NH(C_1$-$C_3$ alkyl) and $N(C_1$-$C_3$ alkyl)$_2$, (e) $C_3$-$C_6$ cycloalkyl optionally substituted with one or more groups selected from $OR^f$ and $R^g$, (f) phenyl optionally substituted with one or more groups selected from $OR^f$ and $R^g$, (g) a 3 to 7 membered heterocycle optionally substituted with one or more groups selected from $OR^f$ and $R^g$, and (h) a 5 to 6 membered heteroaryl optionally substituted with one or more groups selected from $OR^f$ and $R^g$;
$R^3$ is selected from (a) $(CR^hR^i)_x$-phenyl, wherein the phenyl may be optionally substituted with one or more $R^j$ groups, (b) $(CR^hR^i)_x$-(5 to 6 membered heteroaryl), wherein the heteroaryl may be optionally substituted with one or more $R^j$ groups, (c) $(CR^hR^i)_x$-(9 to 10 membered bicyclic heterocycle), wherein the heterocycle may be optionally substituted with one or more $R^j$ groups, and (d) $(CR^hR^i)_x$-(9 to 10 membered bicyclic heteroaryl), wherein the heteroaryl may be optionally substituted with one or more $R^j$ groups;
each $R^4$, $R^5$, $R^6$ and $R^7$ is independently selected from hydrogen, halogen and $C_1$-$C_3$ alkyl;
each $R^a$, $R^b$, $R^c$, $R^d$ and $R^e$ is independently selected from hydrogen and $C_1$-$C_6$ alkyl;
$R^f$ is selected from hydrogen and $C_1$-$C_6$ alkyl optionally substituted with one or more groups selected from oxo, $NH_2$, $NH(C_1$-$C_3$ alkyl) and $N(C_1$-$C_3$ alkyl)$_2$;
each $R^g$ is $C_1$-$C_6$ alkyl;
$R^h$ and $R^i$ are independently selected from hydrogen, $OR^k$ and $C_1$-$C_6$ alkyl optionally substituted with $OR^m$;
each $R^j$ is independently selected from halogen, CN, cyclopropyl, $C_1$-$C_6$ alkyl optionally substituted with halogen, and $C_1$-$C_6$ alkoxy optionally substituted with halogen;
$R^k$ and $R^m$ are independently hydrogen or $C_1$-$C_3$ alkyl; and
x is 0 or 1.

12. A process for preparing a compound of Formula I, comprising:
reacting a compound of Formula 10.8:

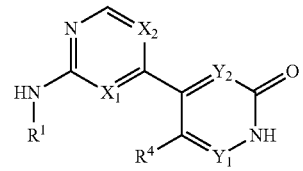

10.8 with a compound having the structure:

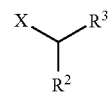

to prepare a compound of Formula I:

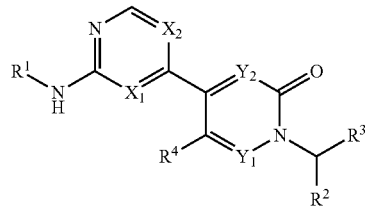

I wherein:

$X_1$ is selected from CH and N;

$X_2$ is selected from $CR^5$ and N;

$Y_1$ is selected from $CR^6$ and N;

$Y_2$ is selected from $CR^7$ and N;

$R^1$ is selected from (a) $C_1$-$C_6$ alkyl optionally substituted with one or more groups independently selected from halogen, $OR^a$, $NR^bR^c$, oxo, CN, $C_3$-$C_6$ cycloalkyl and a 3 to 7 membered heterocycle, (b) $C_3$-$C_7$ cycloalkyl optionally substituted with one or more groups independently selected from halogen, $OR^a$, CN and $C_1$-$C_3$ alkyl optionally substituted with one or more groups independently selected from halogen and $OR^d$, (c) phenyl optionally substituted with one or more groups independently selected from halogen, $OR^a$, CN, $C_3$-$C_6$ cycloalkyl and $C_1$-$C_3$ alkyl optionally substituted with one or more groups independently selected from halogen and $OR^d$, (d) a 3 to 7 membered saturated or partially unsaturated heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$, (e) a 5 to 6 membered heteroaryl optionally substituted with one or more groups independently selected from halogen, $OR^e$, oxide, CN, $C_3$-$C_6$ cycloalkyl and $C_1$-$C_3$ alkyl optionally substituted with one or more groups independently selected from halogen, oxo and $OR^d$, and (f) a 7 to 10 membered bicyclic heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$;

$R^2$ is selected from (a) hydrogen, (b) $C_1$-$C_6$ alkyl optionally substituted with one or more groups selected from $OR^f$, oxo, $NH_2$, $NH(C_1$-$C_3$ alkyl) and $N(C_1$-$C_3$ alkyl)$_2$, (c) $C_1$-$C_6$ alkenyl optionally substituted with one or more groups selected from $OR^f$, oxo, $NH_2$, $NH(C_1$-$C_3$ alkyl) and $N(C_1$-$C_3$ alkyl)$_2$, (d) $C_1$-$C_6$ alkynyl optionally substituted with one or more groups selected from $OR^f$, oxo, $NH_2$, $NH(C_1$-$C_3$ alkyl) and $N(C_1$-$C_3$ alkyl)$_2$, (e) $C_3$-$C_6$ cycloalkyl optionally substituted with one or more groups selected from $OR^f$ and $R^g$, (f) phenyl optionally substituted with one or more groups selected from $OR^f$ and $R^g$, (g) a 3 to 7 membered heterocycle optionally substituted with one or more groups selected from $OR^f$ and $R^g$, and (h) a 5 to 6 membered heteroaryl optionally substituted with one or more groups selected from $OR^f$ and $R^g$;

$R^3$ is selected from (a) $(CR^hR^i)_x$-phenyl, wherein the phenyl may be optionally substituted with one or more $R^j$ groups, (b) $(CR^hR^i)_x$-(5 to 6 membered heteroaryl), wherein the heteroaryl may be optionally substituted with one or more $R^j$ groups, (c) $(CR^hR^i)_x$-(9 to 10 membered bicyclic heterocycle), wherein the heterocycle may be optionally substituted with one or more $R^j$ groups, and (d) $(CR^hR^i)_x$-(9 to 10 membered bicyclic heteroaryl), wherein the heteroaryl may be optionally substituted with one or more $R^j$ groups;

each $R^4$, $R^5$, $R^6$ and $R^7$ is independently selected from hydrogen, halogen and $C_1$-$C_3$ alkyl;

each $R^a$, $R^b$, $R^c$, $R^d$ and $R^e$ are independently selected from hydrogen and $C_1$-$C_6$ alkyl;

$R^f$ is selected from hydrogen and $C_1$-$C_6$ alkyl optionally substituted with one or more groups selected from oxo, $NH_2$, $NH(C_1$-$C_3$ alkyl) and $N(C_1$-$C_3$ alkyl)$_2$;

each $R^g$ is $C_1$-$C_6$ alkyl;

$R^h$ and $R^i$ are independently selected from hydrogen, $OR^k$ and $C_1$-$C_6$ alkyl optionally substituted with $OR^m$;

each $R^j$ is independently selected from halogen, CN, cyclopropyl, $C_1$-$C_6$ alkyl optionally substituted with halogen, and $C_1$-$C_6$ alkoxy optionally substituted with halogen;

$R^k$ and $R^m$ are independently hydrogen or $C_1$-$C_3$ alkyl;

x is 0 or 1; and

X is Cl, Br, I, OMs or OTf.

* * * * *